(12) United States Patent
Bramson et al.

(10) Patent No.: US 11,878,035 B2
(45) Date of Patent: *Jan. 23, 2024

(54) T CELL-ANTIGEN COUPLER WITH VARIOUS CONSTRUCT OPTIMIZATIONS

(71) Applicants: Triumvira Immunologics USA, Inc., Austin, TX (US); McMaster University, Hamilton (CA)

(72) Inventors: Jonathan Lorne Bramson, Oakville (CA); Christopher W. Helsen, Oakville (CA); Joanne Alicia Hammill, Hamilton (CA); Kenneth Anthony Mwawasi, Vancouver (CA)

(73) Assignees: Triumvira Immunologics USA, Inc., Austin, TX (US); McMaster University, Hamilton (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/188,326

(22) Filed: Mar. 22, 2023

(65) Prior Publication Data

US 2023/0210905 A1 Jul. 6, 2023

Related U.S. Application Data

(63) Continuation of application No. 17/810,238, filed on Jun. 30, 2022, which is a continuation of application No. 17/394,280, filed on Aug. 4, 2021, now Pat. No. 11,406,667, which is a continuation of application No. 15/929,513, filed on May 6, 2020, now Pat. No. 11,110,123, which is a continuation of application No. PCT/US2019/042297, filed on Jul. 17, 2019, which is a continuation of application No. 16/442,274, filed on Jun. 14, 2019, now Pat. No. 10,640,562.

(60) Provisional application No. 62/874,426, filed on Jul. 15, 2019, provisional application No. 62/839,235, filed on Apr. 26, 2019, provisional application No. 62/828,879, filed on Apr. 3, 2019, provisional application No. 62/826,853, filed on Mar. 29, 2019, provisional application No. 62/773,120, filed on Nov. 29, 2018, provisional application No. 62/703,037, filed on Jul. 25, 2018, provisional application No. 62/699,173, filed on Jul. 17, 2018.

(51) Int. Cl.
| | |
|---|---|
| A61K 48/00 | (2006.01) |
| A61K 35/17 | (2015.01) |
| C07K 14/725 | (2006.01) |
| A61P 35/00 | (2006.01) |
| C07K 14/82 | (2006.01) |
| C07K 14/73 | (2006.01) |
| C07K 14/705 | (2006.01) |
| C07K 16/28 | (2006.01) |
| C07K 16/32 | (2006.01) |

(52) U.S. Cl.
CPC .............. *A61K 35/17* (2013.01); *A61P 35/00* (2018.01); *C07K 14/7051* (2013.01); *C07K 14/70514* (2013.01); *C07K 14/70517* (2013.01); *C07K 14/82* (2013.01); *C07K 16/2803* (2013.01); *C07K 16/2809* (2013.01); *C07K 16/32* (2013.01); *C07K 2317/622* (2013.01); *C07K 2319/03* (2013.01)

(58) Field of Classification Search
None
See application file for complete search history.

(56) References Cited

U.S. PATENT DOCUMENTS

| | | | |
|---|---|---|---|
| 7,083,785 B2 | 8/2006 | Browning et al. |
| 7,947,805 B2 | 5/2011 | Belloir et al. |
| 8,084,030 B2 | 12/2011 | Kalled et al. |
| 9,718,893 B2 | 8/2017 | Jung et al. |
| 10,435,453 B2 | 10/2019 | Bramson et al. |
| 10,640,562 B2 | 5/2020 | Bramson et al. |
| 10,822,408 B2 | 11/2020 | Hamburger et al. |
| 11,001,621 B1 | 5/2021 | Bramson et al. |
| 11,008,376 B2 | 5/2021 | Bramson et al. |
| 11,110,123 B2 | 9/2021 | Bramson et al. |
| 11,111,298 B2 | 9/2021 | Bramson et al. |
| 11,198,737 B2 | 12/2021 | Helsen et al. |
| 11,406,667 B2 | 8/2022 | Bramson et al. |
| 11,421,014 B2 | 8/2022 | Bader et al. |

(Continued)

FOREIGN PATENT DOCUMENTS

| | | |
|---|---|---|
| CN | 1229436 | 9/1999 |
| CN | 101679966 A | 3/2010 |

(Continued)

OTHER PUBLICATIONS

Borst et al 1988 J. Exp. MED. pp. 1625-1644 Distinct Molecular Forms of Human T Cell Receptor ,y/8 Detected on Viable T Cells by a Monoclonal Antibody.*

(Continued)

*Primary Examiner* — Maria G Leavitt
(74) *Attorney, Agent, or Firm* — Goodwin Procter LLP

(57) ABSTRACT

A trifunctional molecule is provided, comprising (i) a target-specific ligand, (ii) a ligand that binds a protein associated with a TCR complex, and (iii) a T cell receptor signaling domain polypeptide. Variants of the molecule are provided, including variants that exhibit optimized surface expression, transduction efficiency, and effector functionality. Variations include, for example, different ligands that bind CD3 epsilon (e.g., OKT3, L2K, F6A, UCHT1 and humanized UCHT1), different signaling domains, and different linkers between domains.

6 Claims, 57 Drawing Sheets

Specification includes a Sequence Listing.

(56) References Cited

U.S. PATENT DOCUMENTS

| | | |
|---|---|---|
| 11,453,723 B1 | 9/2022 | Bramson et al. |
| 2002/0081296 A1 | 6/2002 | Theill et al. |
| 2002/0107869 A1 | 8/2002 | Leroy |
| 2003/0012783 A1 | 1/2003 | Kindsvogel |
| 2003/0095967 A1 | 5/2003 | MacKay et al. |
| 2004/0162411 A1 | 8/2004 | Lanzavecchia |
| 2006/0233791 A1 | 10/2006 | Tedder et al. |
| 2007/0048221 A1 | 3/2007 | Kindsvogel |
| 2007/0048319 A1 | 3/2007 | Kindsvogel |
| 2007/0049735 A1 | 3/2007 | Kindsvogel |
| 2008/0044413 A1 | 2/2008 | Hammond et al. |
| 2008/0095766 A1 | 4/2008 | Koenig et al. |
| 2008/0260737 A1 | 10/2008 | Ponce et al. |
| 2008/0267965 A1 | 10/2008 | Kalled et al. |
| 2009/0004186 A1 | 1/2009 | Shitara et al. |
| 2012/0009190 A1 | 1/2012 | Gaffen et al. |
| 2012/0082661 A1 | 4/2012 | Kalled et al. |
| 2012/0213768 A1 | 8/2012 | Oh et al. |
| 2013/0101599 A1 | 4/2013 | Borges et al. |
| 2013/0156770 A1 | 6/2013 | Kufer et al. |
| 2013/0171152 A1 | 7/2013 | Spriggs et al. |
| 2013/0273055 A1 | 10/2013 | Borges et al. |
| 2013/0280280 A1 | 10/2013 | Algate et al. |
| 2013/0330323 A1 | 12/2013 | Dunn et al. |
| 2015/0119555 A1 | 4/2015 | Jung et al. |
| 2015/0322169 A1 | 11/2015 | June et al. |
| 2016/0228546 A1 | 8/2016 | Stagliano et al. |
| 2016/0362472 A1 | 12/2016 | Bitter et al. |
| 2016/0368964 A1 | 12/2016 | Bramson et al. |
| 2019/0153115 A1 | 5/2019 | Schellenberger et al. |
| 2020/0024345 A1 | 1/2020 | Bramson et al. |
| 2020/0071377 A1 | 3/2020 | Bramson et al. |
| 2020/0239571 A1 | 7/2020 | Bramson et al. |
| 2020/0261500 A1 | 8/2020 | Bramson et al. |
| 2020/0270330 A1 | 8/2020 | Bramson et al. |
| 2020/0308278 A1 | 10/2020 | Bramson et al. |
| 2020/0392247 A1 | 12/2020 | Helsen et al. |
| 2021/0369780 A1 | 12/2021 | Bramson et al. |
| 2022/0127372 A1 | 4/2022 | Ll et al. |
| 2022/0331364 A1 | 10/2022 | Bramson et al. |
| 2022/0332790 A1 | 10/2022 | Bramson et al. |
| 2023/0212258 A1 | 7/2023 | Bramson et al. |

FOREIGN PATENT DOCUMENTS

| | | |
|---|---|---|
| CN | 103562221 | 2/2014 |
| JP | 2003111595 A | 4/2003 |
| WO | WO 88/00290 * | 1/1988 |
| WO | WO-199744461 A2 | 11/1997 |
| WO | WO-9957268 A1 | 11/1999 |
| WO | WO-2004106380 A2 | 12/2004 |
| WO | WO-2005040220 A1 | 5/2005 |
| WO | WO-2010037835 A2 | 4/2010 |
| WO | WO-2012066058 A1 | 5/2012 |
| WO | WO-2012106587 A1 | 8/2012 |
| WO | WO-2012135345 A1 | 10/2012 |
| WO | WO-2012163805 A1 | 12/2012 |
| WO | WO-2013059885 A2 | 5/2013 |
| WO | WO-2013092001 A1 | 6/2013 |
| WO | WO-2013/123061 A1 | 8/2013 |
| WO | WO-2013132268 A1 | 9/2013 |
| WO | WO-2014011988 A2 | 1/2014 |
| WO | WO-2014122144 A1 | 8/2014 |
| WO | WO-2015006749 A2 | 1/2015 |
| WO | WO-2015117229 A1 | 8/2015 |
| WO | WO-2016166139 A1 | 10/2016 |
| WO | WO-2017040344 A2 | 3/2017 |
| WO | WO-2017087723 A1 | 5/2017 |
| WO | WO-2018027155 A1 | 2/2018 |
| WO | WO-2018121605 A1 | 7/2018 |
| WO | WO-2019071358 A1 | 4/2019 |
| WO | WO-2020018727 A1 | 1/2020 |
| WO | WO-2020156554 A1 | 8/2020 |
| WO | WO-2022099076 A1 | 5/2022 |
| WO | WO-2022256449 A1 | 12/2022 |
| WO | WO-2022266778 A1 | 12/2022 |

OTHER PUBLICATIONS

Acuto et al. T cell activation and the cytoskeleton. Annu. Rev. Immunol. 18:165-184 (2000).

Alabanza et al. Function of Novel Anti-CD19 Chimeric Antigen Receptors with Human Variable Regions Is Affected by Hinge and Transmembrane Domains. Mol Ther 25(11):2452-2465 (2017).

Anderson et al. Comodulation of CD3 and CD4. Evidence for a specific association between CD4 and approximately 5% of the CD3:T cell receptor complexes on helper T lymphocytes. J Immunol 140:1732-1737 (1988).

Apuri, S., et al., "Outcomes in Patients with Acute Myeloid Leukemia Preceded by Breast Cancer", Blood, 120(21): 4316 (2012).

Arcaro et al. Essential role of CD8 palmitoylation in CD8 coreceptor function. J. Immunol. 165:2068-2076 (2000).

Bezverbnaya, K., et al., Preclinical evaluation of BCMA-specific TAC receptor-engineered T cells for multiple myeloma, 32nd annual meeting and pre-conference programs of the society for immunotherapy of cancer (SITC 2017): Part one, J Immunother Cancer, 5(Suppl 2): 86 (2017).

Carpenter, R.O., et al., B-cell maturation antigen is a promising target for adoptive T-cell therapy of multiple myeloma, Clin Cancer Res, 19(8): 2048-2060 (2013).

Chames et al. Bispecific antibodies for cancer therapy: the light at the end of the tunnel? MAbs 1:539-547 (2009).

Chervin et al. The impact of TCR-binding properties and antigen presentation format on T cell responsiveness. J. Immunol. 183:1166-1178 (2009).

Chiu, A., et al., Hodgkin lymphoma cells express TACI and BCMA receptors and generate survival and proliferation signals in response to BAFF and APRIL, Blood, 109(2): 729-739 (2007).

Compte et al. Inhibition of tumor growth in vivo by in situ secretion of bispecific anti-CEA x anti-CD3 diabodies from lentivirally transduced human lymphocytes. Cancer Gene Therapy 14:380-388 (2007).

De Novo, New Products from R&D Systems, Antibody catalog including BCMA mAB, pp. 1-10 (Mar. 2004).

Deans et al. Interaction of CD4:lck with the T cell receptor/CD3 complex induces early signaling events in the absence of CD45 tyrosine phosphatase. Eur J Immunol 22:661-668 (1992).

Deng, S., et al., B-lymphocyte-induced maturation protein1 up-regulates the expression of B-cell maturation antigen in mouse plasma cells, Mol Biol Rep, 37(8): 3747-3755 (2010).

Deshayes, S., et al., Cell-penetrating peptides: tools for intracellular delivery of therapeutics, Cell Mol Life Sci, 62(16): 1839-1849 (2005).

Dotti et al. Fifteen years of gene therapy based on chimeric antigen receptors: "are we nearly there yet?" Hum. Gene Ther. 20:1229-1239 (2009).

EP15746948.7 Communication pursuant to Rule 114(2) EPC dated Jan. 21, 2019.

Finney et al. Activation of resting human primary T cells with chimeric receptors: costimulation from CD28, inducible costimulator, CD134, and CD137 in series with signals from the TCR zeta chain. J. Immunol. 172:104-113 (2004).

Fournier et al. Bispecific antibodies and trispecific immunocytokines for targeting the immune system against cancer: preparing for the future. BioDrugs 27:35-53 (2013).

Fragoso et al. Lipid raft distribution of CD4 depends on its palmitoylation and association with Lek, and evidence for CD4-induced lipid raft aggregation as an additional mechanism to enhance CD3 signaling. J. Immunol. 170:913-921 (2003).

Frankel et al. Targeting T cells to tumor cells using bispecific antibodies. Curr Opin Chem Biol 17(3):385-392 (2013).

Fry et al. T-cell adoptive immunotherapy for acute lymphoblastic leukemia. Hematology Am. Soc. Hematol. Educ. Program 2013:348-353 (2013).

(56) References Cited

OTHER PUBLICATIONS

Geiger et al. Integrated src kinase and costimulatory activity enhances signal transduction through single-chain chimeric receptors in T lymphocytes. Blood 98(8):2364-2371 (2001).
Geyer et al. Review: Current clinical applications of chimeric antigen receptor (CAR) modified T cells. Cytotherapy 18(11):1393-1409 (2016).
Guadagnoli, M., et al., Development and characterization of APRIL antagonistic monoclonal antibodies for treatment of B-cell lymphomas, Blood, 117(25): 6856-6865 (2011).
Hammill, J.A., Pre-clinical development of synthetic receptor-engineered T lymphocytes for the treatment of cancer-novel receptors and understanding toxicity, Thesis submitted to McMaster Univerisity, pp. 1-220 (2017).
Hammond et al. Selective targeting and potent control of tumor growth using an EphA2/CD3-Bispecific single-chain antibody construct. 67(8):3927-3935 (2007).
Han et al. Chimeric antigen receptor-engineered T cells for cancer immunotherapy: progress and challenges. J. Hematol. Oncol. 6:4 7 (2013).
He et al. T-cell antigen receptor triggering and lipid rafts: a matter of space and time scales. Talking Point on the involvement of lipid rafts in T-cell activation. EMBO Rep. 9:525-530 (2008).
Helsen et al. The chimeric TAC receptor co-opts the T cell receptor yielding robust anti-tumor activity without toxicity. Nature Communications 9:3049 (2018).
Helsen et al. Tri-functional T cell receptor antigen coupler (Tri-TAC): a novel methodto direct T cells against tumors. J Immunother Cancer 2(Supp 3):P17 (2014).
Hexham et al. Optimization of the anti-(human CD3) immunotoxin DT389-scFv(UCHT1) N-terminal sequence to yield a homogeneous protein. Biotechnol Appl Biochem 34(Pt 3):183-187 (2010).
Humphries. Adoptive cell therapy: Honing that killer instinct. Nature 504:S13-15 (2013).
Itano et al. The cytoplasmic domain of CD4 promotes the development of CD4 lineage T cells. J Exp Med. 183(3):731-741 (1996).
Jamal, S., et al., "Immunophenotypic Analysis of Peripheral T-Cell Neoplasms", Am. J. Clin. Pathol., vol. 116, pp. 512-526, (2001).
Kiewe, P., et al., "Phase I Trial of the Trifunctional Anti-HER2 x Anti-CD3 Antibody Ertumaxomab in Matastatic Breast Cancer", Clin. Cancer Res., 12(10), pp. 3085-3091, (2006).
Kim et al. A zinc clasp structure tethers Lek to T cell coreceptors CD4 and CD8. Science 301:1725-1728 (2003).
Kimchi-Sarfaty, C., et al., "A 'silent' polymorphiosm in the MDR1 gene changes substrate specificity", Science, 315:525-528, (2007).
Klinger et al. Harnessing T cells to fight cancer with BITER antibody constructs—past developments and future directions. Immunol Rev. 270(1):193-208 (2016).
Kochenderfer et al. Treating B-cell cancer with T cells expressing anti-CD19 chimeric antigen receptors. Nat. Rev. Clin. Oncol. 10:267-276 (2013).
Kuhns et al. TCR Signaling Emerges from the Sum of Many Parts. Front. Immunol. 3:159 (2012).
Löffler et al. A recombinant bispecific single-chain antibody, CD19 X CD3, induces rapid and high lymphoma-directed cytotoxicity by unstimulated T lymphocytes. Blood 95(6):2098-2103 (2000).
Marsden, H.R., et al., Model systems for membrane fusion, Chem Soc Rev, 40(3): 1572-1585 (2011).
Methi et al. Short-interfering RNA-mediated Lek knockdown results in augmented downstream T cell responses. J. Immunol. 175(11):7398-7406 (2005).
Milone et al. Chimeric receptors containing CD137 signal transduction domains mediate enhanced survival of T cells and increased antileukemic efficacy in vivo. Mol. Ther. 17: 1453-1464 (2009).
Molhoj, et al. CD19-/CD3-bispecific antibody of the BiTE class is far superior to tandem diabody with respect to redirected tumor cell lysis. Mol Immunol. Mar. 2007;44(8):1935-43. Epub Nov. 2, 2006.
Nagorsen et al. Immunomodulatory therapy of cancer with T cell-engaging BiTE antibody blinatumomab. Exp Cell Res 317(9):1255-1260 (2011).
Nagorsen et al. Immunotherapy of lymphoma and leukemia with T-cell engaging BiTE antibody blinatumomab. Leuk Lymph 50(6): 886-891 (2009).
Novak, A.J., et al., Expression of BLyS and its receptors in B-cell non-Hodgkin lymphoma: correlation with disease activity and patient outcome, Blood, 104(8): 2247-2253 (2004).
Panka et al. Variable region framework differences result in decreased or increased affinity of variant anti-digoxin antibodies. PNAS USA 85:3080-3084 (1988).
PCT/CA2015/000068 International Preliminary Report on Patentability dated Aug. 9, 2016.
PCT/CA2015/000068 International Search Report and Written Opinion dated May 4, 2015.
PCT/CA2018/051290 International Search Report and Written Opinion dated Jan. 17, 2019.
PCT/US2019/042297 International Search Report and Written Opinion dated Oct. 30, 2019.
Pilozzi et al. Co-expression of CD79a (JCB117) and CD3 by lymphoblastic lymphoma. J Pathol 186(2):140-143. (1998).
Popik, et al. CD4 receptor localized to non-raft membrane microdomains supports HIV-1 entry. Identification of a novel raft localization marker in CD4. J Biol Chem 279(1):704-712 (2004).
Portell et al. Clinical and pharmacologic aspects of blinatumomab in the treatment of B-cell acute lymphoblastic leukemia. Clin. Pharmacol. 5(Suppl 1):5-11 (2013).
Rosenberg, et al. Use of tumor-infiltrating lymphocytes and interleukin-2 in the immunotherapy of patients with matastatic melanoma. A preliminary report. NEJM 319: 1676 (1988).
Rudikoff et al. Single amino acid substitution altering antigen-binding specificity. PNAS USA 79:1979-1983 (1982).
Ryan, M.C., et al., Antibody targeting of B-cell maturation antigen on malignant plasma cells, Mol Cancer Ther, 6(11): 3009-3018 (2007).
Tai, Y-T., et al., Novel Fc-Engineered Anti-B Cell Maturation Antigen-Monomethyl Auristatin F Antibody-Drug Conjugate (GSK2857916) Induces Potent and Selective Anti-Multiple Myeloma Activity Via Enhanced Effector Function and Direct Tumor Cell Killing, Blood, 122(21): 877 (2013).
Thompson et al. CLUSTAL W: improving the sensitivity of progressive multiple sequence alignment through sequence weighting, position-specific gap penalties and weight matrix choice. Nucleic Acid Res. 22:4673-4680 (1994).
Till et al. CD20-specific adoptive immunotherapy for lymphoma using a chimeric antigen receptor with both CD28 and 4-1 BB domains: pilot clinical trial results. Blood 119(17):3940-3950 (2012).
U.S. Appl. No. 15/117,173 Office Action dated Jan. 24, 2018.
U.S. Appl. No. 15/117,173 Office Action dated Jun. 21, 2019.
U.S. Appl. No. 15/117,173 Office Action dated Oct. 24, 2018.
U.S. Appl. No. 15/929,510 Office Action dated Nov. 9, 2020.
U.S. Appl. No. 15/929,513 Office Action dated May 11, 2021.
U.S. Appl. No. 15/929,513 Office Action dated Nov. 30, 2020.
U.S. Appl. No. 16/442,274 Office Action dated Nov. 6, 2019.
U.S. Appl. No. 16/547,421 Office Action dated Nov. 24, 2021.
U.S. Appl. No. 16/904,451 Office Action dated Dec. 1, 2020.
U.S. Appl. No. 16/904,451 Office Action dated May 10, 2021.
U.S. Appl. No. 17/248,174 Office Action dated Mar. 11, 2021.
U.S. Appl. No. 17/304,924, filed Jun. 28, 2021.
U.S. Appl. No. 17/394,280, filed Aug. 4, 2021.
U.S. Appl. No. 17/394,280 Office Action dated Dec. 10, 2021.
Velasquez. T cells expressing CD19-specific Engager Molecules for the Immunotherapy of CD19-positive Malignancies. Sci Rep 6:27130 (2016).
Voet, D., et al., Biochemistry, John Wiley and Sons, New York, pp. 126-128, (1990).
Wang, M., et al., Efficient delivery of genome-editing proteins using bioreducible lipid nanoparticles, PNAS, 113(11): 2868-2873 (2016).
Wels et al. Construction, Bacterial Expression and Characterization of a Bifunctional Single-Chain Antibody-Phosphatase Fusion Protein Targeted to the human ERBB-2 receptor. Nature Biotech 10: 1128-1132 (1992).
Wittlich et al. Structural characterization of the transmembrane and cytoplasmic domains of human CD4. Biochimica et Biophysica Acta 1768:2949-2960 (2007).

(56) References Cited

OTHER PUBLICATIONS

Wykosky, J., et al. The EphA2 repector and ephrinA1 ligand in solid tumors: function and therapeutic targeting, Mol Cancer Res, 6(12):1795-1806 (2008).

Yin et al. Crystal structure of a complete ternary complex of T-cell receptor, peptide-MHC, and CD4. PNAS USA 109:5405-5410 (2012).

Yong, K. L., et al., Evaluation Of Bcma As a Therapeutic Target In Multiple Myeloma Using An Antibody-Drug Conjugate, Blood, 122(21): 4447 (2013).

Zahnd et al. Efficient Tumor Targeting with High-Affinity Designed Ankyrin Repeat Proteins: Effects of Affinity and Molecular Size. Cancer Res 70: 1595-1605 (2010).

Zahnd et al. Selection and Characterization of Her2 Binding-designed Ankyrin Repeat Proteins. The Journal Of Biological Chemistry 281 (46):35167-35175 (2006).

Zhang et al. Sequestration of CD4-associated Lck from the TCR complex may elicit T cell hyporesponsiveness in nonobese diabetic mice. J Immunol 160:1148-1157 (1998).

Zhukovsky et al. Bispecific antibodies and CARs: generalized immunotherapeutics harnessing T cell redirection. Curr Opin Immunol 40:24-35 (2016).

Bezverbnaya, K., et al., Development of a B-cell maturation antigen-specific T-cell antigen coupler receptor for multiple myeloma, Cytotherapy, 23(9): 820-832 (2021).

PCT/CA2022/051024 International Search Report and Written Opinion dated Aug. 22, 2022.

PCT/US2022/031836 International Search Report and Written Opinion dated Nov. 3, 2022.

Borst, J., et al., Distinct molecular forms of human T cell receptor γ/δ detected on viable T cells by a monoclonal antibody, J Exp Med, 167(5): 1625-1644 (1988).

Lang, J.M., et al., Pilot trial of interleukin-2 and zoledronic acid to augment γδ T cells as treatment for patients with refractory renal cell carcinoma, Cancer Immunol Immunother, 60(10): 1447-1460 (2011).

PCT/US2021/058339 International Search Report and Written Opinion dated Mar. 10, 2022.

U.S. Appl. No. 16/826,053 Office Action dated Aug. 14, 2023.

U.S. Appl. No. 16/753,577, filed Mar. 22, 2023, now U.S. Pat. No. 11,643,472, May 8, 2023.

* cited by examiner

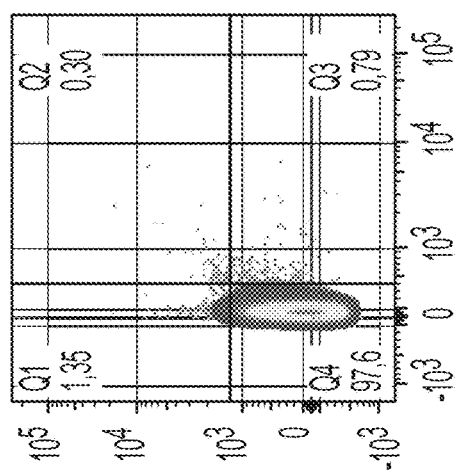
FIG. 6C
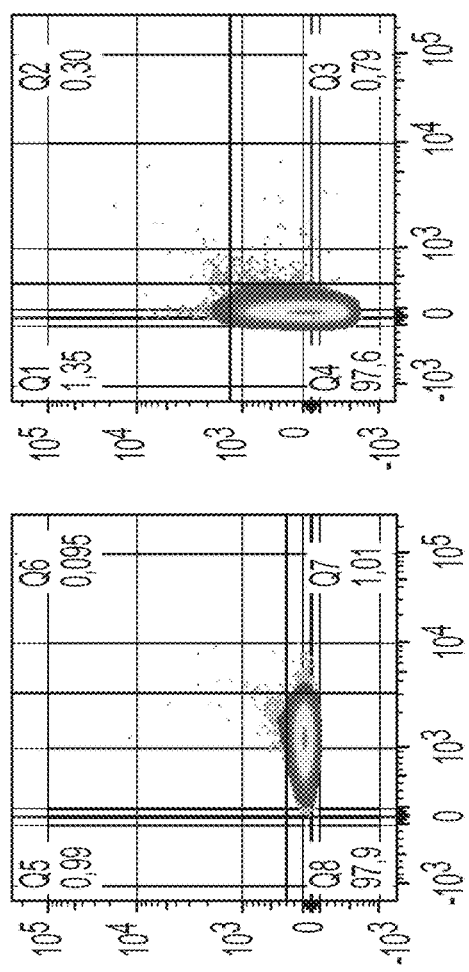
FIG. 6B
FIG. 6A
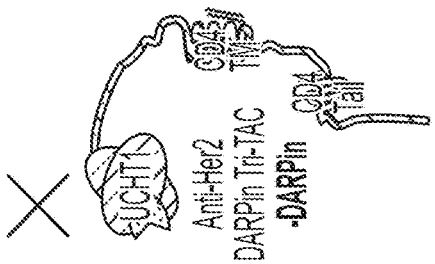
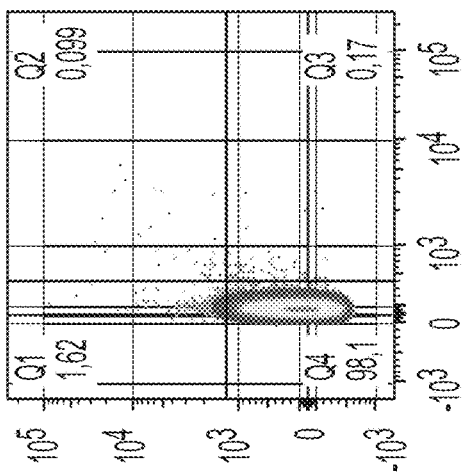
FIG. 6F
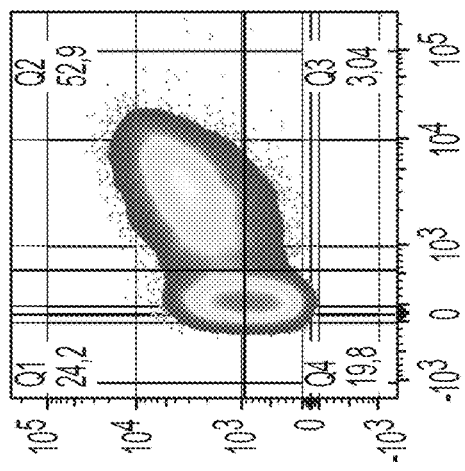
FIG. 6E
FIG. 6D
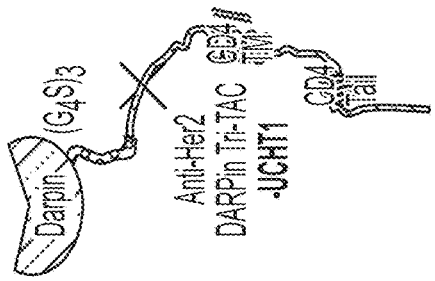

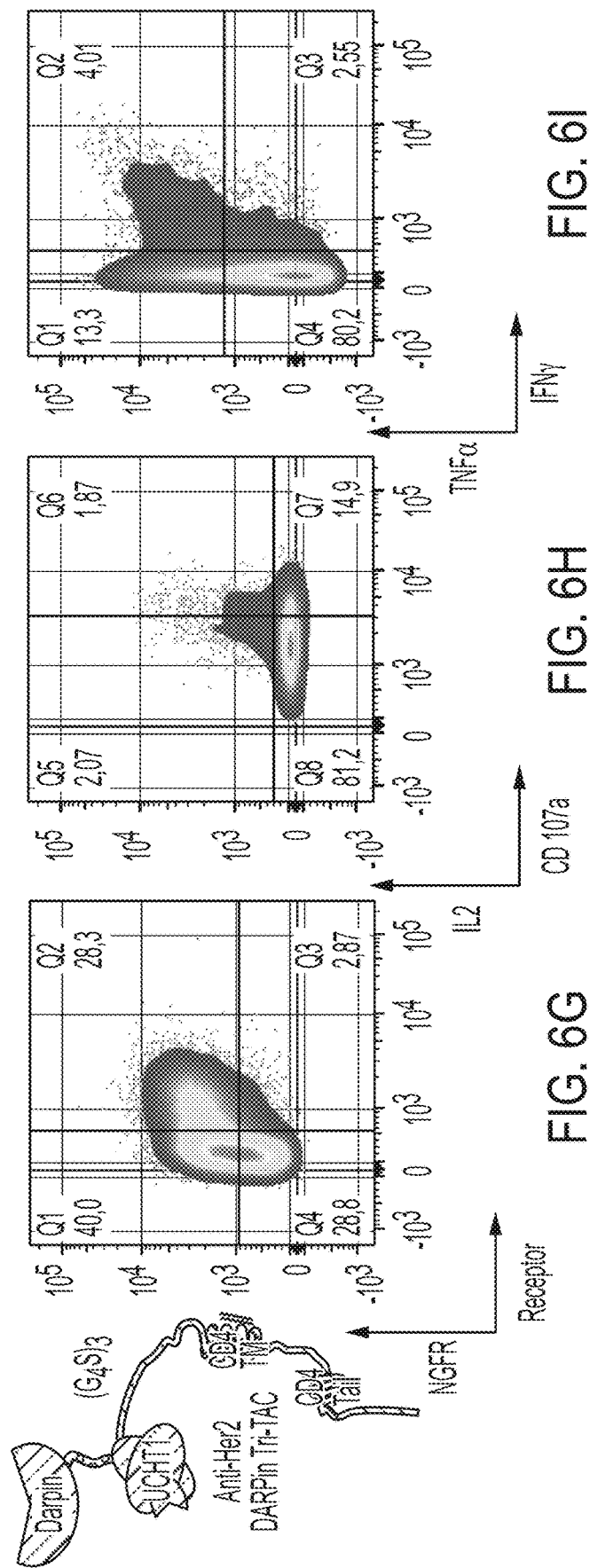

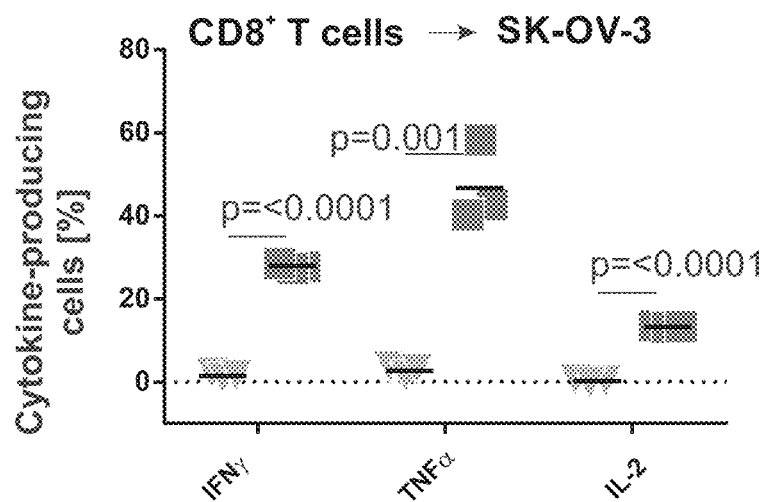
FIG. 8C
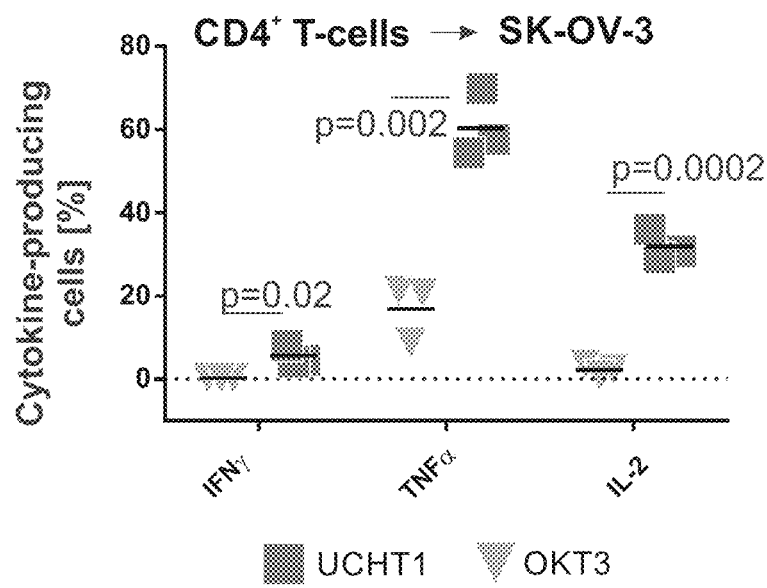
FIG. 8C1

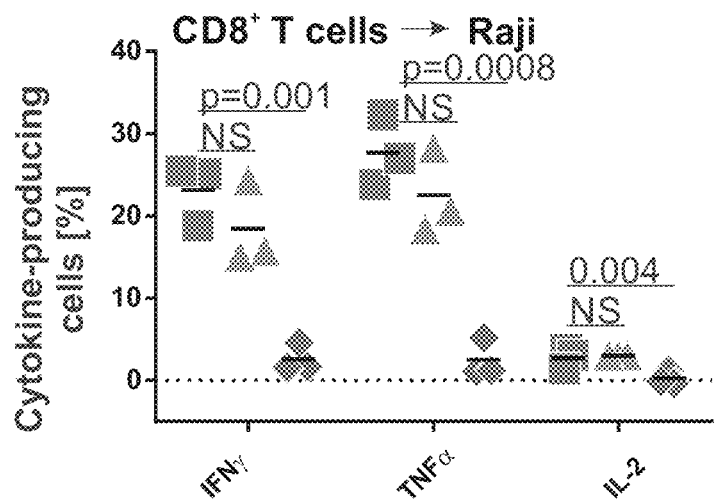
FIG. 8G
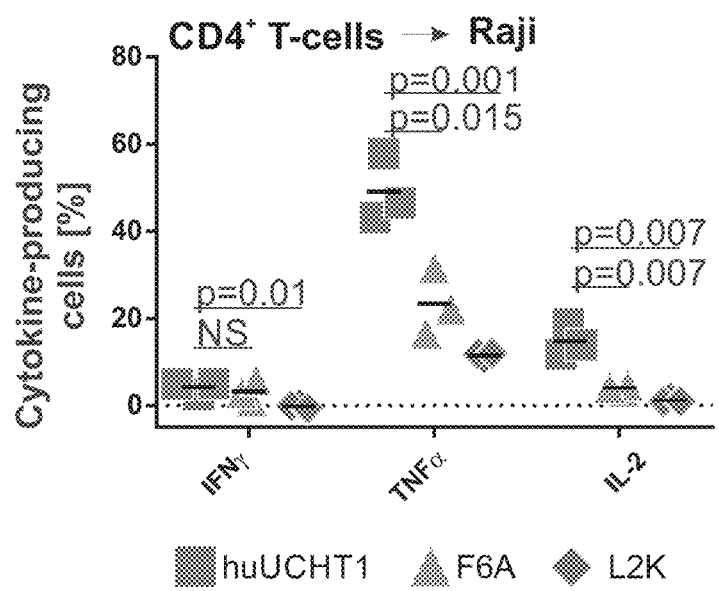
FIG. 8G1

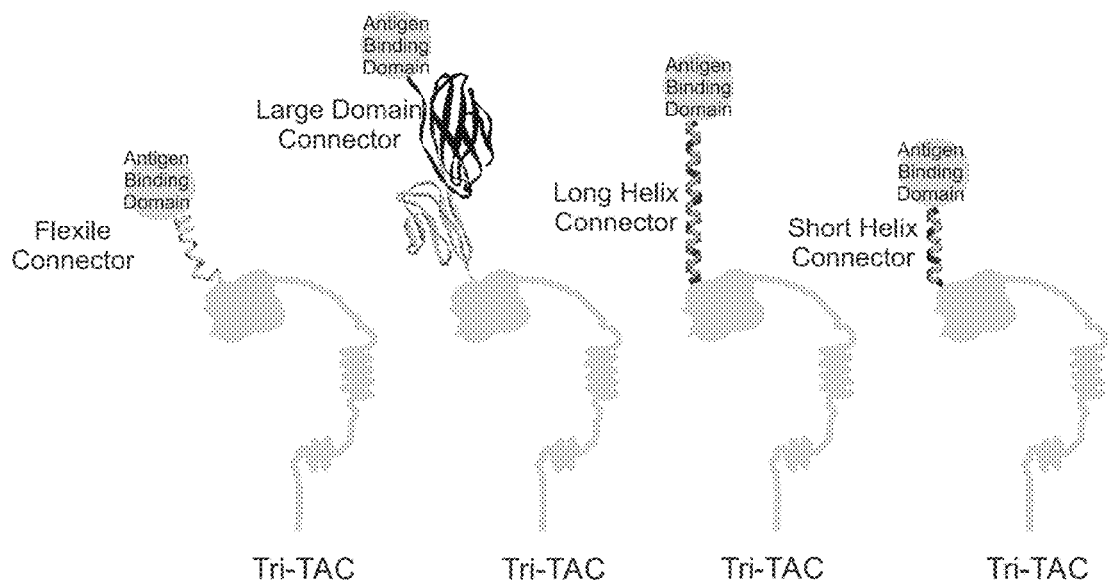

Fig. 10A

Flexible connector
GGGGSGGGGSGGGGSGGGGS

Short Helix connector
AEAAAKEAAAKEAAAKA

Long Helix connector
AEAAAKEAAAKEAAAKEAAAKA

Large Domain connector
IVVLAFQKASSIVYKKEGEQVEFSFPLAFTVEKLTGSGELWWQAERASSSKSWITFDLKNKE
VSVKRVTQDPKLQMGKKLPLHLTLPQALPQYAGSGNLTLALEAKTGKLHQEVNLVVMRATQ
LQKNLTCEVWGPTSPKLMLSLKLENKEAKVSKREKAVWVLNPEAGMWQCLLSDSGQVLLE
SNIKVLPAA

Fig. 10B

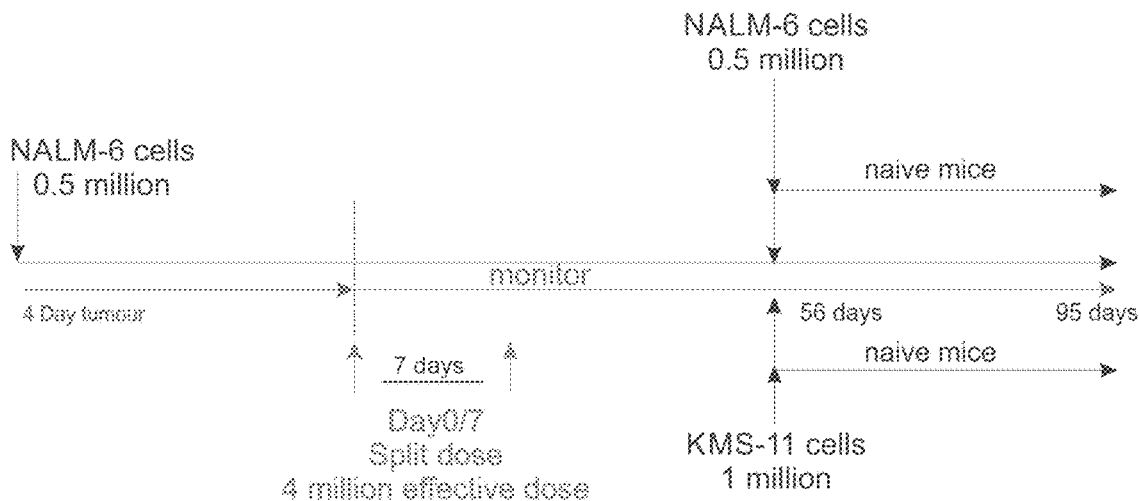
FIG. 20A
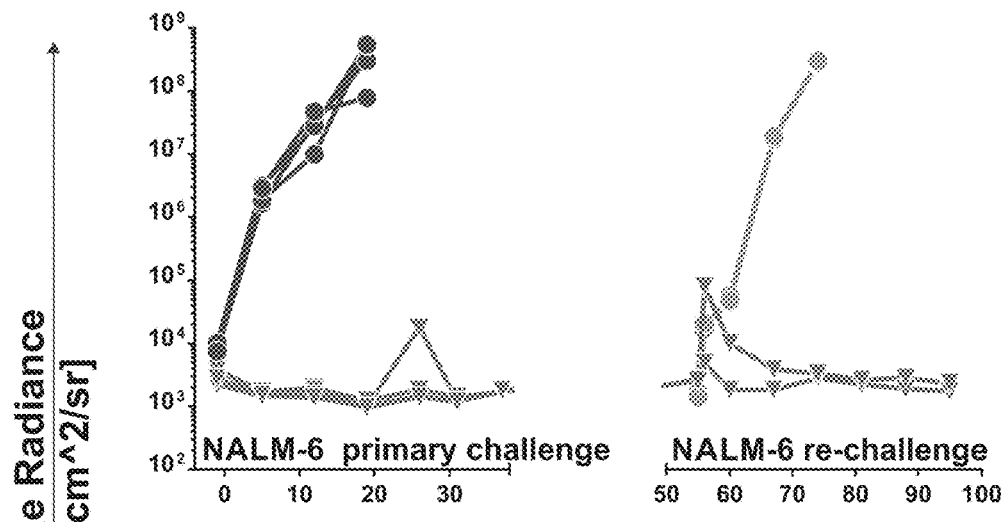
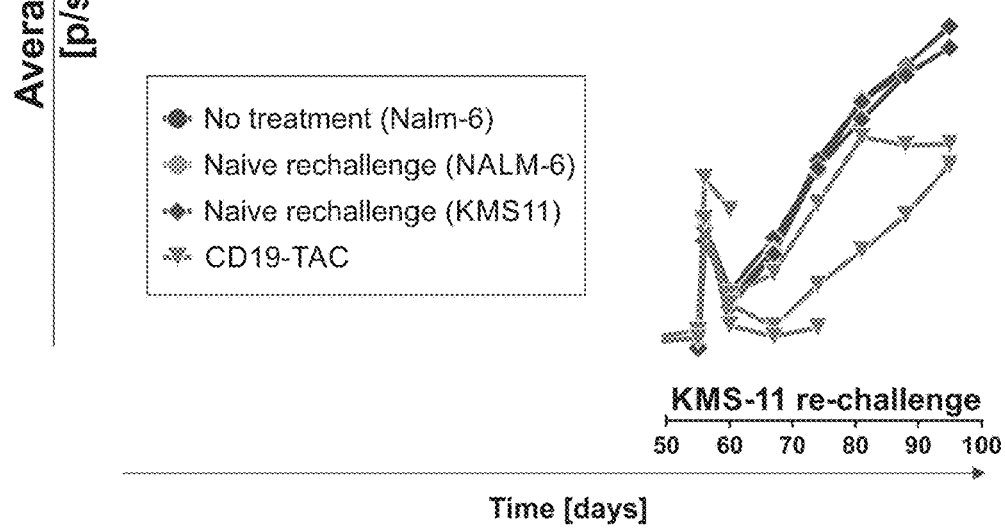
FIG. 20B

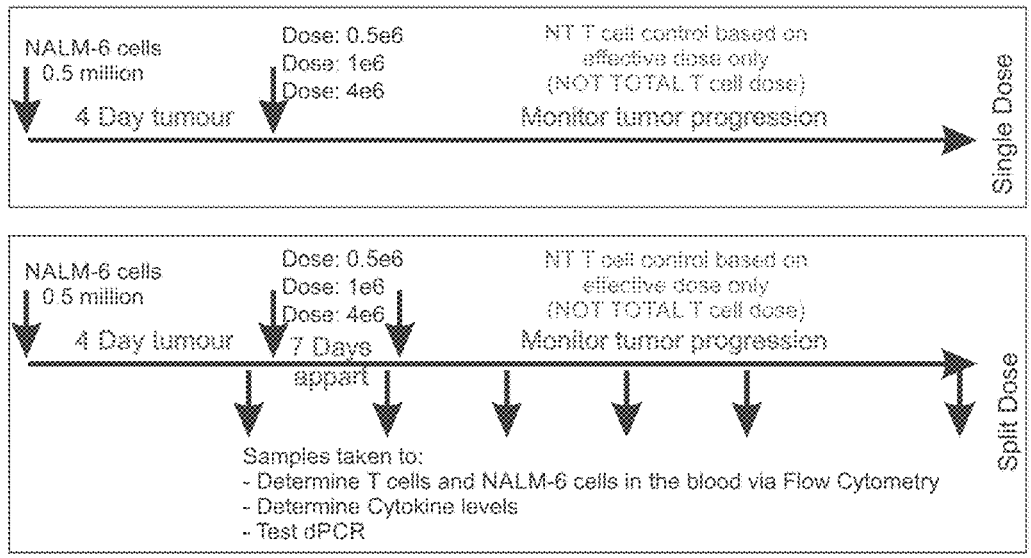
FIG. 21A
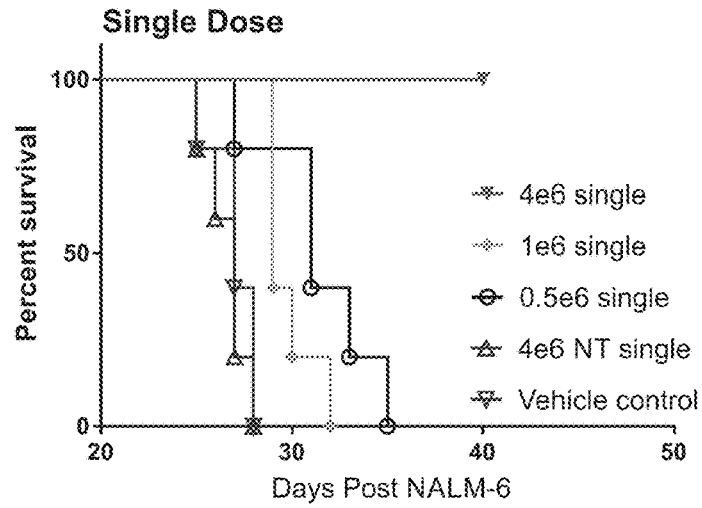
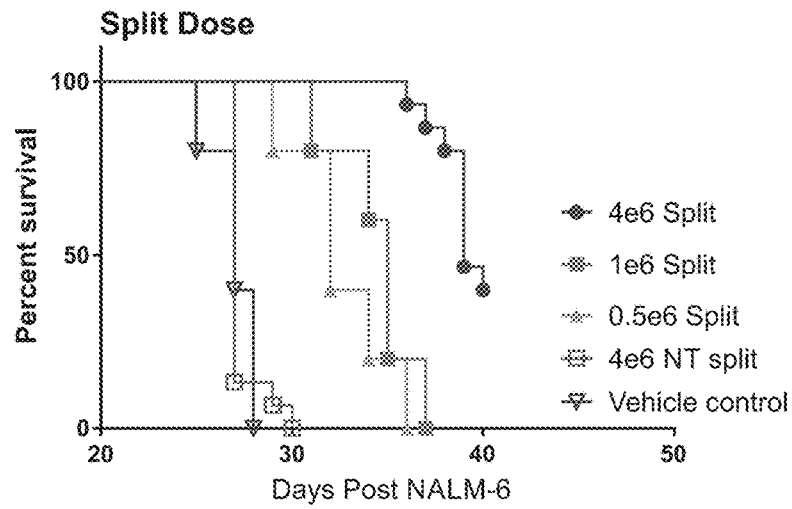
FIG. 21B

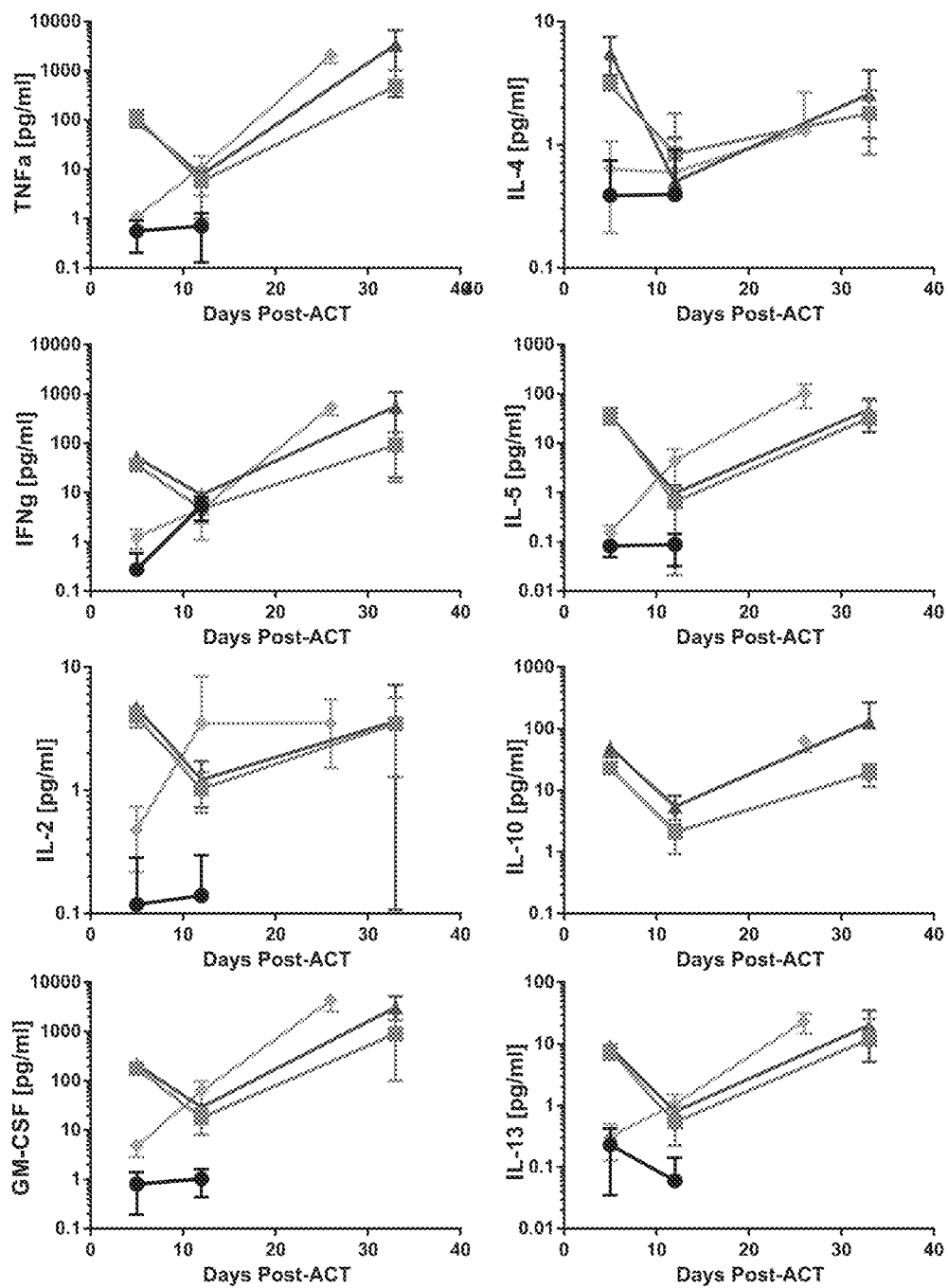
IL-6 was below detection level at all time points
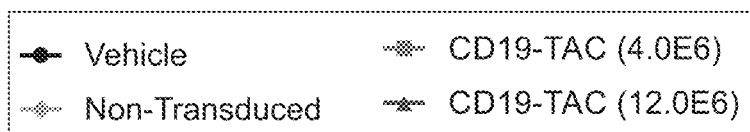
FIG. 25

| ID | Linker | Single chain |
|---|---|---|
| 872 | G4S | --------- |
| 888 | G4S | C11D5.3 |
| 1001 | G4S | 3625 H-L |
| 1002 | Short Helix | 3625 L-H |
| 1042 | Short Helix | 3625 H-L |
| 1043 | G4S | 3625 L-H |

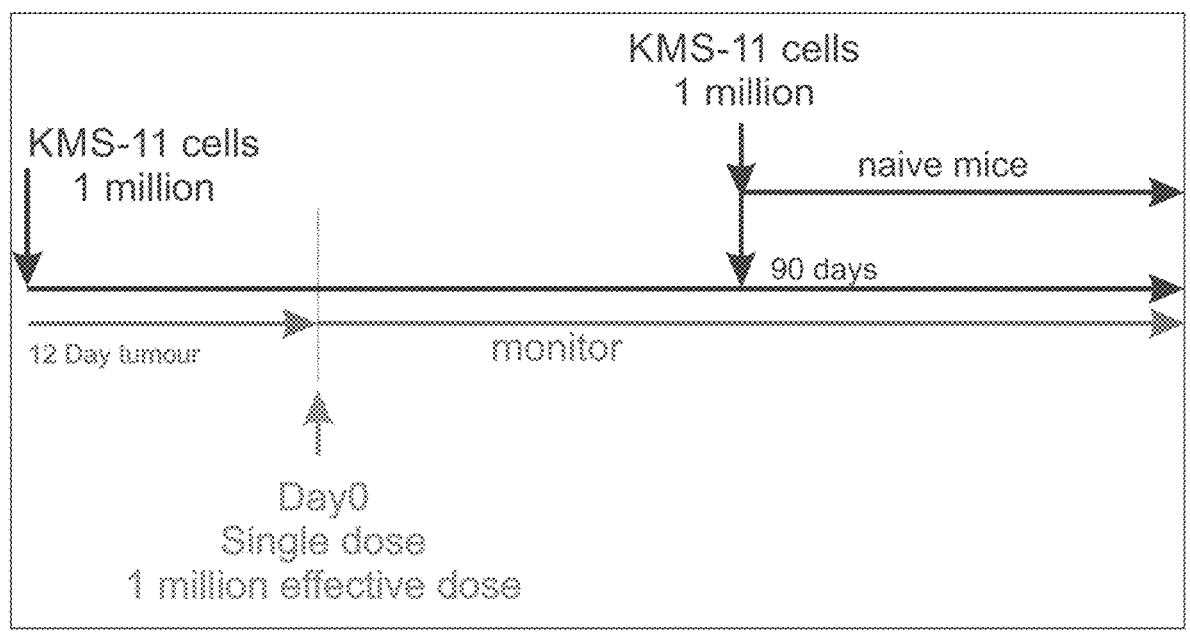
FIG. 28-A

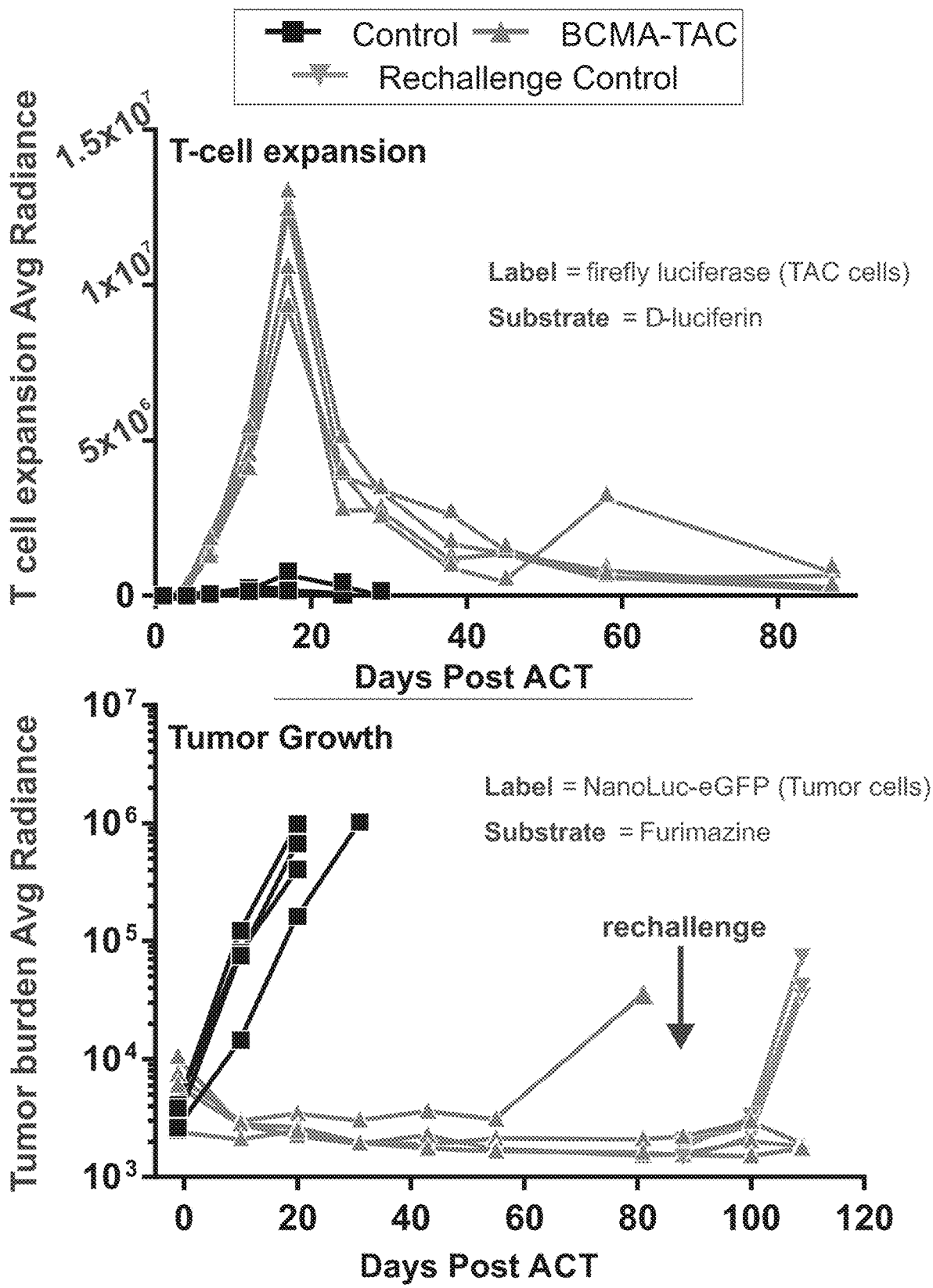
FIG. 28-B

```
                                  SEQUENCE LISTING

Sequence total quantity: 77
SEQ ID NO: 1            moltype = DNA   length = 1521
FEATURE                 Location/Qualifiers
misc_feature            1..1521
                        note = Description of Artificial Sequence: Synthetic
                        polynucleotide
source                  1..1521
                        mol_type = other DNA
                        organism = synthetic construct
SEQUENCE: 1
atgtcacggg gctccgacct gggcaaaaag ctgctggagg ccgctagggc cgggcaggac   60
gatgaagtga gaatcctgat ggccaacggg gctgacgtga atgctaagga tgagtacggc  120
ctgacccccc tgtatctggc tacagcacac ggccatctgg agatcgtgga agtcctgctg  180
aaaaacggag ccgacgtgaa tgcagtcgat gccattgggt tcactcctct gcacctggca  240
gcctttatcg gacatctgga gattgcagaa gtgctgctga agcacggcgc tgacgtgaac  300
gcacaggata agttcggaaa aaccgctttt gacatcagca ttggcaacgg aaatgaagac  360
ctggctgaaa tcctgcagaa actgaatgaa cagaaactga ttagcgaaga agacctgaac  420
cccggggag  gaggagggag cggggagga ggcagcggcg ggggaggctc tggaggagga  480
gggagcggat ccatggacat ccagatgact cagaccacaa gctccctgtc tgcaagtctg  540
ggcgaccggg tgacaatctc ctgcagagcc tctcaggata ttaggaacta cctgaattgg  600
tatcagcaga aacctgatgg cacagtcaag ctgctgatct actataccag ccggctgcac  660
tcaggcgtgc caagcaaatt ctcaggaagc ggctccggga ctgactactc cctgaccatc  720
tctaacctgg agcaggaaga tattgctacc tatttctgcc agcagggcaa tacactgccc  780
tggacttttg ccggaggcac caaactggag atcaaggggg gaggcgggag tggaggcggg  840
ggatcaggag gaggaggcag cggaggagga gggtccgagg tccagctgca gcagagcgga  900
ccagaactgt gaagcccgg agcaagtatg aaaatctcct gtaaggcctc aggatacagc  960
ttcaccggct ataatgaa ctgggtgaaa cagtcccatg gcaagaacct ggaatggatg  1020
gggctgatta atcettacaa aggcgtcagc acctataatc agaagtttaa agacaaggcc  1080
acactgactg tggataagtc tagttcaacc gcttacatgg agctgctgtc cctgacatct  1140
gaagacagtg ccgtgtacta ttgtgctcgg tctggctact atggggacag tgattggtac  1200
ttcgatgtct ggggacaggg cactaccctg accgtgtttt ctactagtgg cggaggagga  1260
tcactcgaga gcggacaggt gctgctgaa tccaatatca aagtcctgcc cacttggtct  1320
acccccgtgc agcctatggc tctgattgtg ctgggaggag tcgcaggact gctgctgttt  1380
atcgggctgg aattttcctt ttgcgtgcgc tgccggcacc ggagaaggca ggccgagcgc  1440
atgagccaga tcaagcgact gctgagcgag aagaaaacct gtcagtgtcc ccatagattc  1500
cagaagacct gttcacccat t                                            1521

SEQ ID NO: 2            moltype = AA    length = 525
FEATURE                 Location/Qualifiers
REGION                  1..525
                        note = Description of Artificial Sequence: Synthetic
                        polypeptide
source                  1..525
                        mol_type = protein
                        organism = synthetic construct
SEQUENCE: 2
MDFQVQIFSF LLISASVIMS RGSDLGKKLL EAARAGQDDE VRILMANGAD VNAKDEYGLT   60
PLYLATAHGH LEIVEVLLKN GADVNAVDAI GFTPLHLAAF IGHLEIAEVL LKHGADVNAQ  120
DKFGKTAFDI SIGNGNEDLA EILQKLNEQK LISEEDLNPG GGGSGGGGS GGGGSGGGGS  180
GSMDIQMTQT TSSLSASLGD RVTISCRASQ DIRNYLNWYQ QKPDGTVKLL IYYTSRLHSG  240
VPSKFSGSGS GTDYSLTISN LEQEDIATYF CQQGNTLPWT FAGGTKLEIK GGGGSGGGGS  300
GGGGSGGGGS EVQLQQSGPE LVKPGASMKI SCKASGYSFT GYTMNWVKQS HGKNLEWMGL  360
INPYKGVSTY NQKFKDKATL TVDKSSSTAY MELLSLTSED SAVYYCARSG YYGDSDWYFD  420
VWGQGTTLTV FSTSGGGGSL ESGQVLLESN IKVLPTWSTP VQPMALIVLG GVAGLLLFIG  480
LGIFFCVRCR HRRRQAERMS QIKRLLSEKK TCQCPHRFQK TCSPI                  525

SEQ ID NO: 3            moltype = DNA   length = 1647
FEATURE                 Location/Qualifiers
misc_feature            1..1647
                        note = Description of Artificial Sequence: Synthetic
                        polynucleotide
source                  1..1647
                        mol_type = other DNA
                        organism = synthetic construct
SEQUENCE: 3
atggactttc aggtgcagat tttctctttt ctgctgattt ccgcaagcgt catcgagctc   60
gggggggggg ggtcaggatc catggacatc cagatgactc agaccacaag ctccctgagc  120
gcatccctgg gcgaccgagt gacaatctca tgcagagcca gcaggatat taggaactac  180
ctgaattggt atcagcagaa acctgacggc acagtcaagc tgctgatcta ctatacttcc  240
cggctgcact ctggcgtgcc aagtaaattc tctggagtg atcaggcac tgactactca  300
ctgaccatca gcaacctgga gcaggaagat attgctacct atttctgcca gcagggcaat  360
```

```
acactgccct ggacttttgc aggcgggacc aaactggaga tcaagggcgg cggcggaagt    420
ggaggaggag gctcaggcgg aggagggagc ggcggaggag gcagcgaggt ccagctgcag    480
cagagcggac cagaactggt gaagcctggc gcatccatga aaatctcctg taaggcctct    540
gggtacagtt tcaccggata tacaatgaac tgggtgaaac agtctcatgg caagaacctg    600
gaatggatgg gcctgattaa tccttacaaa ggcgtcagca cctataatca gaagtttaaa    660
gacaaggcca cactgactgt ggataagtct agttcaaccg cttacatgga gctgctgtca    720
ctgacaagcg aagactccgc cgtgtactat tgcgctagga gcggatacta tggcgactcc    780
gattggtact tcgatgtctg ggggcaggga actaccctga ccgtgtttag cactagtgga    840
ggaggaggct ctggaggagg agggagtgga ggcggggat caggaggagg aggcagcgat    900
atcatgtcac ggggctccga cctgggcaaa agctgctgg aggccgctag ggccgggcag    960
gacgatgaag tgagaatcct gatggccaac ggggctgacg tgaatgctaa ggatgagtac   1020
ggcctgaccc ccctgtatct ggctacagca cacggccatc tggagatcgt ggaagtcctg   1080
ctgaaaaacg gagccgacgt gaatgcagtc gatgccattg ggttcactcc tctgcacctg   1140
gcagccttta tcggacatct ggagattgca gaagtgctgc tgaagcacgg cgctgacgtg   1200
aacgcacagg ataagttcgg aaaaaccgct tttgacatca gcattggcaa cggaaatgaa   1260
gacctggctg aaatcctgca gaaactgaat aacagaaac tgattagcga agaagacctg   1320
aacgtcgacg gaggaggagg gtctggagga ggggaagtg gcggggagg cagcggggga   1380
ggcgggtctc tcgagagtgg ccaggtgctc tggaaaagca atatcaaggt cctgccaact   1440
tggtccaccc cagtgcagcc tatggctctg attgtgctgg gaggagtcgc aggactgctg   1500
ctgtttatcg gcctggggat tttctttgc gtgcgctgcc ggcaccggag aaggcaggct   1560
gagcgcatgt ctcagattaa gcgactgctg agcgagaaga gacctgtca gtgccccat   1620
agattccaga aaacctgttc acccatt                                      1647

SEQ ID NO: 4              moltype = AA   length = 547
FEATURE                   Location/Qualifiers
REGION                    1..547
                          note = Description of Artificial Sequence: Synthetic
                          polypeptide
source                    1..547
                          mol_type = protein
                          organism = synthetic construct
SEQUENCE: 4
MDFQVQIFSF LLISASVIEL GGGGSGSMDI QMTQTTSSLS ASLGDRVTIS CRASQDIRNY    60
LNWYQQKPDG TVKLLIYYTS RLHSGVPSKF SGSGSGTDYS LTISNLEQED IATYFCQNTL   120
PWTFAGGTKL EIKGGGGSGG GGSGGGGSGG GGSEVQLQQS GPELVKPGAS MKISCKASGY   180
SFTGYTMNWV KQSHGKNLEW MGLINPYKGV STYNQKFKDK ATLTVDKSSS TAYMELLSLT   240
SEDSAVYYCA RSGYYGDSDW YFDVWGQGTT LTVFSTSGGG GSGGGGSGGG GSGGGGSDIM   300
SRGSDLGKKL LEAARAGQDD EVRILMANGA DVNAKDEYGL TPLYLATAHG HLEIVEVLLK   360
NGADVNAVDA IGFTPLHLAA FIGHLEIAEV LLKHGADVNA QDKFGKTAFD ISIGNGNEDL   420
AEILQKLNEQ KLISEEDLNV DGGGGSGGGG SGGGGSGGGG SLESGQVLLE SNIKVLPTWS   480
TPVQPMALIV LGGVAGLLLF IGLGIFFCVR CRHRRRQAER MSQIKRLLSE KKTCQCPHRF   540
QKTCSPI                                                            547

SEQ ID NO: 5              moltype = DNA   length = 54
FEATURE                   Location/Qualifiers
misc_feature              1..54
                          note = Description of Artificial Sequence: Synthetic
                          oligonucleotide
source                    1..54
                          mol_type = other DNA
                          organism = synthetic construct
SEQUENCE: 5
atggatttcc aggtccagat tttctccttc ctgctgattt ccgcaagcgt catt           54

SEQ ID NO: 6              moltype = AA   length = 18
FEATURE                   Location/Qualifiers
REGION                    1..18
                          note = Description of Artificial Sequence: Synthetic peptide
source                    1..18
                          mol_type = protein
                          organism = synthetic construct
SEQUENCE: 6
MDFQVQIFSF LLISASVI                                                  18

SEQ ID NO: 7              moltype = DNA   length = 387
FEATURE                   Location/Qualifiers
misc_feature              1..387
                          note = Description of Artificial Sequence: Synthetic
                          polynucleotide
source                    1..387
                          mol_type = other DNA
                          organism = synthetic construct
SEQUENCE: 7
atgtcacggg gctccgacct gggcaaaaag ctgctggagg ccgctagggc cgggcaggac    60
gatgaagtga gaatcctgat ggccaacggg gctgacgtga atgctaagga tgagtacggc   120
ctgaccccc tgtatctggc tacagcacac ggccatctgg agatcgtgga agtcctgctg   180
aaaaacggag ccgacgtgaa tgcagtcgat gccattgggt tcactcctct gcacctggca   240
gcctttatcg gacatctgga gattgcagaa gtgctgctga agcacggcgc tgacgtgaac   300
gcacaggata agttcggaaa aaccgctttt gacatcagca ttggcaacgg aaatgaagac   360
```

```
ctggctgaaa tcctgcagaa actgaat                                    387

SEQ ID NO: 8           moltype = AA  length = 129
FEATURE                Location/Qualifiers
REGION                 1..129
                       note = Description of Artificial Sequence: Synthetic
                       polypeptide
source                 1..129
                       mol_type = protein
                       organism = synthetic construct
SEQUENCE: 8
MSRGSDLGKK LLEAARAGQD DEVRILMANG ADVNAKDEYG LTPYLYLATAH GHLEIVEVLL  60
KNGADVNAVD AIGFTPLHLA AFIGHLEIAE VLLKHGADVN AQDKFGKTAF DISIGNGNED 120
LAEILQKLN                                                        129

SEQ ID NO: 9           moltype = DNA  length = 30
FEATURE                Location/Qualifiers
misc_feature           1..30
                       note = Description of Artificial Sequence: Synthetic
                       oligonucleotide
source                 1..30
                       mol_type = other DNA
                       organism = synthetic construct
SEQUENCE: 9
gaacagaaac tgattagcga agaagacctg                                  30

SEQ ID NO: 10          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 10
EQKLISEEDL                                                        10

SEQ ID NO: 11          moltype = DNA  length = 75
FEATURE                Location/Qualifiers
misc_feature           1..75
                       note = Description of Artificial Sequence: Synthetic
                       oligonucleotide
source                 1..75
                       mol_type = other DNA
                       organism = synthetic construct
SEQUENCE: 11
aaccccgggg gaggaggagg gagcggggga ggaggcagcg gcgggggagg ctctggagga  60
ggagggagcg gatcc                                                  75

SEQ ID NO: 12          moltype = AA  length = 25
FEATURE                Location/Qualifiers
REGION                 1..25
                       note = Description of Artificial Sequence: Synthetic peptide
source                 1..25
                       mol_type = protein
                       organism = synthetic construct
SEQUENCE: 12
NPGGGGGSGG GGSGGGGSGG GGSGS                                       25

SEQ ID NO: 13          moltype = DNA  length = 750
FEATURE                Location/Qualifiers
misc_feature           1..750
                       note = Description of Artificial Sequence: Synthetic
                       polynucleotide
source                 1..750
                       mol_type = other DNA
                       organism = synthetic construct
SEQUENCE: 13
atggacatcc agatgactca gaccacaagc tccctgtctg caagtctggg cgaccgggtg  60
acaatctcct gcagagcctc tcaggatatt aggaactacc tgaattggta tcagcagaaa 120
cctgatggca cagtcaagct gctgatctac tataccagcc ggctgcactc aggcgtgcca 180
agcaaattct caggaagcgg ctccgggact gactactccc tgaccatctc taacctggag 240
caggaagata ttgctaccta tttctgccag cagggcaata cactgccctg gacttttgcc 300
ggaggcacca aactggagat caaggggga ggcgggagtg gaggcggggg atcaggagga 360
ggaggcagcg gaggaggagg gtccgaggtc cagctgcagc agagcggacc agaactggtg 420
aagcccggag caagtatgaa aatctcctgt aaggcctcag atacagcttc accggctat 480
acaatgaact gggtgaaaca gtcccatggc aagaacctgg aatggatggg gctgattaat 540
ccttacaaag cgtcagcac ctataatcag aagtttaaag acaaggccac actgactgtg 600
gataagtcta gttcaaccgc ttacatggag ctgctgtccc tgacatctga agacagtgcc 660
gtgtactatt gtgctcggtc tggctactat ggggacagtg attggtactt cgatgtctgg 720
```

```
ggacagggca ctaccctgac cgtgttttct                                       750

SEQ ID NO: 14           moltype = AA   length = 250
FEATURE                 Location/Qualifiers
REGION                  1..250
                        note = Description of Artificial Sequence: Synthetic
                        polypeptide
source                  1..250
                        mol_type = protein
                        organism = synthetic construct
SEQUENCE: 14
MDIQMTQTTS SLSASLGDRV TISCRASQDI RNYLNWYQQK PDGTVKLLIY YTSRLHSGVP       60
SKFSGSGSGT DYSLTISNLE QEDIATYFCQ QGNTLPWTFA GGTKLEIKGG GGSGGGGSGG      120
GGSGGGGSEV QLQQSGPELV KPGASMKISC KASGYSFTGY TMNWVKQSHG KNLEWMGLIN      180
PYKGVSTYNQ KFKDKATLTV DKSSSTAYME LLSLTSEDSA VYYCARSGYY GDSDWYFDVW      240
GQGTTLTVFS                                                             250

SEQ ID NO: 15           moltype = DNA   length = 27
FEATURE                 Location/Qualifiers
misc_feature            1..27
                        note = Description of Artificial Sequence: Synthetic
                        oligonucleotide
source                  1..27
                        mol_type = other DNA
                        organism = synthetic construct
SEQUENCE: 15
actagtggcg gaggaggatc actcgag                                           27

SEQ ID NO: 16           moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 16
TSGGGGSLE                                                               9

SEQ ID NO: 17           moltype = DNA   length = 252
FEATURE                 Location/Qualifiers
misc_feature            1..252
                        note = Description of Artificial Sequence: Synthetic
                        polynucleotide
source                  1..252
                        mol_type = other DNA
                        organism = synthetic construct
SEQUENCE: 17
agcggacagg tgctgctgga atccaatatc aaagtcctgc ccacttggtc taccccgtg        60
cagcctatgg ctctgattgt gctgggagga gtcgcaggac tgctgctgtt tatcgggctg      120
ggaattttct tttgcgtgcg ctgccggcac cggagaaggc aggccgagcg catgagccag      180
atcaagcgac tgctgagcga gaagaaaacc tgtcagtgtc cccatagatt ccagaagacc      240
tgttcaccca tt                                                          252

SEQ ID NO: 18           moltype = AA   length = 84
FEATURE                 Location/Qualifiers
REGION                  1..84
                        note = Description of Artificial Sequence: Synthetic
                        polypeptide
source                  1..84
                        mol_type = protein
                        organism = synthetic construct
SEQUENCE: 18
SGQVLLESNI KVLPTWSTPV QPMALIVLGG VAGLLLFIGL GIFFCVRCRH RRRQAERMSQ       60
IKRLLSEKKT CQCPHRFQKT CSPI                                              84

SEQ ID NO: 19           moltype = DNA   length = 66
FEATURE                 Location/Qualifiers
misc_feature            1..66
                        note = Description of Artificial Sequence: Synthetic
                        oligonucleotide
source                  1..66
                        mol_type = other DNA
                        organism = synthetic construct
SEQUENCE: 19
agcggacagg tgctgctgga atccaatatc aaagtcctgc ccacttggtc taccccgtg        60
cagcct                                                                  66

SEQ ID NO: 20           moltype = AA   length = 22
FEATURE                 Location/Qualifiers
```

| | | |
|---|---|---|
| REGION | 1..22 | |
| | note = Description of Artificial Sequence: Synthetic peptide | |
| source | 1..22 | |
| | mol_type = protein | |
| | organism = synthetic construct | |
| SEQUENCE: 20 | | |
| SGQVLLESNI KVLPTWSTPV QP | | 22 |

| | | |
|---|---|---|
| SEQ ID NO: 21 | moltype = DNA   length = 769 | |
| FEATURE | Location/Qualifiers | |
| misc_feature | 1..769 | |
| | note = Description of Artificial Sequence: Synthetic polynucleotide | |
| source | 1..769 | |
| | mol_type = other DNA | |
| | organism = synthetic construct | |
| SEQUENCE: 21 | | |

```
atggccgaca tcgtgctgac acagagcccc gccatcatgt ctgccagccc tggcgagaaa   60
gtgaccatga cctgtagcgc cagcagcagc gtgtcctaca tgaactggta tcagcagaag  120
tccggcacca gccccaagcg gtggatctac gacacaagca gctggcctc tggcgtgccc   180
gcccactta gaggctctgg cagcggcaca agctacagcc tgaccatcag cggcatggaa   240
gccgaggatg ccgccaccta ctactgccag cagtggtcca gcaaccctt caccttggc    300
tccggcacaa agctgaaat caaccgggc gacaccgccc ctacaggcgg cggaggatct    360
ggcggaggcg atctgggggg cggaggaagt gggggggggag atctatggc tcaggtgcag   420
ctgcagcagt ctggcgccga actggctaga cctggcgcct ccgtgaagat gagctgcaag   480
gccagcggct acaccttcac ccggtacaca atgcactgga tcaagcagag gcctggacag   540
ggcctggaat ggatcggcta catcaacccc agccggggct acaccaacta caaccagaag   600
ttcaaggaca aggccaccct gaccaccgac aagagcagca gcaccgccta catgcagctg   660
tcctccctga ccagcgagga cagcgccgtg tactactgcg cccggtacta cgacgaccac   720
tactccctgg actactgggg ccagggcacc acactgaccg tgtctagta              769
```

| | | |
|---|---|---|
| SEQ ID NO: 22 | moltype = AA   length = 256 | |
| FEATURE | Location/Qualifiers | |
| REGION | 1..256 | |
| | note = Description of Artificial Sequence: Synthetic polypeptide | |
| source | 1..256 | |
| | mol_type = protein | |
| | organism = synthetic construct | |
| SEQUENCE: 22 | | |

```
MADIVLTQSP AIMSASPGEK VTMTCSASSS VSYMNWYQQK SGTSPKRWIY DTSKLASGVP    60
AHFRGSGSGT SYSLTISGME AEDAATYYCQ QWSSNPFTFG SGTKLEINRA DTAPTGGGGS  120
GGGGSGGGGS GGGGSMAQVQ LQQSGAELAR PGASVKMSCK ASGYTFTRYT MHWVKQRPGQ  180
GLEWIGYINP SRGYTNYNQK FKDKATLTTD KSSSTAYMQL SSLTSEDSAV YYCARYYDDH  240
YSLDYWGQGT TLTVSS                                                 256
```

| | | |
|---|---|---|
| SEQ ID NO: 23 | moltype = DNA   length = 747 | |
| FEATURE | Location/Qualifiers | |
| misc_feature | 1..747 | |
| | note = Description of Artificial Sequence: Synthetic polynucleotide | |
| source | 1..747 | |
| | mol_type = other DNA | |
| | organism = synthetic construct | |
| SEQUENCE: 23 | | |

```
cagaccgtgg tgacccagga gcccagcctg accgtgagcc ccggcggcac cgtgaccctg    60
acctgcggca gcagcaccgg cgccgtgacc agcggctact accccaactg ggtgcagcag  120
aagcccggcc aggcccccag gggcctgatc ggcggcacca gttcctggc ccccggcacc   180
cccgccaggt tcagcggcag cctgctgggc ggcaaggccg ccctgaccct gagcggcgtg  240
cagcccgagg acgaggccga gtactactgc gccctgtggt acagcaacag gtgggtgttc  300
ggcggcggca ccaagctgac cgtgctgggc ggcggcggca gcggcggcgg cggcagcggc  360
ggcggcggca gcgaggtgca gctgctggag agcggcggcg gcctggtgca gcccggcggc  420
agcctgaagc tgagctgcgc cgccagcggc ttcaccttca acatctacgc catgaactgg  480
gtgagggcag gccccggcaa gggcctggag tgggtgccca gcatcaggta caactacgcc  540
cctactacgc cgacagcgtg aagagcaggt tcaccatcag cagggacgac                    600
agcaagaaca ccgcctacct gcagatgaac aacctgaaga ccgaggacac cgccgtgtac  660
tactgcgtga ggcacggcaa cttcggcaac agctacgtga gcttcttcgc ctactgggc   720
cagggcaccc tggtgaccgt gagcagc                                      747
```

| | | |
|---|---|---|
| SEQ ID NO: 24 | moltype = AA   length = 249 | |
| FEATURE | Location/Qualifiers | |
| REGION | 1..249 | |
| | note = Description of Artificial Sequence: Synthetic polypeptide | |
| source | 1..249 | |
| | mol_type = protein | |
| | organism = synthetic construct | |
| SEQUENCE: 24 | | |

```
QTVVTQEPSL TVSPGGTVTL TCGSSTGAVT SGYYPNWVQQ KPGQAPRGLI GGTKFLAPGT    60
```

```
PARFSGSLLG GKAALTLSGV QPEDEAEYYC ALWYSNRWVF GGGTKLTVLG GGGSGGGGSG   120
GGGSEVQLLE SGGGLVQPGG SLKLSCAASG FTFNIYAMNW VRQAPGKGLE WVARIRSKYN   180
NYATYYADSV KSRFTISRDD SKNTAYLQMN NLKTEDTAVY YCVRHGNFGN SYVSFFAYWG   240
QGTLVTVSS                                                          249

SEQ ID NO: 25           moltype = DNA   length = 720
FEATURE                 Location/Qualifiers
misc_feature            1..720
                        note = Description of Artificial Sequence: Synthetic
                         polynucleotide
source                  1..720
                        mol_type = other DNA
                        organism = synthetic construct
SEQUENCE: 25
gacatccagc tgacccagag ccccgccatc atgagcgcca gccccggcga gaaggtgacc   60
atgacctgca gggccagcag cagcgtgagc tacatgaact ggtaccagca gaagagcggc   120
accagcccca gaggtggat ctacgacacc agcaaggtgg ccagcggcgt gccctacagg    180
ttcagcggca gcggcagcgg caccagctac agcctgacca tcagcagcat ggaggccgaa   240
gacgccgcca cctactactg ccagcagtgg agcagcaacc ccctgacctt cggcgccggc   300
accaagctgg agctgaaggg cggcggcggc agcggcggcg gcggcagcgg cggcggcggc   360
agcgacatca agctgcagca gagcggcgcc gagctggcca ggcccggcgc cagcgtgaag   420
atgagctgca agaccagcgg ctacaccttc accaggtaca ccatgcactg ggtgaagcag   480
aggcccggcc agggcctgga gtggatcggc tacatcaacc ccagcagggg ctacaccaac   540
tacaaccaga agttcaagga caaggccacc ctgaccaccg acaagagcag cagcaccgcc   600
tacatgcagc tgagcagcct gaccagcgag gacagcgccg tgtactactg cgccaggtac   660
tacgacgacc actactgcct ggactactgg ggccagggca ccaccctgac cgtgagcagc   720

SEQ ID NO: 26           moltype = AA   length = 240
FEATURE                 Location/Qualifiers
REGION                  1..240
                        note = Description of Artificial Sequence: Synthetic
                         polypeptide
source                  1..240
                        mol_type = protein
                        organism = synthetic construct
SEQUENCE: 26
DIQLTQSPAI MSASPGEKVT MTCRASSSVS YMNWYQQKSG TSPKRWIYDT SKVASGVPYR   60
FSGSGSGTSY SLTISSMEAE DAATYYCQQW SSNPLTFGAG TKLELKGGGG SGGGGSGGGG   120
SDIKLQQSGA ELARPGASVK MSCKTSGYTF TRYTMHWVKQ RPGQGLEWIG YINPSRGYTN   180
YNQKFKDKAT LTTDKSSSTA YMQLSSLTSE DSAVYYCARY YDDHYCLDYW GQGTTLTVSS   240

SEQ ID NO: 27           moltype = DNA   length = 51
FEATURE                 Location/Qualifiers
misc_feature            1..51
                        note = Description of Artificial Sequence: Synthetic
                         oligonucleotide
source                  1..51
                        mol_type = other DNA
                        organism = synthetic construct
SEQUENCE: 27
gccgaagcag cagcaaagga ggccgcagcg aaggaagcag ctgcgaaggc c             51

SEQ ID NO: 28           moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 28
AEAAAKEAAA KEAAAKA                                                  17

SEQ ID NO: 29           moltype = DNA   length = 81
FEATURE                 Location/Qualifiers
misc_feature            1..81
                        note = Description of Artificial Sequence: Synthetic
                         oligonucleotide
source                  1..81
                        mol_type = other DNA
                        organism = synthetic construct
SEQUENCE: 29
gccgaggcag ctgcaaagga agctgcggcg aaggaggccg cagcgaaaga agcagcggca   60
aaagaagcag ccgccaaagc c                                             81

SEQ ID NO: 30           moltype = AA   length = 27
FEATURE                 Location/Qualifiers
REGION                  1..27
                        note = Description of Artificial Sequence: Synthetic peptide
source                  1..27
```

```
                            mol_type = protein
                            organism = synthetic construct
SEQUENCE: 30
AEAAAKEAAA KEAAAKEAAA KEAAAKA                                      27

SEQ ID NO: 31               moltype = DNA   length = 576
FEATURE                     Location/Qualifiers
misc_feature                1..576
                            note = Description of Artificial Sequence: Synthetic
                             polynucleotide
source                      1..576
                            mol_type = other DNA
                            organism = synthetic construct
SEQUENCE: 31
atcgtagtgt tggcatttca aaaagcgtct agcatcgtct ataagaagga aggtgaacaa   60
gtcgagtttt ctttccccct tgcatttacg gtggaaaagc ttacgggtag cggcgagctg  120
tggtggcaag ctgaacgggc ttcaagctca aaatcttgga ttacttttga cttgaagaac  180
aaagaggtga gtgtcaaaag agttactcag gacccaaagc ttcaaatggg aagaaactt   240
ccgctgcacc tgacgttgcc tcaggccctg cctcaatatg ccggctcagg caatctgacc  300
ctcgcgctgg aagctaagac cggaaaattg caccaggaag tcaatttggt tgtgatgcgc  360
gccactcagc tccaaaaaaa tctcacttgc gaggtatggg ggcctacgag cccaaaactt  420
atgctgtctt tgaagcttga aaacaaggaa gcgaaagttt ctaagcgcga gaaagcggta  480
tgggttttga atcctgaggc tggaatgtgg caatgcctcc tgagcgatag cgggcaggtg  540
ctgttggaga gcaacatcaa ggttttgcca gcagcc                            576

SEQ ID NO: 32               moltype = AA   length = 192
FEATURE                     Location/Qualifiers
REGION                      1..192
                            note = Description of Artificial Sequence: Synthetic
                             polypeptide
source                      1..192
                            mol_type = protein
                            organism = synthetic construct
SEQUENCE: 32
IVVLAFQKAS SIVYKKEGEQ VEFSFPLAFT VEKLTGSGEL WWQAERASSS KSWITFDLKN   60
KEVSVKRVTQ DPKLQMGKKL PLHLTLPQAL PQYAGSGNLT LALEAKTGKL HQEVNLVVMR  120
ATQLQKNLTC EVWGPTSPKL MLSLKLENKE AKVSKREKAV WVLNPEAGMW QCLLSDSGQV  180
LLESNIKVLP AA                                                     192

SEQ ID NO: 33               moltype = DNA   length = 801
FEATURE                     Location/Qualifiers
misc_feature                1..801
                            note = Description of Artificial Sequence: Synthetic
                             polynucleotide
source                      1..801
                            mol_type = other DNA
                            organism = synthetic construct
SEQUENCE: 33
atggatttc aggtgcagat tttcagcttc ctgctaatca gtgcctcagt cataatgtct    60
agagacatcg tgctgaccca gagccccccc agcctggcca tgtctctggg caagagagcc  120
accatcagct gccgggccag cgagagcgtg accatcctgg gcagccacct gatccactgg  180
tatcagcaga agccccggcca gccccccacc ctgctgatcc agctcgccag caatgtgcag  240
accggcgtgc cgccagatt cagcggcagc ggcagcagaa ccgacttcac cctgaccatc  300
gaccccgtgg aagaggacga cgtggccgtg tactactgcc tgcagagccg gaccatcccc  360
cggacccttg gcggagggac caaactggaa atcaaggcca gccagcggcc tccggcaag   420
cctggctctg gcgagggcag cacaaaggga cagattcagc tggtgcagag cggccctgga  480
ctgaagaaac ccggcgagac agtgaagatc agctgcaagg cctccggcta caccttcacc  540
gactacagca tcaactgggt gaaaagagcc cctggcaagg gcctgaagtg gatgggctgg  600
atcaacaccg agacaagaga gccgcctac gcctacgact ccggggcag attcgccttc  660
agcctggaaa ccagcgccag caccgcctac ctgcagatca caaacctgaa gtacgaggac  720
accgccacct acttttgcgc cctggactac agctacgcca tggactactg gggccaggc   780
accagcgtga ccgtgtccag c                                            801

SEQ ID NO: 34               moltype = AA   length = 267
FEATURE                     Location/Qualifiers
REGION                      1..267
                            note = Description of Artificial Sequence: Synthetic
                             polypeptide
source                      1..267
                            mol_type = protein
                            organism = synthetic construct
SEQUENCE: 34
MDFQVQIFSF LLISASVIMS RDIVLTQSPP SLAMSLGKRA TISCRASESV TILGSHLIHW   60
YQQKPGQPPT LLIQLASNVQ TGVPARFSGS GSRTDFTLTI DPVEEDDVAV YYCLQSRTIP  120
RTFGGGTKLE IKSTSGSGK PGSGEGSTKG QIQLVQSGPE LKKPGETVKI SCKASGYTFT   180
DYSINWVKRA PGKGLKWMGW INTETREPAY AYDFRGRFAF SLETSASTAY LQINNLKYED  240
TATYFCALDY SYAMDYWGQG TSVTVSS                                     267

SEQ ID NO: 35               moltype = DNA   length = 735
```

```
FEATURE                     Location/Qualifiers
misc_feature                1..735
                            note = Description of Artificial Sequence: Synthetic
                             polynucleotide
source                      1..735
                            mol_type = other DNA
                            organism = synthetic construct
SEQUENCE: 35
gatatccaga tgactcagac gacctcatca ttgtccgcca gtttggggga cagggttaca    60
atatcctgcc gggcgagcca agacatcagt aaatatctta attggtacca gcagaaacca   120
gatggtacag taaaacttct tatctaccac acctctcggc tccactctgg ggttcccctct  180
aggttcagtg gtagtgggtc aggcaccgac tacagcctta cgataagcaa cttgaacag    240
gaggatatcg caacttactt ctgccaacag ggaaataccc tgcctacac gttcggtgga    300
ggcactaaac tggagatcac tgggtcaacc tctggtagcg gtaagcctgg ctccggcgaa   360
ggctccacaa agggtgaggt gaaactccaa gagtcaggtc ccggtttggt agcccccctca  420
caaagtttgt cagttacttg taccgtaagc ggcgtttccc tgcccgatta cggtgtgagc   480
tggataaggc agccaccgag aaaaggtctt gaatggctgg gagtgatctg ggggtctgag   540
acaacgtatt acaactcagc tcttaagagc aggcttacga tcattaaaga taacagcaaa   600
tctcaagtgt tcctcaaaat gaatagcctt caaactgatg atactgccat ctattattgt   660
gctaagcatt attactatgg cggcagttac gcaatggatt attgggggca aggtacctca   720
gtcactgtaa gcagc                                                    735

SEQ ID NO: 36               moltype = AA  length = 245
FEATURE                     Location/Qualifiers
REGION                      1..245
                            note = Description of Artificial Sequence: Synthetic
                             polypeptide
source                      1..245
                            mol_type = protein
                            organism = synthetic construct
SEQUENCE: 36
DIQMTQTTSS LSASLGDRVT ISCRASQDIS KYLNWYQQKP DGTVKLLIYH TSRLHSGVPS    60
RFSGSGSGTD YSLTISNLEQ EDIATYFCQQ GNTLPYTFGG GTKLEITGST SGSGKPGSGE   120
GSTKGEVKLQ ESGPGLVAPS QSLSVTCTVS GVSLPDYGVS WIRQPPRKGL EWLGVIWGSE   180
TTYYNSALKS RLTIIKDNSK SQVFLKMNSL QTDDTAIYYC AKHYYYGGSY AMDYWGQGTS   240
VTVSS                                                               245

SEQ ID NO: 37               moltype = DNA  length = 237
FEATURE                     Location/Qualifiers
misc_feature                1..237
                            note = Description of Artificial Sequence: Synthetic
                             polynucleotide
source                      1..237
                            mol_type = other DNA
                            organism = synthetic construct
SEQUENCE: 37
ctcgagctga ggcccgaggc ttctagacct gctgccggcg gagccgtgca caccagaggc    60
ctggacttcg ccagcgacat ctacatctgg gcccctctgg ccggcacctg tggcgtgctg   120
ctgctgagcc tggtcatcac cctgtactgc aaccaccgga accggcggag agtgtgcaag   180
tgccccagac ccgtggtcaa gagcggcgac aagcccagcc tgagcgccag atacgtg      237

SEQ ID NO: 38               moltype = AA  length = 79
FEATURE                     Location/Qualifiers
REGION                      1..79
                            note = Description of Artificial Sequence: Synthetic
                             polypeptide
source                      1..79
                            mol_type = protein
                            organism = synthetic construct
SEQUENCE: 38
LELRPEASRP AAGGAVHTRG LDFASDIYIW APLAGTCGVL LLSLVITLYC NHRNRRRVCK    60
CPRPVVKSGD KPSLSARYV                                                 79

SEQ ID NO: 39               moltype = DNA  length = 234
FEATURE                     Location/Qualifiers
misc_feature                1..234
                            note = Description of Artificial Sequence: Synthetic
                             polynucleotide
source                      1..234
                            mol_type = other DNA
                            organism = synthetic construct
SEQUENCE: 39
ctcgagctga ggcccgaggc ttctagacct gctgccggcg gagccgtgca caccagaggc    60
ctggacttcg ccagcgacat ctacatctgg gcccctctgg ccggcacctg tggcgtgctg   120
ctgctgagcc tggtcatcac cctgtacctg tgctgcagca ggcggagagt gtgcaagtgc   180
cccagacccg tggtcaagag cggcgacaag cccagcctga cgccagata cgtg          234

SEQ ID NO: 40               moltype = AA  length = 78
FEATURE                     Location/Qualifiers
```

| | | |
|---|---|---|
| REGION | 1..78 | |
| | note = Description of Artificial Sequence: Synthetic polypeptide | |
| source | 1..78 | |
| | mol_type = protein | |
| | organism = synthetic construct | |

SEQUENCE: 40
```
LELRPEASRP AAGGAVHTRG LDFASDIYIW APLAGTCGVL LLSLVITLYL CCRRRRVCKC    60
PRPVVKSGDK PSLSARYV                                                 78
```

| | | |
|---|---|---|
| SEQ ID NO: 41 | moltype = DNA  length = 213 | |
| FEATURE | Location/Qualifiers | |
| misc_feature | 1..213 | |
| | note = Description of Artificial Sequence: Synthetic polynucleotide | |
| source | 1..213 | |
| | mol_type = other DNA | |
| | organism = synthetic construct | |

SEQUENCE: 41
```
ctcgagaaga agtccaccct gaagaaacgg gtgtcccggc tgcccagacc cgagacacag    60
aagggccccc tgagcagccc tatcaccctg ggactgctgg tggccggcgt gctggtgctg   120
ctggtgtctc tgggagtggc catccacctg tgctgccggc ggagaagggc ctgcaagtgc   180
cccagactgc ggttcatgaa gcagttctac aag                                213
```

| | | |
|---|---|---|
| SEQ ID NO: 42 | moltype = AA  length = 71 | |
| FEATURE | Location/Qualifiers | |
| REGION | 1..71 | |
| | note = Description of Artificial Sequence: Synthetic polypeptide | |
| source | 1..71 | |
| | mol_type = protein | |
| | organism = synthetic construct | |

SEQUENCE: 42
```
LEKKSTLKKR VSRLPRPETQ KGPLSSPITL GLLVAGVLVL LVSLGVAIHL CCRRRRACKC    60
PRLRFMKQFY K                                                         71
```

| | | |
|---|---|---|
| SEQ ID NO: 43 | moltype = DNA  length = 735 | |
| FEATURE | Location/Qualifiers | |
| misc_feature | 1..735 | |
| | note = Description of Artificial Sequence: Synthetic polynucleotide | |
| source | 1..735 | |
| | mol_type = other DNA | |
| | organism = synthetic construct | |

SEQUENCE: 43
```
atggatatcc agatgaccca gtccccgagc tccctgtccg cctctgtggg cgatagggtc    60
accatcacct gccgtgccag tcaggacatc cgtaattatc tgaactggta tcaacagaaa   120
ccaggaaaag ctccgaaact actgatttac tatacctccc gcctggagtc tggagtccct   180
tctcgcttct ctggttctgg ttctgggacg gattacactc tgaccatcag cagtctgcaa   240
ccggaagact tcgcaactta ttactgtcag caaggtaata ctctgccgtg gacgttcgga   300
cagggcacca aggtggagat caaaggcggc ggcggaagtg gaggaggagg ctcaggcgga   360
ggagggagcg aggttcagct ggtggagtct ggcggtggcc tggtgcagcc aggggggctca  420
ctccgtttgt cctgtgcagc ttctggctac tcctttaccg gctacactat gaactgggtg   480
cgtcaggccc caggtaaggg cctggaatgg gttgcactga ttaatcctta taaggtgtt    540
agtacctaca accagaagtt caaggaccgt ttcactatca gcgtagataa atccaaaaac   600
acagcctacc tgcaaatgaa cagcctgcgt gctgaggaca ctgccgtcta ttattgtgct   660
agaagcggat actacggcga tagtgactgg tattttgacg tgtgggtca aggaaccctg   720
gtcaccgtct cctcg                                                    735
```

| | | |
|---|---|---|
| SEQ ID NO: 44 | moltype = AA  length = 245 | |
| FEATURE | Location/Qualifiers | |
| REGION | 1..245 | |
| | note = Description of Artificial Sequence: Synthetic polypeptide | |
| source | 1..245 | |
| | mol_type = protein | |
| | organism = synthetic construct | |

SEQUENCE: 44
```
MDIQMTQSPS SLSASVGDRV TITCRASQDI RNYLNWYQQK PGKAPKLLIY YTSRLESGVP    60
SRFSGSGSGT DYTLTISSLQ PEDFATYYCQ QGNTLPWTFG QGTKVEIKGG GGSGGGGSGG   120
GGSEVQLVES GGGLVQPGGS LRLSCAASGY SFTGYTMNWV RQAPGKGLEW VALINPYKGV   180
STYNQKFKDR FTISVDKSKN TAYLQMNSLR AEDTAVYYCA RSGYYGDSDW YFDVWGQGTL   240
VTVSS                                                               245
```

| | | |
|---|---|---|
| SEQ ID NO: 45 | moltype = DNA  length = 735 | |
| FEATURE | Location/Qualifiers | |
| misc_feature | 1..735 | |
| | note = Description of Artificial Sequence: Synthetic polynucleotide | |

```
                       source          1..735
                                       mol_type = other DNA
                                       organism = synthetic construct
SEQUENCE: 45
atggatatcc agatgaccca gtccccgagc tccctgtccg cctctgtggg cgatagggtc   60
accatcacct gccgtgccag tcaggacatc cgtaattatc tgaactggta tcaacagaaa  120
ccaggaaaag ctccgaaact actgatttac tatacctccc gcctggagtc tggagtccct  180
tctcgcttct ctggttctgg ttctgggacg gattacactc tgaccatcag cagtctgcaa  240
ccggaagact cgcaacttta ttactgtcag caaggtaata tctgccgtgt gacgttcgga  300
cagggcacca aggtggagat caaaggcggg ggcggaagtg gaggaggagg ctcaggcgga  360
ggagggagcg aggttcagct ggtggagtct ggcggtggcc tggtgcagcc aggggggctca  420
ctccgtttgt cctgtgcagc ttctggctac tcctttaccg gctacactat gaactgggtg  480
cgtcaggccc aggtaaggg cctggaatgg gttgcactga ttaatcctac caaaggtgtt  540
agtacctaca accagaagtt caaggaccgt ttcactataa gcgtagataa atccaaaaac  600
acagcctacc tgcaaatgaa cagcctgcgt gctgaggaca ctgccgtcta ttattgtgct  660
agaagcggat actacggcga tagtgactgg tatttgacg tgtggggtca aggaaccctg  720
gtcaccgtct cctcg                                                  735

SEQ ID NO: 46         moltype = AA   length = 245
FEATURE               Location/Qualifiers
REGION                1..245
                      note = Description of Artificial Sequence: Synthetic
                       polypeptide
source                1..245
                      mol_type = protein
                      organism = synthetic construct
SEQUENCE: 46
MDIQMTQSPS SLSASVGDRV TITCRASQDI RNYLNWYQQK PGKAPKLLIY YTSRLESGVP   60
SRFSGSGSGT DYTLTISSLQ PEDFATYYCQ QGNTLPWTFG QGTKVEIKGG GGSGGGGSGG  120
GGSEVQLVES GGGLVQPGGS LRLSCAASGY SFTGYTMNWV RQAPGKGLEW VALINPTKGV  180
STYNQKFKDR FTISVDKSKN TAYLQMNSLR AEDTAVYYCA RSGYYGDSDW YFDVWGQGTL  240
VTVSS                                                             245

SEQ ID NO: 47         moltype = DNA   length = 60
FEATURE               Location/Qualifiers
misc_feature          1..60
                      note = Description of Artificial Sequence: Synthetic
                       oligonucleotide
source                1..60
                      mol_type = other DNA
                      organism = synthetic construct
SEQUENCE: 47
atggagaccc ccgcccagct gctgttcctg ctgctgctgt ggctgcccga caccaccggc   60

SEQ ID NO: 48         moltype = AA   length = 20
FEATURE               Location/Qualifiers
REGION                1..20
                      note = Description of Artificial Sequence: Synthetic peptide
source                1..20
                      mol_type = protein
                      organism = synthetic construct
SEQUENCE: 48
METPAQLLFL LLLWLPDTTG                                              20

SEQ ID NO: 49         moltype = DNA   length = 63
FEATURE               Location/Qualifiers
misc_feature          1..63
                      note = Description of Artificial Sequence: Synthetic
                       oligonucleotide
source                1..63
                      mol_type = other DNA
                      organism = synthetic construct
SEQUENCE: 49
atggctttgc ctgtcacggc tcttctgctc cctctggccc tgcttctgca cgcggcgcga   60
ccc                                                                63

SEQ ID NO: 50         moltype = AA   length = 21
FEATURE               Location/Qualifiers
REGION                1..21
                      note = Description of Artificial Sequence: Synthetic peptide
source                1..21
                      mol_type = protein
                      organism = synthetic construct
SEQUENCE: 50
MALPVTALLL PLALLLHAAR P                                            21

SEQ ID NO: 51         moltype = DNA   length = 732
FEATURE               Location/Qualifiers
misc_feature          1..732
```

```
                        note = Description of Artificial Sequence: Synthetic
                            polynucleotide
source                  1..732
                        mol_type = other DNA
                        organism = synthetic construct
SEQUENCE: 51
gaggtgcagc tggtggagtc tggaggaggc ctggtgcagc ctggcggctc cctgaggctg     60
tcttgcgcag caagcggctt caacatctac tatagctaca tgcactgggt cgcgcaggcc    120
cctggcaagg gcctggagtg ggtggcctcc atctctccat actatggcta cacctcctat    180
gccgactctg tgaagggccg gtttacaatc agcgccgata cctccaagaa cacagcctat    240
ctgcagatga attccctgag ggcagaggac accgccgtgt actattgcgc agacacggc     300
tacgccctgg attattgggg ccagggcacc ctggtgacag tgagctccgg cagcacatcc    360
ggatctggca agccaggctc tggagaggga agcaccaagg gcgacatcca gatgacacag    420
tccccatcta gcctgagcgc ctccgtgggc gatagggtga ccatcacatg tcgcgccatct   480
cagagcgtgt cctctgccgt ggcatggtac cagcagaagc ccggcaaggc ccctaagctg    540
ctgatctaca gcgccagctc cctgtattcc ggcgtgcctt ctcggttctc cggctctaga    600
agcggcaccg actttaccct gacaatctct agcctgcagc ccgaggattt cgccacatac    660
tattgtcagc agagcgtgtg ggtgggctac tccctgatca ccctttggcca gggcacaaag    720
gtgggagatca ag                                                       732

SEQ ID NO: 52           moltype = AA   length = 244
FEATURE                 Location/Qualifiers
REGION                  1..244
                        note = Description of Artificial Sequence: Synthetic
                            polypeptide
source                  1..244
                        mol_type = protein
                        organism = synthetic construct
SEQUENCE: 52
EVQLVESGGG LVQPGGSLRL SCAASGFNIY YSYMHWVRQA PGKGLEWVAS ISPYYGYTSY     60
ADSVKGRFTI SADTSKNTAY LQMNSLRAED TAVYYCARHG YALDYWGQGT LVTVSSGSTS    120
GSGKPGSGEG STKGDIQMTQ SPSSLSASVG DRVTITCRAS QSVSSAVAWY QQKPGKAPKL    180
LIYSASSLYS GVPSRFSGSR SGTDFTLTIS SLQPEDFATY YCQQSVWVGY SLITFGQGTK    240
VEIK                                                                 244

SEQ ID NO: 53           moltype = DNA   length = 732
FEATURE                 Location/Qualifiers
misc_feature            1..732
                        note = Description of Artificial Sequence: Synthetic
                            polynucleotide
source                  1..732
                        mol_type = other DNA
                        organism = synthetic construct
SEQUENCE: 53
gacatccaga tgacacagtc cccaagctcc ctgtccgcct ctgtgggcga tagggtgacc     60
atcacatgca gggcaagcca gtccgtgtct agcgccgtgg catggtacca gcagaagccc    120
ggcaaagccc ctaagctgct gatctacagc gcctcctctc tgtattccgg cgtgccatct    180
cggttctctg gcagcagatc cggcaccgac tttaccctga caatcagctc cctgcagccc    240
gaggatttcg ccacatacta ttgccagcag agcgtgtggg tgggctactc cctgatcacc    300
tttggccagg gcacaaaggt ggagatcaag ggatctacca gcggatccgg caagcctggc    360
agcggagagg gatccacaaa gggagaggtg cagctgggtga agtctggagg aggcctggtg    420
cagcctggcg gctctctgag gctgagctgt gcagcatccg gcttcaacat ctactatagc    480
tacatgcact gggtgcgcca ggcccccggc aaggggcctgg agtgggtggc ctctatcagc    540
ccttactatg gctacacctc ttatgccgac agcgtgaagg gccggtttac aatctccgcc    600
gataccttcta gaacacagc ctatctgcag atgaattccc tgagggcaga ggacaccgcc    660
gtgtactatt gtgccagaca cggctacgcc ctggattatt ggggccaggg caccctggtg    720
acagtgtcta gc                                                        732

SEQ ID NO: 54           moltype = AA   length = 244
FEATURE                 Location/Qualifiers
REGION                  1..244
                        note = Description of Artificial Sequence: Synthetic
                            polypeptide
source                  1..244
                        mol_type = protein
                        organism = synthetic construct
SEQUENCE: 54
DIQMTQSPSS LSASVGDRVT ITCRASQSVS SAVAWYQQKP GKAPKLLIYS ASSLYSGVPS     60
RFSGSRSGTD FTLTISSLQP EDFATYYCQQ SVWVGYSLIT FGQGTKVEIK GSTSGSGKPG    120
SGEGSTKGEV QLVESGGGLV QPGGSLRLSC AASGFNIYYS YMHWVRQAPG KGLEWVASIS    180
PYYGYTSYAD SVKGRFTISA DTSKNTAYLQ MNSLRAEDTA VYYCARHGYA LDYWGQGTLV    240
TVSS                                                                 244

SEQ ID NO: 55           moltype = DNA   length = 1905
FEATURE                 Location/Qualifiers
misc_feature            1..1905
                        note = Description of Artificial Sequence: Synthetic
                            polynucleotide
source                  1..1905
```

```
                        mol_type = other DNA
                        organism = synthetic construct
SEQUENCE: 55
atggccctgc cagtgaccgc cctgctgctg ccactggccc tgctgctgca cgccgccaga    60
cccgaggtgc agctggtgga gtctggagga ggcctggtgc agcctggcgg ctccctgagg   120
ctgtcttgcg cagcaagcgg cttcaacatc tactatagct acatgcactg ggtgcgccaa   180
gcccctggca agggcctgga gtgggtggcc tccatctctc catactatgg ctacacctcc   240
tatgccgact ctgtgaaggg ccggtttaca atcagcgccg atacctccaa gaacacagcc   300
tatctgcaga tgaattccct gagggcagag gacaccgccg tgtactattg cgccagacac   360
ggctacgccc tggattattg gggccagggc accctggtga cagtgagctc cggcagcaca   420
tccggatctg gcaagccagg ctctggagag ggaagcacca agggcgacat ccagatgaca   480
cagtccccat ctagcctgag cgcctccgtg ggcgataggg tgaccatcac atgtcgcgcc   540
tctcagagcg tgtcctctgc cgtggcatgg taccagcaga agcccggcaa ggcccctaag   600
ctgctgatct acagcgccag ctccctgtat tccggctgc cttctcggtt ctccggctct   660
agaagcggca ccgactttac cctgacaatc tctagcctgc agcccgagga tttcgccaca   720
tactattgtc agcagagcgt gtgggtggc tactccctga tcacctttgg ccagggcaca   780
aaggtggaga tcaaggagca aagctgatc agcgaggagg acctgaatcc cggggccgaa   840
gcagcagcaa aggaggccgc agcgaaggaa gcagctgcga aggccggatc catgagtatc   900
cagatgaccc agtccccgag ctccctgtcc gcctctgtgg gcgataggt caccatcacc   960
tgccgtgcca gtcaggacat ccgtaattat ctgaactggt atcaacagaa accaggaaaa  1020
gctccgaaac tactgattta ctataccctc cgcctggagt ctggagtccc ttctcgcttc  1080
tctggttctg gttctgggac ggattacact ctgaccatca gcagtctgca accggaagac  1140
ttcgcaactt attactgtca gcaaggtaat actctgccgt ggacgttcgg acagggcacc  1200
aaggtggaga tcaaaggcgg cggcggaagt ggaggaggag gctcaggcgg aggagggagc  1260
gaggttcagc tggtggagtc tggcggtggc ctggtgcagc caggggggctc actccgtttg  1320
tcctgtgcag cttctggctt ctccttacc ggctacacta tgaactgggt gcgtcaggcc  1380
ccaggtaagg gcctgaatg ggttgcactg attaatcctt ataaaggtgt tagtacctac  1440
aaccagaagt tcaaggaccg tttcactata agcgtagata atccaaaaa cacagcctac  1500
ctgcaaatga acagcctgcg tgctgaggac actgccgtct attattgtgc tagaagcgga  1560
tactacggcg atagtgactg gtatttgac tgtgggggtc aaggaaccct ggtcaccgtc  1620
tcctcgacta gtggcggagg aggatcactc gagagcggac aggtgctgct ggaatccaat  1680
atcaaagtcc tgcccacttg gtctaccccc gtgcagccta tggctctgat tgtgctggga  1740
ggagtcgcag gactgctgct gtttatcggg ctgggaattt tcttttgcgt gcgctgccgg  1800
caccggagaa ggcaggccga cgcatgagc cagatcaagc gactgctgag cgagaagaaa  1860
acctgtcagt gtccccatag attccagaag acctgttcac ccatt              1905

SEQ ID NO: 56          moltype = AA  length = 635
FEATURE                Location/Qualifiers
REGION                 1..635
                        note = Description of Artificial Sequence: Synthetic
                         polypeptide
source                 1..635
                        mol_type = protein
                        organism = synthetic construct
SEQUENCE: 56
MALPVTALLL PLALLLHAAR PEVQLVESGG GLVQPGGSLR LSCAASGFNI YYSYMHWVRQ    60
APGKGLEWVA SISPYYGYTS YADSVKGRFT ISADTSKNTA YLQMNSLRAE DTAVYYCARH   120
GYALDYWGQG TLVTVSSGST SGSGKPGSGE GSTKGDIQMT QSPSSLSASV GDRVTITCRA   180
SQSVSSAVAW YQQKPGKAPK LLIYSASSLY SGVPSRFSGS RSGTDFTLTI SSLQPEDFAT   240
YYCQQSVWVG YSLITFGQGT KVEIKEQKLI SEEDLNPGAE AAAKEAAAKE AAAKAGSMDI   300
QMTQSPSSLS ASVGDRVTIT CRASQDIRNY LNWYQQKPGK APKLLIYYTS RLESGVPSRF   360
SGSGSGTDYT LTISSLQPED FATYYCQQGN TLPWTFGQGT KVEIKGGGGS GGGGSGGGGS   420
EVQLVESGGG LVQPGGSLRL SCAASGYSFT GYTMNWVRQA PGKGLEWVAL INPYKGVSTY   480
NQKFKDRFTI SVDKSKNTAY LQMNSLRAED TAVYYCARSG YYGDSDWYFD VWGQGTLVTV   540
SSTSGGGGSL ESGQVLLESN IKVLPTWSTP VQPMALIVLG GVAGLLLFIG LGIFFCVRCR   600
HRRRQAERMS QIKRLLSEKK TCQCPHRFQK TCSPI                              635

SEQ ID NO: 57          moltype = DNA  length = 1905
FEATURE                Location/Qualifiers
misc_feature           1..1905
                        note = Description of Artificial Sequence: Synthetic
                         polynucleotide
source                 1..1905
                        mol_type = other DNA
                        organism = synthetic construct
SEQUENCE: 57
atggccctgc cagtgaccgc cctgctgctg ccactggccc tgctgctgca cgccgcccgg    60
cctgacatcc agatgacaca gtccccaagc tccctgtccg cctctgtggg cgataggtgt   120
accatcacat gcagggccaa gcagtccgtg tctagcgccg tggcatggta ccagcagaaa   180
cccggcaagg cccctaagct gctgatctac agcgcctcct ctctgtattc cggcgtgcca   240
tctcggttct ctggcagcag atccggcacc gactttaccc tgacaatcag ctccctgcag   300
cccgaggatt tcgccacata ctattgccag cagagcgtgt gggtgggcta ctccctgatc   360
acctttggc agggcacaaa ggtggagatc aagggatcta ccagcggatc cggcaagcct   420
ggcagcggag agggatccac aaagggagag gtgcagctgg tggagtctgg aggaggcctg   480
gtgcagcctg gcggctctct gaggctgagc tgtgcagcat ccggcttcaa catctactat   540
agctacatgc actgggtgcg ccaggccccc ggcaagggcc tggagtgggt ggcctctatc   600
agcccttact atggctacac ctcttatgcc gacagcgtga agggcggtt tacaatctcc   660
gccgatacct ctaagaacac agcctatctg cagatgaatt ccctgagggc agaggacacc   720
gccgtgtact attgtgccag acacggctac gcccttggatt attgggggcca gggcaccctg   780
```

```
gtgacagtgt ctagcgagca gaagctgatc agcgaggagg acctgaatcc cggggccgaa    840
gcagcagcaa aggaggccgc agcgaaggaa gcagctgcga aggccggatc catggatatc    900
cagatgaccc agtccccgag ctccctgtcc gcctctgtgg gcgataggt  caccatcacc    960
tgccgtgcca gtcaggacat ccgtaattat ctgaactggt atcaacagaa accaggaaaa   1020
gctccgaaac tactgattta ctatacctcc cgcctgagtc ctggagtccc ttctcgcttc   1080
tctggttctg gttctgggac ggattacact ctgaccatca gcagtctgca accggaagac   1140
ttcgcaactt attactgtca gcaaggtaat actctgccgt ggacgttcgg acagggcacc   1200
aaggtggaga tcaaaggcgg cggcggaagt ggaggaggag gctcaggcgg aggagggagc   1260
gaggttcagc tggtggagtc tggcggtggc ctggtgcagc cagggggctc actccgtttg   1320
tcctgtgcag cttctggcta ctccttacc  ggctacacta tgaactgggt gcgtcaggcc   1380
ccaggtaagg gcctgaatgg ggttgcactg attaatcctt ataaaggtgt tagtacctac   1440
aaccagaagt tcaaggaccg tttcactata agcgtagata atccaaaaa  cacagcctac   1500
ctgcaaatga acagcctgcg tgctgaggac actgccgtct attattgtgc tagaagcgga   1560
tactacggcg atagtggctg gtattttgac gtgtggggtc aaggaacccct ggtcaccgtc   1620
tcctcgacta gtggcggagg aggatcactc gagagcggac aggtgctgct ggaatccaat   1680
atcaaagtcc tgcccacttg gtctacccc  gtgcagccta tggctctgat tgtgctggga   1740
ggagtcgcag gactgctgct gtttatcggg ctgggaattt tcttttgcgt gcgctgccgg   1800
caccggagaa ggcaggccga gcgcatgagc cagatcaagc gactgctgag cgagaagaaa   1860
acctgtcagt gtccccatag attccagaag acctgttcac ccatt                   1905

SEQ ID NO: 58          moltype = AA  length = 635
FEATURE                Location/Qualifiers
REGION                 1..635
                       note = Description of Artificial Sequence: Synthetic
                       polypeptide
source                 1..635
                       mol_type = protein
                       organism = synthetic construct
SEQUENCE: 58
MALPVTALLL PLALLLHAAR PDIQMTQSPS SLSASVGDRV TITCRASQSV SSAVAWYQQK     60
PGKAPKLLIY SASSLYSGVP SRFSGSRSGT DFTLTISSLQ PEDFATYYCQ QSVWVGYSLI    120
TFGQGTKVEI KGSTSGSGKP GSGEGSTKGE VQLVESGGGL VQPGGSLRLS CAASGFNIYY    180
SYMHWVRQAP GKGLEWVASI SPYYGYTSYA DSVKGRFTIS ADTSKNTAYL QMNSLRAEDT    240
AVYYCARHGY ALDYWGQGTL VTVSSEQKLI SEEDLNPGAE AAAKEAAAKE AAAKAGSMDI    300
QMTQSPSSLS ASVGDRVTIT CRASQDIRNY LNWYQQKPGK APKLLIYYTS RLESGVPSRF    360
SGSGSGTDYT LTISSLQPED FATYYCQQGN TLPWTFGQGT KVEIKGGGGS GGGGSGGGGS    420
EVQLVESGGG LVQPGGSLRL SCAASGYSFT GYTMNWVRQA PGKGLEWVAL INPYKGVSTY    480
NQKFKDRFTI SVDKSKNTAY LQMNSLRAED TAVYYCARSG YYGDSDWYFD VWGQGTLVTV    540
SSTSGGGGSL ESGQVLLESN IKVLPTWSTP VQPMALIVLG GVAGLLLFIG LGIFFCVRCR    600
HRRRQAERMS QIKRLLSEKK TCQCPHRFQK TCSPI                               635

SEQ ID NO: 59          moltype = DNA  length = 1914
FEATURE                Location/Qualifiers
misc_feature           1..1914
                       note = Description of Artificial Sequence: Synthetic
                       polynucleotide
source                 1..1914
                       mol_type = other DNA
                       organism = synthetic construct
SEQUENCE: 59
atggcccctgc cagtgaccgc cctgctgctg ccactggccc tgctgctgca cgccgccaga     60
cccgaggtgc agctggtgga gtctggagga ggcctggtgc agcctggcgg ctccctgagg    120
ctgtcttgcg cagcaagcgg cttcaacatc tactatagct acatgcactg ggtgcgccag    180
gcccctggca agggcctgga gtgggtggcc tccatctctc catactatgg ctacacctcc    240
tatgccgact ctgtgaaggg ccggtttaca atcagcgcag ataccccaa  gaacacagcc    300
tatctgcaga tgaattccct gagggcagag gacaccgccg tgtactattg cgccagacac    360
ggctacgccc tggattattg gggccagggc accctggtga cagtgagctc cggcagcaca    420
tccggatctg gcaagccagg ctctggagag ggaagcacca agggcgacat ccagatgaca    480
cagtccccat cctagcctgag cgcctccgtg ggcgataggg tgaccatcac atgtcgcgcc    540
tctcagagcg tgtcctctgc cgtggcatgg taccagcaga gcccggcaa  ggcccctaag    600
ctgctgatct acagcgccag ctccctgtat tccggcgtgc cttctcggtt ctccggctct    660
ggaagcggca ccgacttaac cctgacaatc tctagcctgc agcccgagga tttcgccaca    720
tactattgtc agcagagcgt gtgggtggc  tactcccctga tcacctttgg ccagggcaca    780
aaggtggaga tcaaggagca gaagctgatc agcgaggaga acctgaatcc cggggagaga    840
ggagggagcg gggaggagg  cagcggcggg ggaggctctg gaggaggagg gagcggatcc    900
atggatatcc agatgaccca gtccccgagc tccctgtccg cctctgtggg cgataggtc    960
accatcacct gccgtgccag tcaggacatc cgtaattatc tgaactggta tcaacagaaa   1020
ccaggaaaag ctccgaaact actgatttac tatacctccc gcctgagtc tggagtccct   1080
tctcgcttct ctggttctgg ttctgggacg gattacactc tgaccatcag cagtctgca    1140
ccggaagact tcgcaactta ttactgtcag caaggtaata ctctgccgtg gacgttcgga   1200
cagggcacca aggtggagat caaaggcggc ggcggaagtg gaggaggagg ctcaggcgga   1260
ggagggagcg aggttcagct ggtggagtct ggcggtggcc tggtgcagcc agggggctca   1320
ctccgtttgt cctgtgcagc ttctggctac tccttaccg  gctacactat gaactgggtg   1380
cgtcaggccc caggtaaggg cctgaatggg gttgcactga ttaatcctta taaaggtgtt   1440
agtacctaca accagaagtt caaggaccgt ttcactataa gcgtagataa tccaaaaac    1500
acagcctacc tgcaaatgaa cagcctgcgt gctgaggaca ctgccgtcta ttattgtgct   1560
agaagcggat actacggcga tagtgactgg tattttgacg tgtggggtca aggaaccctg   1620
gtcaccgtct cctcgactag tggcggagga ggatcactcg agagcggaca ggtgctgctg   1680
gaatccaata tcaaagtcct gcccacttgg tctacccccg tgcagcctat ggctctgatt   1740
```

```
gtgctgggag gagtcgcagg actgctgctg tttatcgggc tgggaatttt cttttgcgtg   1800
cgctgccggc accggagaag gcaggccgag cgcatgagcc agatcaagcg actgctgagc   1860
gagaagaaaa cctgtcagtg tcccatcaga ttccagaaga cctgttcacc catt         1914

SEQ ID NO: 60            moltype = AA   length = 638
FEATURE                  Location/Qualifiers
REGION                   1..638
                         note = Description of Artificial Sequence: Synthetic
                          polypeptide
source                   1..638
                         mol_type = protein
                         organism = synthetic construct
SEQUENCE: 60
MALPVTALLL PLALLLHAAR PEVQLVESGG GLVQPGGSLR LSCAASGFNI YYSMHWVRQ    60
APGKGLEWVA SISPYYGYTS YADSVKGRFT ISADTSKNTA YLQMNSLRAE DTAVYYCARH  120
GYALDYWGQG TLVTVSSGST SGSGKPGSGE GSTKGDIQMT QSPSSLSASV GDRVTITCRA  180
SQSVSSAVAW YQQKPGKAPK LLIYSASSLY SGVPSRFSGS RSGTDFTLTI SSLQPEDFAT  240
YYCQQSVWVG YSLITFGQGT KVEIKEQKLI SEEDLNPGGG GGSGGGGSGG GGSGGGGSGS  300
MDIQMTQSPS SLSASVGDRV TITCRASQDI RNYLNWYQQK PGKAPKLLIY YTSRLESGVP  360
SRFSGSGSGT DYTLTISSLQ PEDFATYYCQ QGNTLPWTFG QGTKVEIKGG GGSGGGGSGG  420
GGSEVQLVES GGGLVQPGGS LRLSCAASGY SFTGYTMNWV RQAPGKGLEW VALINPYKGV  480
STYNQKFKDR FTISVDKSKN TAYLQMNSLR AEDTAVYYCA RSGYYGDSDW YFDVWGQGTL  540
VTVSSTSGGG GSLESGQVLL ESNIKVLPTW STPVQPMALI VLGGVAGLLL FIGLGIFFCV  600
RCRHRRRQAE RMSQIKRLLS EKKTCQCPHR FQKTCSPI                          638

SEQ ID NO: 61            moltype = DNA   length = 1914
FEATURE                  Location/Qualifiers
misc_feature             1..1914
                         note = Description of Artificial Sequence: Synthetic
                          polynucleotide
source                   1..1914
                         mol_type = other DNA
                         organism = synthetic construct
SEQUENCE: 61
atggccctgc cagtgaccgc cctgctgctg ccactggccc tgctgctgca cgccgcccgg    60
cctgacatcc agatgacaca gtccccaagc tccctgtccg cctctgtggg cgatagggtg   120
accatcacat gcagggcaag ccagtccgtt tctagcgccg tggcatggta ccagcagaag   180
cccggcaagg cccctaagct gctgatctac agcgcctcct ctctgtattc cggcgtgcca   240
tctcggttct ctggcagcag atccggcacc gactttgacc tgacaatcag ctccctgcag   300
cccgaggatt tcgccacata ctattgccag cagagcgtgt gggtgggcta ctccctgatc   360
accttttggc agggcacaaa ggtggagatc aaggatcta ccagcggatc cggcaagcct   420
ggcagcggag agggatccac aaaggagag gtgcagctgg tggagtctgg aggaggcctg   480
gtgcagcctg gcggctctct gaggctgagc tgtgcagcat ccggcttcaa catctactat   540
agctacatgc actgggtgcg ccaggccccc ggcaagggcc tggagtgggt ggcctctatc   600
agcccttact atggctacac ctcttatgcc gacagcgtga agggccggtt tacaatctcc   660
gccgatacct ctaagaacac agcctatctg cagatgaatt ccctgagggc agaggacacc   720
gccgtgtact attgtgccag acacggctac gccctggatt attgggggcca gggcacccgt   780
gtgacagtgt ctagcgagca gagctgatc agcgaggagg acctgaatcc gggggggagga   840
ggagggagcg gggaggagg cagcggcggg ggaggcctg gaggaggag gagcggatcc   900
atggatatcc agatgaccca gtccccgagc tccctgtccg cctctgtggg cgataggggtc   960
accatcacct gccgtgccag tcaggacatc cgtaattatc tgaactggta tcaacagaaa  1020
ccaggaaaag ctccgaaact actgatttac tatacctccc gcctggagtc tggagtccct  1080
tctcgcttct ctggttctgg ttctgggacg gattacactc tgaccatcag cagtctgcaa  1140
ccggaagact tcgcaactta ttactgtcag caaggtaata ctctgccgtg gacgttcgga  1200
cagggcacca aggtggagat caaaggcggc ggcggaagtg gaggaggaag ctcaggcgga  1260
ggagggagcg aggttcagct ggtggagtct ggcggtggcc tggtcagcc agggggctca  1320
ctccgttttgt cctgtgcagc ttctggctac tcctttaccg gctacactat gaactggggtg  1380
cgtcaggccc caggtaaggg cctggaatgg gttgcactga ttaatcctta taaaggtgtt  1440
agtacctaca ccagaagtt caaggaccgt ttcactataa gcgtagataa atccaaaaac  1500
acagcctacc tgcaaatgaa cagcctgcgt gctgaggaca ctgccgtcta ttattgtgct  1560
agaagcggat actacggcga tagtgactgg tattttgacg tgtgggggtca aggaaccctg  1620
gtcaccgtct cctcgactag tggcggagga ggatcactcg agagcggaca ggtgctgctg  1680
gaatccaata tcaaagtcct gcccacttgg tctaccccg tgcagcctat ggctctgatt  1740
gtgctgggag gagtcgcagg actgctgctg tttatcgggc tgggaatttt cttttgcgtg  1800
cgctgccggc accggagaag gcaggccgag cgcatgagcc agatcaagcg actgctgagc  1860
gagaagaaaa cctgtcagtg tcccatcaga ttccagaaga cctgttcacc catt         1914

SEQ ID NO: 62            moltype = AA   length = 638
FEATURE                  Location/Qualifiers
REGION                   1..638
                         note = Description of Artificial Sequence: Synthetic
                          polypeptide
source                   1..638
                         mol_type = protein
                         organism = synthetic construct
SEQUENCE: 62
MALPVTALLL PLALLLHAAR PDIQMTQSPS SLSASVGDRV TITCRASQSV SSAVAWYQQK    60
PGKAPKLLIY SASSLYSGVP SRFSGSRSGT DFTLTISSLQ PEDFATYYCQ QSVWVGYSLI  120
TFGQGTKVEI KGSTSGSGKP GSGEGSTKGE VQLVESGGGL VQPGGSRLS CAASGFNIYY  180
```

```
SYMHWVRQAP GKGLEWVASI SPYYGYTSYA DSVKGRFTIS ADTSKNTAYL QMNSLRAEDT    240
AVYYCARHGY ALDYWGQGTL VTVSSEQKLI SEEDLNPGGG GGSGGGGSGG GGSGGGGSGS    300
MDIQMTQSPS SLSASVGDRV TITCRASQDI RNYLNWYQQK PGKAPKLLIY YTSRLESGVP    360
SRFSGSGSGT DYTLTISSLQ PEDFATYYCQ QGNTLPWTFG QGTKVEIKGG GGSGGGGSGG    420
GGSEVQLVES GGGLVQPGGS LRLSCAASGY SFTGYTMNWV RQAPGKGLEW VALINPYKGV    480
STYNQKFKDR FTISVDKSKN TAYLQMNSLR AEDTAVYYCA RSGYYGDSDW YFDVWGQGTL    540
VTVSSTSGGG GSLESGQVLL ESNIKVLPTW STPVQPMALI VLGGVAGLLL FIGLGIFFCV    600
RCRHRRRQAE RMSQIKRLLS EKKTCQCPHR FQKTCSPI                           638

SEQ ID NO: 63           moltype = DNA   length = 1917
FEATURE                 Location/Qualifiers
misc_feature            1..1917
                        note = Description of Artificial Sequence: Synthetic
                         polynucleotide
source                  1..1917
                        mol_type = other DNA
                        organism = synthetic construct
SEQUENCE: 63
atggctttgc ctgtcacggc tcttctgctc cctctggccc tgcttctgca cgcggcgcga     60
cccgatatcc agatgactca gacgacctca tcattgtccg ccagtttggg ggacagggtt    120
acaatatcct gccgggcgag ccaagacatc agtaaatatc ttaattggta ccagcagaaa    180
ccagatggta cagtaaaact tctttatcta cacacctctc ggctccactc tggggttccc    240
tctaggttca gtggtagtgg gtcaggcacc gactacagcc ttacgataag caacttggaa    300
caggaggata tcgcaactta cttctgccaa cagggaaata ccctgcctta cacgttcggt    360
ggaggcacta aactggagat cactgggtca acctctggta gcgtaagcc tggctccggc     420
gaaggctcca caaagggtga ggtgaaactc caagagtcga gtgagggaga aggctcaggc    480
tcacaaagtt tgtcagttac ttgtaccgta agcggcgttt ccctgccgcga ttacggtgtg    540
agctggataa ggcagccacc gagaaaaggt cttgaatggc tgggagtgat ctgggggtct    600
gagacaacgt attacaactc agctcttaag agcaggctta cgatcattaa agataacagc    660
aaatctcaag tgttcctcaa aatgaatagc cttcaaactg atgatactgc catctattat    720
tgtgctaagc attattacta tggcggcagt tacgcaatgg attattgggg gcaaggtacc    780
tcagtcactg taagcagcga acagaagctc atttctgaag aagacctcaa ccccggaggg    840
ggaggggga gtgggggagg gggtagtggt ggcggaggat caggcggggg gggatcagga    900
tccatgatga tccagatgac ccagtccccg agctccctgt ccgcctctgt gggcgatagg    960
gtcaccatca cctgccgtgc cagtcaggac atccgtaatt atctgaactg gtatcaacag   1020
aaaccaggaa aagctccgaa actactgatt tactatacct cccgcctgga gtctggagtc   1080
ccttctcgct tctctggttc tggttctggg acggattaca ctctgaccat cagcagtctg   1140
caaccggaag acttcgcaac ttattactgt cagcaaggta atactctgcc gtggacgttc   1200
ggacagggca caaggtgga gatcaaaggc ggcggcggaa gtggaggagg aggctcaggc   1260
ggaggaggga gcgaggttca gctggtggag tctggcggtg gcctggtgca gccagggggc   1320
tcactccgtt tgtcctgtgc agcttctggc tactcctta ccggctacac tatgaactgg    1380
gtgcgtcagg cccccaggtaa gggcctgaa tgggttgcac tgattaatcc taccaaaggt   1440
gttagtacct acaaccagaa gttcaaggac cgtttcacta taagcgtaga taaatccaaa    1500
aacacagcct acctgcaaat gaacagcctg cgtgctgagg acactgccgt ctattattgt   1560
gctagaagcg gatactacgg cgatagtgac tggtattttg acgtgtgggg tcaaggaacc    1620
ctggtcaccg tctcctcgac tagtggcgga ggaggatcac tcgagagcgg acaggtgctg   1680
ctggaatcca atatcaaagt cctgcccact tggtctacc ccgtgcagcc tatggctctg    1740
attgtgctgg gaggagtcgc aggactgctg ctgtttatcg gctgggaat tttcttttgc    1800
gtgcgctgcc ggcaccggag aaggcaggcc gagcgcatga gccagatcaa gcgactgctg   1860
agcgagaaga aacctgtca gtgtccccat agattccaga gacctgttc acccatt         1917

SEQ ID NO: 64           moltype = AA    length = 639
FEATURE                 Location/Qualifiers
REGION                  1..639
                        note = Description of Artificial Sequence: Synthetic
                         polypeptide
source                  1..639
                        mol_type = protein
                        organism = synthetic construct
SEQUENCE: 64
MALPVTALLL PLALLLHAAR PDIQMTQTTS SLSASLGDRV TISCRASQDI SKYLNWYQQK     60
PDGTVKLLIY HTSRLHSGVP SRFSGSGSGT DYSLTISNLE QEDIATYFCQ QGNTLPYTFG    120
GGTKLEITGS TSGSGKPGSG EGSTKGEVKL QESGPGVLAP SQSLSVTCTV SGVSLPDYGV    180
SWIRQPPRKG LEWLGVIWGS ETTYYNSALK SRLTIIKDNS KSQVFLKMNS LQTDDTAIYY    240
CAKHYYGGS YAMDYWGQGT SVTVSSEQKL ISEEDLNPGG GGSGGGGSG GGGSGGGGSG    300
SMDIQMTQSP SSLSASVGDR VTITCRASQD IRNYLNWYQQ KPGKAPKLLI YYTSRLESGV    360
PSRFSGSGSG TDYTLTISSL QPEDFATYYC QQGNTLPWTF GQGTKVEIKG GGGSGGGGSG    420
GGGSEVQLVE SGGGLVQPGG SLRLSCAASG YSFTGYTMNW VRQAPGKGLE WVALINPTKG    480
VSTYNQKFKD RFTISVDKSK NTAYLQMNSL RAEDTAVYYC ARSGYYGDSD WYFDVWGQGT    540
LVTVSSTSGG GGSLESGQVL LESNIKVLPT WSTPVQPMAL IVLGGVAGLL LFIGLGIFFC    600
VRCRHRRRQA ERMSQIKRLL SEKKTCQCPH RFQKTCSPI                          639

SEQ ID NO: 65           moltype = DNA   length = 1566
FEATURE                 Location/Qualifiers
misc_feature            1..1566
                        note = Description of Artificial Sequence: Synthetic
                         polynucleotide
source                  1..1566
                        mol_type = other DNA
```

```
                        organism = synthetic construct
SEQUENCE: 65
atggagaccc ccgcccagct gctgttcctg ctgctgctgt ggctgcccga caccaccggc    60
atgtcacggg gctccgacct gggcaaaaag ctgctggagg ccgctagggc cggggcaggac   120
gatgaagtga gaatcctgat ggccaacggg gctgacgtga atgctaagga tgagtacggc   180
ctgaccccc  tgtatctggc tacagcacac ggccatctgg agatcgtgga agtcctgctg   240
aaaaacggag ccgacgtgaa tgcagtcgat gccattgggt tcactcctct gcacctggca   300
gcctttatcg gacatctgga gattgcagaa gtgctgctga agcacggcgc tgacgtgaac   360
gcacaggata agttcggaaa aaccgctttt gacatcagca ttggcaacgg aaatgaagac   420
ctggctgaaa tcctgcagaa actgaatgaa cagaaactga ttagcgaaga agacctgaac   480
cccgggggag gaggagggag cggggaggga ggcagcggcg ggggaggctc tggaggagga   540
gggagcggat ccatggatat ccagatgacc cagtccccga gctccctgtc cgcctctgtg   600
ggcgatagg  tcaccatcac ctgccgtgcc agtcaggaca tccgtaatta tctgaactgg   660
tatcaacaga aaccaggaaa agctccgaaa ctactgattt actatacctc ccgcctggag   720
tctggagtcc cttctcgctt ctctggttct ggttctggga cggattacac tctgaccatc   780
agcagtctgc aaccggaaga cttcgcaact tattactgtc agcaaggtaa tactctgccg   840
tggacgttcg gacagggcac caaggtggag atcaaaggcg gcggcggaag tggaggagga   900
ggctcaggcg gaggagggag cgaggttcag ctggtggagt ctggcggtgg cctggtggga   960
ccagggggct cactccgttt gtcctgtgca gcttctggct actcctttac cggctacact  1020
atgaactggg tgcgtcaggc cccaggtaag ggcctggaat gggttgcact gattaatcct  1080
tataaagtg  ttagtaccta caaccagaag ttcaaggacc gtttcactat aagcgtagat  1140
aaatccaaaa acacagccta cctgcaaatg aacagcctgc gtgctgagga cactgccgtc  1200
tattattgtg ctagaagcgg atactacggc gatagtgact ggtattttga cgtgtgggt  1260
caaggaaccc tggtcaccgt ctcctcgact agtggcggag aggatcact  cgagagcgga  1320
caggtgctgc tggaatccaa tatcaaagtc ctgcccactt ggtctacccc cgtgcagcct  1380
atggcctga  ttgtgctggg aggagtcgca ggactgctgc tgtttatcgg gctgggaatt  1440
ttcttttgcg tgcgctgccg gcaccggaga aggcaggccg agcgcatgag ccagatcaag  1500
cgactgctga gcgaagaga  aacctgtcag tgtccccata gattccagaa gacctgttca  1560
cccatt                                                             1566

SEQ ID NO: 66       moltype = AA  length = 522
FEATURE             Location/Qualifiers
REGION              1..522
                    note = Description of Artificial Sequence: Synthetic
                    polypeptide
source              1..522
                    mol_type = protein
                    organism = synthetic construct
SEQUENCE: 66
METPAQLLFL LLLWLPDTTG MSRGSDLGKK LLEAARAGQD DEVRILMANG ADVNAKDEYG     60
LTPLYLATAH GHLEIVEVLL KNGADVNAVD AIGFTPLHLA AFIGHLEIAE VLLKHGADVN    120
AQDKFGKTAF DISIGNGNED LAEILQKLNE QKLISEEDLN PGGGGSGGG  GSGGGGSGGG    180
GSGSMDIQMT QSPSSLSASV GDRVTITCRA SQDIRNYLNW YQQKPGKAPK LLIYYTSRLE    240
SGVPSRFSGS GSGTDYTLTI SSLQPEDFAT YYCQQGNTLP WTFGQGTKVE IKGGGGSGGG    300
GSGGGGSEVQ LVESGGGLVQ PGGSLRLSCA ASGYSFTGYT MNWVRQAPGK GLEWVALINP    360
YKGVSTYNQK FKDRFTISVD KSKNTAYLQM NSLRAEDTAV YYCARSGYYG DSDWYFDVWG    420
QGTLVTVSST SGGGGSLESG QVLLESNIKV LPTWSTPVQP MALIVGGVA  GLLLFIGLGI    480
FFCVRCRHRR RQAERMSQIK RLLSEKKTCQ CPHRFQKTCS PI                       522

SEQ ID NO: 67       moltype = DNA  length = 1569
FEATURE             Location/Qualifiers
misc_feature        1..1569
                    note = Description of Artificial Sequence: Synthetic
                    polynucleotide
source              1..1569
                    mol_type = other DNA
                    organism = synthetic construct
SEQUENCE: 67
atggccttac cagtgaccgc cttgctcctg ccgctggcct tgctgctcca cgccgccagg     60
ccgatgtcac ggggctccga cctgggcaaa aagctgctgg aggccgctag ggccggggcag  120
gacgatgaag tgagaatcct gatggccaac ggggctgacg tgaatgctaa ggatgagtac   180
ggcctgaccc cctgtatct  ggctacagca cacggccatc tggagatcgt ggaagtcctg   240
ctgaaaaacg gagccgacgt gaatgcagtc gatgccattg ggttcactcc tctgcacctg   300
gcagccttta tcggacatct ggagattgca gaagtgctga tgaagcacgg cgctgacgtg   360
aacgcacagg ataagttcgg aaaaaccgct tttgacatca gcattggcaa cggaaatgaa   420
gacctggctg aaatcctgca gaaactgaat gaacagaaac tgattagcga agaagacctg   480
aaccccgggg gaggaggagg gagcggggga ggaggcagcg gcgggggagg ctctggagga   540
ggagggagcg gatccatgga tatccagatg acccagtccc cgagctccct gtccgcctct   600
gtgggcgata gggtcaccat cacctgccgt gccagtcagg acatccgtaa ttatctgaac   660
tggtatcaac agaaaccagg aaaagctccg aaactactga tttactatac ctcccgcctg   720
gagtctggag tcccttctcg cttctctggt tctggttctg ggacggatta cactctgacc   780
atcagcagtc tgcaaccgga agacttcgca acttattact gtcagcaagg taatactctg   840
ccgtggacgt tcggacaggg caccaaggtg gagatcaaag gcggcggcgg aagtggagga   900
ggaggctcag gcggaggagg gagcgaggtt cagctggtgg agtctggcgg tggcctggtg   960
ggaccagggg gctcactccg tttgtcctgt gcagcttctg gctactcctt taccggctac  1020
actatgaact gggtgcgtca ggccccaggt aagggcctgg aatgggttgc actgattaat  1080
ccttataaag tgttagtac  ctacaaccag aagttcaagg accgtttcac tataagcgta  1140
gataaatcca aaaacacagc ctacctgcaa atgaacagcc tgcgtgctga ggacactgcc  1200
gtctattatt gtgctagaag cggatactac ggcgatagtg actggtattt tgacgtgtgg  1260
```

```
ggtcaaggaa ccctggtcac cgtctcctcg actagtggcg gaggaggatc actcgagagc    1320
ggacaggtgc tgctggaatc caatatcaaa gtcctgccca cttggtctac ccccgtgcag    1380
cctatggctc tgattgtgct gggaggagtc gcaggactgc tgctgtttat cgggctggga    1440
attttctttt gcgtgcgctg ccggcaccgg agaaggcagg ccgagcgcat gagccagatc    1500
aagcgactgt gagcgagaa  gaaaacctgt cagtgtcccc atagattcca gaagacctgt    1560
tcacccatt                                                            1569
```

```
SEQ ID NO: 68           moltype = AA  length = 523
FEATURE                 Location/Qualifiers
REGION                  1..523
                        note = Description of Artificial Sequence: Synthetic
                        polypeptide
source                  1..523
                        mol_type = protein
                        organism = synthetic construct
SEQUENCE: 68
MALPVTALLL PLALLLHAAR PMSRGSDLGK KLLEAARAGQ DDEVRILMAN GADVNAKDEY     60
GLTPLYLATA HGHLEIVEVL LKNGADVNAV DAIGFTPLHL AAFIGHLEIA EVLLKHGADV    120
NAQDKFGKTA FDISIGNGNE DLAEILQKLN EQKLISEEDL NPGGGGGSGG GGSGGGGSGG    180
GGSGSMDIQM TQSPSSLSAS VGDRVTITCR ASQDIRNYLN WYQQKPGKAP KLLIYYTSRL    240
ESGVPSRFSG SGSGTDYTLT ISSLQPEDFA TYYCQQGNTL PWTFGQGTKV EIKGGGGSGG    300
GGSGGGGSEV QLVESGGGLV QPGGSLRLSC AASGYSFTGY TMNWVRQAPG KGLEWVALIN    360
PYKGVSTYNQ KFKDRFTISV DKSKNTAYLQ MNSLRAEDTA VYYCARSGYY GDSDWYFDVW    420
GQGTLVTVSS TSGGGGSLES GQVLLESNIK VLPTWSTPVQ PMALIVLGGV AGLLLFIGLG    480
IFFCVRCRHR RRQAERMSQI KRLLSEKKTC QCPHRFQKTC SPI                      523
```

```
SEQ ID NO: 69           moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 69
GGGGSGGGGS GGGGSGGGGS                                                 20
```

```
SEQ ID NO: 70           moltype = DNA  length = 60
FEATURE                 Location/Qualifiers
misc_feature            1..60
                        note = Description of Artificial Sequence: Synthetic
                        oligonucleotide
source                  1..60
                        mol_type = other DNA
                        organism = synthetic construct
SEQUENCE: 70
ggaggaggag ggagcggggg aggaggcagc ggcggggag gctctggagg aggagggagc      60
```

```
SEQ ID NO: 71           moltype = DNA  length = 750
FEATURE                 Location/Qualifiers
misc_feature            1..750
                        note = Description of Artificial Sequence: Synthetic
                        polynucleotide
source                  1..750
                        mol_type = other DNA
                        organism = synthetic construct
SEQUENCE: 71
atggacatcc agatgactca gaccacaagc tccctgtctg caagtctggg cgaccgggtg     60
acaatctcct gcagagcctc tcaggatatt aggaactacc tgaattggta tcagcagaaa    120
cctgatggca cagtcaagct gctgatctac tataccagcc ggctgcactc aggcgtgcca    180
agcaaattct caggaagcgg ctccgggact gactactccc tgaccatctc taacctggaa    240
caggaagata ttgctaccta tttctgccag cagggcaata cactgccctg gacttttgcc    300
ggaggcacca aactggagat caaggggga ggcgggagtg gaggcggggg atcaggagga    360
ggaggcagcg gaggaggagg gtccgaggtc cagctgcagc agagcggacc agaactggtg    420
aagcccggag caagtatgaa aatctcctgt aaggcctcag gatacagctt caccggctat    480
acaatgaact gggtgaaaca gtcccatggc aagaacctgg aatggatggg gctgattaat    540
cctaccaaag gcgtcagcac ctataatcag aagtttaaag acaaggccac actgactgtg    600
gataagtcta gttcaaccgc ttacatggag ctgctgtccc tgacatcga agacagtgcc    660
gtgtactatt gtgctcggtc tggctactat ggggacagta ttggtactt cgatgtctgg    720
ggacagggca tacccctgac cgtgttttct                                     750
```

```
SEQ ID NO: 72           moltype = AA  length = 250
FEATURE                 Location/Qualifiers
REGION                  1..250
                        note = Description of Artificial Sequence: Synthetic
                        polypeptide
source                  1..250
                        mol_type = protein
                        organism = synthetic construct
SEQUENCE: 72
```

```
MDIQMTQTTS SLSASLGDRV TISCRASQDI RNYLNWYQQK PDGTVKLLIY YTSRLHSGVP  60
SKFSGSGSGT DYSLTISNLE QEDIATYFCQ QGNTLPWTFA GGTKLEIKGG GGSGGGGSGG 120
GGSGGGGSEV QLQQSGPELV KPGASMKISC KASGYSFTGY TMNWVKQSHG KNLEWMGLIN 180
PTKGVSTYNQ KFKDKATLTV DKSSSTAYME LLSLTSEDSA VYYCARSGYY GDSDWYFDVW 240
GQGTTLTVFS                                                      250

SEQ ID NO: 73           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 73
GGGGS                                                             5

SEQ ID NO: 74           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 74
GGGGSGGGGS GGGGS                                                 15

SEQ ID NO: 75           moltype = DNA  length = 1560
FEATURE                 Location/Qualifiers
misc_feature            1..1560
                        note = Description of Artificial Sequence: Synthetic
                         polynucleotide
source                  1..1560
                        mol_type = other DNA
                        organism = synthetic construct
SEQUENCE: 75
atggatttcc aggtccagat tttctccttc ctgctgattt ccgcaagcgt cattatgtca   60
cggggctccg acctgggcaa aaagctgctg gaggccgcta gggccgggca ggacgatgaa  120
gtgagaatcc tgatggccaa cggggctgac gtgaatgcta aggatgagta cggcctgacc  180
cccctgtatc tggctacagc acacggccat ctggagatcg tggaagtcct gctgaaaaac  240
ggagccgacg tgaatgcagt cgatgccatt gggttcactc ctctgcacct ggcagccttt  300
atcggacatc tggagattgc agaagtgctg ctgaagcacg gcgctgacgt gaacgcacag  360
gataagttcg gaaaaccgc ttttgacatc agcattggca acggaaatga agacctggct  420
gaaatcctgc agaaactgaa tgaacagaaa ctgattagcg aagaagacct gaaccccggg  480
ggaggaggag ggagcggggg aggaggcagc ggcggggag ctctggaggaggagggagc   540
ggatccatgg atatccagat gacccagtcc ccgagctccc tgtccgcctc tgtgggcgat  600
agggtcacca tcacctgccg tgccagtcag gacatccgta ttatctgaa ctggtatcaa  660
cagaaaccag gaaaagctcc gaaactactg atttactata cctcccgcct ggagtctgga  720
gtcccttctc gcttctctgg ttctggttct gggacggatt acactctgac catcagcagt  780
ctgcaaccgg aagacttcgc aacttattac tgtcagcaag gtaatactct gccgtggacg  840
ttcggacagg gcaccaaggt ggagatcaaa gcggcggcg aagtggagg aggaggctca  900
ggcggaggag ggagcgaggt tcagctggtg gagtctggag gtggcctggt gcagccaggg  960
ggctcactcc gtttgtcctg tgcagcttct ggctactcct ttaccggcta cactatgaac 1020
tgggtgcgtc aggcccccagg taagggcctg aatgggttgc actgattaa tccttataaa 1080
ggtgttagta cctacaacca aagttcaag accgtttca ctataagcgt agataaatcc  1140
aaaaacacag cctacctgca aatgaacagc ctgcgtgctg aggacactgc cgtctattat  1200
tgtgctagaa gcggatacta cggcgatagt gactggtatt ttgacgtgtg gggtcaagga  1260
accctggtca ccgtctcctc gactagtggc ggaggaggat cactcgagag cggacaggtg  1320
ctgctggaat ccaatatcaa agtcctgccc acttggtcta cccccgtgca gcctatggct  1380
ctgattgtgc tgggaggagt cgcaggactg ctgctgttta cgggctggg aattttcttt  1440
tgcgtgcgct gccggacccg gagaaggcag gccgagcgca tgagccagat caagcgactg  1500
ctgagcgaga agaaacctg tcagtgtccc catagattcc agaagacctg ttcacccatt  1560

SEQ ID NO: 76           moltype = AA  length = 520
FEATURE                 Location/Qualifiers
REGION                  1..520
                        note = Description of Artificial Sequence: Synthetic
                         polypeptide
source                  1..520
                        mol_type = protein
                        organism = synthetic construct
SEQUENCE: 76
MDFQVQIFSF LLISASVIMS RGSDLGKKLL EAARAGQDDE VRILMANGAD VNAKDEYGLT  60
PLYLATAHGH LEIVEVLLKN GADVNAVDAI GFTPLHLAAF IGHLEIAEVL LKHGADVNAQ 120
DKFGKTAFDI SIGNNEDLA EILQKLNEQK LISEEDLNPG GGGSGGGGS GGGGSGGGGS 180
GSMDIQMTQS PSSLSASVGD RVTITCRASQ DIRNYLNWYQ QKPGKAPKLL IYYTSRLESG 240
VPSRFSGSGS GTDYTLTISS LQPEDFATYY CQQGNTLPWT FGQGTKVEIK GGGGSGGGGS 300
GGGGSEVQLV ESGGGLVQPG GSLRLSCAAS GYSFTGYTMN WVRQAPGKGL EWVALINPYK 360
GVSTYNQKFK DRFTISVDKS KNTAYLQMNS LRAEDTAVYY CARSGYYGDS DWYFDVWGQG 420
TLVTVSSTSG GGGSLESGQV LLESNIKVLP TWSTPVQPMA LIVLGGVAGL LLFIGLGIFF 480
```

```
CVRCRHRRRQ AERMSQIKRL LSEKKTCQCP HRFQKTCSPI                            520

SEQ ID NO: 77           moltype = DNA   length = 45
FEATURE                 Location/Qualifiers
misc_feature            1..45
                        note = Description of Artificial Sequence: Synthetic
                        oligonucleotide
source                  1..45
                        mol_type = other DNA
                        organism = synthetic construct
SEQUENCE: 77
ggcggcggcg gaagtggagg aggaggctca ggcggaggag ggagc              45
```

T CELL-ANTIGEN COUPLER WITH VARIOUS CONSTRUCT OPTIMIZATIONS

CROSS-REFERENCE

This application is a continuation of U.S. application Ser. No. 17/810,238, filed on Jun. 30, 2022, which is a continuation of U.S. application Ser. No. 17/394,280, filed on Aug. 4, 2021, now issued as U.S. Pat. No. 11,406,667 on Aug. 9, 2022, which is a continuation of U.S. application Ser. No. 15/929,513, filed on May 6, 2020, now issued as U.S. Pat. No. 11,110,123 on Sep. 7, 2021, which is a continuation of International Application No. PCT/US2019/042297, filed on Jul. 17, 2019, which claims the benefit of U.S. Provisional Application No. 62/699,173, filed on Jul. 17, 2018, U.S. Provisional Application No. 62/703,037, filed on Jul. 25, 2018, U.S. Provisional Application No. 62/773,120, filed on Nov. 29, 2018, U.S. Provisional Application No. 62/826,853, filed on Mar. 29, 2019, U.S. Provisional Application No. 62/828,879, filed on Apr. 3, 2019, U.S. Provisional Application No. 62/839,235, filed on Apr. 26, 2019, U.S. Non-Provisional application Ser. No. 16/442,274, filed on Jun. 14, 2019, now issued as U.S. Pat. No. 10,640,562 on May 5, 2020, and U.S. Provisional Application No. 62/874,426, filed on Jul. 15, 2019, each of which are incorporated herein by reference in their entireties.

REFERENCE TO AN ELECTRONIC SEQUENCE LISTING

The contents of the electronic sequence listing (TMV-003C6_SL.xml; Size: 137,136 bytes; and Date of Creation: Mar. 22, 2023) is herein incorporated by reference in its entirety.

SUMMARY

Disclosed herein, in certain embodiments, are nucleic acid sequences encoding a CD19 Trifunctional T cell-antigen coupler (CD19-TAC). In some embodiments, the nucleic acid sequence encoding a CD19 Trifunctional T cell-antigen coupler (CD19-TAC) comprises: (a) a first polynucleotide encoding a ligand that selectively binds a CD19 antigen. In some embodiments, the nucleic acid sequence encoding a CD19 Trifunctional T cell-antigen coupler (CD19-TAC) comprises: (b) a second polynucleotide encoding a UCHT1 ligand that binds CD3. In some embodiments, the nucleic acid sequence encoding a CD19 Trifunctional T cell-antigen coupler (CD19-TAC) comprise: (c) a third polynucleotide encoding a TCR signaling domain polypeptide comprising a cytosolic domain and a transmembrane domain. In some embodiments, the components encoded by the first, second, and/or third polynucleotides are connected in any suitable manner, such as in any suitable order and/or comprising any suitable linker(s). In some embodiments, the components encoded by (a), components encoded by (b), and components encoded by (c) are fused directly to each other, or joined by at least one linker. In some embodiments, the ligand that selectively binds the CD19 antigen is a single chain variable fragment (scFv). In some embodiments, the ligand that selectively binds the CD19 antigen comprises an amino acid sequence having at least 80%, at least 85%, at least 90%, at least 95%, at least 96%, at least 97%, at least 98%, at least 99%, or 100% sequence identity with SEQ ID NO: 36. In some embodiments, the UCHT1 ligand is a single chain antibody. In some embodiments, the UCHT1 ligand comprises a Y182T mutation (SEQ ID NO: 72). In some embodiments, the UCHT1 ligand is a humanized variant of UCHT1 (huUCHT1) ligand (SEQ ID NO: 44). In some embodiments, the UCHT1 ligand is a humanized variant of UCHT1 comprising a Y177T mutation (huUCHT1 (Y177T)) (SEQ ID NO: 46). In some embodiments, the UCHT1 ligand comprises an amino acid sequence having at least 80%, at least 85%, at least 90%, at least 95%, at least 96%, at least 97%, at least 98%, at least 99%, or 100% sequence identity with SEQ ID NO: 14, SEQ ID NO: 72, SEQ ID NO: 44, or SEQ ID NO: 46. In some embodiments, the cytosolic domain is a CD4 cytosolic domain and the transmembrane domain is a CD4 transmembrane domain. In some embodiments, the third polynucleotide encodes a polypeptide comprises an amino acid sequence having at least 80%, at least 85%, at least 90%, at least 95%, at least 96%, at least 97%, at least 98%, at least 99%, or 100% sequence identity with SEQ ID NO: 18. In some embodiments, the component encoded by (a) and the component encoded by (c) are fused to the component encoded by (b). In some embodiments, the component encoded by (b) and the component encoded by (c) are fused to the component encoded by (a). In some embodiments, at least one linker joins the component encoded by (a) to the component encoded by (b). In some embodiments, the at least one linker is a $G_4S$ flexible linker (SEQ ID NO: 73), a large protein domain, a long helix structure, or a short helix structure. In some embodiments, the at least one linker comprises an amino acid sequence having at least 80%, at least 85%, at least 90%, at least 95%, at least 96%, at least 97%, at least 98%, at least 99%, or 100% sequence identity with SEQ ID NO: 12 ($G_4S$ flexible linker ("$G_4S$" disclosed as SEQ ID NO: 73)), SEQ ID NO: 32 (large protein domain), SEQ ID NO: 30 (long helix structure), or SEQ ID NO: 28 (short helix structure). In some embodiments, the CD3 is of a TCR complex on a cell expressing the second polynucleotide. In some embodiments, the binding of the CD3 induces activation of a cell expressing the second polynucleotide. In some embodiments, the CD19-TAC comprises a nucleic acid sequence having at least 80%, at least 85%, at least 90%, at least 95%, at least 96%, at least 97%, at least 98%, at least 99%, or 100% sequence identity with SEQ ID NO: 63. In some embodiments, the CD19-TAC comprises an amino acid sequence having at least 80%, at least 85%, at least 90%, at least 95%, at least 96%, at least 97%, at least 98%, at least 99%, or 100% sequence identity with SEQ ID NO: 64. In some embodiments, the nucleic acid sequence does not encode a co-stimulatory domain. In some embodiments, the nucleic acid sequence does not encode an activation domain.

Disclosed herein, in certain embodiments, are vector constructs comprising: (a) a nucleic acid sequence disclosed herein (e.g., a nucleic acid sequence encoding a CD19-TAC); and (b) a promoter functional in a mammalian cell.

Disclosed herein, in certain embodiments, are T cells comprising a nucleic acid sequence disclosed herein (e.g., a nucleic acid sequence encoding a CD19-TAC).

Disclosed herein, in certain embodiments, are pharmaceutical compositions comprising the T cell disclosed herein, and a pharmaceutically acceptable excipient.

Disclosed herein, in certain embodiments, are methods of treating cancer expressing CD19 in an individual in need thereof, comprising administering to the individual a pharmaceutical composition disclosed herein. (e.g., a pharmaceutical composition comprising a T cell comprising any nucleic acid sequence described herein, such as any nucleic acid sequence or sequences described herein as encoding a CD19 Trifunctional T cell-antigen coupler (CD19-TAC)). In some embodiments, the cancer is a B cell malignancy. In some embodiments, the cancer is B cell lymphoma, acute lymphoblastic leukemia (ALL), chronic lymphocytic leukemia (CLL), or Non-Hodgkins Lymphoma. In some embodiments, the pharmaceutical composition is administered transarterially, subcutaneously, intradermally, intratumorally, intranodally, intramedullary, intramuscularly, intravenously or intraperitoneally.

Disclosed herein, in certain embodiments, are nucleic acid sequences encoding a Trifunctional T cell-antigen coupler (Tri-TAC) comprising: (a) a first polynucleotide encoding a target-specific ligand; (b) a second polynucleotide encoding a ligand that binds a protein associated with a TCR complex; and (c) a third polynucleotide encoding a T cell receptor signaling domain polypeptide; wherein the ligand that binds the protein associated with the TCR complex is selected from OKT3, F6A or L2K. In some embodiments, component encoded by (a), component encoded by (b), and component encoded by (c) are fused directly to each other, or joined by at least one linker. In some embodiments, the component encoded by (a) and the component encoded by (b) are directly fused and joined to the component encoded by (c) by a linker. In some embodiments, the component encoded by (b) and the component encoded by (c) are directly fused and joined to the component encoded by (a) by a linker. In some embodiments, the at least one linker is a $G_4S$ flexible linker (SEQ ID NO: 73), a large protein domain, a long helix structure, or a short helix structure. In some embodiments, the at least one linker has an amino acid sequence having at least 80%, at least 85%, at least 90%, at least 95%, at least 96%, at least 97%, at least 98%, at least 99%, or 100% sequence identity with SEQ ID NO: 12 ($G_4S$ flexible linker ("$G_4S$" disclosed as SEQ ID NO: 73)), SEQ ID NO: 32 (large protein domain), SEQ ID NO: 30 (long helix structure), or SEQ ID NO: 28 (short helix structure). In some embodiments, the ligand that binds the protein associated with the TCR complex is OKT3. In some embodiments, the ligand that binds a protein associated with the TCR complex comprises an amino acid sequence having at least 80%, at least 85%, at least 90%, at least 95%, at least 96%, at least 97%, at least 98%, at least 99%, or 100% sequence identity with SEQ ID NO: 22. In some embodiments, the ligand that binds the protein associated with the TCR complex is F6A. In some embodiments, the ligand that binds the protein associated with the TCR complex comprises an amino acid sequence having at least 80%, at least 85%, at least 90%, at least 95%, at least 96%, at least 97%, at least 98%, at least 99%, or 100% sequence identity with SEQ ID NO: 24. In some embodiments, the ligand that binds the protein associated with the TCR complex is L2K. In some embodiments, the ligand that binds the protein associated with the TCR complex comprises an amino acid sequence having at least 80%, at least 85%, at least 90%, at least 95%, at least 96%, at least 97%, at least 98%, at least 99%, or 100% sequence identity with SEQ ID NO: 26. In some embodiments, the protein associated with the TCR complex is CD3. In some embodiments, the target-specific ligand selectively binds a tumor antigen. In some embodiments, the target-specific ligand is a designed ankyrin repeat (DARPin) polypeptide, or a single chain variable fragment (scFv). In some embodiments, the target-specific ligand selectively binds a CD19 antigen, a HER2 antigen, or a BCMA antigen. In some embodiments, the target-specific ligand selectively binds a HER-2 antigen comprises an antigen binding domain of an antibody selected from Trastuzumab, Pertuzumab, Lapatinib, Neratinib, Ado-trastuzmab Emtansine, Gancotamab, Margetuximab, Timigutuzumab, and Ertumaxomab. In some embodiments, the target-specific ligand selectively binds a BCMA antigen comprises an antigen binding domain of an antibody selected from Belantamab mafodotin, and GSK2857916. In some embodiments, the target-specific ligand comprises an amino acid sequence having at least 80%, at least 85%, at least 90%, at least 95%, at least 96%, at least 97%, at least 98%, at least 99%, or 100% sequence identity with SEQ ID NO: 36, SEQ ID NO: 8 or SEQ ID NO: 34. In some embodiments, the T cell receptor signaling domain polypeptide comprises a cytosolic domain and a transmembrane domain. In some embodiments, the cytosolic domain is a CD4 cytosolic domain and the transmembrane domain is a CD4 transmembrane domain, or wherein the cytosolic domain is a CD8 cytosolic domain and the transmembrane domain is a CD8 transmembrane domain. In some embodiments, the nucleic acid sequences further comprise a leader sequence. In some embodiments, the leader sequence comprises an amino acid sequence having at least 80%, at least 85%, at least 90%, at least 95%, at least 96%, at least 97%, at least 98%, at least 99%, or 100% sequence identity with SEQ ID NO: 6, SEQ ID NO: 48, or SEQ ID NO: 50. In some embodiments, the CD3 is of a TCR complex on a cell expressing the second polynucleotide. In some embodiments, the binding of the CD3 induces activation of a cell expressing the second polynucleotide. In some embodiments, the Tri-TAC comprises a nucleic acid sequence having at least 80%, at least 85%, at least 90%, at least 95%, at least 96%, at least 97%, at least 98%, at least 99%, or 100% sequence identity with SEQ ID NO: 63, SEQ ID NO: 65, SEQ ID NO: 67, SEQ ID NO: 75, SEQ ID NO: 55, SEQ ID NO: 57, SEQ ID NO: 59, or SEQ ID NO: 61. In some embodiments, the Tri-TAC comprises an amino acid sequence having at least 80%, at least 85%, at least 90%, at least 95%, at least 96%, at least 97%, at least 98%, at least 99%, or 100% sequence identity with SEQ ID NO: 64, SEQ ID NO: 66, SEQ ID NO: 68, SEQ ID NO: 76, SEQ ID NO: 56, SEQ ID NO: 58, SEQ ID NO: 60, or SEQ ID NO: 62. In some embodiments, the nucleic acid sequence does not encode a co-stimulatory domain. In some embodiments, the nucleic acid sequence does not encode an activation domain.

Disclosed herein, in certain embodiments, are nucleic acid sequences encoding a Trifunctional T cell-antigen coupler (Tri-TAC) comprising: (a) a first polynucleotide encoding a target-specific ligand; (b) a second polynucleotide encoding a ligand that binds a protein associated with a TCR complex; and (c) a third polynucleotide encoding a T cell receptor signaling domain polypeptide; wherein the nucleic acid sequence further comprises a leader sequence, and wherein component encoded by (a), component encoded by (b), and component encoded by (c) are fused directly to each other, or joined by at least one linker. In some embodiments, the target-specific ligand selectively binds a tumor antigen. In some embodiments, the target-specific ligand is a designed ankyrin repeat (DARPin) polypeptide, or a single chain variable fragment (scFv). In some embodiments, the target-specific ligand selectively binds a CD19 antigen, a HER2 antigen, or a BCMA antigen. In some embodiments, the target-specific ligand selectively binds a HER-2 antigen comprises an antigen binding domain of an antibody selected from Trastuzumab, Pertuzumab, Lapatinib, Neratinib, Ado-trastuzmab Emtansine, Gancotamab, Margetuximab, Timigutuzumab, and Ertumaxomab. In some embodiments, the target-specific ligand selectively binds a BCMA antigen comprises an antigen binding domain of an antibody selected from Belantamab mafodotin, and GSK2857916. In some embodiments, the target-specific ligand comprises an amino acid sequence having at least 80%, at least 85%, at least 90%, at least 95%, at least 96%, at least 97%, at least 98%, at least 99%, or 100% sequence identity with SEQ ID NO: 36, SEQ ID NO: 8, SEQ ID NO: 34, SEQ ID NO: 52, or SEQ ID NO: 54. In some embodiments, the ligand that binds the protein associated with the TCR complex is selected from UCHT1, UCHT1 (Y182T), huUCHT1, huUCHT1 (Y177T), OKT3, F6A, or L2K. In some embodiments, the ligand that binds a protein associated with the TCR complex has an amino acid sequence having at least 80%, at least 85%, at least 90%, at least 95%, at least 96%, at least 97%, at least 98%, at least 99%, or 100% sequence identity with SEQ ID NO: 14, SEQ ID NO: 72, SEQ ID NO: 44, SEQ ID NO: 46, SEQ ID NO: 22, SEQ ID NO: 24, or SEQ ID NO: 26. In some embodiments, the protein associated with the TCR complex is CD3. In some embodiments, the T cell receptor signaling domain polypeptide comprises a cytosolic domain and a transmembrane domain. In some embodiments, the cytosolic domain is a CD4 cytosolic domain and the transmembrane domain is a CD4 transmembrane domain, or wherein the cytosolic domain is a CD8 cytosolic domain and the transmembrane domain is a CD8 transmembrane domain. In some embodiments, the leader sequence comprises an amino acid sequence having at least 80%, at least 85%, at least 90%, at least 95%, at least 96%, at least 97%, at least 98%, at least 99%, or 100% sequence identity with SEQ ID NO: 6, SEQ ID NO: 48, or SEQ ID NO: 50. In some embodiments, the component encoded by (a) and the component encoded by (b) are directly fused and joined to the component encoded by (c) by a linker. In some embodiments, the component encoded by (b) and the component encoded by (c) are directly fused and joined to the component encoded by (a) by a linker. In some embodiments, the at least one linker is a $G_4S$ flexible linker (SEQ ID NO: 73), a large protein domain, a long helix structure, or a short helix structure. In some embodiments, the at least one linker has an amino acid sequence having at least 80%, at least 85%, at least 90%, at least 95%, at least 96%, at least 97%, at least 98%, at least 99%, or 100% sequence identity with SEQ ID NO: 12 ($G_4S$ flexible linker ("$G_4S$" disclosed as SEQ ID NO: 73)), SEQ ID NO: 32 (large protein domain), SEQ ID NO: 30 (long helix structure), or SEQ ID NO: 28 (short helix structure). In some embodiments, the CD3 is of a TCR complex on a cell expressing the second polynucleotide. In some embodiments, the binding of the CD3 induces activation of a cell expressing the second polynucleotide. In some embodiments, the Tri-TAC comprises a nucleic acid sequence having at least 80%, at least 85%, at least 90%, at least 95%, at least 96%, at least 97%, at least 98%, at least 99%, or 100% sequence identity with SEQ ID NO: 63, SEQ ID NO: 65, SEQ ID NO: 67, SEQ ID NO: 75, SEQ ID NO: 55, SEQ ID NO: 57, SEQ ID NO: 59, or SEQ ID NO: 61. In some embodiments, the Tri-TAC comprises an amino acid sequence having at least 80%, at least 85%, at least 90%, at least 95%, at least 96%, at least 97%, at least 98%, at least 99%, or 100% sequence identity with SEQ ID NO: 64, SEQ ID NO: 66, SEQ ID NO: 68, SEQ ID NO: 76, SEQ ID NO: 56, SEQ ID NO: 58, SEQ ID NO: 60, or SEQ ID NO: 62. In some embodiments, the nucleic acid sequence does not encode a co-stimulatory domain. In some embodiments, the nucleic acid sequence does not encode an activation domain.

Disclosed herein, in certain embodiments, are polypeptides encoded by the nucleic acid sequence disclosed herein.

Disclosed herein, in certain embodiments, are vector constructs comprising: (a) a nucleic acid sequence disclosed herein; and (b) a promoter functional in a mammalian cell.

Disclosed herein, in certain embodiments, are T cells comprising the nucleic acid sequence disclosed herein.

Disclosed herein, in certain embodiments, are pharmaceutical compositions comprising the T cell disclosed herein, and a pharmaceutically acceptable excipient.

Disclosed herein, in certain embodiments, are methods of treating a cancer in an individual in need thereof, comprising administering to the individual a pharmaceutical composition disclosed herein. In some embodiments, the subject is a mammal. In some embodiments, the cancer is a solid cancer or a liquid cancer. In some embodiments, the cancer is a lung cancer, a breast cancer, multiple myeloma, glioblastoma, gastric cancer, ovarian cancer, stomach cancer, colorectal cancer, urothelial cancer, endometrial cancer, or a colon cancer. In some embodiments, the cancer comprises a CD19 expressing cancer cell. In some embodiments, the cancer is a B cell malignancy. In some embodiments, the cancer is B cell lymphoma, acute lymphoblastic leukemia (ALL), chronic lymphocytic leukemia (CLL), or Non-Hodgkins Lymphoma. In some embodiments, the cancer comprises a HER-2 expressing cancer cell. In some embodiments, the cancer is breast cancer, bladder cancer, pancreatic cancer, ovarian cancer, or stomach cancer. In some embodiments, the cancer comprises a BCMA expressing cancer cell. In some embodiments, the cancer is leukemia, lymphoma, or multiple myeloma. In some embodiments, the pharmaceutical composition is administered to the individual transarterially, subcutaneously, intradermally, intratumorally, intranodally, intrameduliary, intramuscularly, intravenously or intraperitoneally. In some embodiments, the pharmaceutical composition is in a unit dose form. In some embodiments, the pharmaceutical composition comprises about $0.5-2 \times 10^9$ T cells. In some embodiments, the pharmaceutical composition is administered daily, weekly, bi-weekly, monthly, bi-month or yearly.

Disclosed herein, in certain embodiments, are nucleic acid sequences encoding a CD19 Trifunctional T cell-antigen coupler (CD19-TAC) comprising: (a) a first polynucleotide encoding a ligand that selectively binds a CD19 antigen; (b) a second polynucleotide encoding a humanized variant of a UCHT1 (huUCHT1) ligand comprising a Y177T mutation (huUCHT1 (Y177T)) that binds CD3; and (c) a third polynucleotide encoding a polypeptide comprising a CD4 cytosolic domain and a CD4 transmembrane domain; wherein ligand encoded by (a), ligand encoded by (b), and polypeptide encoded by (c) are fused directly to each other, or joined by at least one linker. In some embodiments, the nucleic acid sequence does not encode a co-stimulatory domain, an activation domain, or both a co-stimulatory domain and an activation domain. In some embodiments, the ligand that selectively binds the CD19 antigen is a single chain variable fragment (scFv). In some embodiments, the ligand that selectively binds the CD19 antigen comprises an amino acid sequence having at least 80%, at least 90%, or at least 95% sequence identity with SEQ ID NO: 36. In some embodiments, the ligand that selectively binds the CD19 antigen comprises an amino acid sequence of SEQ ID NO: 36. In some embodiments, the huUCHT1 (Y177T) ligand is a single chain antibody. In some embodiments, the huUCHT1 (Y177T) ligand comprises an amino acid sequence having at least 80%, at least 90%, or at least 95% sequence identity with SEQ ID NO: 46. In some embodiments, the huUCHT1 (Y177T) ligand comprises an amino acid sequence of SEQ ID NO: 46. In some embodiments, the third polynucleotide encodes a polypeptide comprising an amino acid sequence having at least 80%, at least 90%, or at least 95% sequence identity with SEQ ID NO: 18.

In some embodiments, the third polynucleotide encodes a polypeptide comprising an amino acid sequence of SEQ ID NO: 18. In some embodiments, the at least one linker is a G4S flexible linker, a large protein domain, a long helix structure, or a short helix structure. In some embodiments, the at least one linker comprises an amino acid sequence having at least 80%, at least 90%, or at least 95% sequence identity with SEQ ID NO: 12, SEQ ID NO: 32, SEQ ID NO: 30, or SEQ ID NO: 28. In some embodiments, the at least one linker comprises an amino acid sequence of SEQ ID NO: 12, SEQ ID NO: 32, SEQ ID NO: 30, or SEQ ID NO: 28. In some embodiments, the CD3 is expressed on a cell expressing the second polynucleotide. In some embodiments, the CD19-TAC comprises a nucleic acid sequence having at least 80%, at least 90%, or at least 95% sequence identity with SEQ ID NO: 63. In some embodiments, the CD19-TAC comprises an amino acid sequence having at least 80%, at least 90%, or at least 95% sequence identity with SEQ ID NO: 64. In some embodiments, the CD19-TAC comprises a sequence of SEQ ID NO: 63 or SEQ ID NO: 64. Disclosed herein, in certain embodiments, are vector constructs comprising: (a) a nucleic acid sequence disclosed herein; and (b) a promoter functional in a mammalian cell. Disclosed herein, in certain embodiments, are compositions comprising the vector disclosed herein, and an excipient. Disclosed herein, in certain embodiments, are polypeptides encoded by the nucleic acid sequence disclosed herein.

Disclosed herein, in certain embodiments, are nucleic acid sequences encoding a HER2 Trifunctional T cell-antigen coupler (HER2-TAC) comprising a nucleic acid sequence having at least 80%, at least 85%, at least 90%, at least 95%, at least 96%, at least 97%, at least 98%, at least 99%, or 100% sequence identity with SEQ ID NO: 65, SEQ ID NO: 67, or SEQ ID NO: 75. In some embodiments, the HER2-TAC comprises an amino acid sequence having at least 80%, at least 85%, at least 90%, at least 95%, at least 96%, at least 97%, at least 98%, at least 99%, or 100% sequence identity with SEQ ID NO: 66, SEQ ID NO: 68, or SEQ ID NO: 76. In some embodiments, the nucleic acid sequence does not encode a co-stimulatory domain. In some embodiments, the nucleic acid sequence does not encode an activation domain.

Disclosed herein, in certain embodiments, are nucleic acid sequences encoding a BCMA Trifunctional T cell-antigen coupler (BCMA-TAC) comprising a nucleic acid sequence having at least 80%, at least 85%, at least 90%, at least 95%, at least 96%, at least 97%, at least 98%, at least 99%, or 100% sequence identity with SEQ ID NO: 55, SEQ ID NO: 57, SEQ ID NO: 59, or SEQ ID NO: 61. In some embodiments, the BCMA-TAC comprises an amino acid sequence having at least 80%, at least 85%, at least 90%, at least 95%, at least 96%, at least 97%, at least 98%, at least 99%, or 100% sequence identity with SEQ ID NO: 56, SEQ ID NO: 58, SEQ ID NO: 60, or SEQ ID NO: 62. In some embodiments, the nucleic acid sequence does not encode a co-stimulatory domain. In some embodiments, the nucleic acid sequence does not encode an activation domain.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4A exemplifies the surface expression of the Tri-TAC and CAR compared to T cells that express no chimeric receptor.
FIG. 4B exemplifies growth of three cell populations.
FIG. 4C-FIG. 4D exemplify the percentage of engineered cells positive for various T cell activation markers following stimulation with antigen.
FIG. 6A-FIG. 6J illustrate receptor surface expression and activation of various anti-HER-2 DARPin Tri-TAC controls. T cells were engineered with a Tri-TAC variant that lacks the targeting element (-DARPin), a Tri-TAC variant that lacks UCHT1 (-UCHT1), or the full-length Tri-TAC.
FIG. 6A, FIG. 6D, FIG. 6G illustrate T cell transduction and Her2 binding ability (left);
FIG. 6B, FIG. 6E, FIG. 6H degranulation (middle) and FIG. 6C, FIG. 6F, FIG. 6I cytokine production (right).
FIG. 6J illustrates that only full length anti-HER-2 DARPin Tri-TAC is able to elicit a cytotoxic response.
FIG. 7A exemplifies the change in tumor growth relative to the day of T cell infusion (day 35).
FIG. 7B exemplifies the change in weight, a measure of toxicity, in the same mice.
FIG. 7C illustrates cytokine concentrations in serum of mice on day 7 post T-cell infusion.
FIG. 8A-FIG. 8H illustrate Tri-TACs designed with various alternatives to the UCHT1 scFv-CD3 recruitment domain.
FIG. 8A provides a schematic representation of TAC receptor constructs utilizing the anti-HER-2 DARPin, paired with either the UCHT1 or OKT3 anti-CD3 scFv.
FIG. 8B illustrates HER-2 TAC surface expression of CD8+NGFR+(left) or CD4+NGFR+ T cells (right).
FIG. 8C, FIG. 8C1 illustrate cytokine production by HER-2-specific TAC-T cells stimulated with antigen-positive SK-OV-3 tumor cells.
FIG. 8D illustrates killing of SK-OV-3 tumor cells by HER-2 TAC and vector control (vector only carrying tNGFR) T cells. Vector control T cells (circles) are compared against HER-2-specific TAC-T cells bearing UCHT1 (square) or OKT3 (triangle).
FIG. 8E provides a schematic representation of TAC receptor constructs utilizing the anti-CD19 scFv, paired with either huUCHT1, F6A, or L2K anti-CD3 scFv.
FIG. 8F illustrates CD19-TAC surface expression of CD8+NGFR+(left) or CD4+NGFR+ T cells (right).
FIG. 8G, FIG. 8G1 illustrate cytokine production by CD19-specific TAC-T cells stimulated with antigen-positive Raji tumor cells. Cytokine producing cells are compared from TAC-T cells bearing huUCHT1 (square), F6A (triangle), or L2K (diamond).
FIG. 8H illustrates killing of NALM-6 tumor cells by CD19 TAC and vector control (vector only carrying tNGFR) T cells. Vector control T cells (circles) are compared against CD19-specific TAC-T cells bearing huUCHT1 (square), F6A (triangle), or L2K (diamond).

FIG. 9A, FIG. 9E illustrate TCR surface expression of T cells engineered with either control vector (tNGFR), UCHT1, or OKT3 TAC variants. FIG. 9B, FIG. 9F illustrate that T cells engineered with OKT3-TAC have significantly reduced TCR surface expression relative to UCHT1-TAC. FIG. 9C, FIG. 9G illustrate TCR surface expression of T cells engineered with control vector (tNGFR), huUCHT1, F6A or L2K TAC variants. FIG. 9D, FIG. 9H illustrates that T cells engineered with L2K TAC have significantly reduced TCR surface expression relative to huUCHT1-TAC.

FIG. 10A-FIG. 10B illustrate connector domain variants. The domain the connecting antigen binding domain with the TCR recruitment domain is termed the connector domain. FIG. 10A provides schematics of TAC variants with different connector domains: (i) a flexible connector, (ii) a large domain connector (constructed from domains 3 and 4 derived from the extracellular CD4 domain), (iii) a long helical connector, and (iv) a short helical connector. FIG. 10B provides exemplary amino acid sequence of the domains represented in FIG. 10A. (SEQ ID NOS 69, 28, 30, and 32, respectively, in order of appearance)

FIG. 11A illustrates TAC variant surface expression in both CD4 and CD8 cells. FIG. 11B illustrates surface expression of TAC comprising flexible connectors relative to TAC comprising helical or large domain connectors. FIG. 11C illustrates overall transduction of TAC comprising alternative connectors relative to the flexible connector.

FIG. 11D, FIG. 11E illustrate relative cell reactivity to antigen positive Raji cells.

FIG. 13A, FIG. 13C illustrate surface expression. FIG. 13B illustrates cytokine production.

FIG. 14A illustrates a Tri-TAC comprising a CD4 transmembrane and cytosolic domain (left), and comparable regions of a CD8α/CD8β heterodimer (right). Key regions for co-receptor functionality (arginine rich domain and CXCP motif) are highlighted. FIG. 14B is a schematic of a CD8α Tri-TAC comprising a Cysteine to Serine mutation to ensure a monomeric receptor distribution, and a CD8α cytosolic domain. FIG. 14C is a schematic of a CD8α+Rβ Tri-TAC comprising a Cysteine to Serine mutation to ensure a monomeric receptor distribution, and a chimeric CD8α cytosolic domain where the CD8α arginine rich region is replaced with the CD8β arginine rich region. FIG. 14D is a schematic of a CD8β+Lck Tri-TAC comprising a Cysteine to Serine mutation to ensure a monomeric receptor distribution, and a chimeric CD8β cytosolic domain, where the CD8α CXCP domain, which contains a Lck binding motif, was added to the C-terminus of the CD8β cytosolic domain.

FIG. 15A-FIG. 15B illustrate surface expression of CD8-Tri TAC variants relative to the prototypic Tri-TAC. FIG. 15C illustrates in vitro cytotoxicity of CD8-Tri TAC variants co-cultured with LOX IMVI (HER-2 negative) or A549, SKOV3, SKBR3 or MBA MB 231 (HER-2 positive). FIG. 15D illustrates cell division of T cells engineered with either the CD8 Tri-TAC variants or the prototypic Tri-TAC. FIG. 15E illustrates TCR surface expression of engineered T cells comprising CD8 Tri-TAC variants or the prototypic Tri-TAC.

FIG. 17 illustrates the various domains of a TAC-CD19 (a CD8a leader, FMC63 scFv, Myc Tag, huUCHT1 Y177T mutant and a truncated CD4 anchoring co-receptor domain).

FIG. 19A NALM-6 (acute lymphoblastic leukemia), FIG. 19B Jeko-1 (Mantle Cell Lymphoma) and FIG. 19C Raji (Burkitt's lymphoma).

FIG. 20A illustrates the experimental set up of TAC-CD19 treated mice with NALM-6 tumor. Following successful treatment mice are then re-challenged with either NALM-6 (CD19 positive) or KMS11 (CD19 negative) tumor cells.

FIG. 20B illustrates in vivo efficacy of mice treated with TAC-CD19.

FIG. 21A illustrates the experimental design of evaluating dose regime and dosing impact on efficacy and cell expansion.

FIG. 21B illustrates in vivo survival of NALM-6 bearing mice treated with either a single or split dose of TAC-CD19.

FIG. 22A illustrates the gating strategy used to identify T cells in mouse blood. FIG. 22B illustrates in vivo results of T cell expansion in blood.

FIG. 23A illustrates an experimental protocol of NALM-6 bearing mice being treated with various controls and TAC-CD19 at two dose levels. FIG. 23B illustrates in vivo efficacy of control vs two dose levels of TAC-CD19 treatment groups. FIG. 23C illustrates long term survival of low dose TAC-CD19 treated mice.

FIG. 25 illustrates human cytokine released in mice blood following treatment with TAC-CD19 or non-transduced T cells.

FIG. 26A illustrates an experimental design. FIG. 26B illustrates various controls and test articles. FIG. 26C illustrates in vivo efficacy of various TAC constructs. FIG. 26A-FIG. 26C disclose "G$_4$S" as SEQ ID NO: 73.

FIG. 28A-FIG. 28B illustrate TAC engineered T cells expand in vivo and provide long term protection, indicating cell persistence in a model of myeloma. FIG. 28A-FIG. 28B illustrate BCMA-TAC T cells reject multiple myeloma tumors in a KMS-11 xenograft model engineered with NanoLuc (KMS 11-NanoLuc) (BCMA$^{pos}$). Following tumor engraftment mice were treated with BCMA TAC-T cells (carrying Firefly Luciferase). TAC-T cells expand significantly following administration. This correlates with tumor regression. Treated mice were resistant to tumor rechallenge indicating long term persistence of TAC-T cells.

DETAILED DESCRIPTION

Figure 1A:
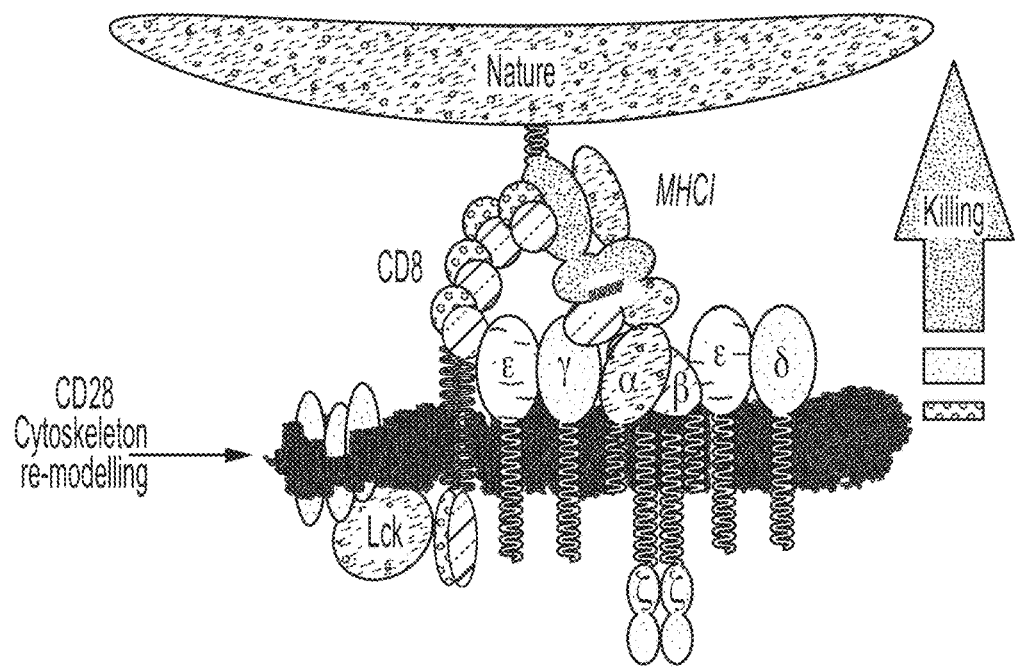
FIG. 1A is a schematic of natural T-cell activation.

Cancer is a major health challenge, with over 150,000 cases of cancer expected to be diagnosed in Canada alone. While patients with early stage disease are sometimes treated effectively by conventional therapies (surgery, radiation, chemotherapy), few options are available to patients with advanced disease, and those options are typically palliative in nature.

Active immunotherapy seeks to employ the patient's immune system to clear tumors and offers an option to patients who have failed conventional therapies. Generally, this treatment involves infusing patients with large numbers of tumor-specific T cells. This approach has proven to be successful in early phase clinical trials for a number of diseases, including melanoma, myeloma, leukemia, lymphoma and synovial sarcoma. As a specific example, several clinical studies have demonstrated that immunotherapy with T cells are curative in patients with advanced melanoma, confirming the utility of this approach. Additionally, patients suffering from chronic lymphocytic leukemia (CLL) and acute lymphoblastic leukemia (ALL) have also been effectively treated and cured with T cell immunotherapy.

A key challenge facing the clinical application of adoptive T cell therapy is the source of the T cells. Typically, T cells isolated from a tumor-bearing patient are grown to large numbers ex vivo and are administered back into the patient to induce a robust anti-tumor immune response. Tumor specificity is achieved by either: (i) isolating naturally-occurring tumor-specific T cells from the patient; or (ii) engineering bulk T cells from the peripheral blood to express tumor-specific receptors. Naturally occurring tumor-specific T cells are rare and isolating such cells in therapeutic quantities from cancer patients is a laborious and costly procedure. In contrast, it is becoming more efficient to engineer readily available peripheral T cells with tumor-specific receptors through genetic manipulation. Techniques have been developed for this engineering process, which are clinically viable, and several clinical trials have demonstrated the feasibility and efficacy of genetically-engineered T cells for the treatment of cancer.

To this point, most engineered T cell therapies involving genetic modification of the T cells yield: (i) forced expression of T cell receptor (TCR); or (ii) a chimeric antigen receptor (CAR) specific for antigen targets on the tumor. To date, the chimeric antigen receptors used for engineering T cells consist of: (i) a targeting domain, usually a single-chain fragment variable (scFv); (ii) a transmembrane domain; and (iii) a cytosolic domain that contains signaling elements from the T cell receptor and associated proteins. Such chimeric antigen receptors have also been referred to as "T-body" or "Chimeric Immune Receptor" (CIR), but currently, most researchers use the term "CAR". One advantage of the CAR approach is that it allows any patient's immune cells to be targeted against any desirable target in a major histocompatibility complex (MHC) independent manner. This is appealing as MHC presentation is often defective in tumor cells.

CARs are considered in modular terms and scientists have spent considerable time investigating the influence of different cytoplasmic signaling domains on CAR function.

Conventional CARs generally share two main components: (i) the CD3 zeta cytoplasmic domain, which contains immunotyrosine activation motifs (ITAMs) critical for T cell activation; and (ii) components of costimulatory receptors that trigger important survival pathways such as the Akt pathway.

The first-generation CARs employed a single signaling domain from either CD3ξ or FcεRIγ. Second-generation CARs combined the signaling domain of CD3ξ with the cytoplasmic domain of costimulatory receptors from either the CD28 or TNFR family of receptors. Most CAR-engineered T cells that are currently being tested in the clinic employ second-generation CARs where CD3ξ is coupled to the cytoplasmic domain of either CD28 or CD137. These second generation CARs have demonstrated anti-tumor activity in CD19-positive tumors. Third-generation CARs combined multiple costimulatory domains, but there is concern that third-generation CARs may lose antigen-specificity.

While CAR-engineered T cells have shown considerable promise in clinical application, they rely on a synthetic method for replacing the native activation signal that is provided by the T cell receptor (TCR). Since this synthetic receptor does not deliver all of the signaling components associated with the TCR (ex. ITAMs on CD3γ, CD3δ, CD3ε), it remains unclear whether the T cells are optimally activated by the CAR or how the CAR activation affects T cell differentiation (ex. progression to memory). Furthermore, since the CAR signaling domains are disconnected from their natural regulatory partners by the very nature of the CAR structure, there is an inherent risk that CARs may lead to a low-level of constitutive activation, which could result in off-target toxicities. Therefore, the synthetic nature of the prototypic CAR may disrupt canonical mechanisms that limit TCR activation, and may underpin the severe toxicity often associated with therapeutic doses of conventional CAR T cells.

Given these limitations, it is preferable to re-direct T cells to attack tumors via their natural TCR. To this end, a class of recombinant proteins termed "Bispecific T-cell Engagers" (BiTEs) has been created. These proteins employ bispecific antibody fragments to crosslink T-cell TCR receptors with target antigens. This leads to efficient T-cell activation, triggering cytotoxicity. Similarly, bi-specific antibodies have been generated that accomplish this goal and some scientists have simply linked anti-CD3 antibodies to tumor-specific antibodies employing chemical linkage. While these bi-specific proteins have demonstrated some activity in vitro, GMP production, short biological half-lives, and limited bioavailability represent significant challenges to the successful use of these molecules in cancer treatment. Additionally, these molecules also fail to properly recapitulate natural TCR signaling because they do not engage the TCR co-receptors (CD8 and CD4).

In view of the above, a need remains for chimeric receptors with enhanced activity and safety.

An alternate chimeric receptor, termed a Trifunctional T cell Antigen Coupler (Tri-TAC or TAC) receptor, has been developed which employs a distinct biology to direct the T cell to attack tumors. While the CAR is a fully synthetic receptor that stitches together components of T cell receptor (TCR) signaling complex, the TAC receptor re-directs the TCR towards tumor targets and recapitulates the native TCR signaling structure. For example, in some embodiments, the TACs disclosed herein activate natural Major Histocompatibility complex (MHC) signaling through the T-cell receptor (TCR), while retaining MHC-unrestricted targeting. Further, the TACs disclosed herein recruit the T-Cell Receptor (TCR) in combination with co-receptor stimulation. Moreover, in some embodiments, Tri-TACs disclosed herein show enhanced activity and safety.

Certain Terminology

The term "T cell" as used herein refers to a type of lymphocyte that plays a central role in cell-mediated immunity. T cells, also referred to as T lymphocytes, are distinguished from other lymphocytes, such as B cells and natural killer cells, by the presence of a T-cell receptor (TCR) on the cell surface. There are several subsets of T cells with distinct functions, including but not limited to, T helper cells, cytotoxic T cells, memory T cells, regulatory T cells and natural killer T cells.

The term "T cell antigen coupler" or TAC is used interchangeably with "trifunctional T cell antigen coupler" or Tri-TAC and refers to an engineered nucleic acid construct or polypeptide, that when expressed on a T cell, helps to facilitate the targeting of the T cell to a particular antigen. In some embodiments, the TAC comprises (a) a target-specific ligand, (b) a ligand that binds a protein associated with a T cell receptor (TCR) complex, and (c) a T cell receptor signaling domain.

The term "polynucleotide" and/or "nucleic acid sequence" and/or "nucleic acid" as used herein refers to a sequence of nucleoside or nucleotide monomers consisting of bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acids of the present disclosure may be isolated from biological organisms, formed by laboratory methods of genetic recombination or obtained by chemical synthesis or other known protocols for creating nucleic acids.

The term "isolated polynucleotide" or "isolated nucleic acid sequence" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived. The term "nucleic acid" is intended to include DNA and RNA and is either double stranded or single stranded, and represents the sense or antisense strand. Further, the term "nucleic acid" includes the complementary nucleic acid sequences.

The term "recombinant nucleic acid" or "engineered nucleic acid" as used herein refers to a nucleic acid or polynucleotide that is not found in a biological organism. For example, recombinant nucleic acids may be formed by laboratory methods of genetic recombination (such as molecular cloning) to create sequences that would not otherwise be found in nature.

Recombinant nucleic acids may also be created by chemical synthesis or other known protocols for creating nucleic acids.

The term "polypeptide" or "protein" as used herein describes a chain of amino acids. A polypeptide or protein of this disclosure is a peptide, which usually describes a chain of amino acids. The term protein as used herein also describes a large molecule comprising one or more chains of amino acids and, in some embodiments, is a fragment or domain of a protein or a full length protein. Furthermore, as used herein, the term protein either refers to a linear chain of amino acids or to a chain of amino acids that has been processed and folded into a functional protein. The protein structure is divided into four distinct levels: (1) primary structure—referring to the sequence of amino acids in the polypeptide chain, (2) secondary structure—referring to the regular local sub-structures on the polypeptide backbone chain, such as α-helix and β-sheets, (3) tertiary structure—referring to the three-dimensional structure if monomeric and multimeric protein molecules, and (4) quaternary structure—referring to the three-dimensional structure comprising the aggregation of two or more individual polypeptide chains that operate as a single functional unit. The proteins of the present disclosure, in some embodiments, are obtained by isolation and purification of the proteins from cells where they are produced naturally, by enzymatic (e.g., proteolytic) cleavage, and/or recombinantly by expression of nucleic acid encoding the proteins or fragments of this disclosure. The proteins and/or fragments of this disclosure, in some embodiments, is obtained by chemical synthesis or other known protocols for producing proteins and fragments.

The term "isolated polypeptide" refers to a polypeptide substantially free of cellular material or culture medium when produced by recombinant DNA techniques, or chemical precursors or other chemicals when chemically synthesized.

The term "antibody" as used herein is intended to include monoclonal antibodies, polyclonal antibodies, single chain antibodies, chimeric antibodies, and antibody fusions. The antibody may be from recombinant sources and/or produced in transgenic animals. The term "antibody fragment" as used herein is intended to include without limitations Fab, Fab', F(ab')2, scFv, dsFv, ds-scFv, dimers, minibodies, diabodies, and multimers thereof, multispecific antibody fragments and Domain Antibodies.

The term "vector" as used herein refers to a polynucleotide that is used to deliver a nucleic acid to the inside of a cell. In some embodiments, a vector is an expression vector comprising expression control sequences (for example, a promoter) operatively linked to a nucleic acid to be expressed in a cell. Vectors known in the art include, but are not limited to, plasmids, phages, cosmids and viruses.

The term "tumor antigen" or "tumor associated antigen" as used herein refers to an antigenic substance produced in tumor cells that triggers an immune response in a host (e.g. which is presented by MHC complexes). In some embodiments, a tumor antigen is on the surface of a tumor cell.

The term "T cell receptor" or TCR as used herein refers to a complex of integral membrane proteins that participates in the activation of T cells in response to the binding of an antigen. The TCR is a disulfide-linked membrane-anchored heterodimer normally consisting of the highly variable alpha (α) and beta (β) chains expressed as part of a complex with the invariant CD3 (cluster of differentiation 3) chain molecules. T cells expressing this receptor are referred to as α:β (or αβ) T cells, though a minority of T cells express an alternate receptor, formed by variable gamma (γ) and delta (δ) chains, referred as γδT cells. CD3 is a protein complex composed of four distinct chains. In mammals, the complex contains a CD3γ chain, a CD3δ chain, two CD3ε chains and two CD3ξ chains.

As used herein, the term "transmembrane and cytosolic domain" refers to a polypeptide that comprises a transmembrane domain and a cytosolic domain of a protein associated with the T cell receptor (TCR) complex. In some embodiments, such transmembrane and cytosolic domain may include, but is not limited to, protein domains that (a) associate with the lipid raft and/or (b) bind Lck.

A "TCR co-receptor" as used herein, refers to a molecule that assists the T cell receptor (TCR) in communicating with an antigen-presenting cell and may be considered part of the first signal that leads to the activation of the TCR. Examples of TCR co-receptors include, but are not limited to, CD4, LAG3, and CD8.

A "TCR co-stimulator" as used herein, refers to a molecule that enhances the response of a T cell to an antigen and may be considered as the second signal that leads to the activation of the TCR. Examples of TCR co-stimulators include, but are not limited to, ICOS, CD27, CD28, 4-1BB (CD 137), OX40 (CD134), CD30, CD40, lymphocyte fiction-associated antigen 1 (LFA-1), CD2, CD7, LIGHT, NKG2C, B7-H3, and a ligand that specifically binds CD83.

A "TCR co-inhibitor" or "checkpoint receptor" as used herein, refers to a molecule that inhibits the response of a T cell to an antigen. Examples of TCR co-inhibitors include, but are not limited to, PD-1, TIM3, LAG-3, TIGIT, BTLA, CD160, and CD37.

The terms "recipient", "individual", "subject", "host", and "patient", are used interchangeably herein and in some embodiments, refer to any mammalian subject for whom diagnosis, treatment, or therapy is desired, particularly humans. "Mammal" for purposes of treatment refers to any animal classified as a mammal, including humans, domestic and farm animals, and laboratory, zoo, sports, or pet animals, such as dogs, horses, cats, cows, sheep, goats, pigs, mice, rats, rabbits, guinea pigs, monkeys etc. In some embodiments, the mammal is human. None of these terms require the supervision of medical personnel.

As used herein, the terms "treatment," "treating," and the like, in some embodiments, refer to administering an agent, or carrying out a procedure, for the purposes of obtaining an effect. The effect may be prophylactic in terms of completely or partially preventing a disease or symptom thereof and/or may be therapeutic in terms of affecting a partial or complete cure for a disease and/or symptoms of the disease. "Treatment," as used herein, may include treatment of a disease or disorder (e.g. cancer) in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. Treating may refer to any indicia of success in the treatment or amelioration or prevention of a cancer, including any objective or subjective parameter such as abatement; remission; diminishing of symptoms; or making the disease condition more tolerable to the patient; slowing in the rate of degeneration or decline; or making the final point of degeneration less debilitating. The treatment or amelioration of symptoms is based on one or more objective or subjective parameters; including the results of an examination by a physician. Accordingly, the term "treating" includes the administration of the compounds or agents of the present invention to prevent, delay, alleviate, arrest or inhibit development of the symptoms or conditions associated with diseases (e.g. cancer). The term "therapeutic effect" refers to the reduction, elimination, or prevention of the disease, symptoms of the disease, or side effects of the disease in the subject.

As used herein, singular forms "a", "and," and "the" include plural referents unless the context clearly indicates otherwise. Thus, for example, reference to "an antibody" includes a plurality of antibodies and reference to "an antibody" in some embodiments includes multiple antibodies, and so forth.

As used herein, all numerical values or numerical ranges include whole integers within or encompassing such ranges and fractions of the values or the integers within or encompassing ranges unless the context clearly indicates otherwise. Thus, for example, reference to a range of 90-100%, includes 91%, 92%, 93%, 94%, 95%, 95%, 96%, 97%, etc., as well as 91.1%, 91.2%, 91.3%, 91.4%, 91.5%, etc., 92.1%, 92.2%, 92.3%, 92.4%, 92.5%, etc., and so forth. In another example, reference to a range of 1-5,000 fold includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and so forth.

"About" a number, as used herein, refers to range including the number and ranging from 10% below that number to 10% above that number. "About" a range refers to 10% below the lower limit of the range, spanning to 10% above the upper limit of the range.

"Percent (%) identity" refers to the extent to which two sequences (nucleotide or amino acid) have the same residue at the same positions in an alignment. For example, "an amino acid sequence is X % identical to SEQ ID NO: Y" refers to % identity of the amino acid sequence to SEQ ID NO: Y and is elaborated as X % of residues in the amino acid sequence are identical to the residues of sequence disclosed in SEQ ID NO: Y. Generally, computer programs are employed for such calculations. Exemplary programs that compare and align pairs of sequences, include ALIGN (Myers and Miller, 1988), FASTA (Pearson and Lipman, 1988; Pearson, 1990) and gapped BLAST (Altschul et al., 1997), BLASTP, BLASTN, or GCG (Devereux et al., 1984).

As used herein, the term "selective binding" refers to the higher affinity with which a molecule (e.g. protein such as a target-binding ligand of TAC) binds its target molecule (e.g. target antigen such as HER-2, BCMA, or CD19) over other molecules.

T Cell Antigen Coupler (Tri-TAC or TAC)

Disclosed herein, in certain embodiments, are nucleic acids encoding a Trifunctional T cell-antigen coupler (Tri-TAC). In some embodiments, the nucleic acids encoding a Tri-TAC comprises: (a) a first polynucleotide encoding a target-specific ligand; (b) a second polynucleotide encoding a ligand that binds a TCR complex; and (c) a third polynucleotide encoding a transmembrane domain and cytosolic domain. In some embodiments, the nucleic acids encoding a Tri-TAC do not encode a co-stimulatory domain. In some embodiments, the nucleic acids encoding a Tri-TAC do not encode a co-activation domain.

Target-Specific Ligand

The target-specific ligand, also referred to as an antigen binding domain, refers to any substance or molecule that binds, directly or indirectly, to a target cell. In some embodiments, the target specific ligand binds to an antigen on the target cell. In some embodiments, a target cell is a cell associated with a disease state, including, but not limited to, cancer, hematologic malignancy, large B-cell lymphoma, diffuse large B-cell lymphoma, primary mediastinal B cell lymphoma, high grade B-cell lymphoma, or large B cell lymphoma arising from follicular lymphoma. In some embodiments, a target cell is a tumor cell. In some embodiments, a target-specific ligand binds to a tumor antigen or tumor associated antigen on a tumor cell. In some embodiments, the target antigen is a tumor antigen. In some embodiments, the tumor antigen when proteinaceous is a sequence of 8 or more amino acids up to the full protein. In some embodiments, the tumor antigen is any number of amino acids in between 8 and the full length protein which comprises at least one antigenic fragment of the full length protein that is presented in a Major Histocompatibility Complex (MHC). Examples of tumor antigens include, but are not limited to, CD19, HER-2 (erbB-2), B-cell maturation antigen (BCMA), alphafetoprotein (AFP), carcinoembryonic antigen (CEA), CA-125, MUC-1, epithelial tumor antigen (ETA), tyrosinase, melanoma-associated antigen (MAGE), prostate-specific antigen (PSA), glioma-associated antigen, β-human chorionic gonadotropin, thyroglobulin, RAGE-1, MN-CA IX, human telomerase reverse transcriptase, RU1, RU2 (AS), intestinal carboxyl esterase, mut hsp70-2, M-CSF, prostase, PAP, NY-ESO-1, LAGE-1a, p53, prostein, PSMA, survivin and telomerase, prostate-carcinoma tumor antigen-1 (PCTA-1), ELF2M, neutrophil elastase, CD22, insulin growth factor (IGF)-I, IGF-II, IGF-I receptor and mesothelin.

In some embodiments, the target-specific ligands include, but are not limited to, antibodies and fragments thereof, for example single chain antibodies such as single-chain antibodies (scFvs), single domain antibodies, peptides, peptidomimetics, proteins, glycoproteins, or proteoglycans that bind to the target cell and/or antigen. In some embodiments, the target-specific ligands include, but are not limited to, designed ankyrin repeat proteins (DARPins), lectins, knottins, centryrins, anticalins, or naturally occurring ligands for the tumor antigen, such as growth factors, enzyme substrates, receptors or binding proteins. In some embodiments, target specific ligands include non-protein compounds that bind to target cells and/or antigens, including but not limited to carbohydrates, lipids, nucleic acids, or small molecules. In some embodiments, a target-specific ligand is a designed ankyrin repeat (DARPin) targeted to a specific cell and/or antigen. In some embodiments, a target-specific ligand is a single-chain variable fragment (ScFv) targeted to a specific cell and/or antigen.

In some embodiments, the tumor antigen is a HER-2 antigen. In some embodiments, the HER-2 specific ligand comprises an antigen binding domain of an antibody selected from Trastuzumab, Pertuzumab, Lapatinib, Neratinib, Ado-trastuzmab Emtansine, Gancotamab, Margetuximab, Timigutuzumab, and Ertumaxomab. In some embodiments, the target-specific ligand is a DARPin that selectively binds a HER-2 (erbB-2) antigen. In some embodiments, the target-specific ligand is a DARPin that specifically binds a HER-2 (erbB-2) antigen. In some embodiments, the DARPin targeted to HER-2 (erb-2) comprises SEQ ID NO: 7 or SEQ ID NO: 8.

In some embodiments, the first polynucleotide comprises a nucleotide sequence having at least 70% sequence identity with SEQ ID NO: 7. In some embodiments, the first polynucleotide comprises a nucleotide sequence having at least 75% sequence identity with SEQ ID NO: 7. In some embodiments, the first polynucleotide comprises a nucleotide sequence having at least 80% sequence identity with SEQ ID NO: 7. In some embodiments, the first polynucleotide comprises a nucleotide sequence having at least 85% sequence identity with SEQ ID NO: 7. In some embodiments, the first polynucleotide comprises a nucleotide sequence having at least 90% sequence identity with SEQ ID NO: 7. In some embodiments, the first polynucleotide comprises a nucleotide sequence having at least 95% sequence identity with SEQ ID NO: 7. In some embodiments, the first polynucleotide comprises a nucleotide sequence of SEQ ID NO: 7.

In some embodiments, the target-specific ligand comprises an amino acid sequence having at least 70% sequence identity with SEQ ID NO: 8. In some embodiments, the target-specific ligand comprises an amino acid sequence having at least 75% sequence identity with SEQ ID NO: 8. In some embodiments, the target-specific ligand comprises an amino acid sequence having at least 80% sequence identity with SEQ ID NO: 8. In some embodiments, the target-specific ligand comprises an amino acid sequence having at least 85% sequence identity with SEQ ID NO: 8. In some embodiments, the target-specific ligand comprises an amino acid sequence having at least 90% sequence identity with SEQ ID NO: 8. In some embodiments, the target-specific ligand comprises an amino acid sequence having at least 95% sequence identity with SEQ ID NO: 8. In some embodiments, the target-specific ligand comprises an amino acid sequence of SEQ ID NO: 8.

In some embodiments, the tumor antigen is a BCMA antigen. In some embodiments, the BCMA specific ligand comprises an antigen binding domain of an antibody selected from Belantamab mafodotin, and GSK2857916. In some embodiments, the target-specific ligand is a scFv that selectively binds BCMA. In some embodiments, the target-specific ligand is a scFv that specifically binds BCMA. In some embodiments, the scFv that binds BCMA comprises SEQ ID NO: 33 or SEQ ID NO: 34.

In some embodiments, the first polynucleotide comprises a nucleotide sequence having at least 70% sequence identity with SEQ ID NO: 33. In some embodiments, the first polynucleotide comprises a nucleotide sequence having at least 75% sequence identity with SEQ ID NO: 33. In some embodiments, the first polynucleotide comprises a nucleotide sequence having at least 80% sequence identity with SEQ ID NO: 33. In some embodiments, the first polynucleotide comprises a nucleotide sequence having at least 85% sequence identity with SEQ ID NO: 33. In some embodiments, the first polynucleotide comprises a nucleotide sequence having at least 90% sequence identity with SEQ ID NO: 33. In some embodiments, the first polynucleotide comprises a nucleotide sequence having at least 95% sequence identity with SEQ ID NO: 33. In some embodiments, the first polynucleotide comprises a nucleotide sequence of SEQ ID NO: 33.

In some embodiments, the target-specific ligand comprises an amino acid sequence having at least 70% sequence identity with SEQ ID NO: 34. In some embodiments, the target-specific ligand comprises an amino acid sequence having at least 75% sequence identity with SEQ ID NO: 34. In some embodiments, the target-specific ligand comprises an amino acid sequence having at least 80% sequence identity with SEQ ID NO: 34. In some embodiments, the target-specific ligand comprises an amino acid sequence having at least 85% sequence identity with SEQ ID NO: 34. In some embodiments, the target-specific ligand comprises an amino acid sequence having at least 90% sequence identity with SEQ ID NO: 34. In some embodiments, the target-specific ligand comprises an amino acid sequence having at least 95% sequence identity with SEQ ID NO: 34. In some embodiments, the target-specific ligand comprises an amino acid sequence of SEQ ID NO: 34.

In some embodiments, the tumor antigen is a CD19 antigen. In some embodiments, the target-specific ligand is a scFv that selectively binds CD19. In some embodiments, the target-specific ligand is a scFv that specifically binds CD19. In some embodiments, the scFv that binds CD19 comprises SEQ ID NO: 35 or SEQ ID NO: 36.

In some embodiments, the first polynucleotide comprises a nucleotide sequence having at least 70% sequence identity with SEQ ID NO: 35. In some embodiments, the first polynucleotide comprises a nucleotide sequence having at least 75% sequence identity with SEQ ID NO: 35. In some embodiments, the first polynucleotide comprises a nucleotide sequence having at least 80% sequence identity with SEQ ID NO: 35. In some embodiments, the first polynucleotide comprises a nucleotide sequence having at least 85% sequence identity with SEQ ID NO: 35. In some embodiments, the first polynucleotide comprises a nucleotide sequence having at least 90% sequence identity with SEQ ID NO: 35. In some embodiments, the first polynucleotide comprises a nucleotide sequence having at least 95% sequence identity with SEQ ID NO: 35. In some embodiments, the first polynucleotide comprises a nucleotide sequence of SEQ ID NO: 35.

In some embodiments, the target-specific ligand comprises an amino acid sequence having at least 70% sequence identity with SEQ ID NO: 36. In some embodiments, the target-specific ligand comprises an amino acid sequence having at least 75% sequence identity with SEQ ID NO: 36. In some embodiments, the target-specific ligand comprises an amino acid sequence having at least 80% sequence identity with SEQ ID NO: 36. In some embodiments, the target-specific ligand comprises an amino acid sequence having at least 85% sequence identity with SEQ ID NO: 36. In some embodiments, the target-specific ligand comprises an amino acid sequence having at least 90% sequence identity with SEQ ID NO: 36. In some embodiments, the target-specific ligand comprises an amino acid sequence having at least 95% sequence identity with SEQ ID NO: 36. In some embodiments, the target-specific ligand comprises an amino acid sequence of SEQ ID NO: 36.

Ligand that Binds a TCR Complex

In some embodiments, the TAC comprises a ligand that binds a protein associated with the TCR complex. In some embodiments, the ligand that binds a protein associated with a TCR complex comprises a substance that binds, directly or indirectly, to a protein of the TCR. In some embodiments, the ligand that binds a protein associated with a TCR complex comprises a substance that selectively binds to a protein of the TCR. In some embodiments, the ligand that binds a protein associated with a TCR complex comprises a substance that specifically binds to a protein of the TCR. Proteins associated with the TCR include, but are not limited, to the TCR alpha (α) chain, TCR beta (β) chain, TCR gamma (γ) chain, TCR delta (δ) chain, CD3γ chain, CD3δ chain and CD3ε chains. In some embodiments, a ligand that binds a protein associated with the TCR complex is an antibody to the TCR alpha (α) chain, TCR beta (β) chain, TCR gamma (γ) chain, TCR delta (δ) chain, CD3γ chain, CD3δ chain and/or CD3ε chain. In some embodiments, the protein associated with a TCR complex is CD3. In some embodiments, the protein associated with a TCR complex is CD3ε. Examples of CD3 antibodies, include, but are not limited to, for. In some embodiments, the antibody that binds CD3 is a single chain antibody, for example a single-chain variable fragment (scFv). In some embodiments, the ligand that binds a TCR is anti-CD3 antibody, or a fragment thereof, such as muromonab, otelixizumab, teplizumab, visilizumab, CD3-12, MEM-57, 4D10A6, CD3D, or TR66.

In some embodiments, the CD3 is of a TCR complex on a cell expressing the second polynucleotide. In some embodiments, the binding of the CD3 induces activation of a cell expressing the second polynucleotide.

In some embodiments, the ligand that binds a TCR complex is UCHT1, or a variant thereof. In some embodiments, the ligand that binds a TCR complex is UCHT1 (SEQ ID NO: 13, SEQ ID NO: 14 or homologs thereof). In some embodiments, the UCHT1 ligand binds CD3. In some embodiments, the UCHT1 ligand selectively binds CD3. In some embodiments, the UCHT1 ligand specifically binds CD3. In some embodiments, the UCHT1 ligand binds CD3ε. In some embodiments, the UCHT1 ligand selectively binds CD3ε. In some embodiments, the UCHT1 ligand specifically binds CD3ε. In some embodiments, the UCHT1 ligand is encoded by SEQ ID NO 13. In some embodiments, the UCHT1 ligand comprises SEQ ID NO 14. In some embodiments, the UCHT1 ligand is mutated. In some embodiments, the UCHT1 ligand comprises a Y182T mutation (also referred to as UCHT1 (Y182T)) (SEQ ID NO: 71 and SEQ ID NO: 72). In some embodiments, the UCHT1 (Y182T) ligand binds CD3. In some embodiments, the UCHT1 (Y182T) ligand selectively binds CD3. In some embodiments, the UCHT1 (Y182T) ligand specifically binds CD3. In some embodiments, the UCHT1 (Y182T) ligand binds CD3ε. In some embodiments, the UCHT1 (Y182T) ligand selectively binds CD3ε. In some embodiments, the UCHT1 (Y182T) ligand specifically binds CD3ε. In some embodiments, the UCHT1 (Y182T) ligand is encoded by SEQ ID NO 71. In some embodiments, the UCHT1 (Y182T) ligand comprises SEQ ID NO 72. In some embodiments, the ligand that binds a TCR complex is a humanized UCHT1 (huUCHT1). In some embodiments, the ligand that binds a TCR complex is huUCHT1 (SEQ ID NO 43, SEQ ID NO: 44 or homologs thereof). In some embodiments, the huUCHT1 ligand binds CD3. In some embodiments, the huUCHT1 ligand selectively binds CD3. In some embodiments, the huUCHT1 ligand specifically binds CD3. In some embodiments, the huUCHT1 ligand binds CD3ε. In some embodiments, the huUCHT1 ligand selectively binds CD3ε. In some embodiments, the huUCHT1 ligand specifically binds CD3ε. In some embodiments, the huUCHT1 ligand is encoded by SEQ ID NO 43. In some embodiments, the huUCHT1 ligand comprises SEQ ID NO 44. In some embodiments, the huUCHT1 has a Y177T mutation (also referred to as huUCHT1 (Y177T)) (SEQ ID NO: 45 and SEQ ID NO: 46). In some embodiments, the huUCHT1 (Y177T) ligand binds CD3. In some embodiments, the huUCHT1 (Y177T) ligand selectively binds CD3. In some embodiments, the huUCHT1 (Y177T) ligand specifically binds CD3. In some embodiments, the huUCHT1 (Y177T) ligand binds CD3ε. In some embodiments, the huUCHT1 (Y177T) ligand selectively binds CD3ε. In some embodiments, the huUCHT1 (Y177T) ligand specifically binds CD3ε. In some embodiments, the huUCHT1 (Y177T) ligand is encoded by SEQ ID NO 45. In some embodiments, the huUCHT1 ligand comprises SEQ ID NO 46.

In some embodiments, the second polynucleotide comprises a nucleotide sequence having at least 70% sequence identity with SEQ ID NO: 13. In some embodiments, the second polynucleotide comprises a nucleotide sequence having at least 75% sequence identity with SEQ ID NO: 13. In some embodiments, the second polynucleotide comprises a nucleotide sequence having at least 80% sequence identity with SEQ ID NO: 13. In some embodiments, the second polynucleotide comprises a nucleotide sequence having at least 85% sequence identity with SEQ ID NO: 13. In some embodiments, the second polynucleotide comprises a nucleotide sequence having at least 90% sequence identity with SEQ ID NO: 13. In some embodiments, the second polynucleotide comprises a nucleotide sequence having at least 95% sequence identity with SEQ ID NO: 13. In some embodiments, the second polynucleotide comprises a nucleotide sequence of SEQ ID NO: 13.

In some embodiments, the ligand that binds a TCR complex comprises an amino acid sequence having at least 70% sequence identity with SEQ ID NO: 14. In some embodiments, the ligand that binds a TCR complex comprises an amino acid sequence having at least 75% sequence identity with SEQ ID NO: 14. In some embodiments, the ligand that binds a TCR complex comprises an amino acid sequence having at least 80% sequence identity with SEQ ID NO: 14. In some embodiments, the ligand that binds a TCR complex comprises an amino acid sequence having at least 85% sequence identity with SEQ ID NO: 14. In some embodiments, the ligand that binds a TCR complex comprises an amino acid sequence having at least 90% sequence identity with SEQ ID NO: 14. In some embodiments, the ligand that binds a TCR complex comprises an amino acid sequence having at least 95% sequence identity with SEQ ID NO: 14. In some embodiments, the ligand that binds a TCR complex comprises an amino acid sequence of SEQ ID NO: 14.

In some embodiments, the second polynucleotide comprises a nucleotide sequence having at least 70% sequence identity with SEQ ID NO: 71. In some embodiments, the second polynucleotide comprises a nucleotide sequence having at least 75% sequence identity with SEQ ID NO: 71. In some embodiments, the second polynucleotide comprises a nucleotide sequence having at least 80% sequence identity with SEQ ID NO: 71. In some embodiments, the second polynucleotide comprises a nucleotide sequence having at least 85% sequence identity with SEQ ID NO: 71. In some embodiments, the second polynucleotide comprises a nucleotide sequence having at least 90% sequence identity with SEQ ID NO: 71. In some embodiments, the second polynucleotide comprises a nucleotide sequence having at least 95% sequence identity with SEQ ID NO: 71. In some embodiments, the second polynucleotide comprises a nucleotide sequence of SEQ ID NO: 71.

In some embodiments, the ligand that binds a TCR complex comprises an amino acid sequence having at least 70% sequence identity with SEQ ID NO: 72. In some embodiments, the ligand that binds a TCR complex comprises an amino acid sequence having at least 75% sequence identity with SEQ ID NO: 72. In some embodiments, the ligand that binds a TCR complex comprises an amino acid sequence having at least 80% sequence identity with SEQ ID NO: 72. In some embodiments, the ligand that binds a TCR complex comprises an amino acid sequence having at least 85% sequence identity with SEQ ID NO: 72. In some embodiments, the ligand that binds a TCR complex comprises an amino acid sequence having at least 90% sequence identity with SEQ ID NO: 72. In some embodiments, the ligand that binds a TCR complex comprises an amino acid sequence having at least 95% sequence identity with SEQ ID NO: 72. In some embodiments, the ligand that binds a TCR complex comprises an amino acid sequence of SEQ ID NO: 72.

In some embodiments, the second polynucleotide comprises a nucleotide sequence having at least 70% sequence identity with SEQ ID NO: 43. In some embodiments, the second polynucleotide comprises a nucleotide sequence having at least 75% sequence identity with SEQ ID NO: 43. In some embodiments, the second polynucleotide comprises a nucleotide sequence having at least 80% sequence identity with SEQ ID NO: 43. In some embodiments, the second polynucleotide comprises a nucleotide sequence having at least 85% sequence identity with SEQ ID NO: 43. In some embodiments, the second polynucleotide comprises a nucleotide sequence having at least 90% sequence identity with SEQ ID NO: 43. In some embodiments, the second polynucleotide comprises a nucleotide sequence having at least 95% sequence identity with SEQ ID NO: 43. In some embodiments, the second polynucleotide comprises a nucleotide sequence of SEQ ID NO: 43.

In some embodiments, the ligand that binds a TCR complex comprises an amino acid sequence having at least 70% sequence identity with SEQ ID NO: 44. In some embodiments, the ligand that binds a TCR complex comprises an amino acid sequence having at least 75% sequence identity with SEQ ID NO: 44. In some embodiments, the ligand that binds a TCR complex comprises an amino acid sequence having at least 80% sequence identity with SEQ ID NO: 44. In some embodiments, the ligand that binds a TCR complex comprises an amino acid sequence having at least 85% sequence identity with SEQ ID NO: 44. In some embodiments, the ligand that binds a TCR complex comprises an amino acid sequence having at least 90% sequence identity with SEQ ID NO: 44. In some embodiments, the ligand that binds a TCR complex comprises an amino acid sequence having at least 95% sequence identity with SEQ ID NO: 44. In some embodiments, the ligand that binds a TCR complex comprises an amino acid sequence of SEQ ID NO: 44.

In some embodiments, the second polynucleotide comprises a nucleotide sequence having at least 70% sequence identity with SEQ ID NO: 45. In some embodiments, the second polynucleotide comprises a nucleotide sequence having at least 75% sequence identity with SEQ ID NO: 45. In some embodiments, the second polynucleotide comprises a nucleotide sequence having at least 80% sequence identity with SEQ ID NO: 45. In some embodiments, the second polynucleotide comprises a nucleotide sequence having at least 85% sequence identity with SEQ ID NO: 45. In some embodiments, the second polynucleotide comprises a nucleotide sequence having at least 90% sequence identity with SEQ ID NO: 45. In some embodiments, the second polynucleotide comprises a nucleotide sequence having at least 95% sequence identity with SEQ ID NO: 45. In some embodiments, the second polynucleotide comprises a nucleotide sequence of SEQ ID NO: 45.

In some embodiments, the ligand that binds a TCR complex comprises an amino acid sequence having at least 70% sequence identity with SEQ ID NO: 46. In some embodiments, the ligand that binds a TCR complex comprises an amino acid sequence having at least 75% sequence identity with SEQ ID NO: 46. In some embodiments, the ligand that binds a TCR complex comprises an amino acid sequence having at least 80% sequence identity with SEQ ID NO: 46. In some embodiments, the ligand that binds a TCR complex comprises an amino acid sequence having at least 85% sequence identity with SEQ ID NO: 46. In some embodiments, the ligand that binds a TCR complex comprises an amino acid sequence having at least 90% sequence identity with SEQ ID NO: 46. In some embodiments, the ligand that binds a TCR complex comprises an amino acid sequence having at least 95% sequence identity with SEQ ID NO: 46. In some embodiments, the ligand that binds a TCR complex comprises an amino acid sequence of SEQ ID NO: 46.

In some embodiments, the ligand that binds to a CD3 is OKT3. In some embodiments, the OKT3 ligand binds CD3. In some embodiments, the OKT3 ligand selectively binds CD3. In some embodiments, the OKT3 ligand specifically binds CD3. In some embodiments, the OKT3 ligand binds CD3ϵ. In some embodiments, the OKT3 ligand selectively binds CD3ϵ. In some embodiments, the OKT3 ligand specifically binds CD3ϵ. In some embodiments, the murine OKT3 ligand is encoded by SEQ ID NO 21. In some embodiments, the OKT3 ligand comprises SEQ ID NO 22.

In some embodiments, the second polynucleotide comprises a nucleotide sequence having at least 70% sequence identity with SEQ ID NO: 21. In some embodiments, the second polynucleotide comprises a nucleotide sequence having at least 75% sequence identity with SEQ ID NO: 21. In some embodiments, the second polynucleotide comprises a nucleotide sequence having at least 80% sequence identity with SEQ ID NO: 21. In some embodiments, the second polynucleotide comprises a nucleotide sequence having at least 85% sequence identity with SEQ ID NO: 21. In some embodiments, the second polynucleotide comprises a nucleotide sequence having at least 90% sequence identity with SEQ ID NO: 21. In some embodiments, the second polynucleotide comprises a nucleotide sequence having at least 95% sequence identity with SEQ ID NO: 21. In some embodiments, the second polynucleotide comprises a nucleotide sequence of SEQ ID NO: 21.

In some embodiments, the ligand that binds a TCR complex comprises an amino acid sequence having at least 70% sequence identity with SEQ ID NO: 22. In some embodiments, the ligand that binds a TCR complex comprises an amino acid sequence having at least 75% sequence identity with SEQ ID NO: 22. In some embodiments, the ligand that binds a TCR complex comprises an amino acid sequence having at least 80% sequence identity with SEQ ID NO: 22. In some embodiments, the ligand that binds a TCR complex comprises an amino acid sequence having at least 85% sequence identity with SEQ ID NO: 22. In some embodiments, the ligand that binds a TCR complex comprises an amino acid sequence having at least 90% sequence identity with SEQ ID NO: 22. In some embodiments, the ligand that binds a TCR complex comprises an amino acid sequence having at least 95% sequence identity with SEQ ID NO: 22. In some embodiments, the ligand that binds a TCR complex comprises an amino acid sequence of SEQ ID NO: 22.

In some embodiments, the ligand that binds to a CD3 is F6A. In some embodiments, the F6A ligand binds CD3. In some embodiments, the F6A ligand selectively binds CD3. In some embodiments, the F6A ligand specifically binds CD3. In some embodiments, the F6A ligand binds CD3ϵ. In some embodiments, the F6A ligand selectively binds CD3ϵ. In some embodiments, the F6A ligand specifically binds CD3ϵ. In some embodiments, the murine F6A ligand is encoded by SEQ ID NO 23. In some embodiments, the F6A ligand comprises SEQ ID NO 24.

In some embodiments, the second polynucleotide comprises a nucleotide sequence having at least 70% sequence identity with SEQ ID NO: 23. In some embodiments, the second polynucleotide comprises a nucleotide sequence having at least 75% sequence identity with SEQ ID NO: 23. In some embodiments, the second polynucleotide comprises a nucleotide sequence having at least 80% sequence identity with SEQ ID NO: 23. In some embodiments, the second polynucleotide comprises a nucleotide sequence having at least 85% sequence identity with SEQ ID NO: 23. In some embodiments, the second polynucleotide comprises a nucleotide sequence having at least 90% sequence identity with SEQ ID NO: 23. In some embodiments, the second polynucleotide comprises a nucleotide sequence having at least 95% sequence identity with SEQ ID NO: 23. In some embodiments, the second polynucleotide comprises a nucleotide sequence of SEQ ID NO: 23.

In some embodiments, the ligand that binds a TCR complex comprises an amino acid sequence having at least 70% sequence identity with SEQ ID NO: 24. In some embodiments, the ligand that binds a TCR complex comprises an amino acid sequence having at least 75% sequence identity with SEQ ID NO: 24. In some embodiments, the ligand that binds a TCR complex comprises an amino acid sequence having at least 80% sequence identity with SEQ ID NO: 24. In some embodiments, the ligand that binds a TCR complex comprises an amino acid sequence having at least 85% sequence identity with SEQ ID NO: 24. In some embodiments, the ligand that binds a TCR complex comprises an amino acid sequence having at least 90% sequence identity with SEQ ID NO: 24. In some embodiments, the ligand that binds a TCR complex comprises an amino acid sequence having at least 95% sequence identity with SEQ ID NO: 24. In some embodiments, the ligand that binds a TCR complex comprises an amino acid sequence of SEQ ID NO: 24.

In some embodiments, the ligand that binds to a CD3 is L2K. In some embodiments, the L2K ligand binds CD3. In some embodiments, the L2K ligand selectively binds CD3. In some embodiments, the L2K ligand specifically binds CD3. In some embodiments, the L2K ligand binds CD3ε. In some embodiments, the L2K ligand selectively binds CD3ε. In some embodiments, the L2K ligand specifically binds CD3ε. In some embodiments, the murine L2K ligand is encoded by SEQ ID NO 25. In some embodiments, the L2K ligand comprises SEQ ID NO 26.

In some embodiments, the second polynucleotide comprises a nucleotide sequence having at least 70% sequence identity with SEQ ID NO: 25. In some embodiments, the second polynucleotide comprises a nucleotide sequence having at least 75% sequence identity with SEQ ID NO: 25. In some embodiments, the second polynucleotide comprises a nucleotide sequence having at least 80% sequence identity with SEQ ID NO: 25. In some embodiments, the second polynucleotide comprises a nucleotide sequence having at least 85% sequence identity with SEQ ID NO: 25. In some embodiments, the second polynucleotide comprises a nucleotide sequence having at least 90% sequence identity with SEQ ID NO: 25. In some embodiments, the second polynucleotide comprises a nucleotide sequence having at least 95% sequence identity with SEQ ID NO: 25. In some embodiments, the second polynucleotide comprises a nucleotide sequence of SEQ ID NO: 25.

In some embodiments, the ligand that binds a TCR complex comprises an amino acid sequence having at least 70% sequence identity with SEQ ID NO: 26. In some embodiments, the ligand that binds a TCR complex comprises an amino acid sequence having at least 75% sequence identity with SEQ ID NO: 26. In some embodiments, the ligand that binds a TCR complex comprises an amino acid sequence having at least 80% sequence identity with SEQ ID NO: 26. In some embodiments, the ligand that binds a TCR complex comprises an amino acid sequence having at least 85% sequence identity with SEQ ID NO: 26. In some embodiments, the ligand that binds a TCR complex comprises an amino acid sequence having at least 90% sequence identity with SEQ ID NO: 26. In some embodiments, the ligand that binds a TCR complex comprises an amino acid sequence having at least 95% sequence identity with SEQ ID NO: 26. In some embodiments, the ligand that binds a TCR complex comprises an amino acid sequence of SEQ ID NO: 26.

Transmembrane Domain and Cytosolic Domain

In some embodiments, a T cell antigen coupler includes a T cell receptor signaling domain polypeptide. In some embodiments, the TCR signaling domain polypeptide comprises a transmembrane domain. In some embodiments, the TCR signaling domain polypeptide comprises a cytosolic domain. In some embodiments, the TCR signaling domain polypeptide comprises a transmembrane domain and a cytosolic domain. In some embodiments, the cytosolic domain and transmembrane domains are optionally joined by a linker. In some embodiments, the T cell receptor signaling domain polypeptide comprises a TCR co-receptor domain. In some embodiments, the T cell receptor signaling domain polypeptide does not comprise a TCR co-stimulator domain. In some embodiments, the TCR signaling domain polypeptide comprises a transmembrane domain and/or a cytosolic domain of a TCR co-receptor. In some embodiments, the TCR co-receptor is CD4, CD8, LAG3, or a chimeric variation thereof.

In some embodiments, the TCR co-receptor is CD4. In some embodiments, the TCR signaling domain polypeptide comprises the transmembrane and cytosolic domains of the CD4 co-receptor encoded by SEQ ID NO: 17. In some embodiments, the TCR signaling domain polypeptide comprises the transmembrane and cytosolic domains of the CD4 co-receptor comprising SEQ ID NO: 18.

In some embodiments, the third polynucleotide comprises a nucleotide sequence having at least 70% sequence identity with SEQ ID NO: 17. In some embodiments, the third polynucleotide comprises a nucleotide sequence having at least 75% sequence identity with SEQ ID NO: 17. In some embodiments, the third polynucleotide comprises a nucleotide sequence having at least 80% sequence identity with SEQ ID NO: 17. In some embodiments, the third polynucleotide comprises a nucleotide sequence having at least 85% sequence identity with SEQ ID NO: 17. In some embodiments, the third polynucleotide comprises a nucleotide sequence having at least 90% sequence identity with SEQ ID NO: 17. In some embodiments, the third polynucleotide comprises a nucleotide sequence having at least 95% sequence identity with SEQ ID NO: 17. In some embodiments, the third polynucleotide comprises a nucleotide sequence of SEQ ID NO: 17.

In some embodiments, the transmembrane domain and cytosolic domain comprise an amino acid sequence having at least 70% sequence identity with SEQ ID NO: 18. In some embodiments, the transmembrane domain and cytosolic domain comprise an amino acid sequence having at least 75% sequence identity with SEQ ID NO: 18. In some embodiments, the transmembrane domain and cytosolic domain comprise an amino acid sequence having at least 80% sequence identity with SEQ ID NO: 18. In some embodiments, the transmembrane domain and cytosolic domain comprise an amino acid sequence having at least 85% sequence identity with SEQ ID NO: 18. In some embodiments, the transmembrane domain and cytosolic domain comprise an amino acid sequence having at least 90% sequence identity with SEQ ID NO: 18. In some embodiments, the transmembrane domain and cytosolic domain comprise an amino acid sequence having at least 95% sequence identity with SEQ ID NO: 18. In some embodiments, the transmembrane domain and cytosolic domain comprise an amino acid sequence of SEQ ID NO: 18.

In some embodiments, the TCR co-receptor is CD8. In some embodiments, the TCR co-receptor is CD8α. In some embodiments, the TCR signaling domain polypeptide comprises the transmembrane and cytosolic domains of the CD8α co-receptor encoded by SEQ ID NO: 37. In some embodiments, the TCR signaling domain polypeptide comprises the transmembrane and cytosolic domains of the CD8α co-receptor comprising SEQ ID NO: 38.

In some embodiments, the third polynucleotide comprises a nucleotide sequence having at least 70% sequence identity with SEQ ID NO: 37. In some embodiments, the third polynucleotide comprises a nucleotide sequence having at least 75% sequence identity with SEQ ID NO: 37. In some embodiments, the third polynucleotide comprises a nucleotide sequence having at least 80% sequence identity with SEQ ID NO: 37. In some embodiments, the third polynucleotide comprises a nucleotide sequence having at least 85% sequence identity with SEQ ID NO: 37. In some embodiments, the third polynucleotide comprises a nucleotide sequence having at least 90% sequence identity with SEQ ID NO: 37. In some embodiments, the third polynucleotide comprises a nucleotide sequence having at least 95% sequence identity with SEQ ID NO: 37. In some embodiments, the third polynucleotide comprises a nucleotide sequence of SEQ ID NO: 37.

In some embodiments, the transmembrane domain and cytosolic domain comprise an amino acid sequence having at least 70% sequence identity with SEQ ID NO: 38. In some embodiments, the transmembrane domain and cytosolic domain comprise an amino acid sequence having at least 75% sequence identity with SEQ ID NO: 38. In some embodiments, the transmembrane domain and cytosolic domain comprise an amino acid sequence having at least 80% sequence identity with SEQ ID NO: 38. In some embodiments, the transmembrane domain and cytosolic domain comprise an amino acid sequence having at least 85% sequence identity with SEQ ID NO: 38. In some embodiments, the transmembrane domain and cytosolic domain comprise an amino acid sequence having at least 90% sequence identity with SEQ ID NO: 38. In some embodiments, the transmembrane domain and cytosolic domain comprise an amino acid sequence having at least 95% sequence identity with SEQ ID NO: 38. In some embodiments, the transmembrane domain and cytosolic domain comprise an amino acid sequence of SEQ ID NO: 38.

In some embodiments, the TCR signaling domain polypeptide comprises a chimera of sequences or domains from co-receptors. In some embodiments, the TCR signaling domain polypeptide comprises a chimera of CD8α and CD8β, wherein the CD8α arginine rich region is replaced with the CD8β arginine rich region. In some embodiments, the T cell receptor signaling domain polypeptide comprises the transmembrane and cytosolic domains of the CD8α+R(β) co-receptor chimera encoded by SEQ ID NO: 39. In some embodiments, the T cell receptor signaling domain polypeptide comprises the transmembrane and cytosolic domains of the CD8α+R(β) co-receptor chimera provided by SEQ ID NO: 40. In some embodiments, the TCR signaling domain polypeptide comprises a chimera of CD8α and CD8β, the CD8β CXCP domain, which contains an Lck binding motif, is appended to the C-terminus of the CD8β cytosolic domain. In some embodiments, the T cell receptor signaling domain polypeptide comprises the transmembrane and cytosolic domains of the CD8β+Lck co-receptor chimera encoded by SEQ ID NO: 41. In some embodiments, the T cell receptor signaling domain polypeptide comprises the transmembrane and cytosolic domains of the CD8β+Lck co-receptor chimera provided by SEQ ID NO: 42.

In some embodiments, the third polynucleotide comprises a nucleotide sequence having at least 70% sequence identity with SEQ ID NO: 39. In some embodiments, the third polynucleotide comprises a nucleotide sequence having at least 75% sequence identity with SEQ ID NO: 39. In some embodiments, the third polynucleotide comprises a nucleotide sequence having at least 80% sequence identity with SEQ ID NO: 39. In some embodiments, the third polynucleotide comprises a nucleotide sequence having at least 85% sequence identity with SEQ ID NO: 39. In some embodiments, the third polynucleotide comprises a nucleotide sequence having at least 90% sequence identity with SEQ ID NO: 39. In some embodiments, the third polynucleotide comprises a nucleotide sequence having at least 95% sequence identity with SEQ ID NO: 39. In some embodiments, the third polynucleotide comprises a nucleotide sequence of SEQ ID NO: 39.

In some embodiments, the transmembrane domain and cytosolic domain comprise an amino acid sequence having at least 70% sequence identity with SEQ ID NO: 40. In some embodiments, the transmembrane domain and cytosolic domain comprise an amino acid sequence having at least 75% sequence identity with SEQ ID NO: 40. In some embodiments, the transmembrane domain and cytosolic domain comprise an amino acid sequence having at least 80% sequence identity with SEQ ID NO: 40. In some embodiments, the transmembrane domain and cytosolic domain comprise an amino acid sequence having at least 85% sequence identity with SEQ ID NO: 40. In some embodiments, the transmembrane domain and cytosolic domain comprise an amino acid sequence having at least 90% sequence identity with SEQ ID NO: 40. In some embodiments, the transmembrane domain and cytosolic domain comprise an amino acid sequence having at least 95% sequence identity with SEQ ID NO: 40. In some embodiments, the transmembrane domain and cytosolic domain comprise an amino acid sequence of SEQ ID NO: 40.

In some embodiments, the third polynucleotide comprises a nucleotide sequence having at least 70% sequence identity with SEQ ID NO: 41. In some embodiments, the third polynucleotide comprises a nucleotide sequence having at least 75% sequence identity with SEQ ID NO: 41. In some embodiments, the third polynucleotide comprises a nucleotide sequence having at least 80% sequence identity with SEQ ID NO: 41. In some embodiments, the third polynucleotide comprises a nucleotide sequence having at least 85% sequence identity with SEQ ID NO: 41. In some embodiments, the third polynucleotide comprises a nucleotide sequence having at least 90% sequence identity with SEQ ID NO: 41. In some embodiments, the third polynucleotide comprises a nucleotide sequence having at least 95% sequence identity with SEQ ID NO: 41. In some embodiments, the third polynucleotide comprises a nucleotide sequence of SEQ ID NO: 41.

In some embodiments, the transmembrane domain and cytosolic domain comprise an amino acid sequence having at least 70% sequence identity with SEQ ID NO: 42. In some embodiments, the transmembrane domain and cytosolic domain comprise an amino acid sequence having at least 75% sequence identity with SEQ ID NO: 42. In some embodiments, the transmembrane domain and cytosolic domain comprise an amino acid sequence having at least 80% sequence identity with SEQ ID NO: 42. In some embodiments, the transmembrane domain and cytosolic domain comprise an amino acid sequence having at least 85% sequence identity with SEQ ID NO: 42. In some embodiments, the transmembrane domain and cytosolic domain comprise an amino acid sequence having at least 90% sequence identity with SEQ ID NO: 42. In some embodiments, the transmembrane domain and cytosolic domain comprise an amino acid sequence having at least 95% sequence identity with SEQ ID NO: 42. In some embodiments, the transmembrane domain and cytosolic domain comprise an amino acid sequence of SEQ ID NO: 42.

In some embodiments, the T cell receptor signaling domain polypeptide comprises a TCR co-stimulator domain. In some embodiments, the TCR co-stimulator is ICOS. In some embodiments, the TCR co-stimulator is CD27. In some embodiments, the TCR co-stimulator is CD28. In some embodiments, the TCR co-stimulator is 4-1BB (CD137). In some embodiments, the TCR co-stimulator is OX40 (CD134). In some embodiments, the TCR co-stimulator is CD30. In some embodiments, the TCR co-stimulator is CD40. In some embodiments, the TCR co-stimulator is lymphocyte fiction-associated antigen 1 (LFA-1). In some embodiments, the TCR co-stimulator is CD2. In some embodiments, the TCR co-stimulator is CD7. In some embodiments, the TCR co-stimulator is LIGHT. In some embodiments, the TCR co-stimulator is NKG2C. In some embodiments, the TCR co-stimulator is B7-H3. In some embodiments, the TCR co-stimulator is a ligand that specifically binds CD83.

In some embodiments, the TCR signaling domain polypeptide comprises a transmembrane domain and/or a cytosolic domain of a TCR co-inhibitor. In some embodiments, the TCR co-inhibitor is PD-1. In some embodiments, the TCR co-inhibitor is TIM3. In some embodiments, the TCR co-inhibitor is LAG-3. In some embodiments, the TCR co-inhibitor is TIGIT. In some embodiments, the TCR co-inhibitor is BTLA. In some embodiments, the TCR co-inhibitor is CD160. In some embodiments, the TCR co-inhibitor is CD37.

In some embodiments, the TCR signaling domain polypeptide includes both a cytosolic domain and a transmembrane domain of a TCR co-receptor or co-stimulator protein. In some embodiments, the cytosolic domain and transmembrane domain are from the same co-receptor or co-stimulator or from different co-receptors or co-stimulators. In some embodiments, the TAC further comprises other polypeptides that directly or indirectly act to target or activate the T cell.

Linkers, Connectors, and Configurations

In some embodiments, a nucleic acid disclosed herein is in an order of (1) a first polynucleotide encoding a target-specific ligand; (2) a second polynucleotide encoding a ligand that binds a TCR complex; (3) a third polynucleotide encoding a transmembrane domain and a cytosolic domain. In some embodiments, a nucleic acid disclosed herein is in an order of (1) a first polynucleotide encoding a target-specific ligand; (2) a second polynucleotide encoding a ligand that binds a TCR complex; (3) a third polynucleotide encoding a transmembrane domain and a cytosolic domain, wherein the order is 5' end to 3' end. In some embodiments, a nucleic acid disclosed herein is in an order of (1) a first polynucleotide encoding a target-specific ligand; (2) a second polynucleotide encoding a ligand that binds a TCR complex; (3) a third polynucleotide encoding a transmembrane domain and a cytosolic domain, wherein the order is 3' end to 5' end. In some embodiments, a nucleic acid described herein is in an order of (1) a first polynucleotide encoding a ligand that binds a TCR complex; (2) a second polynucleotide encoding a target-specific ligand; (3) a third polynucleotide encoding a transmembrane domain and a cytosolic domain. In some embodiments, a nucleic acid described herein is in an order of (1) a first polynucleotide encoding a ligand that binds a TCR complex; (2) a second polynucleotide encoding a target-specific ligand; (3) a third polynucleotide encoding a transmembrane domain and a cytosolic domain, wherein the order is 5' end to 3' end. In some embodiments, a nucleic acid described herein is in an order of (1) a first polynucleotide encoding a ligand that binds a TCR complex; (2) a second polynucleotide encoding a target-specific ligand; (3) a third polynucleotide encoding a transmembrane domain and a cytosolic domain, wherein the order is 3' end to 5' end.

In some embodiments, the first nucleic acid encodes a first polypeptide, the second nucleic acid encodes a second polypeptide, and the third nucleic acid encodes a third polypeptide. In some embodiments, the first polypeptide, the second polypeptide, and the third polypeptide are directly fused. For example, the target-specific ligand and the T cell receptor signaling domain polypeptide are both fused to the ligand that binds the TCR complex. In some embodiments, the first polypeptide, the second polypeptide, and the third polypeptide are joined by at least one linker. In some embodiments, the first polypeptide and the second polypeptide are directly fused, and joined to the third polypeptide by a linker. In some embodiments, the second polypeptide and the third polypeptide are directly fused, and joined to the first polypeptide by a linker.

In some embodiments, the linker is a peptide linker. In some embodiments, the peptide linker comprises 1 to 40 amino acids. In some embodiments, the peptide linker comprises 1 to 30 amino acids. In some embodiments, the peptide linker comprises 1 to 15 amino acids. In some embodiments, the peptide linker comprises 1 to 10 amino acids. In some embodiments, the peptide linker comprises 1 to 6 amino acids. In some embodiments, the peptide linker comprises 30 to 40 amino acids. In some embodiments, the peptide linker comprises 32 to 36 amino acids. In some embodiments, the peptide linker comprises 5 to 30 amino acids. In some embodiments, the peptide linker comprises 5 amino acids. In some embodiments, the peptide linker comprises 10 amino acids. In some embodiments, the peptide linker comprises 15 amino acids. In some embodiments, the peptide linker comprises 20 amino acids. In some embodiments, the peptide linker comprises 25 amino acids. In some embodiments, the peptide linker comprises 30 amino acids.

In some embodiments, the peptide linker comprises a $G_4S_3$ linker (SEQ ID NO: 74). In some embodiments, the peptide linker comprises SEQ ID NOs: 11, 12, 15, 16, 19, 20, or variants or fragments thereof.

In some embodiments, the peptide linker that joins the target-specific ligand to the ligand that binds a TCR complex (e.g. UCHT1) is known as the connector to distinguish this protein domain from other linkers in the Tri-TAC. The connector is of any size. In some embodiments, the connector between ligand that binds a TCR complex and a target-specific ligand is a short helix comprising SEQ ID NO ID: 28. In some embodiments, the connector between ligand that binds a TCR complex and a target-specific ligand is a short helix encoded by SEQ ID NO ID: 27. In some embodiments, the connector between ligand that binds a TCR complex and a target-specific ligand is a long helix comprising SEQ ID NO ID: 30. In some embodiments, the connector between ligand that binds a TCR complex and a target-specific ligand is a long helix encoded by SEQ ID NO ID: 29. In some embodiments, the connector between ligand that binds a TCR complex and a target-specific ligand is a large domain comprising SEQ ID NO ID: 32. In some embodiments, the connector between ligand that binds a TCR complex and a target-specific ligand is a large domain encoded by SEQ ID NO ID: 31.

In some embodiments, a nucleic acid disclosed herein comprises a leader sequence. In some embodiments, the leader sequence comprises a nucleotide sequence having at least 70% sequence identity with SEQ ID NO: 5, 47, or 49. In some embodiments, the leader sequence comprises a nucleotide sequence having at least 75% sequence identity with SEQ ID NO: 5, 47, or 49. In some embodiments, the leader sequence comprises a nucleotide sequence having at least 80% sequence identity with SEQ ID NO: 5, 47, or 49. In some embodiments, the leader sequence comprises a nucleotide sequence having at least 85% sequence identity with SEQ ID NO: 5, 47, or 49. In some embodiments, the leader sequence comprises a nucleotide sequence having at least 90% sequence identity with SEQ ID NO: 5, 47, or 49. In some embodiments, the leader sequence comprises a nucleotide sequence having at least 95% sequence identity with SEQ ID NO: 5, 47, or 49. In some embodiments, the leader sequence comprises a nucleotide sequence of SEQ ID NO: 5, 47, or 49.

In some embodiments, a nucleic acid disclosed herein comprises a leader sequence. In some embodiments, the leader sequence comprises an amino acid sequence having at least 70% sequence identity with SEQ ID NO: 6, 48, or 50. In some embodiments, the leader sequence comprises an amino acid sequence having at least 75% sequence identity with SEQ ID NO: 6, 48, or 50. In some embodiments, the leader sequence comprises an amino acid sequence having at least 80% sequence identity with SEQ ID NO: 6, 48, or 50. In some embodiments, the leader sequence comprises an amino acid sequence having at least 85% sequence identity with SEQ ID NO: 6, 48, or 50. In some embodiments, the leader sequence comprises an amino acid sequence having at least 90% sequence identity with SEQ ID NO: 6, 48, or 50. In some embodiments, the leader sequence comprises an amino acid sequence having at least 95% sequence identity with SEQ ID NO: 6, 48, or 50. In some embodiments, the leader sequence comprises an amino acid sequence of SEQ ID NO: 6, 48, or 50.

The Tri-TAC is contemplated to be present in various configurations and combinations of (a) target-specific ligand, (b) a ligand that binds a TCR complex, and (c) a TCR signaling domain, as disclosed herein.

In some embodiments, the Tri-TAC comprises (a) a target-specific ligand, (b) a single-chain antibody (scFv) that binds CD3ε, and (c) a transmembrane and cytosolic domain of the CD4 co-receptor. In some embodiments, the Tri-TAC comprises (a) a target-specific ligand, (b) UCHT1, and (c) a transmembrane and cytosolic domain of the CD4 co-receptor. In some embodiments, the Tri-TAC comprises (a) a target-specific ligand, (b) UCHT1 (Y182T), and (c) a transmembrane and cytosolic domain of the CD4 co-receptor. In some embodiments, the Tri-TAC comprises (a) a target-specific ligand, (b) huUCHT1, and (c) a transmembrane and cytosolic domain of the CD4 co-receptor. In some embodiments, the Tri-TAC comprises (a) a target-specific ligand, (b) huUCHT1 (Y177T), and (c) a transmembrane and cytosolic domain of the CD4 co-receptor. In some embodiments, the Tri-TAC comprises (a) a target-specific ligand, (b) OKT3, and (c) a transmembrane and cytosolic domain of the CD4 co-receptor. In some embodiments, the Tri-TAC comprises (a) a target-specific ligand, (b) F6A, and (c) a transmembrane and cytosolic domain of the CD4 co-receptor. In some embodiments, the Tri-TAC comprises (a) a target-specific ligand, (b) L2K, and (c) a transmembrane and cytosolic domain of the CD4 co-receptor.

In some embodiments, the Tri-TAC comprises (a) a DARPin, (b) UCHT1, and (c) a transmembrane and cytosolic domain of the CD4 co-receptor. In some embodiments, the Tri-TAC comprises (a) a DARPin, (b) UCHT1 (Y182T), and (c) a transmembrane and cytosolic domain of the CD4 co-receptor. In some embodiments, the Tri-TAC comprises (a) a DARPin, (b) huUCHT1, and (c) a transmembrane and cytosolic domain of the CD4 co-receptor. In some embodiments, the Tri-TAC comprises (a) a DARPin, (b) huUCHT1 (Y177T), and (c) a transmembrane and cytosolic domain of the CD4 co-receptor. In some embodiments, the Tri-TAC comprises (a) a DARPin, (b) OKT3, and (c) a transmembrane and cytosolic domain of the CD4 co-receptor. In some embodiments, the Tri-TAC comprises (a) a DARPin, (b) F6A, and (c) a transmembrane and cytosolic domain of the CD4 co-receptor. In some embodiments, the Tri-TAC comprises (a) a DARPin, (b) L2K, and (c) a transmembrane and cytosolic domain of the CD4 co-receptor.

In some embodiments, the Tri-TAC comprises (a) a scFv, (b) UCHT1, and (c) a transmembrane and cytosolic domain of the CD4 co-receptor. In some embodiments, the Tri-TAC comprises (a) a scFv, (b) UCHT1 (Y182T), and (c) a transmembrane and cytosolic domain of the CD4 co-receptor. In some embodiments, the Tri-TAC comprises (a) a scFv, (b) huUCHT1, and (c) a transmembrane and cytosolic domain of the CD4 co-receptor. In some embodiments, the Tri-TAC comprises (a) a scFv, (b) huUCHT1 (Y177T), and (c) a transmembrane and cytosolic domain of the CD4 co-receptor. In some embodiments, the Tri-TAC comprises (a) a scFv, (b) OKT3, and (c) a transmembrane and cytosolic domain of the CD4 co-receptor. In some embodiments, the Tri-TAC comprises (a) a scFv, (b) F6A, and (c) a transmembrane and cytosolic domain of the CD4 co-receptor. In some embodiments, the Tri-TAC comprises (a) a scFv, (b) L2K, and (c) a transmembrane and cytosolic domain of the CD4 co-receptor.

In some embodiments, the Tri-TAC comprises (a) a HER-2-specific DARPin, (b) UCHT1, and (c) a transmembrane and cytosolic domain of the CD4 co-receptor. In some embodiments, the Tri-TAC comprises (a) a HER-2-specific DARPin, (b) UCHT1 (Y182T), and (c) a transmembrane and cytosolic domain of the CD4 co-receptor. In some embodiments, the Tri-TAC comprises (a) a HER-2-specific DARPin, (b) huUCHT1, and (c) a transmembrane and cytosolic domain of the CD4 co-receptor. In some embodiments, the Tri-TAC comprises (a) a HER-2-specific DARPin, (b) huUCHT1 (Y177T), and (c) a transmembrane and cytosolic domain of the CD4 co-receptor. In some embodiments, the Tri-TAC comprises (a) a HER-2-specific DARPin, (b) OKT3, and (c) a transmembrane and cytosolic domain of the CD4 co-receptor. In some embodiments, the Tri-TAC comprises (a) a HER-2-specific DARPin, (b) F6A, and (c) a transmembrane and cytosolic domain of the CD4 co-receptor. In some embodiments, the Tri-TAC comprises (a) a HER-2-specific DARPin, (b) L2K, and (c) a transmembrane and cytosolic domain of the CD4 co-receptor.

In some embodiments, the Tri-TAC comprises (a) a BCMA-specific ScFv, (b) UCHT1, and (c) a transmembrane and cytosolic domain of the CD4 co-receptor. In some embodiments, the Tri-TAC comprises (a) a BCMA-specific ScFv, (b) UCHT1 (Y182T), and (c) a transmembrane and cytosolic domain of the CD4 co-receptor. In some embodiments, the Tri-TAC comprises (a) a BCMA-specific ScFv, (b) huUCHT1, and (c) a transmembrane and cytosolic domain of the CD4 co-receptor. In some embodiments, the Tri-TAC comprises (a) a BCMA-specific ScFv, (b) huUCHT1 (Y177T), and (c) a transmembrane and cytosolic domain of the CD4 co-receptor. In some embodiments, the Tri-TAC comprises (a) a BCMA-specific ScFv, (b) OKT3, and (c) a transmembrane and cytosolic domain of the CD4 co-receptor. In some embodiments, the Tri-TAC comprises (a) a BCMA-specific ScFv, (b) F6A, and (c) a transmembrane and cytosolic domain of the CD4 co-receptor. In some embodiments, the Tri-TAC comprises (a) a BCMA-specific ScFv, (b) L2K, and (c) a transmembrane and cytosolic domain of the CD4 co-receptor.

In some embodiments, the Tri-TAC comprises (a) a CD19-specific ScFv, (b) UCHT1, and (c) a transmembrane and cytosolic domain of the CD4 co-receptor. In some embodiments, the Tri-TAC comprises (a) a CD19-specific ScFv, (b) UCHT1 (Y182T), and (c) a transmembrane and cytosolic domain of the CD4 co-receptor. In some embodiments, the Tri-TAC comprises (a) a CD19-specific ScFv, (b) huUCHT1, and (c) a transmembrane and cytosolic domain of the CD4 co-receptor. In some embodiments, the Tri-TAC comprises (a) a CD19-specific ScFv, (b) huUCHT1 (Y177T), and (c) a transmembrane and cytosolic domain of the CD4 co-receptor. In some embodiments, the Tri-TAC comprises (a) a CD19-specific ScFv, (b) OKT3, and (c) a transmembrane and cytosolic domain of the CD4 co-receptor. In some embodiments, the Tri-TAC comprises (a) a CD19-specific ScFv, (b) F6A, and (c) a transmembrane and cytosolic domain of the CD4 co-receptor. In some embodiments, the Tri-TAC comprises (a) a CD19-specific ScFv, (b) L2K, and (c) a transmembrane and cytosolic domain of the CD4 co-receptor.

In some embodiments, the Tri-TAC comprises (a) a target-specific ligand, (b) a single-chain antibody (scFv) that binds CD3ε, and (c) a transmembrane and cytosolic domain of the CD8 co-receptor. In some embodiments, the Tri-TAC comprises (a) a target-specific ligand, (b) UCHT1, and (c) a transmembrane and cytosolic domain of the CD8 co-receptor. In some embodiments, the Tri-TAC comprises (a) a target-specific ligand, (b) UCHT1 (Y182T), and (c) a transmembrane and cytosolic domain of the CD8 co-receptor. In some embodiments, the Tri-TAC comprises (a) a target-specific ligand, (b) huUCHT1, and (c) a transmembrane and cytosolic domain of the CD8 co-receptor. In some embodiments, the Tri-TAC comprises (a) a target-specific ligand, (b) huUCHT1 (Y177T), and (c) a transmembrane and cytosolic domain of the CD8 co-receptor. In some embodiments, the Tri-TAC comprises (a) a target-specific ligand, (b) OKT3, and (c) a transmembrane and cytosolic domain of the CD8 co-receptor. In some embodiments, the Tri-TAC comprises (a) a target-specific ligand, (b) F6A, and (c) a transmembrane and cytosolic domain of the CD8 co-receptor. In some embodiments, the Tri-TAC comprises (a) a target-specific ligand, (b) L2K, and (c) a transmembrane and cytosolic domain of the CD8 co-receptor.

In some embodiments, the Tri-TAC comprises (a) a DARPin, (b) UCHT1, and (c) a transmembrane and cytosolic domain of the CD4 co-receptor. In some embodiments, the Tri-TAC comprises (a) a DARPin, (b) UCHT1 (Y182T), and (c) a transmembrane and cytosolic domain of the CD8 co-receptor. In some embodiments, the Tri-TAC comprises (a) a DARPin, (b) huUCHT1, and (c) a transmembrane and cytosolic domain of the CD8 co-receptor. In some embodiments, the Tri-TAC comprises (a) a DARPin, (b) huUCHT1 (Y177T), and (c) a transmembrane and cytosolic domain of the CD8 co-receptor. In some embodiments, the Tri-TAC comprises (a) a DARPin, (b) OKT3, and (c) a transmembrane and cytosolic domain of the CD8 co-receptor. In some embodiments, the Tri-TAC comprises (a) a DARPin, (b) F6A, and (c) a transmembrane and cytosolic domain of the CD8 co-receptor. In some embodiments, the Tri-TAC comprises (a) a DARPin, (b) L2K, and (c) a transmembrane and cytosolic domain of the CD8 co-receptor.

In some embodiments, the Tri-TAC comprises (a) a scFv, (b) UCHT1, and (c) a transmembrane and cytosolic domain of the CD8 co-receptor. In some embodiments, the Tri-TAC comprises (a) a scFv, (b) UCHT1 (Y182T), and (c) a transmembrane and cytosolic domain of the CD8 co-receptor. In some embodiments, the Tri-TAC comprises (a) a scFv, (b) huUCHT1, and (c) a transmembrane and cytosolic domain of the CD8 co-receptor. In some embodiments, the Tri-TAC comprises (a) a scFv, (b) huUCHT1 (Y177T), and (c) a transmembrane and cytosolic domain of the CD8 co-receptor. In some embodiments, the Tri-TAC comprises (a) a scFv, (b) OKT3, and (c) a transmembrane and cytosolic domain of the CD8 co-receptor. In some embodiments, the Tri-TAC comprises (a) a scFv, (b) F6A, and (c) a transmembrane and cytosolic domain of the CD8 co-receptor. In some embodiments, the Tri-TAC comprises (a) a scFv, (b) L2K, and (c) a transmembrane and cytosolic domain of the CD8 co-receptor.

In some embodiments, the Tri-TAC comprises (a) a HER-2-specific DARPin, (b) UCHT1, and (c) a transmembrane and cytosolic domain of the CD8 co-receptor. In some embodiments, the Tri-TAC comprises (a) a HER-2-specific DARPin, (b) UCHT1 (Y182T), and (c) a transmembrane and cytosolic domain of the CD8 co-receptor. In some embodiments, the Tri-TAC comprises (a) a HER-2-specific DARPin, (b) huUCHT1, and (c) a transmembrane and cytosolic domain of the CD8 co-receptor. In some embodiments, the Tri-TAC comprises (a) a target-specific ligand, (b) huUCHT1 (Y177T), and (c) a transmembrane and cytosolic domain of the CD8 co-receptor. In some embodiments, the Tri-TAC comprises (a) a HER-2-specific DARPin, (b) OKT3, and (c) a transmembrane and cytosolic domain of the CD8 co-receptor. In some embodiments, the Tri-TAC comprises (a) a HER-2-specific DARPin, (b) F6A, and (c) a transmembrane and cytosolic domain of the CD8 co-receptor. In some embodiments, the Tri-TAC comprises (a) a HER-2-specific DARPin, (b) L2K, and (c) a transmembrane and cytosolic domain of the CD8 co-receptor.

In some embodiments, the Tri-TAC comprises (a) a BCMA-specific ScFv, (b) UCHT1, and (c) a transmembrane and cytosolic domain of the CD8 co-receptor. In some embodiments, the Tri-TAC comprises (a) a BCMA-specific ScFv, (b) UCHT1 (Y182T), and (c) a transmembrane and cytosolic domain of the CD8 co-receptor. In some embodiments, the Tri-TAC comprises (a) a BCMA-specific ScFv, (b) huUCHT1, and (c) a transmembrane and cytosolic domain of the CD8 co-receptor. In some embodiments, the Tri-TAC comprises (a) a BCMA-specific ScFv, (b) huUCHT1 (Y177T), and (c) a transmembrane and cytosolic domain of the CD8 co-receptor. In some embodiments, the Tri-TAC comprises (a) a BCMA-specific ScFv, (b) OKT3, and (c) a transmembrane and cytosolic domain of the CD8 co-receptor. In some embodiments, the Tri-TAC comprises (a) a BCMA-specific ScFv, (b) F6A, and (c) a transmembrane and cytosolic domain of the CD8 co-receptor. In some embodiments, the Tri-TAC comprises (a) a BCMA-specific ScFv, (b) L2K, and (c) a transmembrane and cytosolic domain of the CD8 co-receptor.

In some embodiments, the Tri-TAC comprises (a) a CD19-specific ScFv, (b) UCHT1, and (c) a transmembrane and cytosolic domain of the CD8 co-receptor. In some embodiments, the Tri-TAC comprises (a) a CD19-specific ScFv, (b) UCHT1 (Y182T), and (c) a transmembrane and cytosolic domain of the CD8 co-receptor. In some embodiments, the Tri-TAC comprises (a) a CD19-specific ScFv, (b) huUCHT1, and (c) a transmembrane and cytosolic domain of the CD8 co-receptor. In some embodiments, the Tri-TAC comprises (a) a CD19-specific ScFv, (b) huUCHT1 (Y177T), and (c) a transmembrane and cytosolic domain of the CD8 co-receptor. In some embodiments, the Tri-TAC comprises (a) a CD19-specific ScFv, (b) OKT3, and (c) a transmembrane and cytosolic domain of the CD8 co-receptor. In some embodiments, the Tri-TAC comprises (a) a CD19-specific ScFv, (b) F6A, and (c) a transmembrane and cytosolic domain of the CD8 co-receptor. In some embodiments, the Tri-TAC comprises (a) a CD19-specific ScFv, (b) L2K, and (c) a transmembrane and cytosolic domain of the CD8 co-receptor.

In some embodiments, the Tri-TAC draws CD3 and TCR into lipid raft regions of the membrane, and brings Lck into the proximity of the TCR, similar to natural MHC binding.

In some embodiments, the TAC disclosed herein is the anti-HER-2 DARPin Tri-TAC (also referred to as configuration 1; SEQ ID NO: 1 and 2) includes, in order:
  i) the anti-HER-2 Tri-TAC leader sequence (secretion signal) (SEQ ID NO: 5 and 6)
  ii) DARPin specific for HER-2 antigen (SEQ ID NO: 7 and 8)
  iii) Myc tag (SEQ ID NO: 9 and 10)
  iv) Connector (SEQ ID NO: 11 and 12)
  v) UCHT1 (SEQ ID NO: 13 and 14)
  vi) Linker (SEQ ID NO: 15 and 16)
  vii) CD4 (SEQ ID NO: 17 and 18).

In some embodiments, the TAC disclosed herein is a HER2-TAC. In some embodiments, the HER2-TAC comprises a nucleotide sequence having at least 70% sequence identity with SEQ ID NO: 65. In some embodiments, the HER2-TAC comprises a nucleotide sequence having at least 75% sequence identity with SEQ ID NO: 65. In some embodiments, the HER2-TAC comprises a nucleotide sequence having at least 80% sequence identity with SEQ ID NO: 65. In some embodiments, the HER2-TAC comprises a nucleotide sequence having at least 85% sequence identity with SEQ ID NO: 65. In some embodiments, the HER2-TAC comprises a nucleotide sequence having at least 90% sequence identity with SEQ ID NO: 65. In some embodiments, the HER2-TAC comprises a nucleotide sequence having at least 95% sequence identity with SEQ ID NO: 65. In some embodiments, the HER2-TAC comprises a nucleotide sequence of SEQ ID NO: 65.

In some embodiments, the HER2-TAC comprises an amino acid sequence having at least 70% sequence identity with SEQ ID NO: 66. In some embodiments, the HER2-TAC comprises an amino acid sequence having at least 75% sequence identity with SEQ ID NO: 66. In some embodiments, the HER2-TAC comprises an amino acid sequence having at least 80% sequence identity with SEQ ID NO: 66. In some embodiments, the HER2-TAC comprises an amino acid sequence having at least 85% sequence identity with SEQ ID NO: 66. In some embodiments, the HER2-TAC an amino acid sequence having at least 90% sequence identity with SEQ ID NO: 66. In some embodiments, the HER2-TAC comprises an amino acid sequence having at least 95% sequence identity with SEQ ID NO: 66. In some embodiments, the HER2-TAC comprises an amino acid sequence of SEQ ID NO: 66.

In some embodiments, the TAC disclosed herein is a HER2-TAC. In some embodiments, the HER2-TAC comprises a nucleotide sequence having at least 70% sequence identity with SEQ ID NO: 67. In some embodiments, the HER2-TAC comprises a nucleotide sequence having at least 75% sequence identity with SEQ ID NO: 67. In some embodiments, the HER2-TAC comprises a nucleotide sequence having at least 80% sequence identity with SEQ ID NO: 67. In some embodiments, the HER2-TAC comprises a nucleotide sequence having at least 85% sequence identity with SEQ ID NO: 67. In some embodiments, the HER2-TAC comprises a nucleotide sequence having at least 90% sequence identity with SEQ ID NO: 67. In some embodiments, the HER2-TAC comprises a nucleotide sequence having at least 95% sequence identity with SEQ ID NO: 67. In some embodiments, the HER2-TAC comprises a nucleotide sequence of SEQ ID NO: 67.

In some embodiments, the HER2-TAC comprises an amino acid sequence having at least 70% sequence identity with SEQ ID NO: 68. In some embodiments, the HER2-TAC comprises an amino acid sequence having at least 75% sequence identity with SEQ ID NO: 68. In some embodiments, the HER2-TAC comprises an amino acid sequence having at least 80% sequence identity with SEQ ID NO: 68. In some embodiments, the HER2-TAC comprises an amino acid sequence having at least 85% sequence identity with SEQ ID NO: 68. In some embodiments, the HER2-TAC an amino acid sequence having at least 90% sequence identity with SEQ ID NO: 68. In some embodiments, the HER2-TAC comprises an amino acid sequence having at least 95% sequence identity with SEQ ID NO: 68. In some embodiments, the HER2-TAC comprises an amino acid sequence of SEQ ID NO: 68.

In some embodiments, the TAC disclosed herein is a HER2-TAC. In some embodiments, the HER2-TAC comprises a nucleotide sequence having at least 70% sequence identity with SEQ ID NO: 75. In some embodiments, the HER2-TAC comprises a nucleotide sequence having at least 75% sequence identity with SEQ ID NO: 75. In some embodiments, the HER2-TAC comprises a nucleotide sequence having at least 80% sequence identity with SEQ ID NO: 75. In some embodiments, the HER2-TAC comprises a nucleotide sequence having at least 85% sequence identity with SEQ ID NO: 75. In some embodiments, the HER2-TAC comprises a nucleotide sequence having at least 90% sequence identity with SEQ ID NO: 75. In some embodiments, the HER2-TAC comprises a nucleotide sequence having at least 95% sequence identity with SEQ ID NO: 75. In some embodiments, the HER2-TAC comprises a nucleotide sequence of SEQ ID NO: 75.

In some embodiments, the HER2-TAC comprises an amino acid sequence having at least 70% sequence identity with SEQ ID NO: 76. In some embodiments, the HER2-TAC comprises an amino acid sequence having at least 75% sequence identity with SEQ ID NO: 76. In some embodiments, the HER2-TAC comprises an amino acid sequence having at least 80% sequence identity with SEQ ID NO: 76. In some embodiments, the HER2-TAC comprises an amino acid sequence having at least 85% sequence identity with SEQ ID NO: 76. In some embodiments, the HER2-TAC an amino acid sequence having at least 90% sequence identity with SEQ ID NO: 76. In some embodiments, the HER2-TAC comprises an amino acid sequence having at least 95% sequence identity with SEQ ID NO: 76. In some embodiments, the HER2-TAC comprises an amino acid sequence of SEQ ID NO: 76.

In some embodiments, the TAC disclosed herein is a BCMA-TAC. In some embodiments, the BCMA-TAC comprises a nucleotide sequence having at least 70% sequence identity with SEQ ID NO: 55, 57, 59 or 61. In some embodiments, the BCMA-TAC comprises a nucleotide sequence having at least 75% sequence identity with SEQ ID NO: 55, 57, 59 or 61. In some embodiments, the BCMA-TAC comprises a nucleotide sequence having at least 80% sequence identity with SEQ ID NO: 55, 57, 59 or 61. In some embodiments, the BCMA-TAC comprises a nucleotide sequence having at least 85% sequence identity with SEQ ID NO: 55, 57, 59 or 61. In some embodiments, the BCMA-TAC comprises a nucleotide sequence having at least 90% sequence identity with SEQ ID NO: 55, 57, 59 or 61. In some embodiments, the BCMA-TAC comprises a nucleotide sequence having at least 95% sequence identity with SEQ ID NO: 55, 57, 59 or 61. In some embodiments, the BCMA-TAC comprises a nucleotide sequence of SEQ ID NO: 55, 57, 59 or 61.

In some embodiments, the BCMA-TAC comprises an amino acid sequence having at least 70% sequence identity with SEQ ID NO: 56, 58, 60 or 62. In some embodiments, the BCMA-TAC comprises an amino acid sequence having at least 75% sequence identity with SEQ ID NO: 56, 58, 60 or 62. In some embodiments, the BCMA-TAC comprises an amino acid sequence having at least 80% sequence identity with SEQ ID NO: 56, 58, 60 or 62. In some embodiments, the BCMA-TAC comprises an amino acid sequence having at least 85% sequence identity with SEQ ID NO: 56, 58, 60 or 62. In some embodiments, the BCMA-TAC comprises an amino acid sequence having at least 90% sequence identity with SEQ ID NO: 56, 58, 60 or 62. In some embodiments, the BCMA-TAC comprises an amino acid sequence having at least 95% sequence identity with SEQ ID NO: 56, 58, 60 or 62. In some embodiments, the BCMA-TAC comprises an amino acid sequence of SEQ ID NO: 56, 58, 60 or 62.

In some embodiments, the TAC disclosed herein is a CD19-TAC. In some embodiments, the CD19-TAC comprises a nucleotide sequence having at least 70% sequence identity with SEQ ID NO: 63. In some embodiments, the CD19-TAC comprises a nucleotide sequence having at least 75% sequence identity with SEQ ID NO: 63. In some embodiments, the CD19-TAC comprises a nucleotide sequence having at least 80% sequence identity with SEQ ID NO: 63. In some embodiments, the CD19-TAC comprises a nucleotide sequence having at least 85% sequence identity with SEQ ID NO: 63. In some embodiments, the CD19-TAC comprises a nucleotide sequence having at least 90% sequence identity with SEQ ID NO: 63. In some embodiments, the CD19-TAC comprises a nucleotide sequence having at least 95% sequence identity with SEQ ID NO: 63. In some embodiments, the CD19-TAC comprises a nucleotide sequence of SEQ ID NO: 63.

In some embodiments, the CD19-TAC comprises an amino acid sequence having at least 70% sequence identity with SEQ ID NO: 64. In some embodiments, the CD19-TAC comprises an amino acid sequence having at least 75% sequence identity with SEQ ID NO: 64. In some embodiments, the CD19-TAC comprises an amino acid sequence having at least 80% sequence identity with SEQ ID NO: 64. In some embodiments, the CD19-TAC comprises an amino acid sequence having at least 85% sequence identity with SEQ ID NO: 64. In some embodiments, the CD19-TAC comprises an amino acid sequence having at least 90% sequence identity with SEQ ID NO: 64. In some embodiments, the CD19-TAC comprises an amino acid sequence having at least 95% sequence identity with SEQ ID NO: 64. In some embodiments, the CD19-TAC comprises an amino acid sequence of SEQ ID NO: 64.

Polypeptides and Vector Constructs

Disclosed herein, in certain embodiments, are polypeptides encoded by the nucleic acid sequence as disclosed herein. Also disclosed herein, are vectors comprising the nucleic acid sequence as disclosed herein. In some embodiments, the vectors further comprise a promoter. In some embodiments, the promoter is functional in a mammalian cell. Promoters, regions of DNA that initiate transcription of a particular nucleic acid sequence, are well known in the art. A "promoter functional in a mammalian cell" refers to a promoter that drives expression of the associated nucleic acid sequence in a mammalian cell. A promoter that drives expression of a nucleic acid sequence is referred to as being "operably connected" to the nucleic acid sequence.

A variety of delivery vectors and expression vehicles are employed to introduce nucleic acids described herein into a cell.

Disclosed herein, in certain embodiments, are polynucleotides comprised in a vector to provide a vector construct, also herein referred to as a vector. In some embodiments, the present disclosure provides a vector comprising:
 a. a first polynucleotide encoding a target-specific ligand;
 b. a second polynucleotide encoding a ligand that binds a protein associated with a TCR complex;
 c. a third polynucleotide encoding a T cell receptor signaling domain polypeptide; and
 d. a promoter that is functional in a mammalian cell.

In some embodiments, the target of the target-specific ligand binds to HER-2, BCMA, or CD19. In some embodiments, the target-specific ligand is a DARPin that selectively binds a HER-2 (erbB-2) antigen. In some embodiments, the target-specific ligand is a DARPin that specifically binds a HER-2 (erbB-2) antigen. In some embodiments, the DARPin targeted to HER-2 (erb-2) comprises SEQ ID NO: 7 or SEQ ID NO: 8. In some embodiments, the target-specific ligand is a scFv that selectively binds BCMA. In some embodiments, the target-specific ligand is a scFv that specifically binds BCMA. In some embodiments, the scFv that binds BCMA comprises SEQ ID NO: 33 or SEQ ID NO: 34. In some embodiments, the target-specific ligand is a scFv that selectively binds CD19. In some embodiments, the target-specific ligand is a scFv that specifically binds CD19. In some embodiments, the scFv that binds CD19 comprises SEQ ID NO: 35 or SEQ ID NO: 36.

In some embodiments, the ligand that binds a protein associated with a TCR complex is UCHT1, humanized UCHT1 (huUCHT1), OKT3, F6A, or L2K. In some embodiments, the ligand that binds a protein associated with a TCR complex is UCHT1, or a variant thereof. In some embodiments, the ligand that binds a protein associated with a TCR complex is UCHT1 and is encoded by SEQ ID NO: 13. In some embodiments, the ligand that binds a protein associated with a TCR complex is UCHT1 and comprises SEQ ID NO: 14 In some embodiments, the UCHT1 ligand that binds a protein associated with a TCR complex has a Y182T mutation (UCHT1 (Y182T)) and is encoded by SEQ ID NO: 71. In some embodiments, the ligand that binds a protein associated with a TCR complex is UCHT1 (Y182T) and comprises SEQ ID NO: 72. In some embodiments, the ligand that binds a protein associated with a TCR complex is humanized UCHT1 (huUCHT1), or a variant thereof. In some embodiments, the ligand that binds a protein associated with a TCR complex is humanized UCHT1 (huUCHT1) and is encoded by SEQ ID NO: 43. In some embodiments, the ligand that binds a protein associated with a TCR complex is huUCHT1 and comprises SEQ ID NO: 44. In some embodiments, the huUCHT1 ligand that binds a protein associated with a TCR complex has a Y177T mutation (huUCHT1 (Y177T)) and is encoded by SEQ ID NO: 45. In some embodiments, the ligand that binds a protein associated with a TCR complex is huUCHT1 (Y177T) and comprises SEQ ID NO: 46.

In some embodiments, the ligand that binds a protein associated with a TCR complex is OKT3, or a variant thereof. In some embodiments, the ligand that binds a protein associated with a TCR complex is OKT3 and is encoded by SEQ ID NO: 21. In some embodiments, the ligand that binds a protein associated with a TCR complex is OKT3 and comprises SEQ ID NO: 22.

In some embodiments, the ligand that binds a protein associated with a TCR complex is F6A, or a variant thereof. In some embodiments, the ligand that binds a protein associated with a TCR complex is F6A and is encoded by SEQ ID NO: 23. In some embodiments, the ligand that binds a protein associated with a TCR complex is F6A and comprises SEQ ID NO: 24.

In some embodiments, the ligand that binds a protein associated with a TCR complex is L2K, or a variant thereof. In some embodiments, the ligand that binds a protein associated with a TCR complex is L2K and is encoded by SEQ ID NO: 25. In some embodiments, the ligand that binds a protein associated with a TCR complex is L2K and comprises SEQ ID NO: 26.

In some embodiments, the protein associated with a TCR complex is CD3. In some embodiments, the protein associated with a TCR complex is CD3ε.

In some embodiments, the TCR signaling domain polypeptide comprises a transmembrane domain and/or a cytosolic domain of a TCR co-receptor. In some embodiments, the TCR co-receptor is CD4, CD8, LAG3, or a chimeric variation thereof.

In some embodiments, the first polynucleotide and third polynucleotide are fused to the second polynucleotide and the coding sequence is operably connected to the promoter. In some embodiments, the second polynucleotide and third polynucleotide are fused to the first polynucleotide and the coding sequence is operably connected to the promoter. In some embodiments, the vector is designed for expression in mammalian cells such as T cells. In some embodiments, the vector is a viral vector. In some embodiments, the viral vector is a retroviral vector.

In some embodiments, vectors that are useful comprise vectors derived from lentiviruses, Murine Stem Cell Viruses (MSCV), pox viruses, oncoretroviruses, adenoviruses, and adeno-associated viruses. Other delivery vectors that are useful comprise vectors derived from herpes simplex viruses, transposons, vaccinia viruses, human papilloma virus, Simian immunodeficiency viruses, HTLV, human foamy virus and variants thereof. Further vectors that are useful comprise vectors derived from spumaviruses, mammalian type B retroviruses, mammalian type C retroviruses, avian type C retroviruses, mammalian type D retroviruses and HTLV/BLV type retroviruses. One example of a lentiviral vector useful in the disclosed compositions and methods is the pCCL4 vector.

In some embodiments, the nucleic acid is a recombinant, or engineered, nucleic acid. In some embodiments, the first, second and/or third polynucleotides are recombinant, or engineered, polynucleotides. In some embodiments, the polynucleotides described herein are be modified or mutated to optimize the function of the encoded polypeptide and/or the function, activity and/or expression of the T cell antigen coupler. In some embodiments, the nucleic acid encodes a polypeptide.

In some embodiments, modifications are made to the polynucleotide sequences including vector sequences and polypeptides sequences disclosed herein. Modifications include substitution, insertion or deletion of nucleotides or amino acids or altering the relative positions or order of nucleotides or amino acids.

Expression in T Cells

Disclosed herein, in certain embodiments, are engineered T cells comprising the nucleic acid sequences disclosed herein, or the vectors disclosed herein. Disclosed herein, in certain embodiments, are human T cells engineered to express a Tri-TAC disclosed herein. In some embodiments, the T cell expresses a Tri-TAC disclosed herein. Further disclosed herein, are T cells transduced or transfected with T cell antigen coupler or a vector comprising a Tri-TAC. In some embodiments, the T cell is an isolated T cell.

In some embodiments, the human T cells engineered to express a Tri-TAC demonstrate functionality equivalent to a conventional CAR in vitro. In some embodiments, T cells engineered with the Tri-TAC demonstrate functionality superior to a conventional CAR in vitro. Disclosed herein, in some embodiments, are human T cells engineered with a Tri-TAC that demonstrate enhanced safety compared to traditional CARs. In some embodiments, human T cells engineered to express a Tri-TAC demonstrate enhanced safety compared to traditional CARs.

T cells, in some embodiments, are obtained from a number of sources, including, but not limited to blood (for example, peripheral blood mononuclear cells), bone marrow, thymus tissue, lymph node tissue, cord blood, thymus tissue, tissue from an infection site, spleen tissue, or tumors. In some embodiments, the T cells are autologous T cells. In some embodiments, the T cells are obtained from a cell line of T cells. In some embodiments, the T cells are obtained from donors (allogeneic T cells). In some embodiments, the T cells are obtained by differentiation of embryonic or adult stem cells or from induced pluripotent stem cells. In some embodiments, regardless of the source of T cells, the T cells have been modified so that they lack expression of an endogenous TCR and/or permanently or transiently lack expression of MHC/HLA molecules (universal donor T cells). In some embodiments, the T cells are autologous with respect to the subject. In some embodiments, the cells are allogeneic, syngeneic, or xenogeneic with respect to the subject.

In some embodiments, once obtained, the T cells are optionally enriched in vitro. In some embodiments, a population of cells is enriched by positive or negative selection. Further, the T cells are optionally frozen or cryopreserved and then thawed at a later date.

In some embodiments, T cells are activated and/or expanded before or after introducing the Tri-TAC to the T cells. In some embodiments, the T cells are expanded by contact with a surface having attached thereto an agent that stimulates a CD3/TCR complex associated signal and a ligand that stimulates a co-stimulator molecule on the surface of the T cells. In some embodiments, the T cells are expanded by contact with one or more soluble agents that stimulate CD3/TCR complex signaling and co-stimulator molecule signaling.

In some embodiments, the T cells are transduced or transfected with nucleic acid sequences. The transduced or transfected T cells express proteins coded for by the transfected or transduced nucleic acid sequences. A nucleic acid may be introduced into a cell by physical, chemical, or biological means. Physical means include, but are not limited to, microinjection, electroporation, particle bombardment, lipofection and calcium phosphate precipitation. Biological means include the use of DNA and RNA vectors.

Viral vectors, including retroviral vectors, are used to introduce and express a nucleic acid into a T cell. Viral vectors include vectors derived from lentivirus, Murine Stem Cell Viruses (MSCV), pox viruses, herpes simplex virus I, adenovirus and adeno-associated viruses. The vector optionally includes a promoter that drives expression of the transduced nucleic acid molecule in a T cell (e.g., a CMV promoter, eF1a promoter, or MSCV promoter).

Any suitable assay is used to confirm the presence and/or expression of the transduced nucleic acid sequence and/or the polypeptide encoded by the nucleic acid in the T cell. Assays include, but are not limited to, Southern and Northern blotting, RT-PCR and PCR, ELISA, Western blotting, and flow cytometry.

A T cell expressing a TAC has increased T cell activation in the presence of an antigen compared to a T cell not expressing a TAC and/or as compared to a T cell expressing a traditional CAR. Increased T cell activation is ascertained by numerous methods, including but not limited to, increased tumor cell line killing, increased cytokine production, increased cytolysis, increased degranulation and/or increased expression of activation markers such as CD107α, IFNγ, IL2 or TNFα. In some embodiments, increases are measured in an individual cell or in a population of cells.

The terms "increased" or "increasing" as used herein refer to at least a 1%, 2%, 5%, 10%, 25%, 50%, 100% or 200% increase in a T cell or population of T cells expressing a TAC compared to a T cell or population of T cells not expressing a TAC and/or as compared to a T cell or population of T cells expressing a traditional CAR.

Pharmaceutical Compositions

Disclosed herein, in certain embodiments, are pharmaceutical compositions comprising an engineered T cell disclosed herein (transduced with and/or expressing a TAC), and a pharmaceutically acceptable carrier. Pharmaceutically acceptable carriers include, but are not limited to, buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); or preservatives. In some embodiments, the engineered T cells are formulated for intravenous administration.

Pharmaceutical compositions are administered in a manner appropriate to the disease to be treated (or prevented). The quantity and frequency of administration is determined by such factors as the condition of the patient, and the type and severity of the patient's disease, although appropriate dosages are determined by clinical trials. When "an immunologically effective amount," "an anti-tumor effective amount," "a tumor-inhibiting effective amount," or "therapeutic amount" is indicated, the precise amount of the compositions of the present invention to be administered is determined by a physician with consideration of individual differences in age, weight, tumor size, extent of infection or metastasis, and condition of the patient (subject).

In some embodiments, the modified T cells and/or pharmaceutical compositions described herein are administered at a dosage of $10^1$ to $10^{15}$ cells per kg body weight, $10^4$ to $10^9$ cells per kg body weight, optionally $10^5$ to $10^8$ cells per kg body weight, $10^6$ to $10^7$ cells per kg body weight or $10^5$ to $10^6$ cells per kg body weight, including all integer values within those ranges. In some embodiments, the modified T cells and/or pharmaceutical compositions described herein are administered at a dosage of greater than $10^1$ cells per kg body weight. In some embodiments, the modified T cells and/or pharmaceutical compositions described herein are administered at a dosage of less than $10^{15}$ cells per kg body weight.

In some embodiments, the modified T cells and/or pharmaceutical compositions described herein are administered at a dosage of $0.5 \times 10^6$ cells, $2 \times 10^6$ cells, $4 \times 10^6$ cells, $5 \times 10^6$ cells, $1.2 \times 10^7$ cells, $2 \times 10^7$ cells, $5 \times 10^7$ cells, $2 \times 10^8$ cells, $5 \times 10^8$ cells, $2 \times 10^9$ cells, $0.5$-$2000 \times 10^6$ cells, $0.5$-$2 \times 10^6$ cells, $0.5$-$2 \times 10^7$ cells, $0.5$-$2 \times 10^8$ cells, or $0.5$-$2 \times 10^9$ cells, including all integer values within those ranges.

In some embodiments, T cell compositions are administered multiple times at these dosages. In some embodiments, the dosage is administered a single time or multiple times, for example daily, weekly, biweekly, or monthly, hourly, or is administered upon recurrence, relapse or progression of the cancer being treated. The cells, in some embodiments, are administered by using infusion techniques that are commonly known in immunotherapy (see, e.g., Rosenberg et al., New Eng. J. of Med. 319:1676, 1988).

The pharmaceutical composition is substantially free of, e.g., there are no detectable levels of a contaminant, e.g., selected from the group consisting of endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium a fungus, mycoplasma, IL-2, and IL-7.

In some embodiments, engineered T-cells disclose herein are administered to a subject and blood is subsequently redrawn (or apheresis performed), T-cells therefrom are activated and reinfused into the patient with engineered T cells. This process, in some embodiments, is carried out multiple times every few weeks. T-cells are activated from blood draws of from 10 cc to 400 cc. T-cells are activated from blood draws of 20 cc, 30 cc, 40 cc, 50 cc, 60 cc, 70 cc, 80 cc, 90 cc, or 100 cc.

The modified/engineered T cells and/or pharmaceutical compositions are administered by methods including, but not limited to, aerosol inhalation, injection, infusion, ingestion, transfusion, implantation or transplantation. The modified T cells and/or pharmaceutical compositions are administered to a subject transarterially, subcutaneously, intradermally, intratumorally, intranodally, intramedullary, intramuscularly, by intravenous (i.v.) injection, by intravenous (i.v.) infusion, or intraperitoneally. The modified/engineered T cells and/or pharmaceutical compositions thereof are administered to a patient by intradermal or subcutaneous injection. The modified/engineered T cells and/or pharmaceutical compositions thereof are administered by i.v. injection. The modified/engineered T cells and/or pharmaceutical compositions thereof are injected directly into a tumor, lymph node, or site of infection.

The modified/engineered T cells T cells and/or pharmaceutical compositions are administered in a volume of about 5 mL, 10 mL, 15 mL, 20 mL, 25 mL, 30 mL, 35 mL, 40 mL, 45 mL, 50 mL, 60 mL, 70 mL, 80 mL, 90 mL, 100 mL, 110 mL, 120 mL, 130 mL, 140 mL, 150 mL, 200 mL, 300 mL, 400 mL, or 500 mL.

The modified/engineered T cells T cells and/or pharmaceutical compositions are administered in a volume of at greater than at most about 5 mL, 10 mL, 15 mL, 20 mL, 25 mL, 30 mL, 35 mL, 40 mL, 45 mL, 50 mL, 60 mL, 70 mL, 80 mL, 90 mL, 100 mL, 110 mL, 120 mL, 130 mL, 140 mL, 150 mL, 200 mL, 300 mL, 400 mL, or 500 mL.

The modified/engineered T cells T cells and/or pharmaceutical compositions are administered in a volume of at least about 5 mL, 10 mL, 15 mL, 20 mL, 25 mL, 30 mL, 35 mL, 40 mL, 45 mL, 50 mL, 60 mL, 70 mL, 80 mL, 90 mL, 100 mL, 110 mL, 120 mL, 130 mL, 140 mL, 150 mL, 200 mL, 300 mL, 400 mL, or 500 mL.

A pharmaceutical composition is prepared by per se known methods for the preparation of pharmaceutically acceptable compositions that are administered to subjects, such that an effective quantity of the T cells is combined in a mixture with a pharmaceutically acceptable carrier. Suitable carriers are described, for example, in Remington's Pharmaceutical Sciences (Remington's Pharmaceutical Sciences, 20$^{th}$ ed., Mack Publishing Company, Easton, Pa., USA, 2000). On this basis, the compositions include, albeit not exclusively, solutions of the substances in association with one or more pharmaceutically acceptable carriers or diluents, and contained in buffered solutions with a suitable pH and iso-osmotic with the physiological fluids.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, N-(1(2,3-dioleyloxy)propyl)N,N,N-trimethylammonium chloride (DOTMA), diolesylphosphotidyl-ethanolamine (DOPE), and liposomes. In some embodiments, such compositions contain a therapeutically effective amount of the compound, together with a suitable amount of carrier so as to provide the form for direct administration to the patient.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions.

A pharmaceutical composition disclosed herein is formulated into a variety of forms and administered by a number of different means. A pharmaceutical formulation is administered orally, rectally, or parenterally, in formulations containing conventionally acceptable carriers, adjuvants, and vehicles as desired. The term "parenteral" as used herein includes subcutaneous, intravenous, intramuscular, or intrasternal injection and infusion techniques. Administration includes injection or infusion, including intra-arterial, intracardiac, intracerebroventricular, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration. In some exemplary embodiments, a route of administration is via an injection such as an intramuscular, intravenous, subcutaneous, or intraperitoneal injection.

Liquid formulations include an oral formulation, an intravenous formulation, an intranasal formulation, an ocular formulation, an otic formulation, an aerosol, and the like. In certain embodiments, a combination of various formulations is administered. In certain embodiments a composition is formulated for an extended release profile.

Methods of Treatment and Use

Disclosed herein, in certain embodiments, are methods of use of Tri-TACs disclosed herein in the treatment of cancer in an individual in need thereof. In some embodiments, a target-specific ligand of the TACs disclosed herein bind to a tumor antigen or tumor associated antigen on a tumor cell. In some embodiments, a target-specific ligand of the TACs disclosed herein selectively bind to a tumor antigen or tumor associated antigen on a tumor cell. In some embodiments, a target-specific ligand of the TACs disclosed herein specifically bind to a tumor antigen or tumor associated antigen on a tumor cell. In some embodiments, the target antigen is a tumor antigen. Examples of tumor antigens include, but are not limited to, CD19, HER-2 (erbB-2), B-cell maturation antigen (BCMA), alphafetoprotein (AFP), carcinoembryonic antigen (CEA), CA-125, MUC-1, epithelial tumor antigen (ETA), tyrosinase, melanoma-associated antigen (MAGE), prostate-specific antigen (PSA), glioma-associated antigen, β-human chorionic gonadotropin, thyroglobulin, RAGE-1, MN-CA IX, human telomerase reverse transcriptase, RU1, RU2 (AS), intestinal carboxyl esterase, mut hsp70-2, M-CSF, prostase, PAP, NY-ESO-1, LAGE-1a, p53, prostein, PSMA, survivin and telomerase, prostate-carcinoma tumor antigen-1 (PCTA-1), ELF2M, neutrophil elastase, CD22, insulin growth factor (IGF)-I, IGF-II, IGF-I receptor and mesothelin.

Disclosed herein, in certain embodiments, are methods of treating a cancer expressing a target antigen in an individual in need thereof, comprising administering to the individual engineered T cells disclosed herein. In some embodiments, the target antigen is CD19. In some embodiments, the method of treating a cancer expressing CD19 in an individual in need thereof comprises administering to the individual engineered T cells comprising a TAC comprising a CD19-targeting ligand. In some embodiments, examples of cancers that are treated by a TAC comprising a CD19-targeting ligand include, but are not limited to B cell malignancies. In some embodiments, examples of cancers that are treated by a TAC comprising a CD19-targeting ligand include, but are not limited to B cell lymphomas, acute lymphoblastic leukemia (ALL), and chronic lymphocytic leukemia (CLL). In some embodiments, examples of cancers that are treated by a TAC comprising a CD19-targeting ligand include, but are not limited to Non-Hodgkin's lymphoma (NHL).

In some embodiments, the target antigen is HER-2. In some embodiments, the method of treating a cancer wherein a cancer cell expresses HER-2 in an individual in need thereof comprises administering to the individual engineered T cells comprising a TAC comprising a HER-2-targeting ligand. In some embodiments, examples of cancers that are treated by a TAC comprising a HER-2-targeting ligand include, but are not limited to breast cancer, bladder cancer, pancreatic cancer, ovarian cancer, and stomach cancer.

In some embodiments, the target antigen is BCMA. In some embodiments, the method of treating a cancer wherein a cancer cell expresses BCMA in an individual in need thereof comprises administering to the individual engineered T cells comprising a TAC comprising a BCMA-targeting ligand. In some embodiments, examples of cancers that are treated by a TAC comprising a BCMA-targeting ligand include, but are not limited to leukemia, lymphomas, and multiple myeloma.

Further disclosed herein is use of an engineered T cell disclosed herein in the preparation of a medicament to treat cancer in an individual in need thereof. Also disclosed herein is the use of a mixture of T cells comprising modified and unmodified cells, or comprising different populations of modified cells with or without unmodified cells. One of ordinary skill in the art would understand that a therapeutic quantity of modified T cells need not be homogenous in nature.

In some embodiment, the engineered T cells disclosed herein are part of a combination therapy. In some embodiments, effectiveness of a therapy disclosure herein is assessed multiple times. In some embodiments, patients are stratified based on a response to a treatment disclosed herein. In some embodiments, an effectiveness of treatment determines entrance into a trial.

In some embodiments, cancers that are treated engineered T cells comprising any one of the TAC disclosed herein include any form of neoplastic disease. In some embodiments, examples of cancers that are treated include, but are not limited to breast cancer, lung cancer and leukemia, for example mixed lineage leukemia (MLL), chronic lymphocytic leukemia (CLL) acute lymphoblastic leukemia (ALL). In some embodiments, examples of cancers that are treated include, but are not limited to large B-cell lymphoma, diffuse large B-cell lymphoma, primary mediastinal B cell lymphoma, high grade B-cell lymphoma, or large B cell lymphoma arising from follicular lymphoma. Other cancers include carcinomas, blastomas, melanomas, sarcomas, hematological cancers, lymphoid malignancies, benign and malignant tumors, and malignancies. In some embodiments, the cancer comprises non-solid tumors or solid tumors. In some embodiments, cancers that are treated include tumors that are not vascularized, or not yet substantially vascularized, as well as vascularized tumors. In some embodiments, the cancer is a solid cancer or comprises a solid tumor. In some embodiments, the cancer is a liquid cancer or comprises a liquid tumor. In some embodiments, the cancer is a lung cancer, a breast cancer, a colon cancer, multiple myeloma, glioblastoma, gastric cancer, ovarian cancer, stomach cancer, colorectal cancer, urothelial cancer, endometrial cancer, or a melanoma. In some embodiments, the cancer is a lung cancer. In some embodiments, the cancer is a breast cancer. In some embodiments, the cancer is a colon cancer. In some embodiments, the cancer is multiple myeloma. In some embodiments, the cancer is a glioblastoma. In some embodiments, the cancer is a gastric cancer. In some embodiments, the cancer is an ovarian cancer. In some embodiments, the cancer is a stomach cancer. In some embodiments, the cancer is a colorectal cancer. In some embodiments, the cancer is urothelial cancer. In some embodiments, the cancer is an endometrial cancer. In some embodiments, the cancer is a melanoma.

TABLE 1

Table of Sequences

| SEQ ID NO | Description | Nucleotide/ Amino Acid |
|---|---|---|
| SEQ ID NO: 1 | Tri TAC Configuration 1 | Nucleotide |
| SEQ ID NO: 2 | Tri TAC Configuration 1 | Amino Acid |
| SEQ ID NO: 3 | Tri TAC Configuration 2 | Nucleotide |
| SEQ ID NO: 4 | Tri TAC Configuration 2 | Amino Acid |
| SEQ ID NO: 5 | muIgG leader (secretion signal) | Nucleotide |
| SEQ ID NO: 6 | muIgG leader (secretion signal) | Amino Acid |
| SEQ ID NO: 7 | DARPin specific for Her2 antigen | Nucleotide |
| SEQ ID NO: 8 | DARPin specific for Her2 antigen | Amino Acid |
| SEQ ID NO: 9 | Myc Tag | Nucleotide |
| SEQ ID NO: 10 | Myc Tag | Amino Acid |
| SEQ ID NO: 11 | Linker 1 | Nucleotide |
| SEQ ID NO: 12 | Linker 1 | Amino Acid |
| SEQ ID NO: 13 | UCHT1[1] | Nucleotide |
| SEQ ID NO: 14 | UCHT1[2] | Amino Acid |
| SEQ ID NO: 15 | Linker 2 | Nucleotide |
| SEQ ID NO: 16 | Linker 2 | Amino Acid |
| SEQ ID NO: 17 | CD4 Domain[3] | Nucleotide |
| SEQ ID NO: 18 | CD4 Domain[4] | Amino Acid |
| SEQ ID NO: 19 | CD4 based linker | Nucleotide |
| SEQ ID NO: 20 | CD4 based linker | Amino Acid |
| SEQ ID NO: 21 | OKT3 | Nucleotide |
| SEQ ID NO: 22 | OKT3 | Amino Acid |
| SEQ ID NO: 23 | F6A | Nucleotide |
| SEQ ID NO: 24 | F6A | Amino Acid |
| SEQ ID NO: 25 | L2K | Nucleotide |
| SEQ ID NO: 26 | L2K | Amino Acid |
| SEQ ID NO: 27 | Short Helix connector | Nucleotide |
| SEQ ID NO: 28 | Short Helix connector | Amino Acid |
| SEQ ID NO: 29 | Long Helix connector | Nucleotide |
| SEQ ID NO: 30 | Long Helix connector | Amino Acid |
| SEQ ID NO: 31 | Large domain connector | Nucleotide |
| SEQ ID NO: 32 | Large domain connector | Amino Acid |
| SEQ ID NO: 33 | ScFv specific for BCMA antigen | Nucleotide |
| SEQ ID NO: 34 | ScFv specific for BCMA antigen | Amino Acid |
| SEQ ID NO: 35 | ScFv specific for CD19 antigen | Nucleotide |
| SEQ ID NO: 36 | ScFv specific for CD19 antigen | Amino Acid |
| SEQ ID NO: 37 | CD8α Domain | Nucleotide |
| SEQ ID NO: 38 | CD8α Domain | Amino Acid |
| SEQ ID NO: 39 | CD8α + R(β) Domain | Nucleotide |
| SEQ ID NO: 40 | CD8α + R(β) Domain | Amino Acid |
| SEQ ID NO: 41 | CD8 α + Lck Domain | Nucleotide |
| SEQ ID NO: 42 | CD8 α + Lck Domain | Amino Acid |
| SEQ ID NO: 43 | huUCHT1 | Nucleotide |
| SEQ ID NO: 44 | huUCHT1 | Amino Acid |
| SEQ ID NO: 45 | huUCHT1 (Y177T) | Nucleotide |
| SEQ ID NO: 46 | huUCHT1 (Y177T) | Amino Acid |
| SEQ ID NO: 47 | huIgG | Nucleotide |
| SEQ ID NO: 48 | huIgG | Amino Acid |
| SEQ ID NO: 49 | huCD8a | Nucleotide |
| SEQ ID NO: 50 | huCD8a | Amino Acid |
| SEQ ID NO: 51 | 3625 scFv BCMA Vh-Vl | Nucleotide |
| SEQ ID NO: 52 | 3625 scFv BCMA Vh-Vl | Amino Acid |
| SEQ ID NO: 53 | 3625 scFv BCMA Vl-Vh | Nucleotide |
| SEQ ID NO: 54 | 3625 scFv BCMA Vl-Vh | Amino Acid |
| SEQ ID NO: 55 | 3625 TAC Helix Vh-Vl huUCHT1 | Nucleotide |
| SEQ ID NO: 56 | 3625 TAC Helix Vh-Vl huUCHT1 | Amino Acid |
| SEQ ID NO: 57 | 3625 TAC Helix Vl-Vh huUCHT1 | Nucleotide |
| SEQ ID NO: 58 | 3625 TAC Helix Vl-Vh huUCHT1 | Amino Acid |
| SEQ ID NO: 59 | 3625 TAC G4S Vh-Vl huUCHT1 | Nucleotide |
| SEQ ID NO: 60 | 3625 TAC G4S Vh-Vl huUCHT1 | Amino Acid |
| SEQ ID NO: 61 | 3625 TAC G4S VL-VH huUCHT1 | Nucleotide |
| SEQ ID NO: 62 | 3625 TAC G4S VL-VH huUCHT1 | Amino Acid |
| SEQ ID NO: 63 | CD19-TAC | Nucleotide |
| SEQ ID NO: 64 | CD19-TAC | Amino Acid |
| SEQ ID NO: 65 | huIgG Her2 TAC huUCHT1 | Nucleotide |
| SEQ ID NO: 66 | huIgG Her2 TAC huUCHT1 | Amino Acid |
| SEQ ID NO: 67 | CD8a Her2 TAC huUCHT1 | Nucleotide |
| SEQ ID NO: 68 | CD8a Her2 TAC huUCHT1 | Amino Acid |
| SEQ ID NO: 69 | Flexible Connector | Amino Acid |
| SEQ ID NO: 70 | Flexible Connector | Nucleotide |
| SEQ ID NO: 71 | UCHT1(Y182T) | Nucleotide |
| SEQ ID NO: 72 | UCHT1 (Y182T) | Amino Acid |
| SEQ ID NO: 73 | G4S flexible linker | Amino Acid |
| SEQ ID NO: 74 | G4S3 linker | Amino Acid |
| SEQ ID NO: 75 | muIgG Her2 TAC huUCHT1 | Nucleotide |
| SEQ ID NO: 76 | muIgG Her2 TAC huUCHT1 | Amino Acid |
| SEQ ID NO: 77 | G4S3 linker | Nucleotide |

[1]Light chain, nucleotides 1-324; Linker, nucleotides 325-387; Heavy chain, nucleotides 388-750
[2]Light chain, amino acids 1-108; Linker, amino acids 109-128; Heavy chain, amino acids 129-250
[3]Extracellular linker, nucleotides 1-66; Transmembrane domain, nucleotides 67-132; Cytosolic domain, nucleotides 133-254
[4]Extracellular linker, amino acids 1-22; Transmembrane domain, amino acids 23-44; Cytosolic domain, amino acids 45-84

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1. Characterization of the Tri-TAC Technology

Figure 1B:
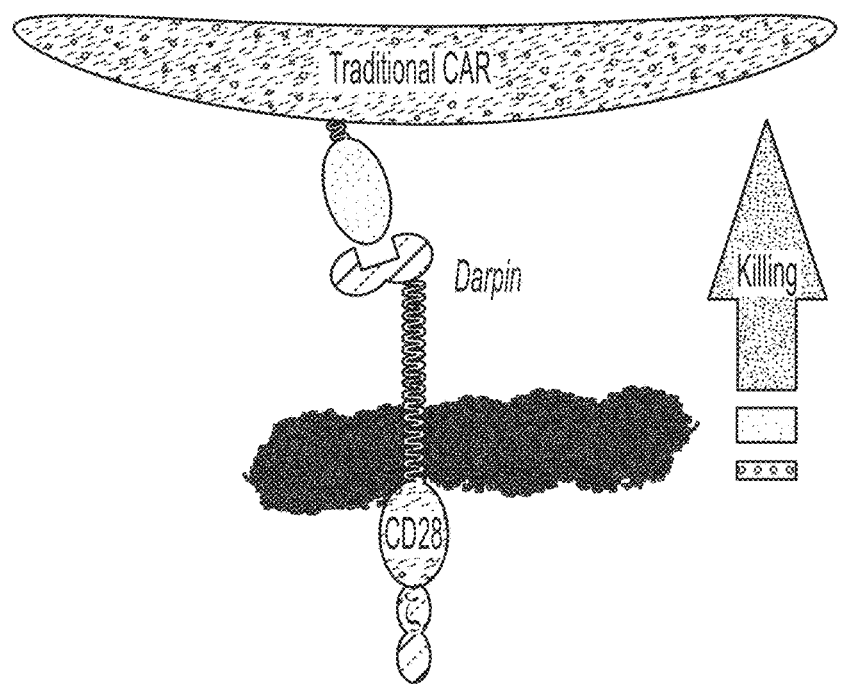
FIG. 1B is a schematic of CAR based T-cell activation.
Figure 1C:
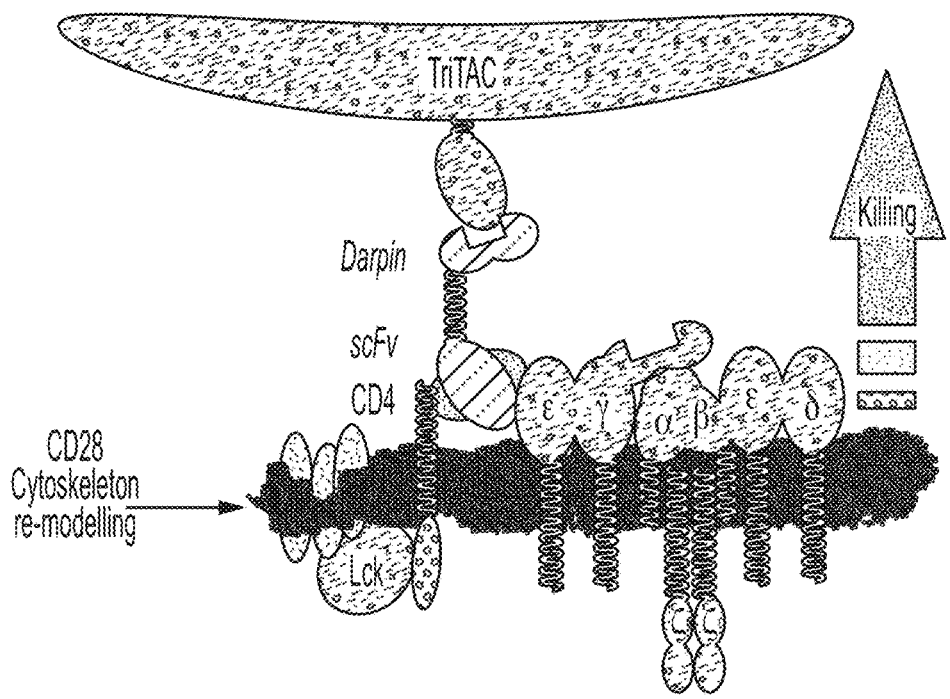
FIG. 1C is a schematic of a trifunctional-T cell-antigen coupler (Tri-TAC) based T cell activation.
Figure 1D:
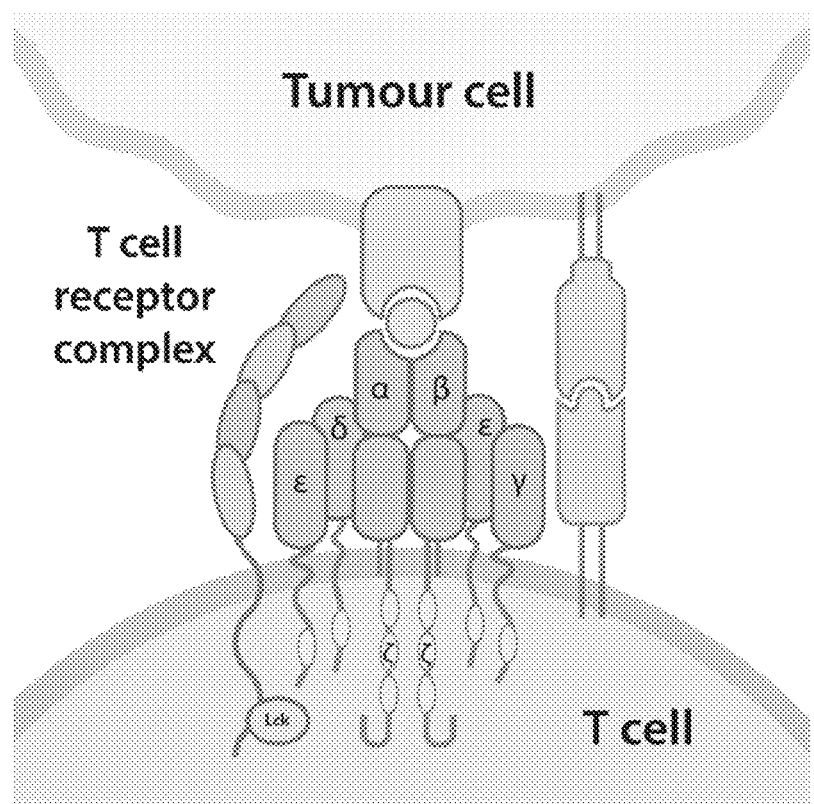
FIG. 1D is a schematic of natural T-cell activation.
Figure 1E:
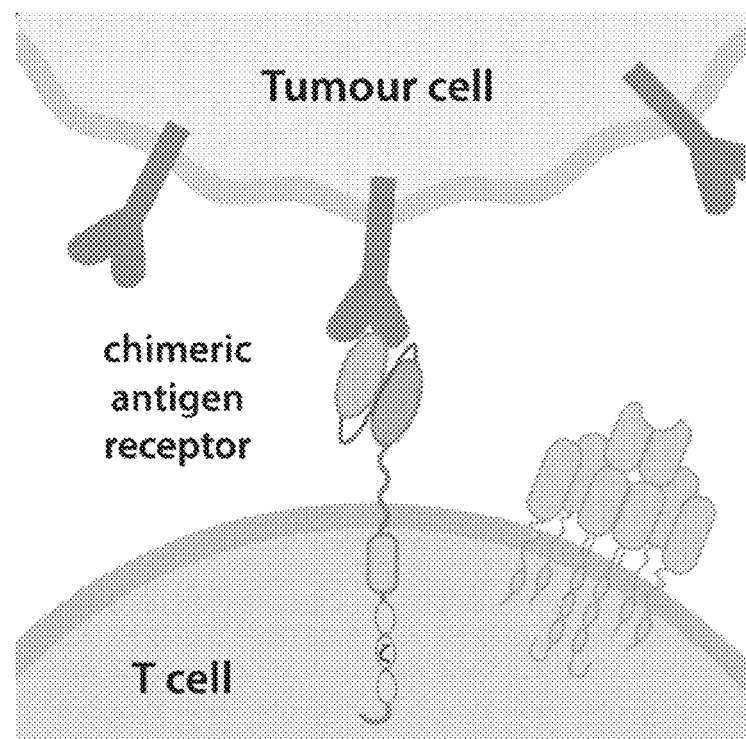
FIG. 1E is a schematic of CAR based T-cell activation.
Figure 1F:
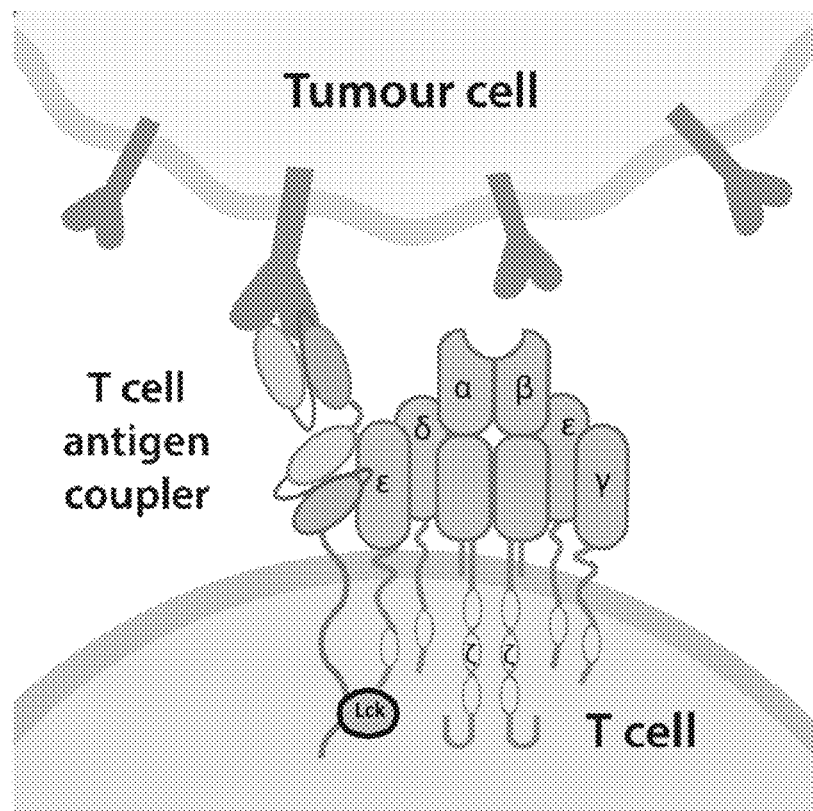
FIG. 1F is a schematic of Tri-TAC based T cell activation.

An overview of the Tri-TAC technology is provided in FIG. 1A-FIG. 1C.

FIG. 1A shows an example of CD8 T-cell activation based on the co-assembly of different receptors and their associated protein partners. Initially, the major histocompatibility complex I is presenting an antigen (helix). This is recognized by a T cell receptor (TCR) complex capable of binding the antigen. The TCR complex contains several individual subunits. The α/β domains are able to interact directly with the antigen presented on MHC-I. The α/β domains then interact with several other domains (ϵ, γ, δ, and ξ), all of which participate in T-cell activation via various intracellular activation domains. The TCR complex interacts with MHC-I concurrently with the CD8 co-receptor. The CD8 co-receptor binds to the MHC-I in an antigen independent manner. CD8 directly interacts with Lck, a protein kinase important for activating the TCR receptor complex. The CD8 and Lck interaction also ensures their association with lipid rafts (membrane portion) microdomains, which are hypothesized to organize and encapsulate other relevant signaling moieties (dark spheres). Later stages of activation then lead to CD28 recruitment. If this interaction cascade occurs several times in parallel, T-cells become activated and are able to exert their cytotoxic effects.

FIG. 1B provides an overview of Chimeric Antigen Receptors (CAR). CARs seek to reproduce the complex mechanism of T-cell activation by combining several key activation domains, such as CD3ξ and CD28 in a single synthetically engineered molecule. The CAR then directly interacts with an antigen of choice using specific binding domains. Depicted here is an ankyrin repeat protein (DARPin). It is believed that several such interactions occurring in parallel lead to T-cell activation.

FIG. 1C is an overview of the Tri-TAC technology mimicking the natural activation process. The Tri-TAC was developed to better recapitulate the natural signaling through the TCR, while retaining MHC unrestricted targeting. T-cell activation occurs following ligation of MHC by the TCR and T cell co-receptor (either CD4 or CD8), which simultaneously bind to conserved regions within the MHC molecule. The co-receptors are specifically located within "lipid rafts", membrane micro domains that are particularly important for TCR signal complex formation. In addition to ensuring the correct microdomain localization of the TCR activation complex, these co-receptors also bind directly to Lck, a protein kinase that is crucial for T-cell activation. None of the traditional chimeric receptors or bi-functional proteins engage the co-receptor molecules or Lck. A molecule was created where the transmembrane and intracellular regions of the CD4 co-receptor, which localize to the lipid raft and bind Lck, respectively, were fused to single-chain antibody that binds CD3 (UCHT1; SEQ ID NO: 13, 14 and homologs thereof). This construct is designed to draw the CD3 molecule and the TCR into regions of lipid rafts and bring Lck into the proximity of the TCR, similar to natural MHC binding. To target this receptor, a designed ankyrin repeat (DARPin) was linked to the CD4-UCHT1 chimera to generate a Trifunctional T cell-antigen coupler (Tri-TAC). In this example, the DARPin was specific for the proto-oncogene, HER-2 (erbB-2).

Figure 2A:
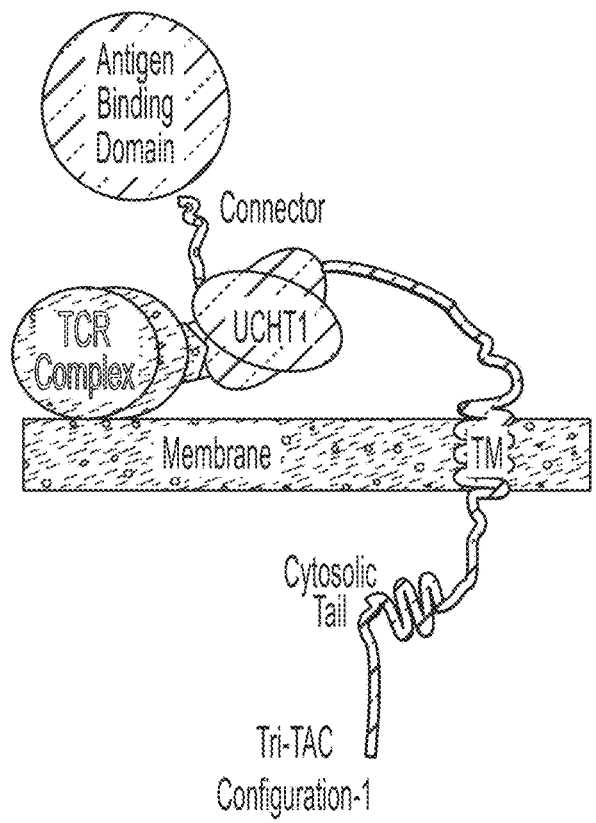
FIG. 2A is a schematic of a Tri-TAC configuration with the UCHT1 domain being centered between the trans-membrane domain (TM) and the antigen binding domain.
Figure 2B:
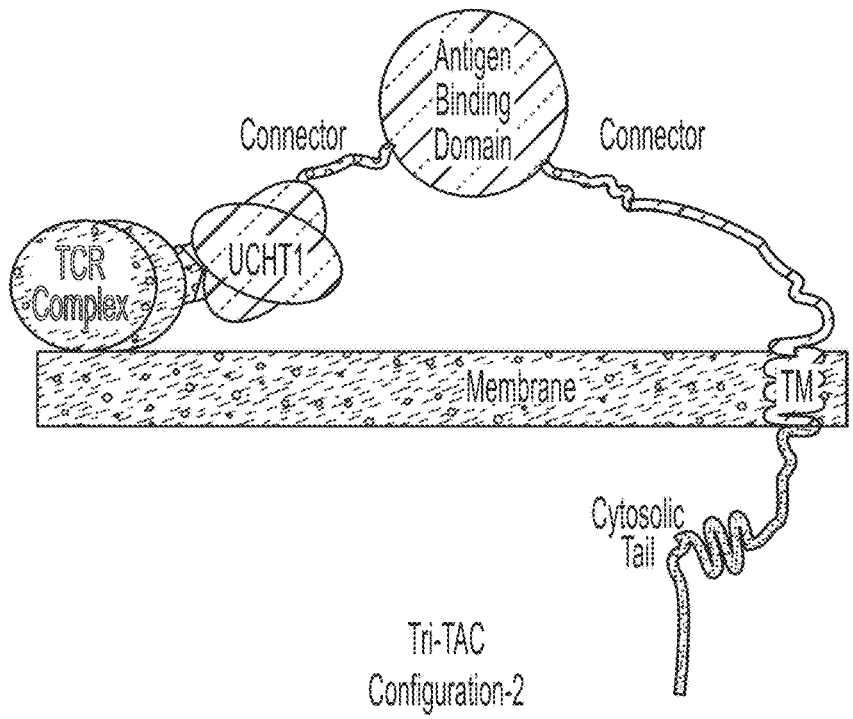
FIG. 2B is a schematic of a Tri-TAC configuration in which the UCHT1 domain is N-terminal, followed by the antigen binding domain and the trans-membrane domain.
Figure 2C:
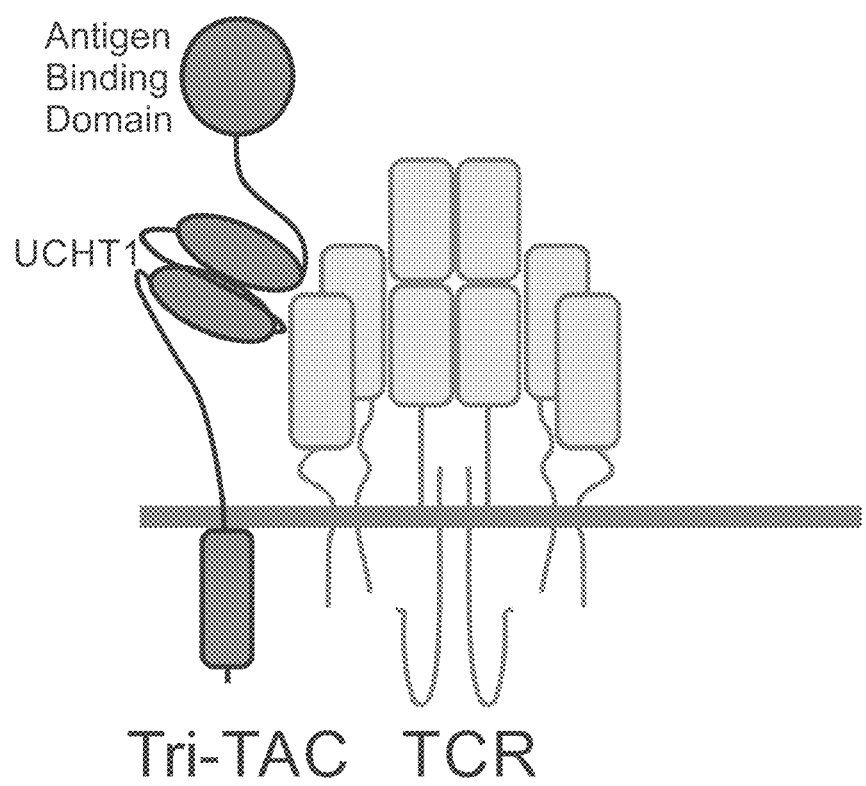
FIG. 2C is a schematic of a Tri-TAC molecule with a generic antigen binding domain and a UCHT1 domain.

Multiple Tri-TAC configurations are possible (FIG. 2A and FIG. 2B). In configuration 1 (FIG. 2A) the Antigen binding domain is located N-terminal, connected to the CD3 ligand binding domain and then the co-receptor domain. In configuration 2 (FIG. 2B) the CD3 ligand binding domain is located N-terminal, connected to the antigen binding domain which in turn connects to the co-receptor domain.

Figure 3A:
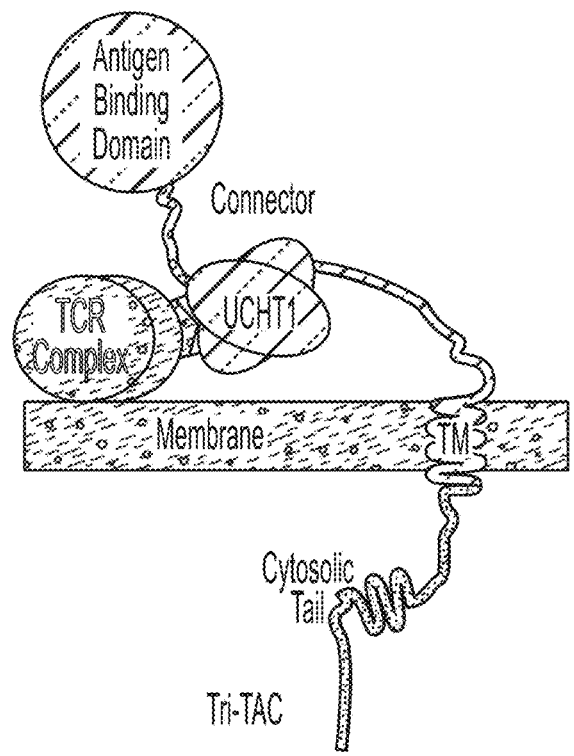
FIG. 3A is a schematic of a Tri-TAC molecule with a generic antigen binding domain.
Figure 3B:
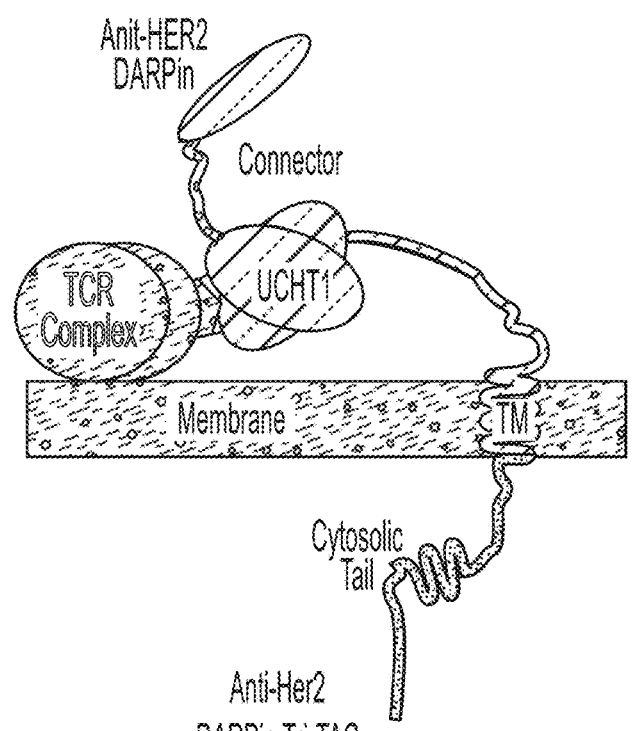
FIG. 3B is a schematic of a Tri-TAC with an anti-HER-2 DARPin antigen binding domain.
Figure 3C:
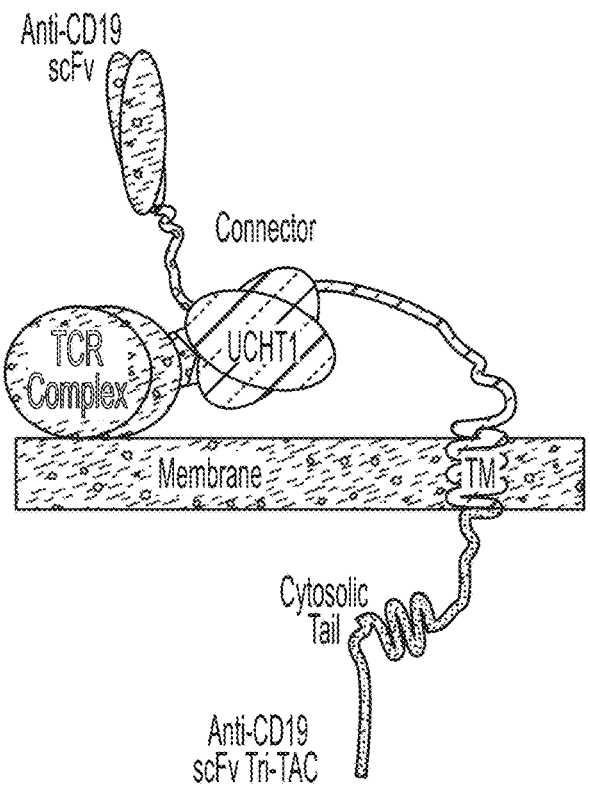
FIG. 3C is a schematic of a Tri-TAC with an anti-CD19 scFv antigen binding domain.
Figure 3D:
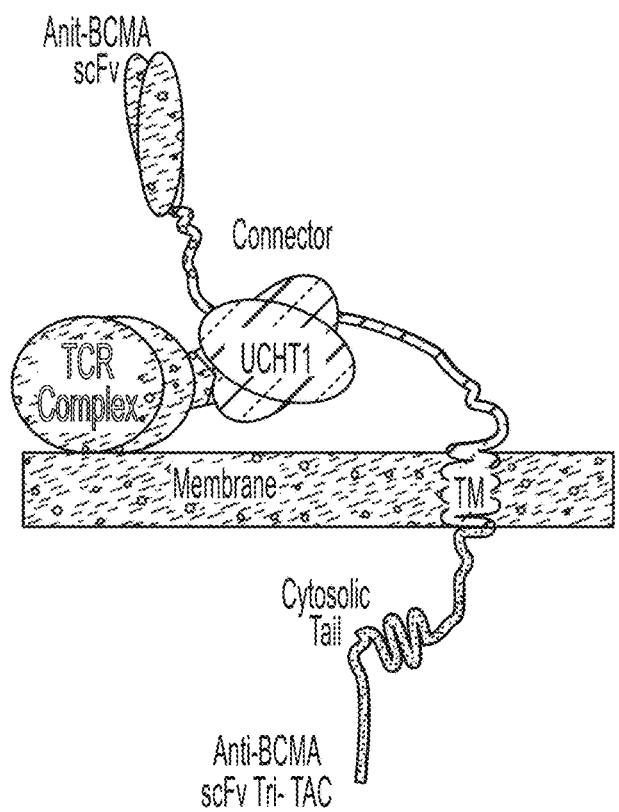
FIG. 3D is a schematic of a Tri-TAC with an anti-BCMA scFv antigen binding domain.
Figure 3E:
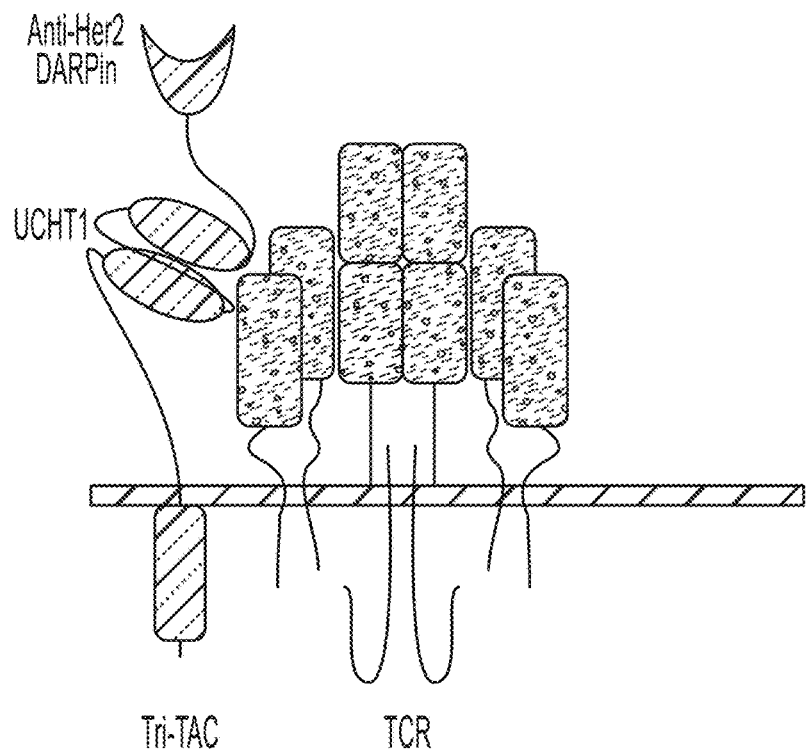
FIG. 3E is a schematic of a Tri-TAC molecule with the Anti-HER-2 DARPin antigen binding domain.
Figure 3F:
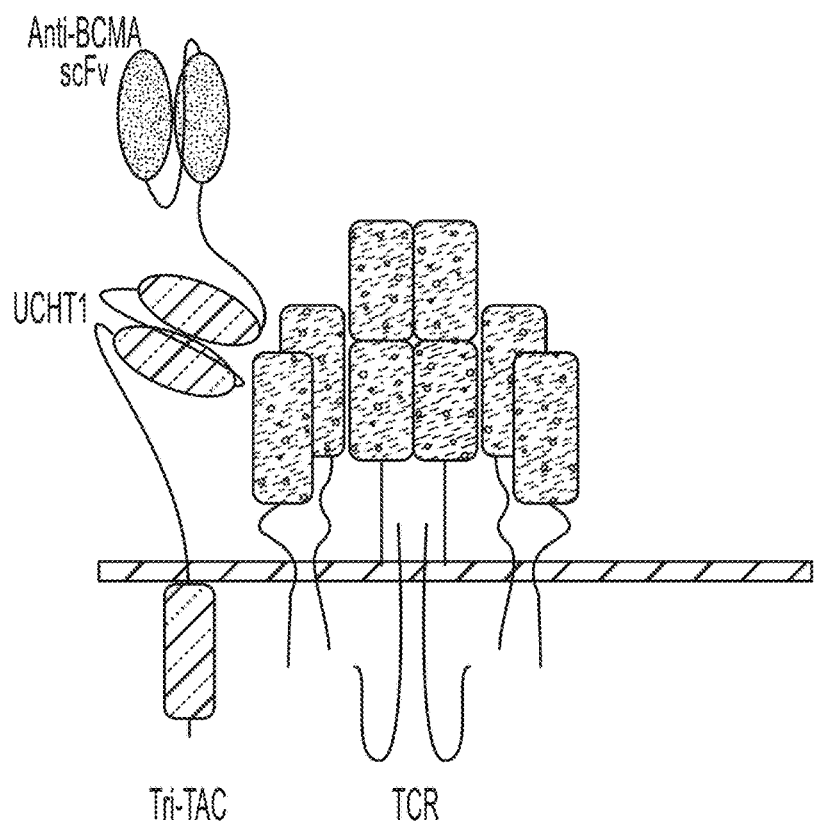
FIG. 3F is a schematic of a Tri-TAC molecule with the Anti-BCMA scFv antigen binding domain.

Multiple classes of ligand binding domains can be incorporated into the Tri-TAC molecule (FIG. 3A-FIG. 3D). The examples herein illustrate a general schematic of a configuration 1 Tri-TAC (FIG. 3A), a Tri-TAC bearing a HER-2-specific DARPin (FIG. 3B), a Tri-TAC bearing a CD19-specific scFv (FIG. 3C), and a Tri-TAC bearing a BCMA-specific scFv (FIG. 3D).

FIG. 4A-FIG. 4D illustrate the functionality of a Tri-TAC bearing the HER-2-specific DARPin. Human T cells were engineered to express either the Tri-TAC as disclosed herein or a conventional CAR with the same DARPin. It was determined that in all aspects, T cells engineered with the Tri-TAC demonstrated functionality at least equivalent to a conventional CAR. Interestingly, with regard to 2 parameters (TNF-α production and CD107a mobilization), it was observed that the Tri-TAC was more active than a conventional CAR in some circumstances.

Figure 4A:
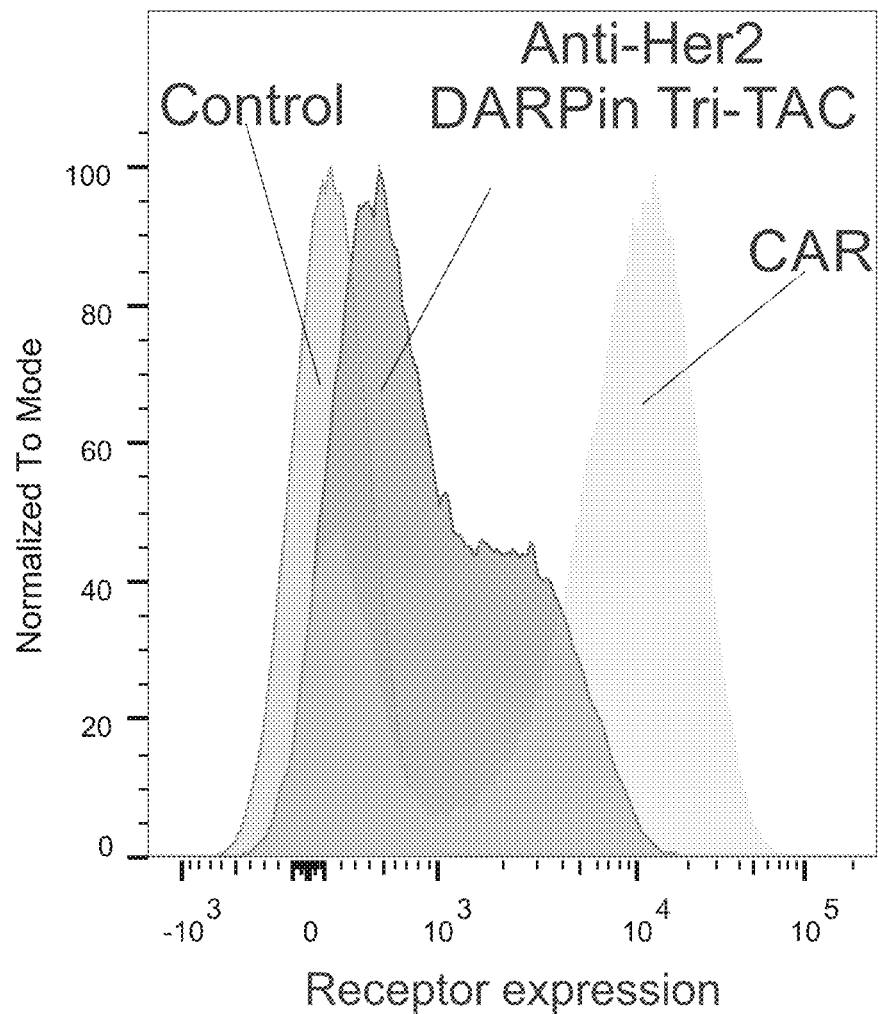
FIG. 4A-FIG. 4D exemplify T cells engineered with a Tri-TAC or a CD28-based CAR directed against HER-2 using a DARPin.
Figure 4B:
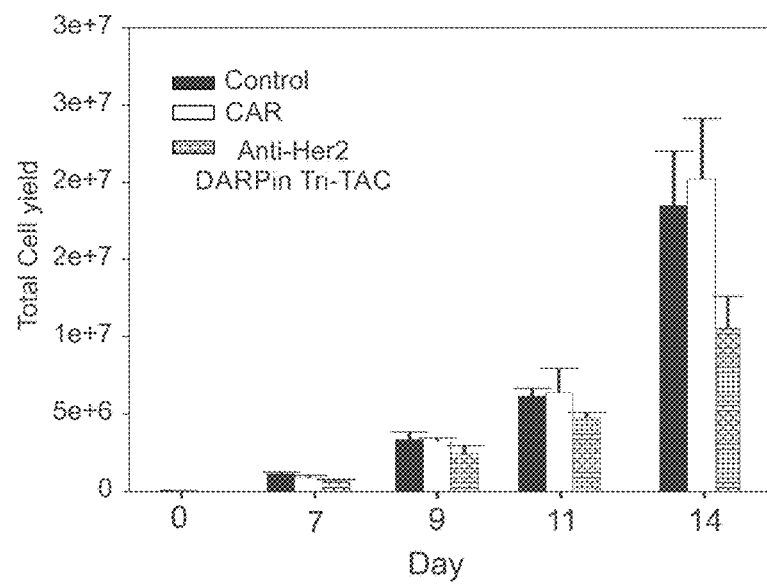
Figure 4C:
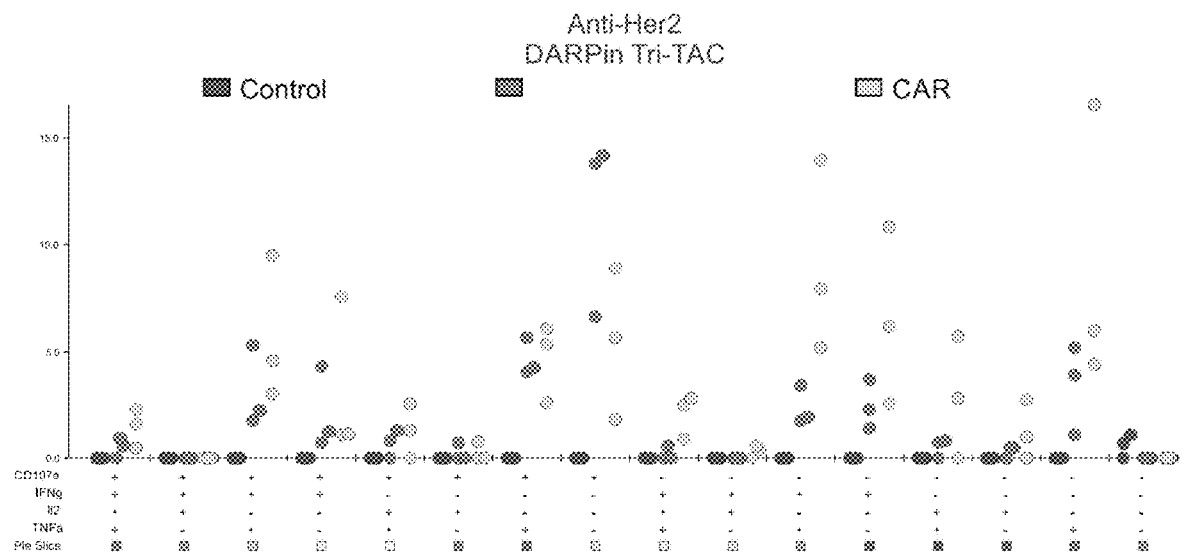
Figure 4D:
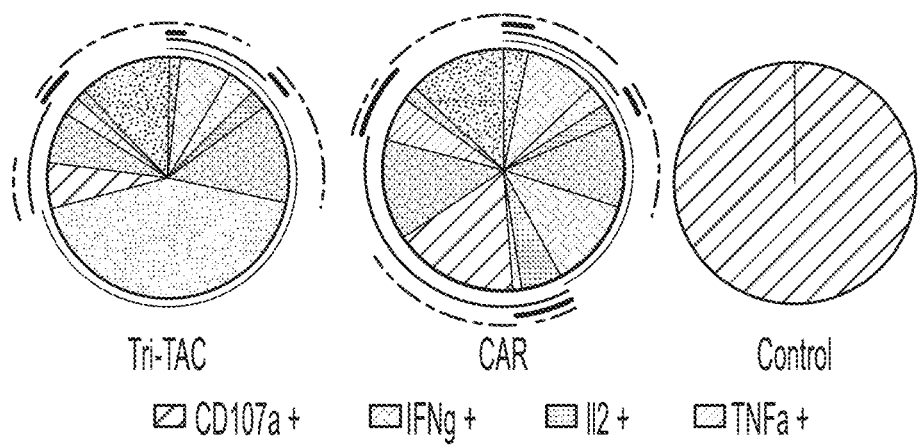
Figure 5:
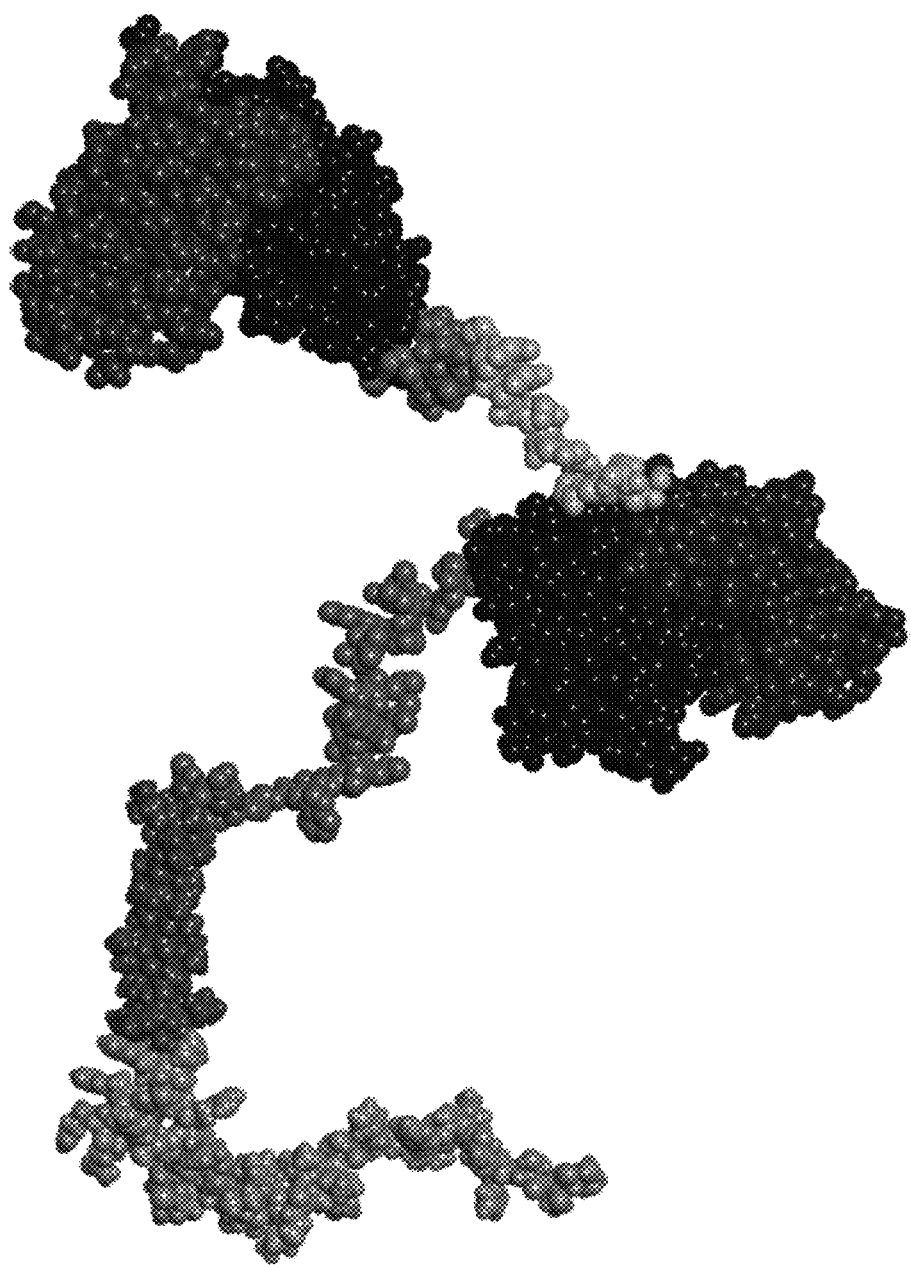
FIG. 5 illustrates a model of the CD19-TAC protein structure.

FIG. 4A shows surface expression of Anti-HER-2 DARPin Tri-TAC compared to Anti-HER-2 DARPin CAR, and control T cells. The chimeric receptors were detected by incubation with recombinant HER-2. The Anti-HER-2 DARPin Tri-TAC was expressed well on the surface of the engineered T cells. FIG. 4B shows growth of the engineered T cells cultures. T cells were activated with anti-CD3/anti-CD28 Dynabeads and engineered with lentiviruses encoding the Tri-TAC, CAR or no receptor (control). After 2 weeks, the CAR and control cultures had grown to similar numbers while the Tri-TAC cultures grew slightly more slowly. FIG. 4C and FIG. 4D show the functional attributes of the engineered T cells. T cells engineered to express the Tri-TAC or the CAR bearing the HER-2 DARPin were stimulated with plate-bound antigen. The T cells engineered to express the Tri-TAC and CAR could elaborate all measured functions (TNF-α production, IFN-7 production and CD107a mobilization, FIG. 3C and FIG. 3D). T cells engineered with the Tri-TAC exhibited elevated frequencies of CD107a-positive cells following stimulation relative to T cells engineered with a CAR (FIG. 3D), suggesting enhanced cytotoxicity on a per-cell basis.

Figure 6J:
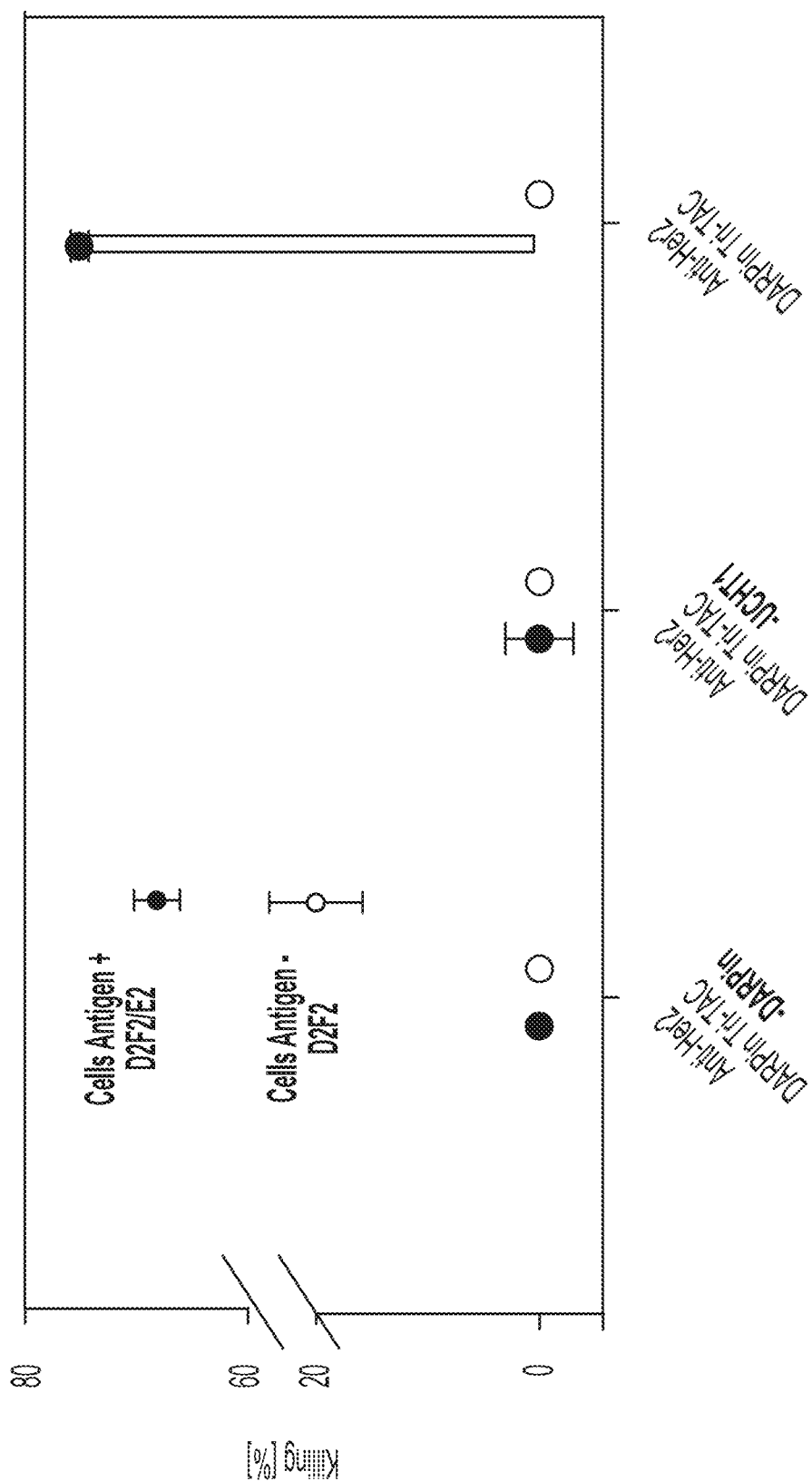

FIG. 6A-FIG. 6J provides data confirming the importance of both ligand binding domain and the UCHT1 CD3 binding domain for Tri-TAC functionality. T cells were engineered with the full-length Tri-TAC bearing the HER-2 DARPin (FIG. 6G, FIG. 6H, FIG. 6I, bottom row), a Tri-TAC variant that lacks the DARPin (FIG. 6A, FIG. 6B, FIG. 6C, top row), or a Tri-TAC variant that lacks the UCHT1 (FIG. 6D, FIG. 6E, FIG. 6F, middle row). All three engineered T cell populations were stimulated with HER-2-positive tumor cells. The T cells engineered with the full-length Tri-TAC could produce IFN-g, TNF- and IL-2 following stimulation, whereas the variants failed to produce any cytokine following stimulation. The three T cell populations were also co-cultured with D2F2/E2 cells (HER-2-expressing) or D2F2 cells (HER-2-negative) at an effector: target of 4:1 (FIG. 6J). T cells engineered with full-length Tri-TAC demonstrated robust killing against D2F2/E2 cells but did not kill the D2F2 cells. The other Tri-TAC variants lacking either the DARPin or the UCHT1, exhibited no killing.

Figure 7A:
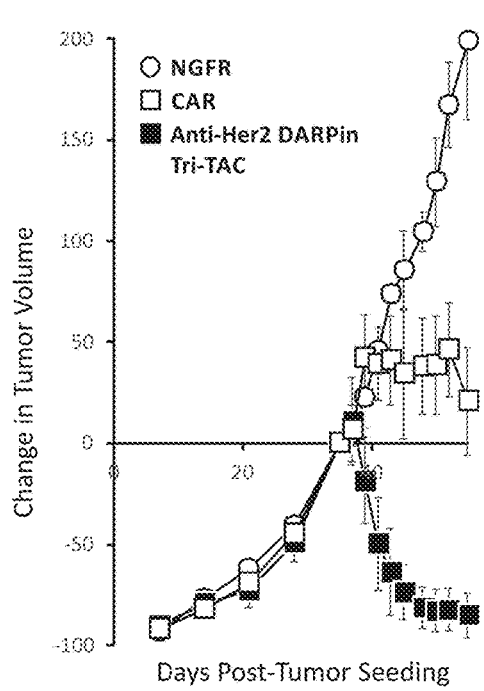
FIG. 7A-FIG. 7C illustrate anti-tumor activity, toxicity, and cytokine production of T cells engineered with either the anti-HER-2 DARPin Tri-TAC or the anti-HER-2 DARPin CD28-based CAR. Mice bearing established OVCAR-3 tumors were treated with T cells engineered with the anti-HER-2 DARPin Tri-TAC or the anti-HER-2 DARPin CAR.
Figure 7B:
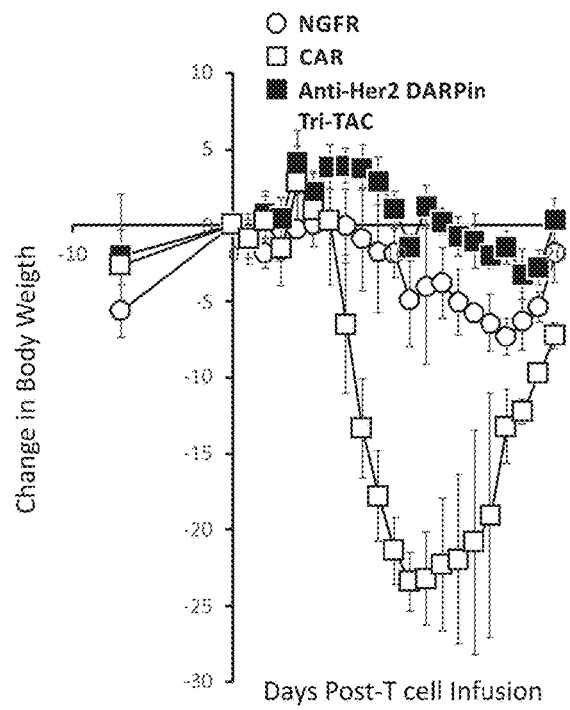
Figure 7C:
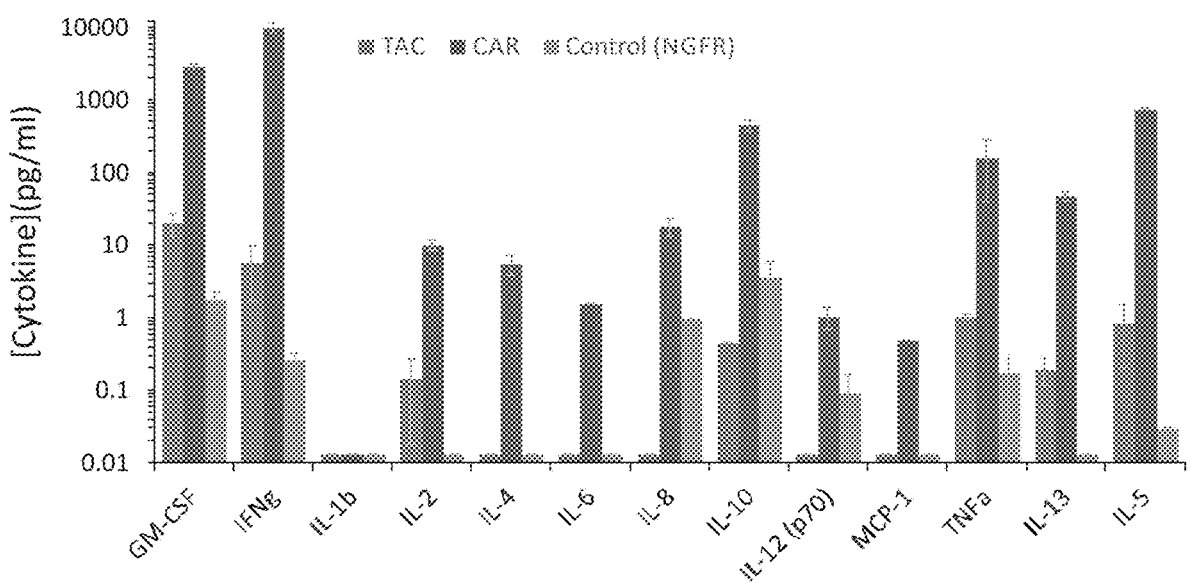

FIG. 7A-FIG. 7C show the results of mice treated with vector control (NGFR), Anti-HER-2 DARPin CAR or Anti-HER-2 DARPin Tri-TAC. A xenograft mouse model was used.

OVCAR-3 tumor cells were administered to mice subcutaneously and allowed to grow until the tumors reached a size of 100-200 mm$^3$. FIG. 7A shows relative tumor progression normalized to tumor size at day of treatment. Anti-HER-2 DARPin Tri-TAC engineered T-cells caused a rapid decrease in tumor volume, control had no effect, and CAR cells slowed tumor growth and showed a delayed reduction in tumor size. FIG. 7B illustrates relative changes in body weight post T-cell infusion. Both control and anti-HER-2 DARPin Tri-TAC engineered cells show no significant changes in mouse body weight post treatment. In contrast, Anti-HER-2 DARPin CAR-treated mice show significant loss in body weight indicative of severe toxicity. FIG. 7C illustrates cytokine concentrations in serum of mice on day 7 post T-cell infusion. Cytokine levels were higher in CAR-treated mice compared to Tri-TAC-treated mice.

Example 2. Substitutions of UCHT1 Influence Tri-TAC Function

Figure 8A:
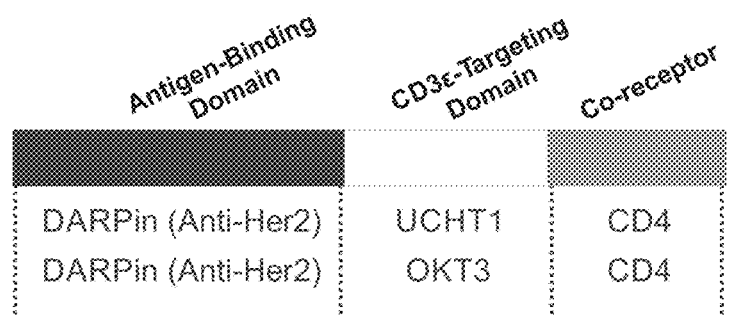
Figure 8B:
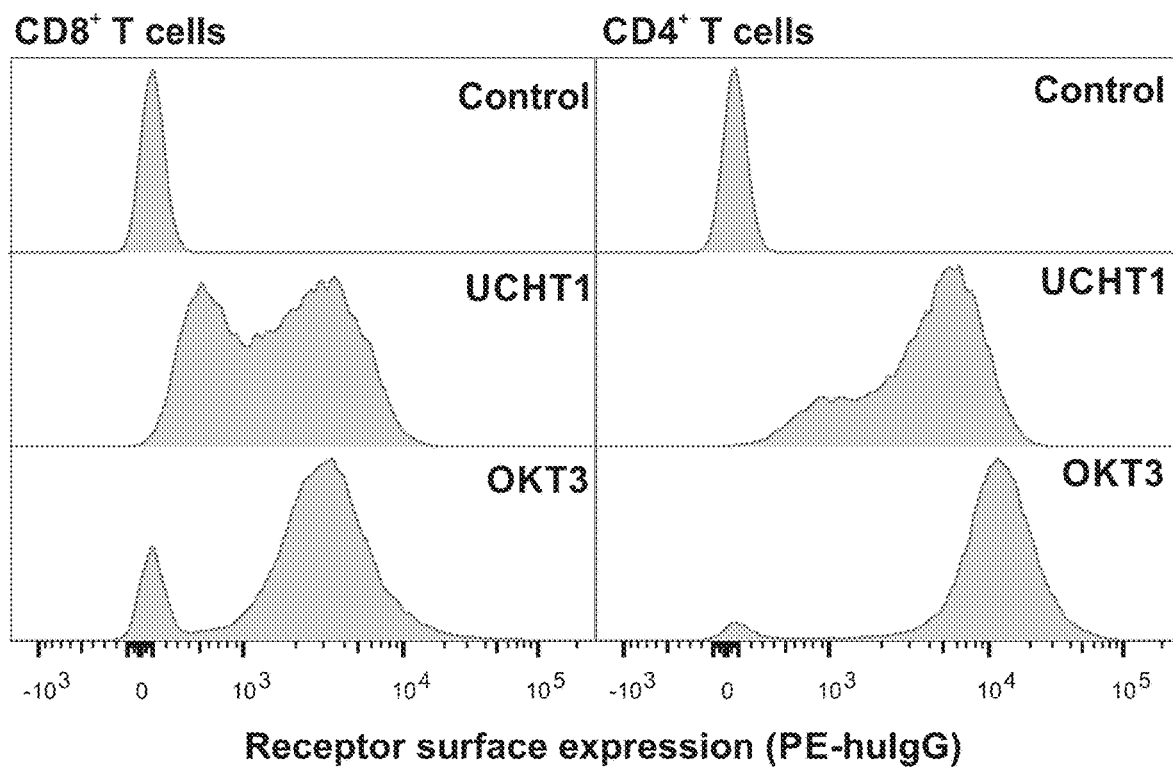
Figure 8D:
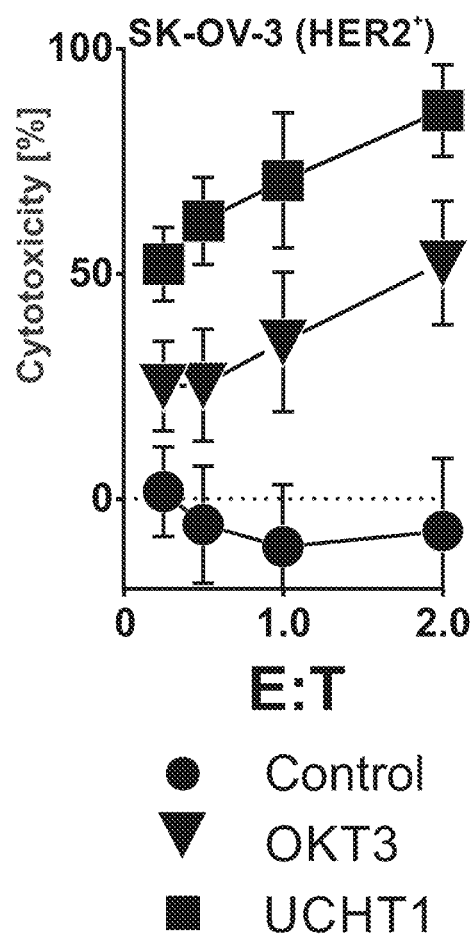
Figure 8E:
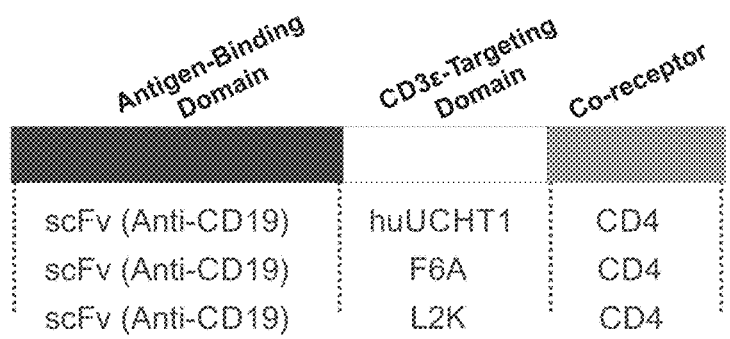
Figure 8F:
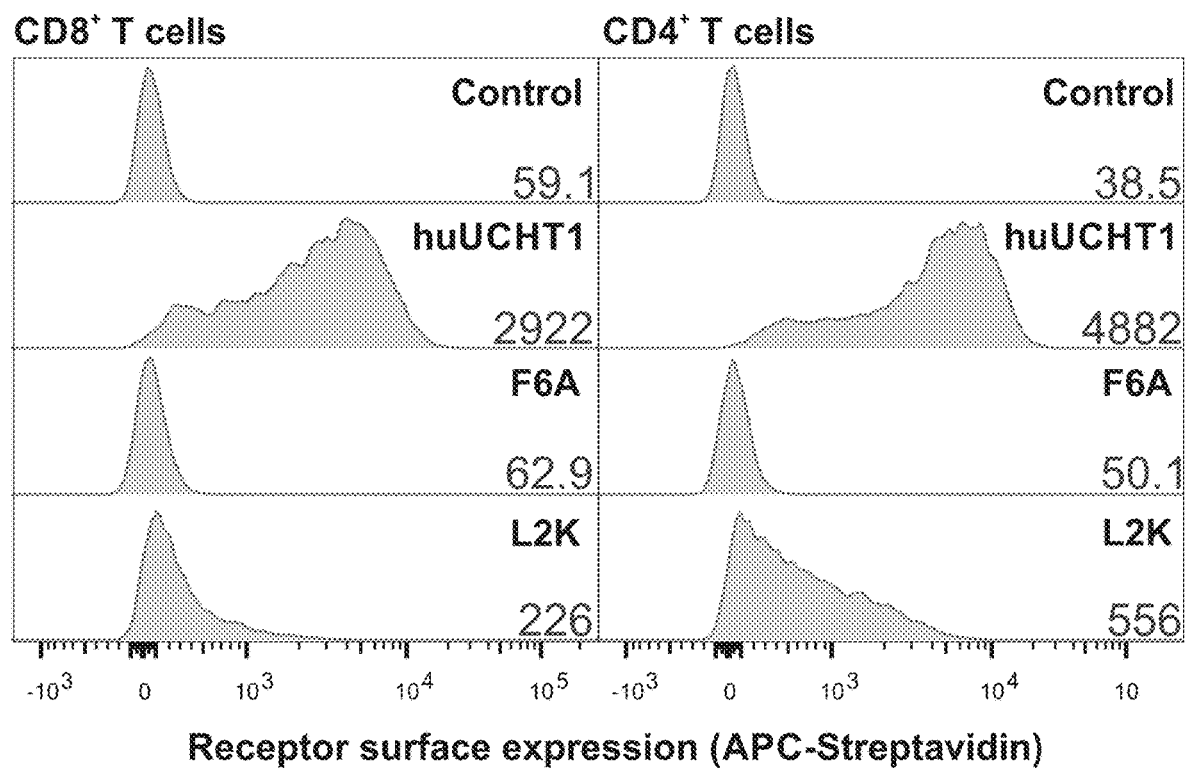
Figure 8H:
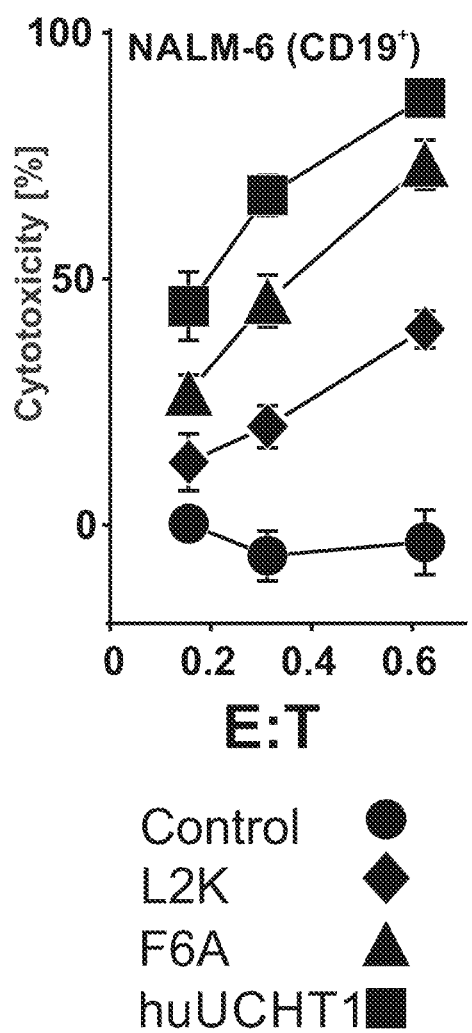
Figures 9A, 9E:
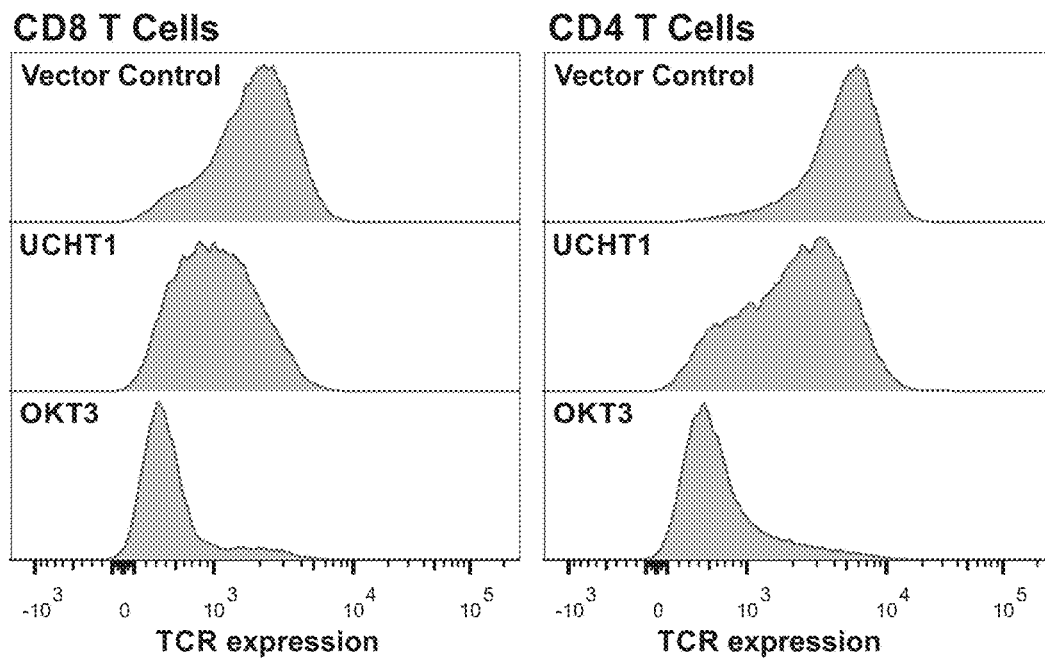
FIG. 9A-FIG. 9H illustrates the effect of various anti-CD3 scFv on TCR surface expression.
Figures 9B, 9F:
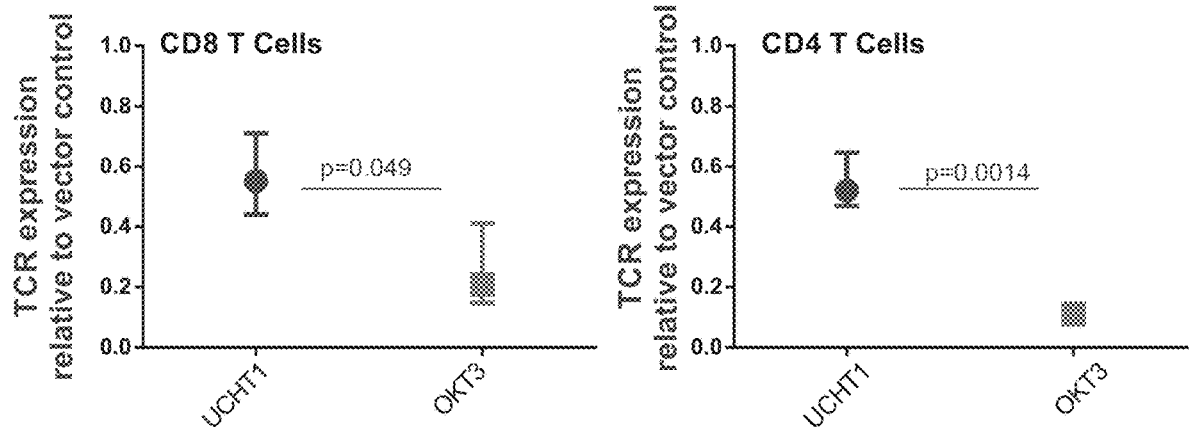
Figure 9C:
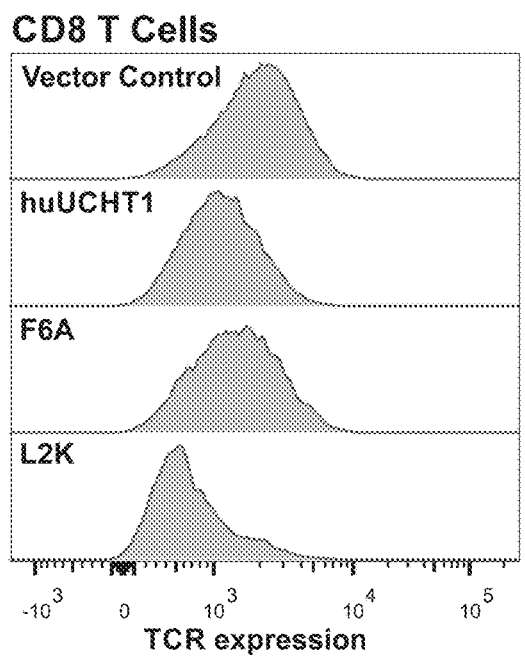
Figure 9G:
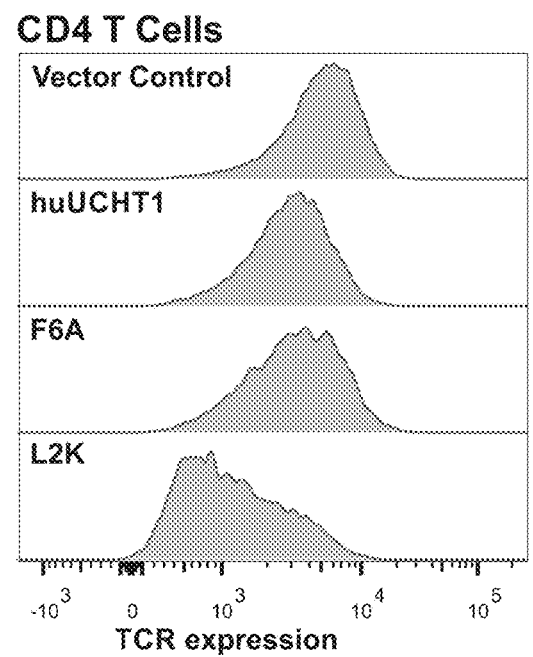
Figure 9D:
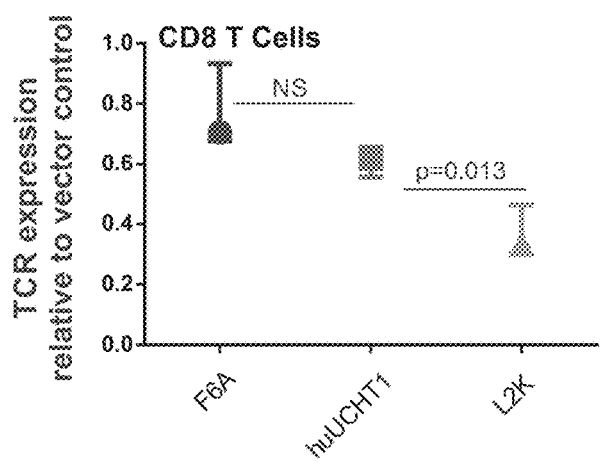
Figure 9H:
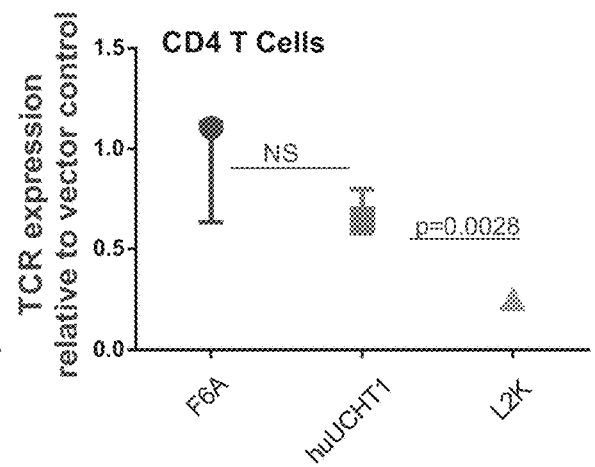

FIG. 8A-FIG. 8H illustrate the functionality of Tri-TACs bearing alternate CD3 binding domains. The domains are listed in FIG. 8A and FIG. 8E. Tri-TACs containing UCHT1 (FIG. 8B), OKT3 (FIG. 8B) and huUCHT1 (FIG. 8F) displayed high surface expression, whereas the Tri-TACs containing F6A (FIG. 8F) and L2K (FIG. 8F) revealed lower surface expression. Cells expressing the Tri-TAC containing OKT3 exhibited low cytokine production (FIG. 8C, FIG. 8C1) and intermediate cytotoxicity (FIG. 8D) upon Tri-TAC ligation. Cells expressing the Tri-TAC containing F6A exhibited strong cytokine production (FIG. 8G, FIG. 8G1) and cytotoxicity (FIG. 8H) following Tri-TAC ligation. Cells expressing the Tri-TAC containing L2K exhibited low cytokine production (FIG. 8G, FIG. 8G1) and intermediate cytotoxicity (FIG. 8H).

FIG. 9A-FIG. 9H illustrates TCR surface expression on T cells engineered with different Tri-TAC variants shown in FIG. 8A and FIG. 8E. T cells engineered with the Tri-TAC variants comprising OKT3 (FIG. 9A, FIG. 9E and FIG. 9B, FIG. 9F) or L2K (FIG. 9C, FIG. 9G and FIG. 9D, FIG. 9H) exhibited lower TCR surface expression relative to the T cells engineered with Tri-TACs comprising UCHT1 or huUCHT1, respectively. In contrast, T cells engineered with the Tri-TAC variant comprising F6A did not reveal TCR downregulation relative to the Tri-TAC carrying huUCHT1 (FIG. 9C, FIG. 9G and FIG. 9D, FIG. 9H). The F6A substitution reduced Tri-TAC receptor surface expression, while retaining moderate cytokine production and cytotoxicity. The L2K substitution moderately reduced surface expression and reduced cytokine production, but retained intermediate cytotoxicity. The OKT3 substitution resulted in high Tri-TAC surface expression, low cytokine production, and intermediate cytotoxicity. These data indicate that Tri-TAC surface expression and T cell effector functions are not inherently proportional, and that Tri-TAC domain substitutions, in some instances, alters effector functions independent of surface expression levels. It is conceivable that a TAC variant with reduced cytotoxicity and low surface expression could be of value in certain clinical applications.

In many cases, the scFv substitutions attenuated the ability of the engineered T cell to elaborate IFN-γ, TNF-α, and IL-2, yet the engineered T cells retained the ability to kill target cells. Excessive cytokine production has been associated with adverse events in clinical settings, limiting current CAR technologies to life-threatening diseases. The ability to modify TAC molecules to reduce their cytokine production while retaining moderate cytotoxicity will allow generation Tri-TAC receptors with the exact level of reactivity required to satisfy clinical efficacy and safety.

The capacity of the Tri-TAC variant comprising OKT3 to suppress TCR surface expression and cytokine production, while retaining cytotoxicity, could be of great value in allogeneic situations where the suppression of TCR could suppress graft versus host disease.

These data demonstrate that scFv substitutions of UCHT1 influences the function of Tri-TACs. Further modifications will be result in Tri-TACs useful in various applications (e.g., oncology, autoimmunity, allergy).

Example 3. Introducing Various Linkers Connecting the Ligand that Binds a TCR Complex to the Target-Binding Ligand Domain FIG. 10A-FIG. 10B illustrate several TAC variants with different linkers connecting the ligand that binds a TCR complex and the target-binding ligand domain. The flexible connector allows movement between the two domains. The large domain connector contains two folded domains and is very large and rigid. The small and long helix connectors also introduce rigidity but are less restrictive when compared to the large domain linker.

Figure 11A:
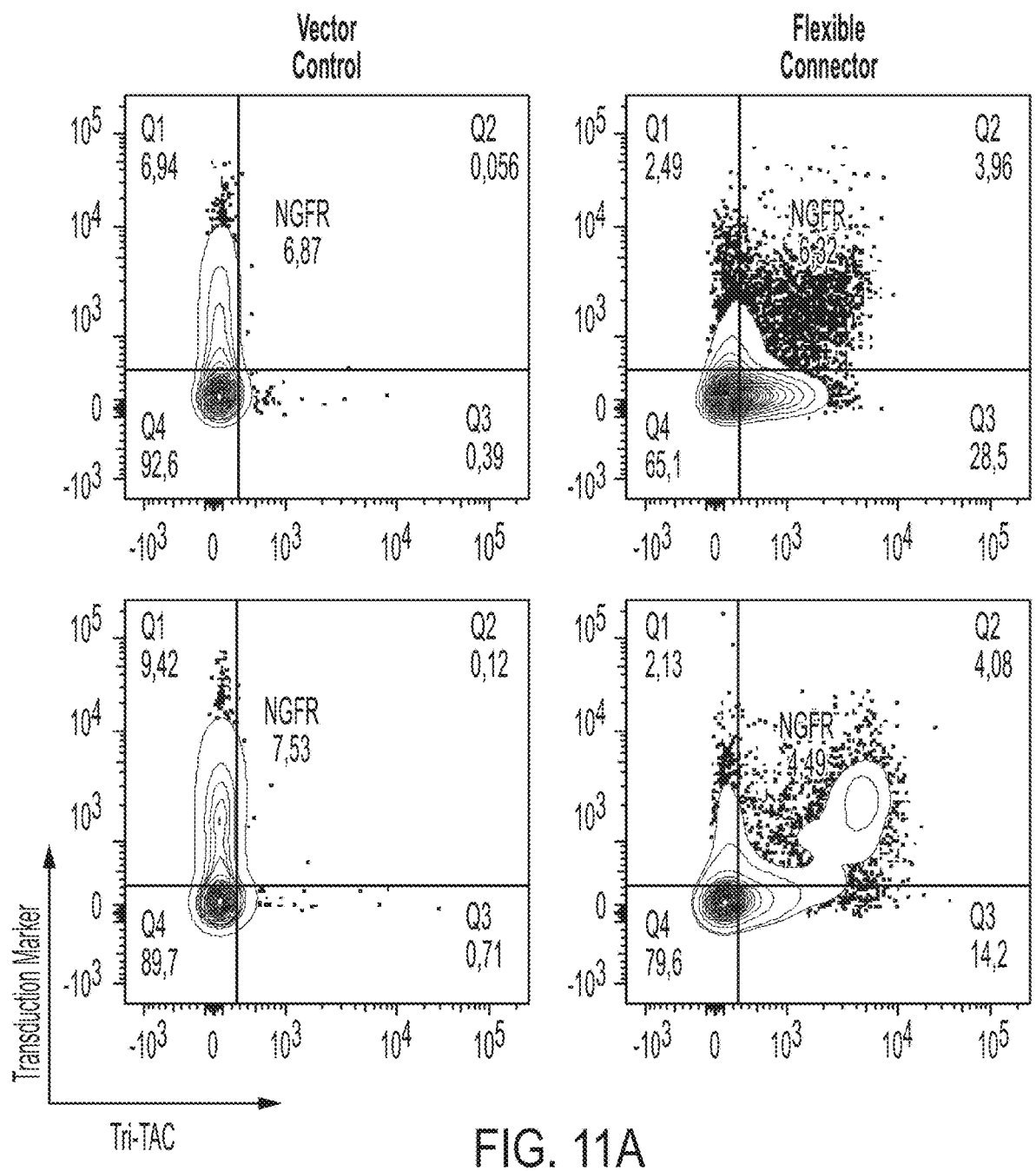
FIG. 11A-FIG. 11E illustrate exemplary in vitro parameters of CD19 TAC engineered with different connector variants.
Figure 11A:
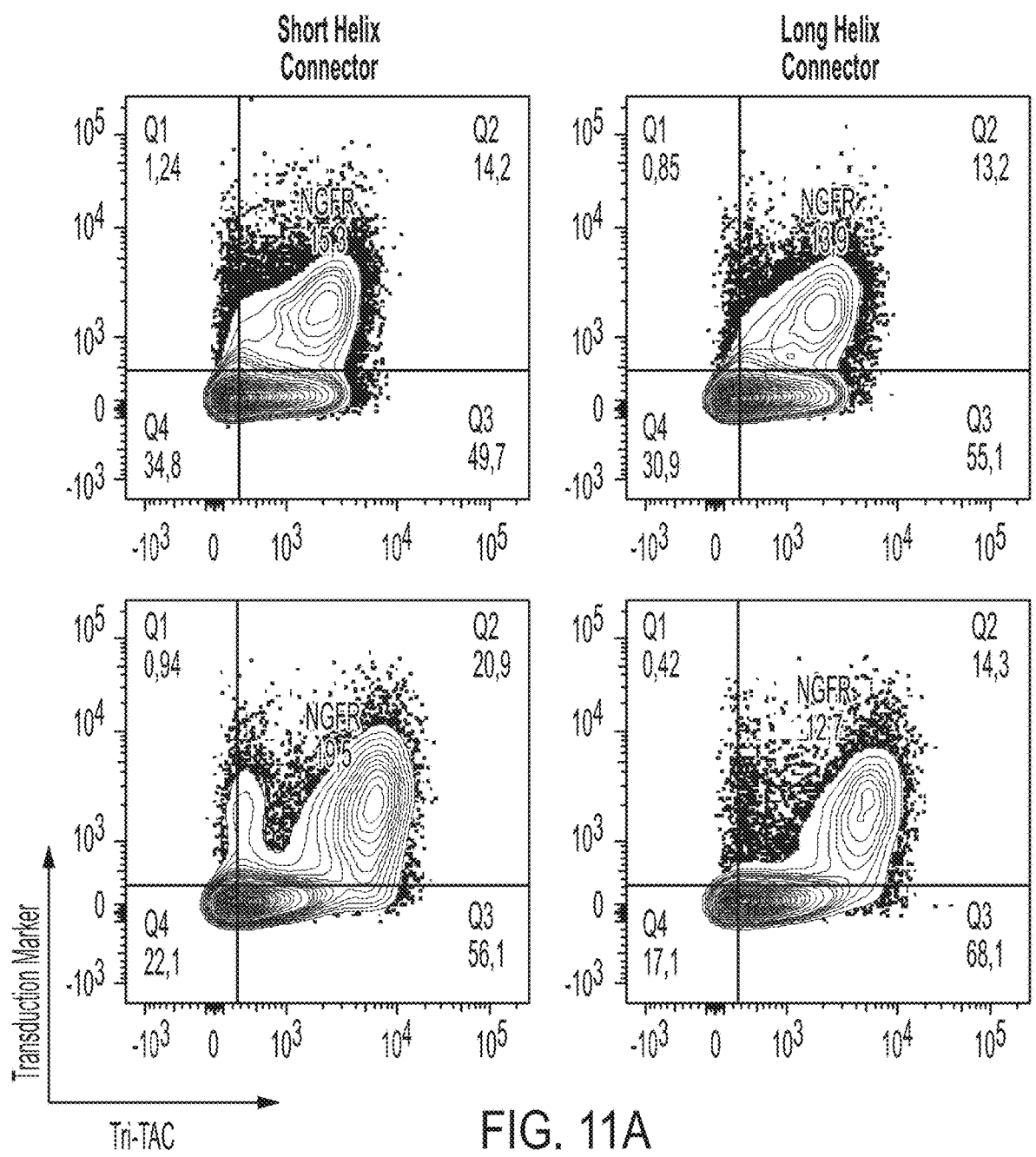
Figure 11A:
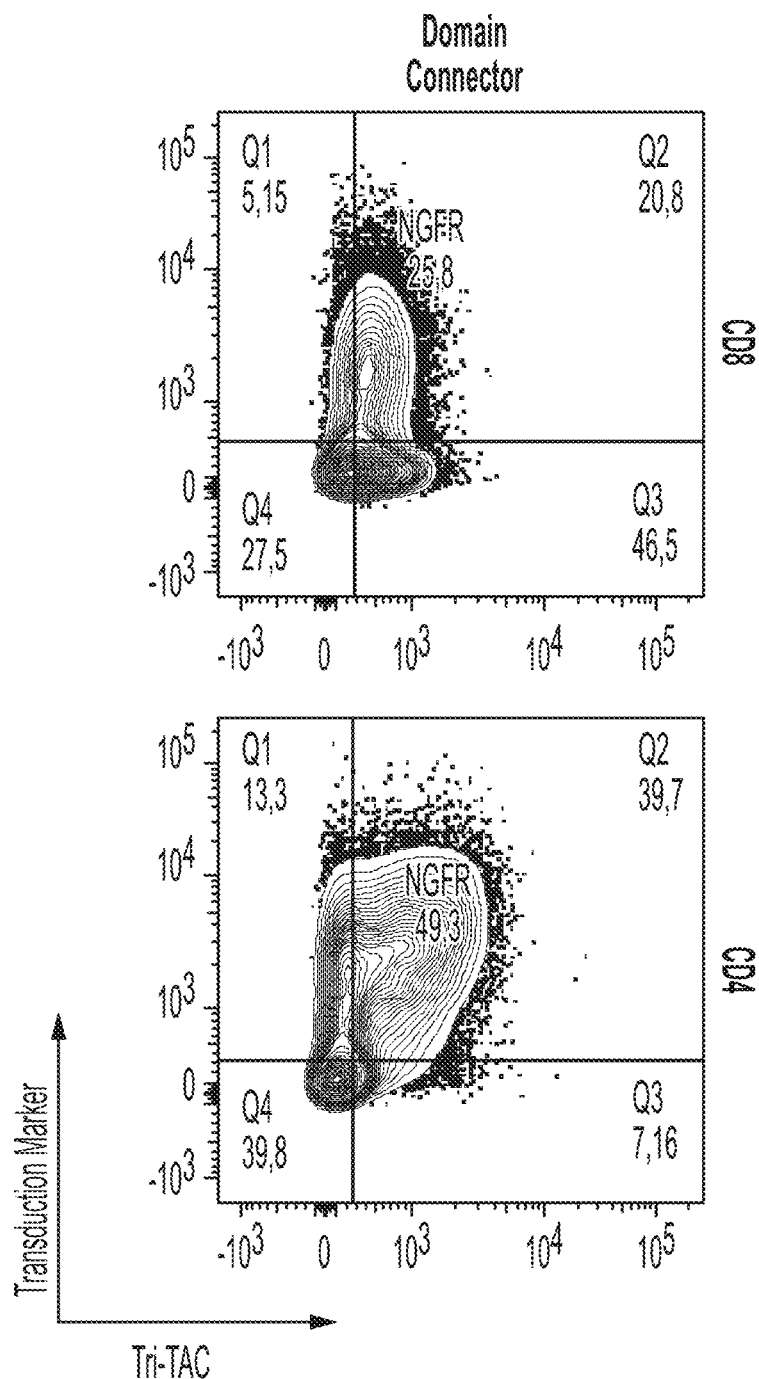
Figure 11B:
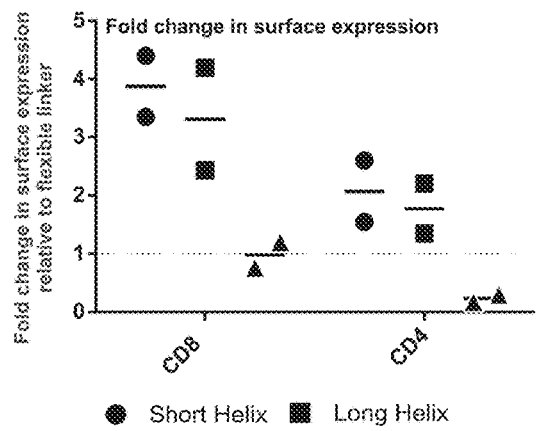
Figure 11C:
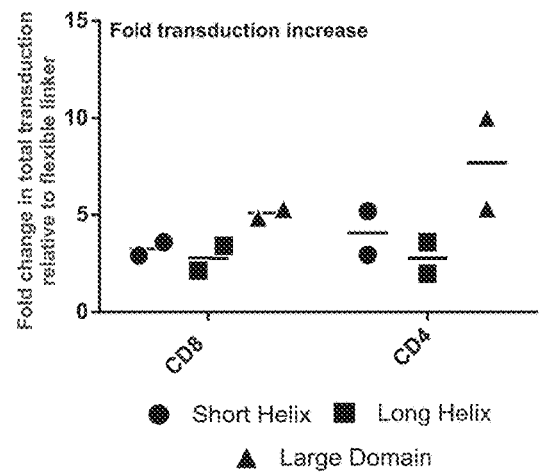
Figure 11D:
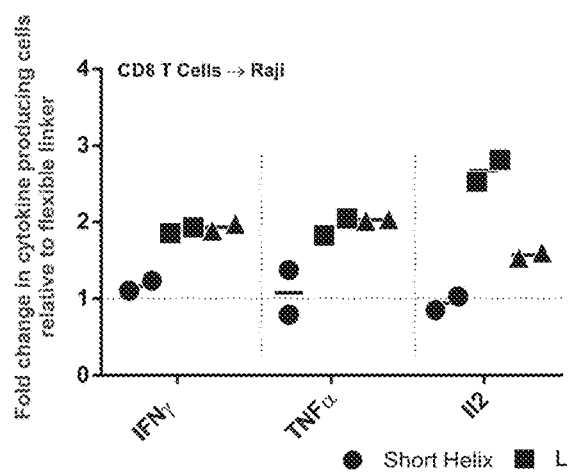
Figure 11E:
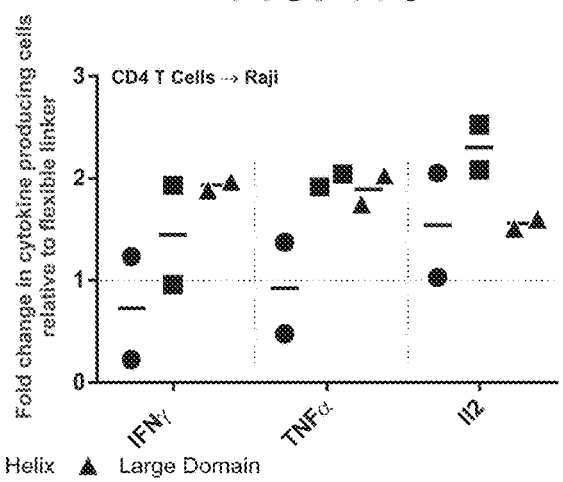

FIG. 11A-FIG. 11E illustrate the impact of connector substitution on Tri-TAC surface expression, Tri-TAC transduction efficiency, and cytokine production upon Tri-TAC ligation. FIG. 11A and FIG. 11B show that the helical linkers enhance surface expression and transduction efficiency when compared to the flexible linker, while the large domain connector enhances transduction efficiency but not surface expression. FIG. 11D, FIG. 11E illustrates cytokine production by cells expressing Tri-TACs with short helix, long helix, or large domain connectors.

Figure 12A:
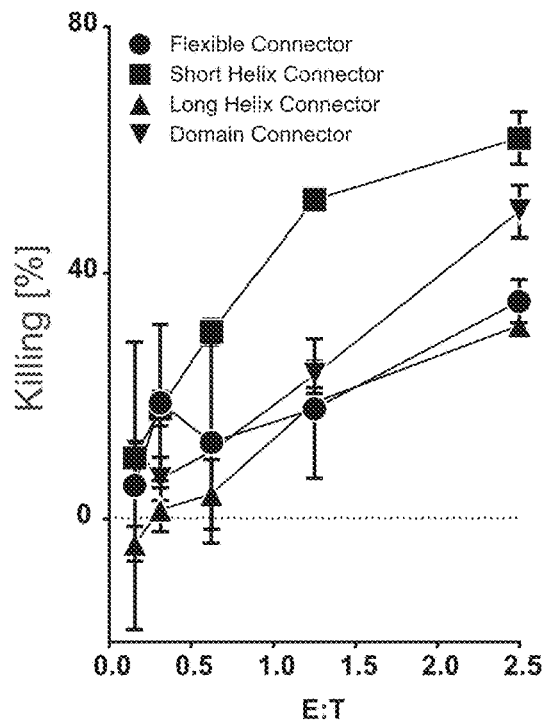
FIG. 12A illustrates in vitro cytotoxicity of BCMA Tri-TAC variants engineered with different connectors.
Figure 12B:
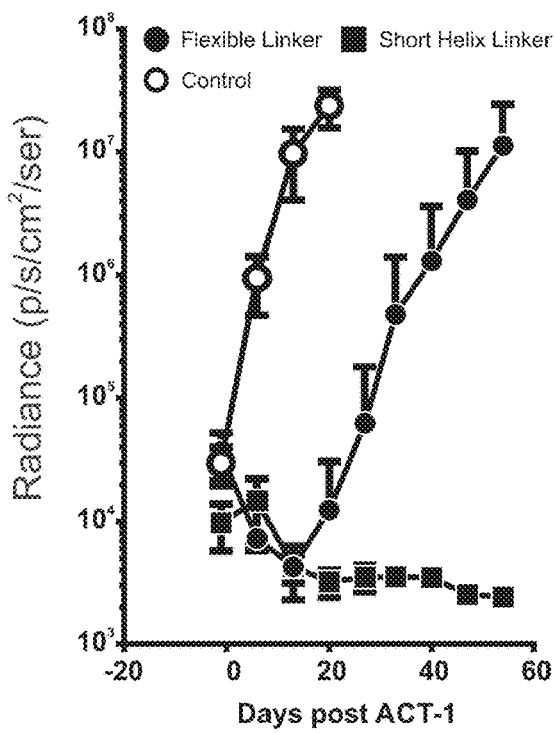
FIG. 12B illustrates in vivo tumor control of BCMA Tri-TAC variants engineered with the flexible connector compared to the short helical connector.

FIG. 12A illustrates enhanced in vitro cytotoxicity of T cells expressing Tri-TACs with the short helix connector. FIG. 12B illustrates enhanced in vivo tumor control of T cells expressing Tri-TACs with the short helix connector. The short helical connector was associated with high in vitro cytotoxicity and effective in vivo tumor control.

Example 4. Introducing a CD8α/β Cytosolic Domain

Figure 13A:
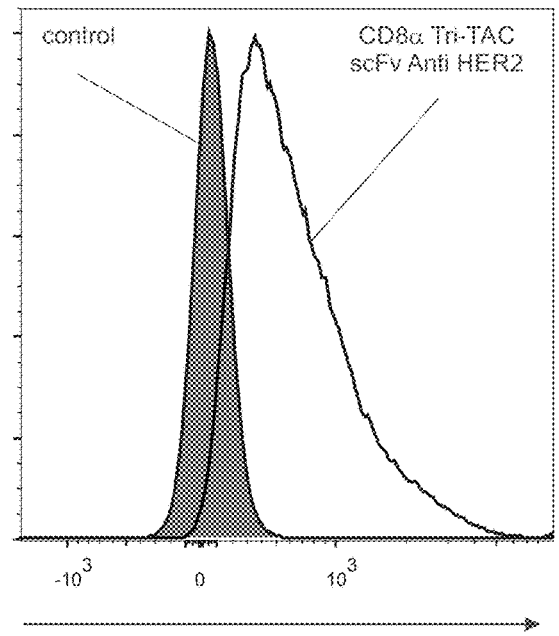
FIG. 13A-FIG. 13C illustrate properties of CD8α Tri-TAC scFv anti HER-2, and CD8α Tri-TAC DARPin anti-HER-2.
Figure 13C:
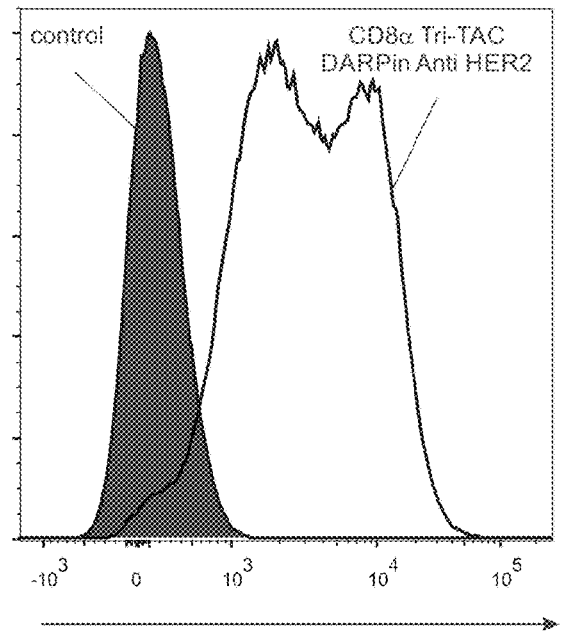
Figure 13B:
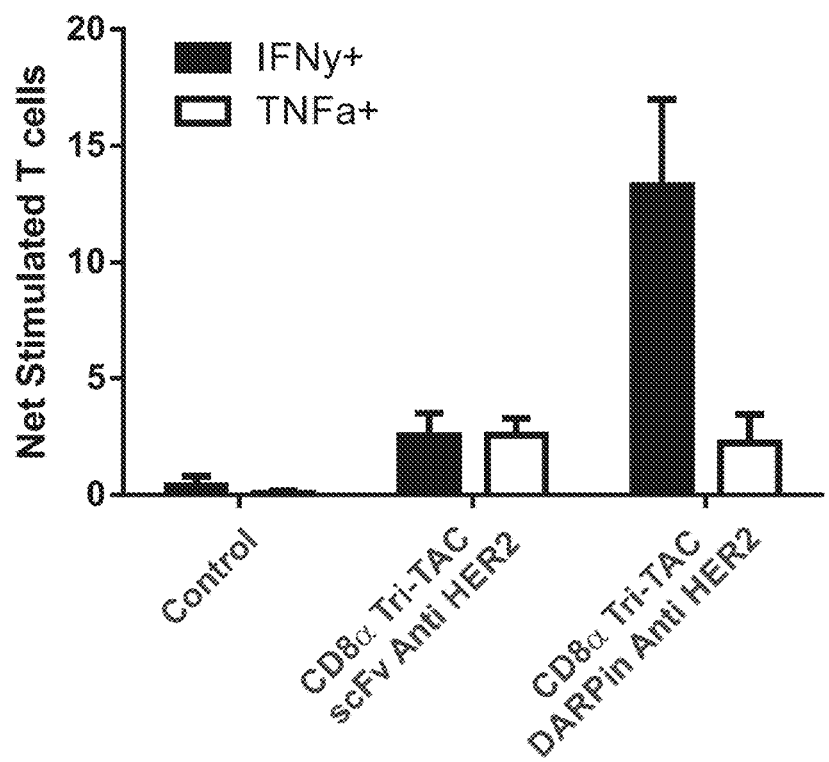

FIG. 13A illustrates surface expression of CD8α Tri-TAC paired with an anti-HER-2 scFv or FIG. 13C anti-HER-2 DARPin. FIG. 13B illustrates cytokine production by T cells expressing CD8α Tri-TAC paired with an anti-HER-2 scFv or anti-HER-2 DARPin.

Figures 14A, 14B, 14C, 14D:
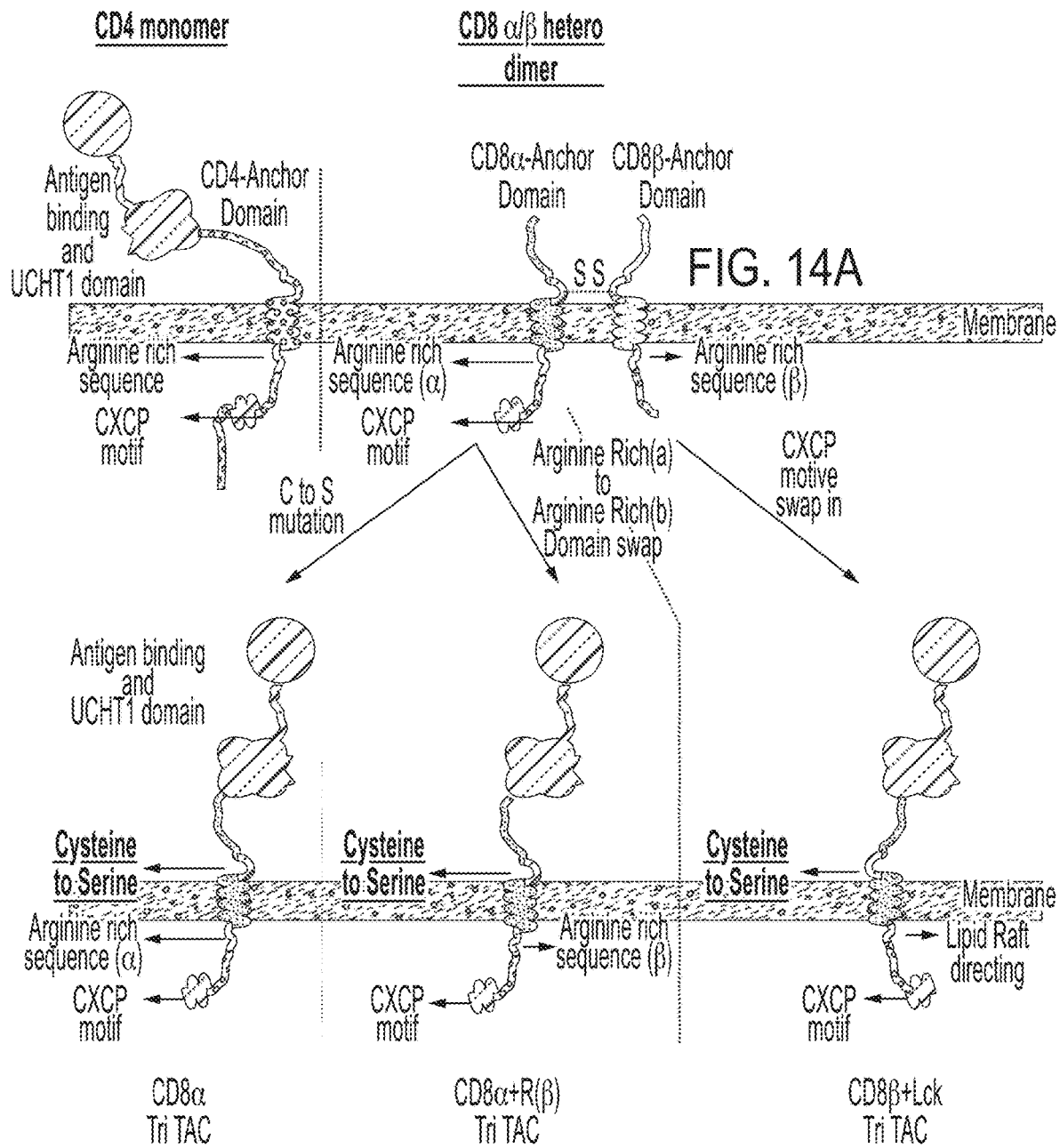
FIG. 14A-FIG. 14D provide schematics of CD8 Tri-TAC variants. The anti HER-2-DARPin is used as an exemplary antigen-binding domain and the UCHT1 CD3 recruitment domain is used as an exemplary recruitment domain.

FIG. 14A illustrates a CD4 Tri-TAC monomer and a CD8α/β heterodimer. TCR co-receptors, both CD4 and CD8, carry functional domains that are important for the co-receptor functionality. These regions include the arginine rich region that is hypothesized to be important for lipid raft association, and the CXCP motif required for Lck binding. Unlike CD4, which is a monomer, the CD8 co-receptor is a heterodimer composed of an a and a p subunit (FIG. 14A).

Both the α and β CD8 subunits contain arginine rich regions, but only the a subunit contains the CXCP motif.

FIG. 14B-FIG. 14D provide schematics of Tri-TAC variants that incorporate elements from the CD8 co-receptor shown in FIG. 14A. The cysteine responsible for dimerizing CD8α and CD8β was replaced with an alanine in all CD8 Tri-TAC variants. FIG. 14B is a schematic of a CD8α Tri-TAC comprising a Cysteine to Serine mutation to ensure a monomeric receptor distribution, and a CD8α cytosolic domain. FIG. 14C is a schematic of a CD8α+RR Tri-TAC comprising a Cysteine to Serine mutation to ensure a monomeric receptor distribution, and a chimeric CD8α cytosolic domain where the CD8α arginine rich region is replaced with the CD8β arginine rich region. FIG. 14D is a schematic of a CD8β+Lck Tri-TAC comprising a Cysteine to Serine mutation to ensure a monomeric receptor distribution, and a chimeric CD8β cytosolic domain, where the CD8α CXCP domain, which contains an Lck binding motif, was added to the C-terminus of the CD8β cytosolic domain.

Figure 15A:
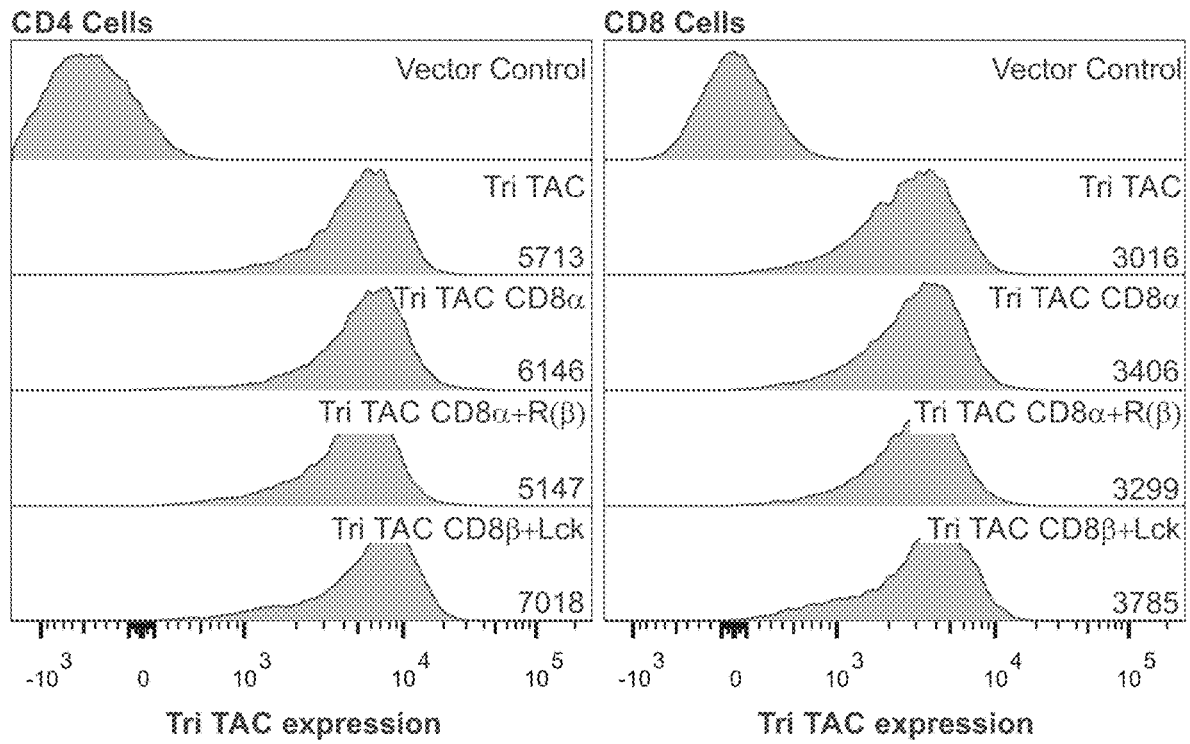
FIG. 15A-FIG. 15E illustrate in vitro characterization of CD8 Tri-TAC variants relative to the prototypic Tri-TAC containing CD4 regions.
Figure 15B:
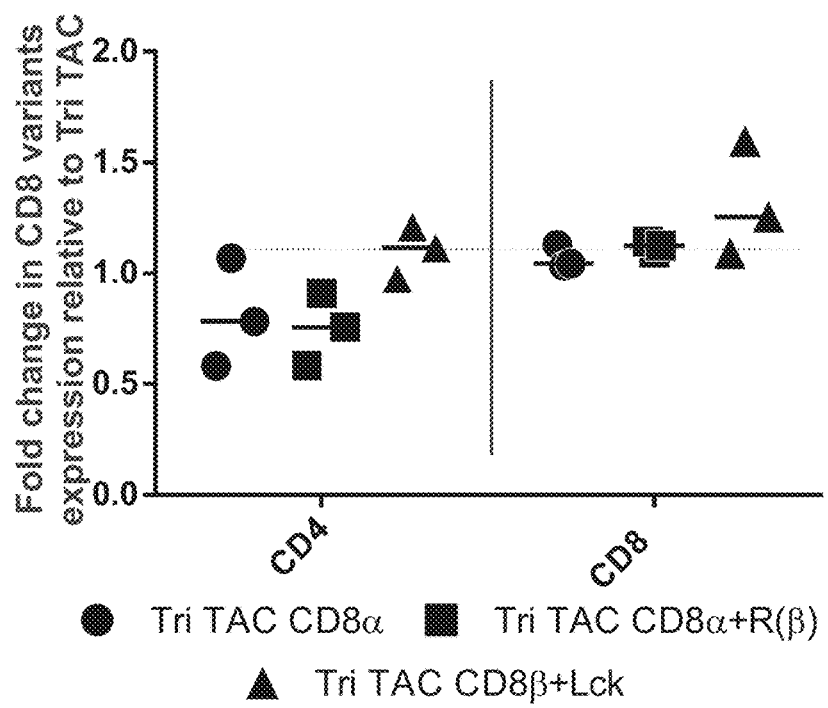
Figure 15C:
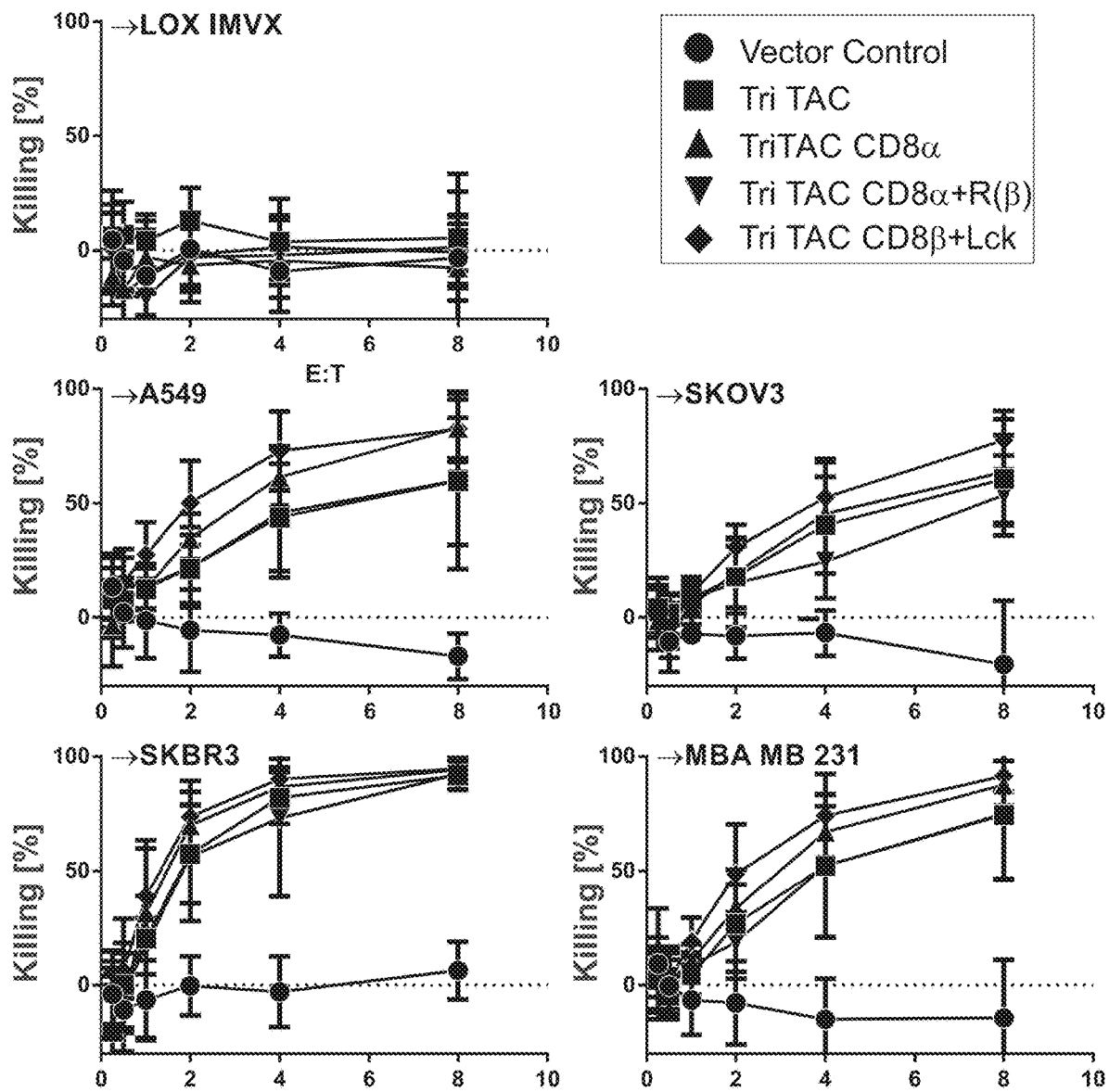
Figure 15D:
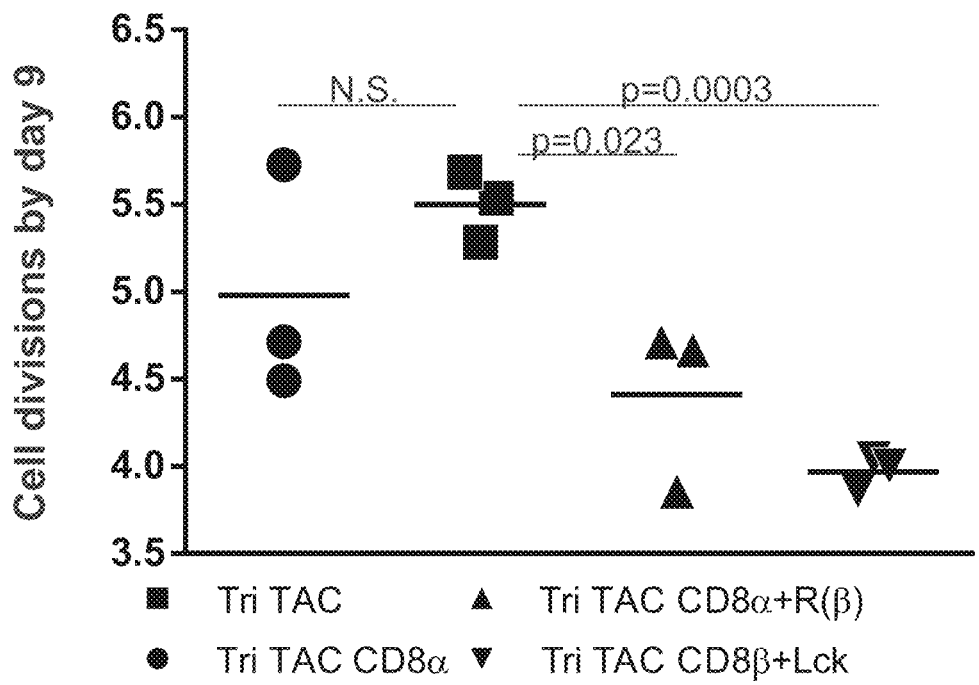
Figure 15E:
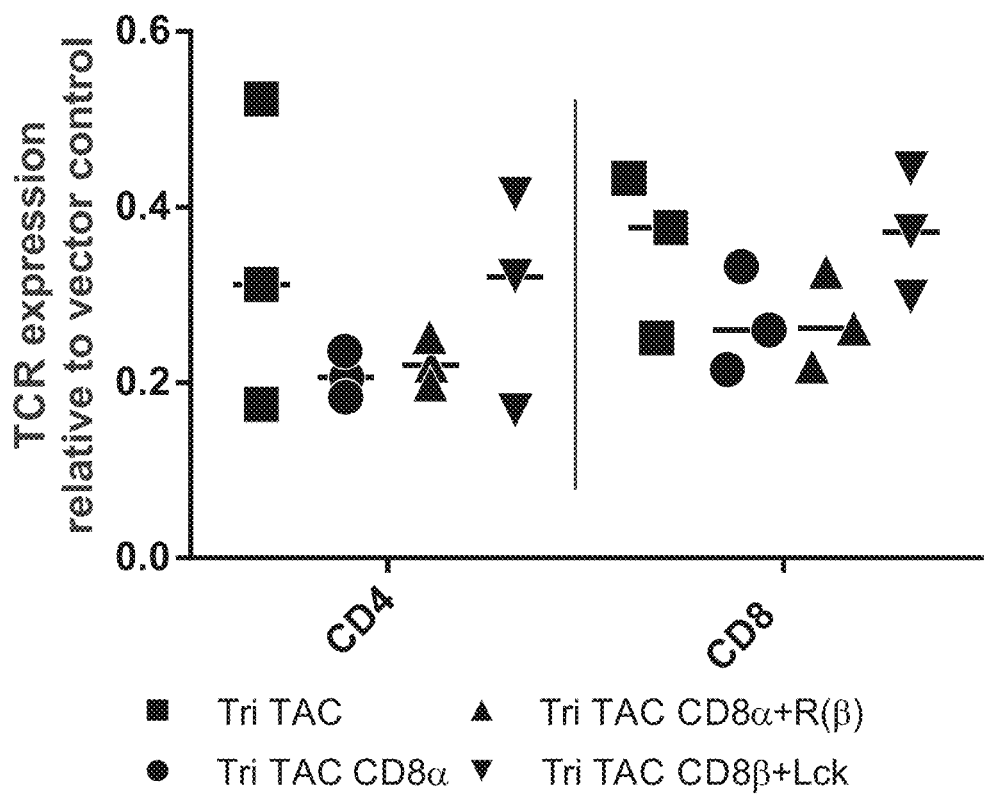

FIG. 15A-FIG. 15D illustrate various phenotypic and functional attributes of the CD8-based Tri-TAC variants relative to the prototypical Tri-TAC. FIG. 15A-FIG. 15B illustrate surface expression of CD8-Tri TAC variants relative to the prototypic Tri-TAC. Surface expression was comparable among the different Tri-TACs. FIG. 15C illustrates in vitro cytotoxicity of CD8-Tri TAC variants co-cultured with LOX IMVI (HER-2 negative) and A549, SKOV3, SKBR3 or MBA MB 231 (all are HER-2 positive). All T cells engineered with Tri-TACs exhibited cytotoxicity. FIG. 15D illustrates cell division of T cells engineered with either the CD8 Tri-TAC variants or the prototypic Tri-TAC (FIG. 15D). FIG. 15E illustrates TCR surface expression of engineered T cells comprising CD8 Tri-TAC variants or the prototypic Tri-TAC. All Tri-TAC variants had a similar effect on TCR expression. While the CD4 co-receptor demonstrated good surface expression and functionality with both the scFv and DARPin anti HER-2, the CD8α construct showed activity only in the context of the DARPin antigen binding domain. When testing different CD8α cytosolic domains, all the configurations contained the reported key sequence attributes associated with co receptor functionality (Arginine rich region and CXCP). All CD8α/β constructs showed similar performance when compared to the CD4 prototype. This emphasizes that the retention of specific biochemical properties, such as lipid raft affinity and Lck binding, is more important to determine Tri TAC performance than a specific cytosolic polypeptide sequence.

The growth of T cells engineered with the CD8α+R(β) and the CD8β+Lck Tri-TACs was significantly impaired relative to the growth of T cells engineered with the other variations. Despite a significant impact on growth, these Tri-TACs all displayed a comparable ability to activate T cells. The reduced growth of the CD8α+R(β) and the CD8β+Lck Tri-TACs may be advantageous for certain application where maximal T cell expansion is not desirable.

Example 5. Development of a CD19-TAC Construct

Figure 16:
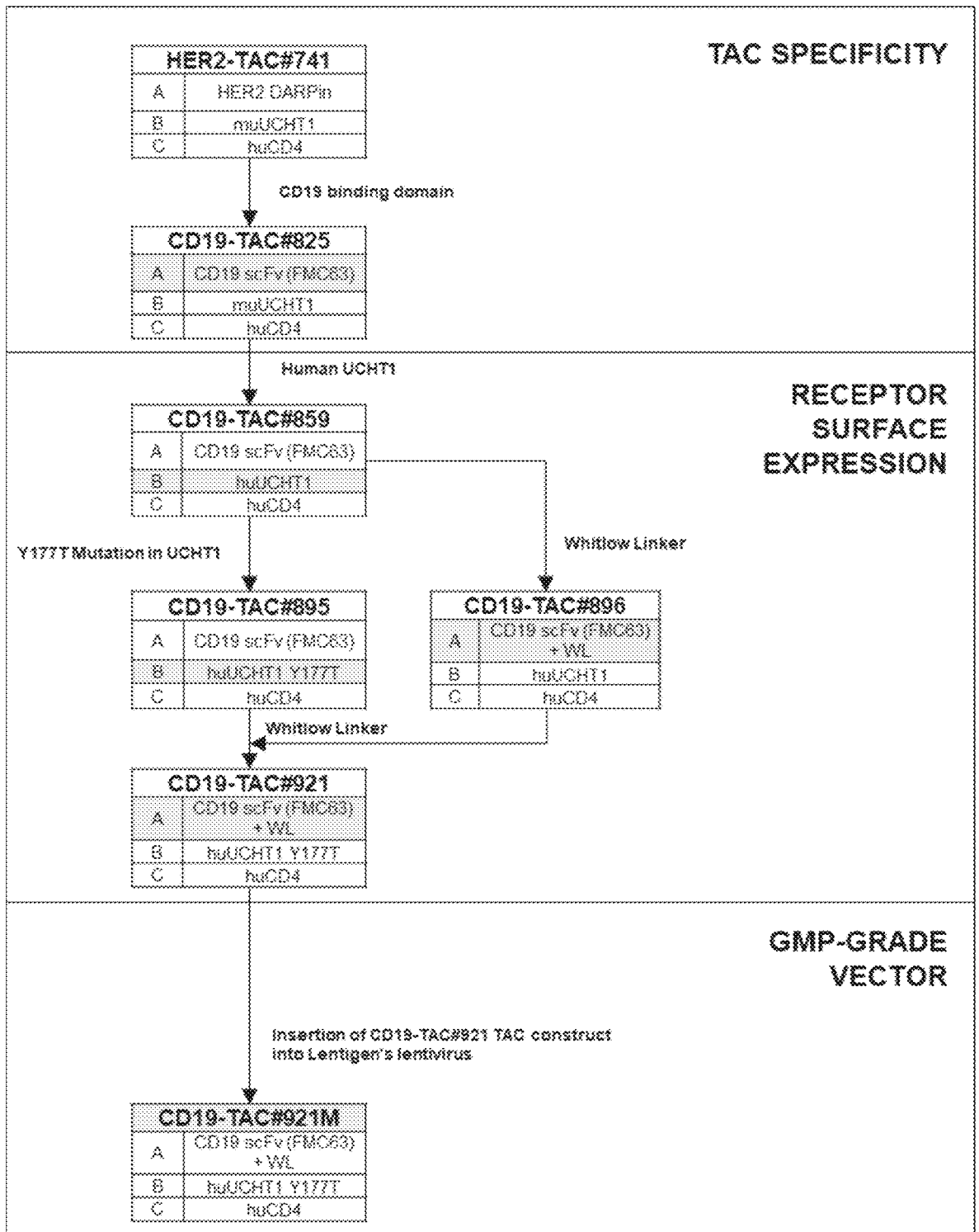
FIG. 16 illustrates various Tri-TACs.

FIG. 16 illustrates the step-wise development of a CD19-TAC construct. Several generations of lentiviral vectors are created with various alterations in design elements to ensure CD19-specificity, proper TAC expression, and GMP-grade lentivirus production. Each box represents a lentiviral vector and specifies the 3 major design elements: (A) the antigen-binding domain, (B) the TCR/CD3-binding domain, and (C) the co-receptor domain. Shaded areas indicate domains that have been the subject of modification during the vector development process.

The TAC in the first step comprises a HER-2-specific designed ankyrin repeat protein (DARPin), a murine UCHT1 CD3-specific scFv, and a flexible transmembrane and cytosolic CD4 polypeptide. The TAC is cloned into a pCCL4 lentiviral vector.

To generate a CD19-specific Tri-TAC, the HER-2-specific DARPin was replaced with a polypeptide comprising an N-terminal CD8a leader peptide fused to an anti-CD19 scFv. The heavy and light chains of the CD19 scFv were connected via glycine-serine linker region.

The UCHT1 domain was replaced with a humanized version (huUCHT1) to reduce immunogenicity. This TAC construct exhibited superior surface expression levels than its precursor.

To further improve receptor expression on the cellular surface of T cells without impairing functionality, two separate modifications were evaluated in parallel. To increase single chain stabilization, the $G_4S$ linker (SEQ ID NO: 73) used in the anti-CD19 scFv was replaced with the more structured Whitlow linker. Separately, a Y177T mutation was introduced into the huUCHT1 domain. Both strategies enhanced the expression of the TAC receptor, and a receptor was generated with both the Whitlow linker and the Y177T mutation.

Figure 17:
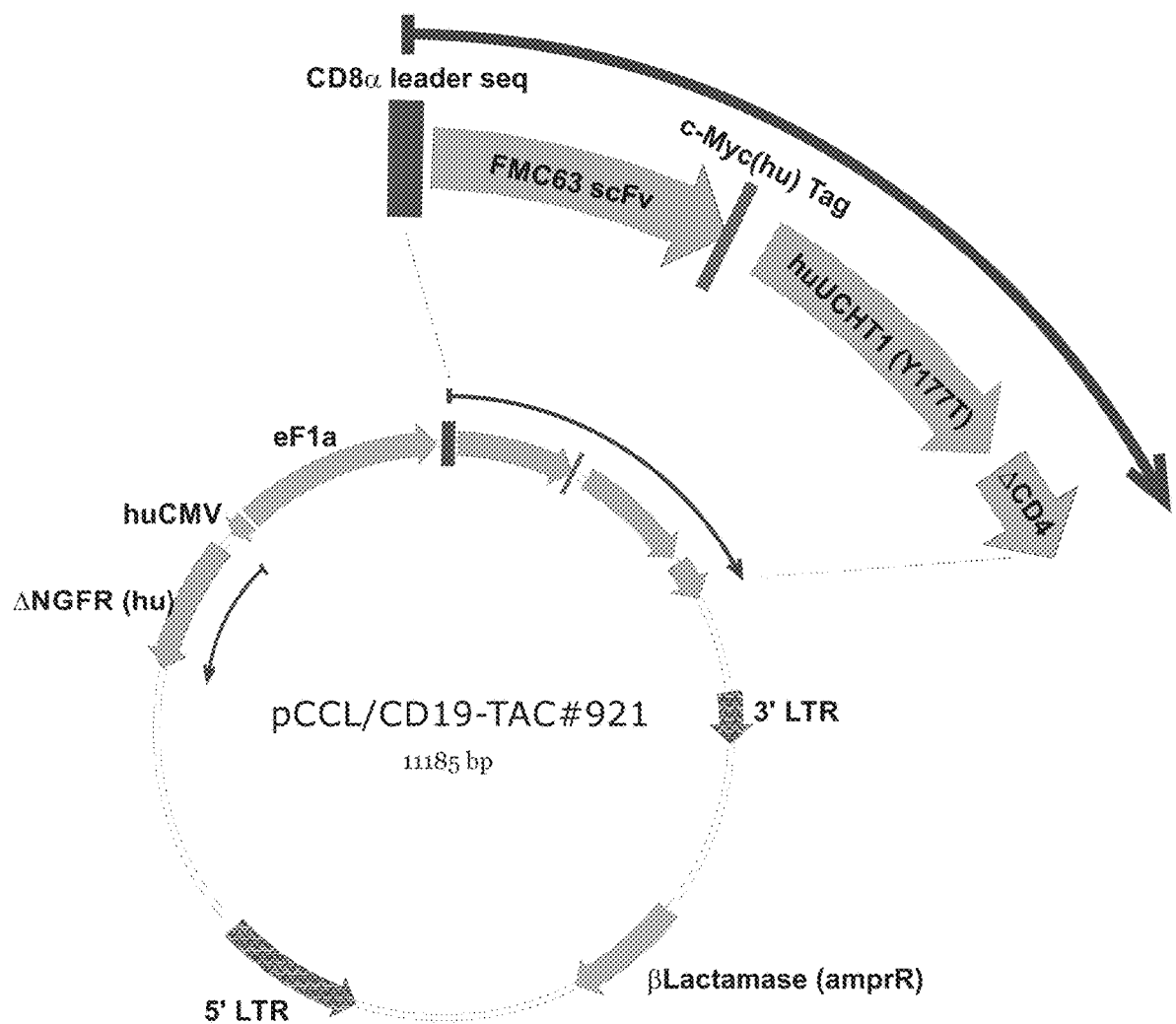
FIG. 17 illustrates TAC-CD19 insert in a pCCL lentiviral vector.

FIG. 17 illustrates a CD19-TAC insert in a pCCL lentiviral vector. The pCCL vector features a bi-directional promoter system with ΔNGFR(hu) under control of the mCMV promoter and TAC expression being driven by the EF-1α promoter. The ΔNGFR(hu) is a truncated human CD271 (Tumor necrosis factor receptor superfamily member 16), with transmembrane domain but lacking the cytosolic signaling domain. The ΔNGFR(hu) expression product is used to quantify lentiviral transduction. The CD19-TAC #921 open reading frame is enlarged to show the key elements of the TAC construct: The CD8α leader, FMC63 single chain (anti-CD19 scFv), the human c-Myc Tag, the huUCHT1 (Y177T) and the ΔCD4 domain. The huUCHT1 (Y177T) mutation was identified by examining point mutations randomly introduced into resides of the murine UCHT1 CD3 epsilon binding interface. In a screen the (Y177T) mutation was successfully identified. The (Y177T) mutation results in better Tri TAC surface expression while retaining T cell activation. ΔCD4 lacks the four CD4 extracellular immunoglobulin like domains and retains the extracellular linker, transmembrane and cytosolic domains.

To generate a GMP-grade lentiviral vector, the CD19-Tri-TAC construct was cloned into a new lentiviral vector under the control of a MSCV promoter. The CD19-Tri-TAC construct is the same as shown in FIG. 17.

Figure 18:
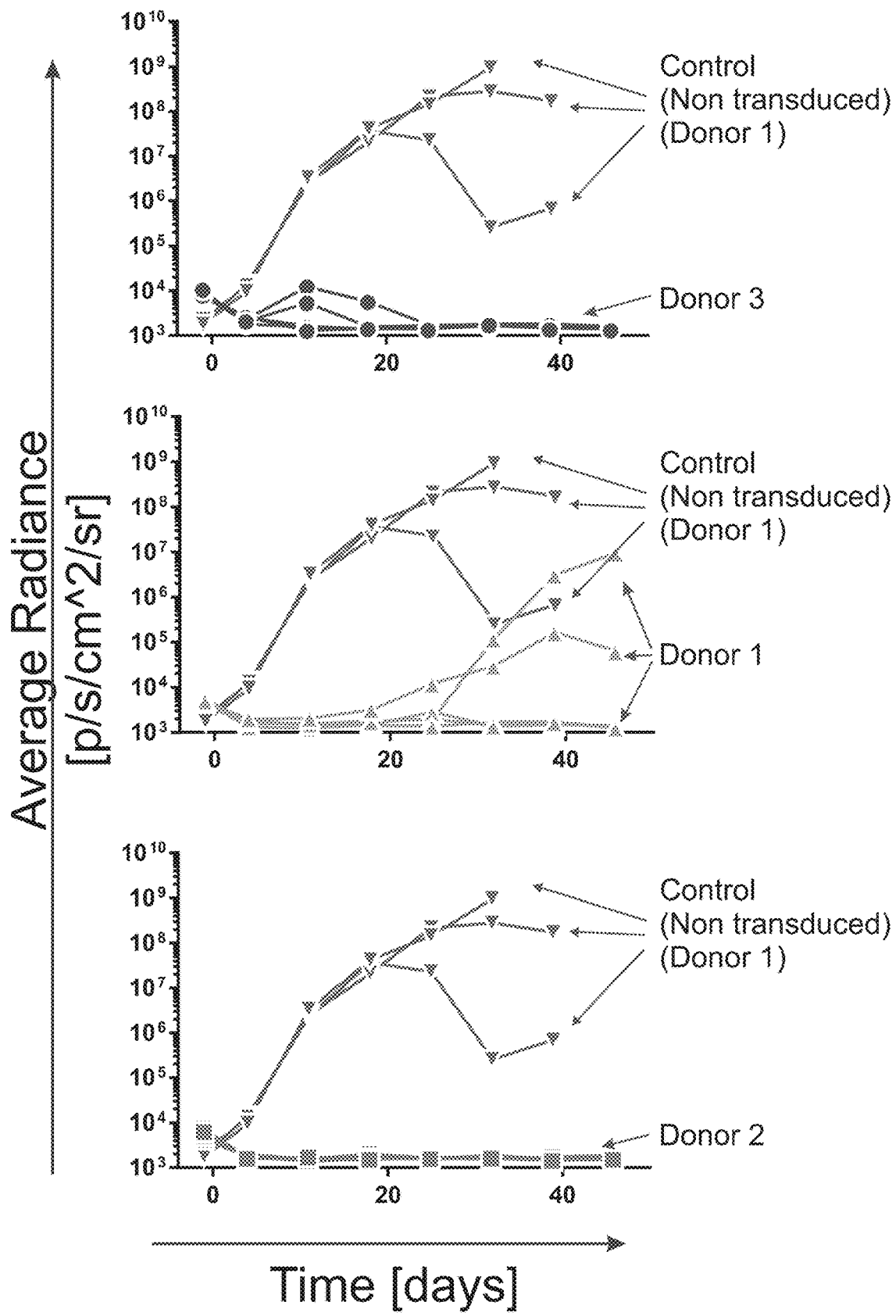
FIG. 18 illustrates the in vivo efficacy of TAC-CD19 generated from different donors.

Example 6. Ability to Manufacture CD19-TAC-Expressing T Cells from Different Donor Material FIG. 18 illustrates the efficacy of CD19 TAC-expressing T cells manufactured from multiple donors. CD19-TAC-expressing T cells were produced using T cells from three different donors, and tested in the NALM-6 tumor model. Mice bearing established NALM-6 tumors were treated with a single dose of $4 \times 10^6$ CD19 TAC-expressing T cells. Control mice showed rapid tumor outgrowth, with all mice reaching endpoint by the termination of the study. T cell products from Donors 1 & 2 resulted in complete control in all mice. T cell product from Donor 3 resulted in robust tumor control in all mice and long-term control in 2/4 treated mice. The study confirms that tumor rejection is achieved by CD19 TAC-expressing T cells derived from multiple healthy donors. The results of the NALM-6 tumor model in FIG. 18 suggest that efficacious CD19 TAC is produced from multiple donor source materials.

Example 7. In Vitro Cytotoxicity and In Vivo Efficacy of CD19-TAC-Expressing T Cells To evaluate the ability of CD19-TAC to effectively engage various CD19-positive cells, Tri-TAC-engineered T cells were co-cultured with either NALM-6 (acute lymphoblastic leukemia), Raji (Burkitt lymphoma) or Jeko-1 (Mantle Cell Lymphoma). NALM-6, Jeko-1 and Raji cells were engineered with enhanced firefly luciferase to enable tracking of tumor burden in vitro and in the live animal via bioluminescence imaging.

Figures 19A, 19B, 19C:
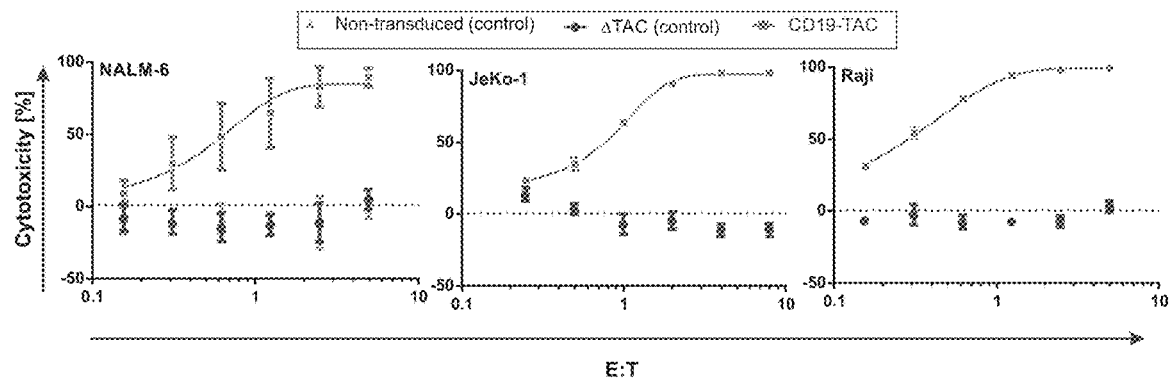
FIG. 19A-FIG. 19C illustrates an in vitro example of TAC-CD19 cytotoxicity against the tumor lines.
Figure 19D:
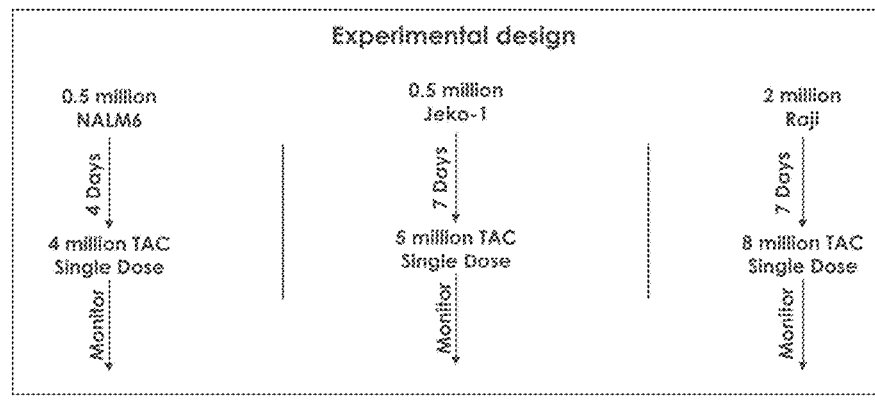
FIG. 19D illustrates the schematic of 3 different in vivo tumor models in NRG mice.

FIG. 19A-FIG. 19C illustrates killing of tumor cell lines by CD19-TAC-expressing T cells. The effects were dose-dependent and increased with increasing effector-to-target (E:T) ratios. As negative controls, cells engineered with ΔTAC (lacking an antigen-binding domain) or non-transduced T cells were used. These results demonstrate that CD19-TAC-expressing T cells kill CD19-positive tumor cells.

FIG. 19D-FIG. 19G illustrates the design and outcome of an in vivo study assessing efficacy of CD19-TAC in mice engrafted with either NALM-6 (acute lymphoblastic leukemia), Raji (Burkitt lymphoma) or Jeko-1 (Mantle Cell Lymphoma) liquid tumors. To initiate NALM-6, Raji and Jeko-1 tumors, mice were inoculated with NALM-6, Raji or Jeko-1 cells and housed 4 or 7 days, respectively, to allow the engraftment of tumors. On day 4 or 7, CD19-TAC-expressing T cells were given as an intravenous tail vein injection. Tumor burden was measured at weekly intervals, and the data are plotted as the average radiance [p/s/cm^2/sr].

Figures 19E, 19F, 19G:
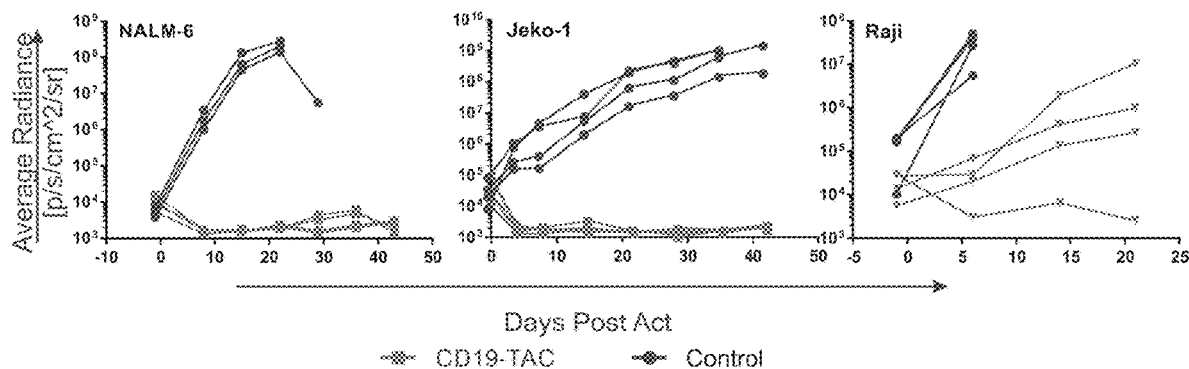
FIG. 19E-FIG. 19G illustrate in vivo efficacy of CD19-TAC in NALM-6 (acute lymphoblastic leukemia) FIG. 19E, Jeko-1 (Mantle Cell Lymphoma) FIG. 19F, and Raji (Burkitt's lymphoma) FIG. 19G.

FIG. 19E-FIG. 19G illustrates that CD19-TAC engineered T cells are efficacious in inducing tumor regression and long-term tumor control in NALM-6 (acute lymphoblastic leukemia), Raji (Burkitt lymphoma) or Jeko-1 (Mantle Cell Lymphoma) liquid tumors.

The results of the NAML-6, Raji or Jeko-1 tumor models in FIG. 19A-FIG. 19G suggest that CD19-TAC is efficacious in a variety of CD19 positive tumor models.

Example 8. CD19-TAC-Expressing T Cell Persistence and Lasting Tumor Immunity

FIG. 20A-FIG. 20B illustrate persistence of tumor immunity and resistance to re-challenge in mice receiving CD19-TAC-expressing T cells. Mice bearing established NALM-6 tumors were treated with CD19-TAC-expressing T cells.

FIG. 20A illustrates the experimental set up to determine CD19-TAC persistence in mice. Mice were first inoculated with NALM-6 cells, which following a 4 day engraftment period were treated with CD19-TAC. All mice showed tumor regression and complete tumor control. 56 days after the initial treatment mice were re-challenged with either NALM-6 (CD19 positive) or KMS11 (CD19 negative) liquid tumors. In all cases naïve mice are co-injected with tumor cells and used as negative controls. Tumor burden is followed via luminescence signal.

FIG. 20B: Mice bearing established NALM-6 tumors were treated with CD19-TAC-expressing T cells given as split dose totaling $4 \times 10^6$ engineered cells. As controls, a group of un-treated animals was used. Following ACT, treated mice presented durable anti-tumor responses. In contrast, control mice showed exponential increases in tumor masses and reached tumor burden related endpoint. On day 56 post-ACT, mice were re-challenged with either NALM-6 tumor cells (CD19 positive) or KMS11 tumor cells (CD19 negative). CD19-TAC-treated mice remain protected from NALM-6 (CD19 positive) tumor cells, but not from KMS11 (CD19 negative) tumor cells.

The results of re-challenge experiments in FIG. 20A and FIG. 20B suggest that CD19-TAC, in some instances, differentiates into long-lived memory cells that retain anti-tumor properties.

Example 9. In Vivo Expansion and Dose Dependency of CD19-TAC-Expressing T Cells

Figure 22A:
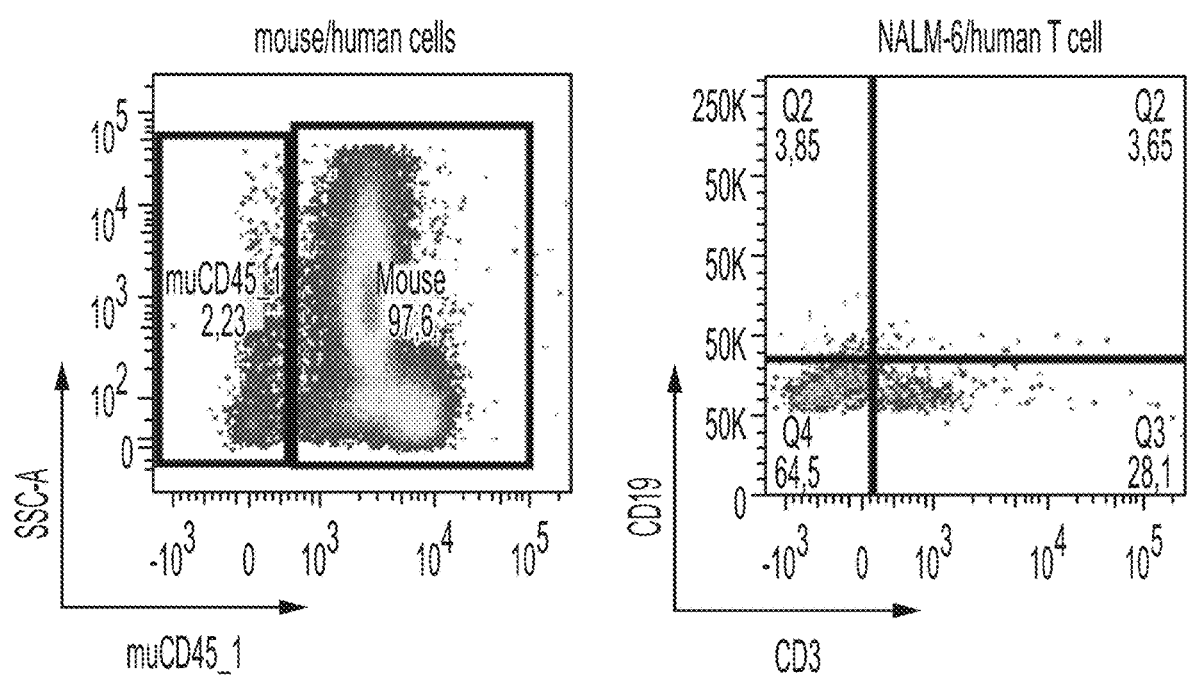
FIG. 22A-FIG. 22B illustrate an experimental setup and data with regard to in vivo expansion of TAC-CD19 following a split dose administration.
Figure 22A:
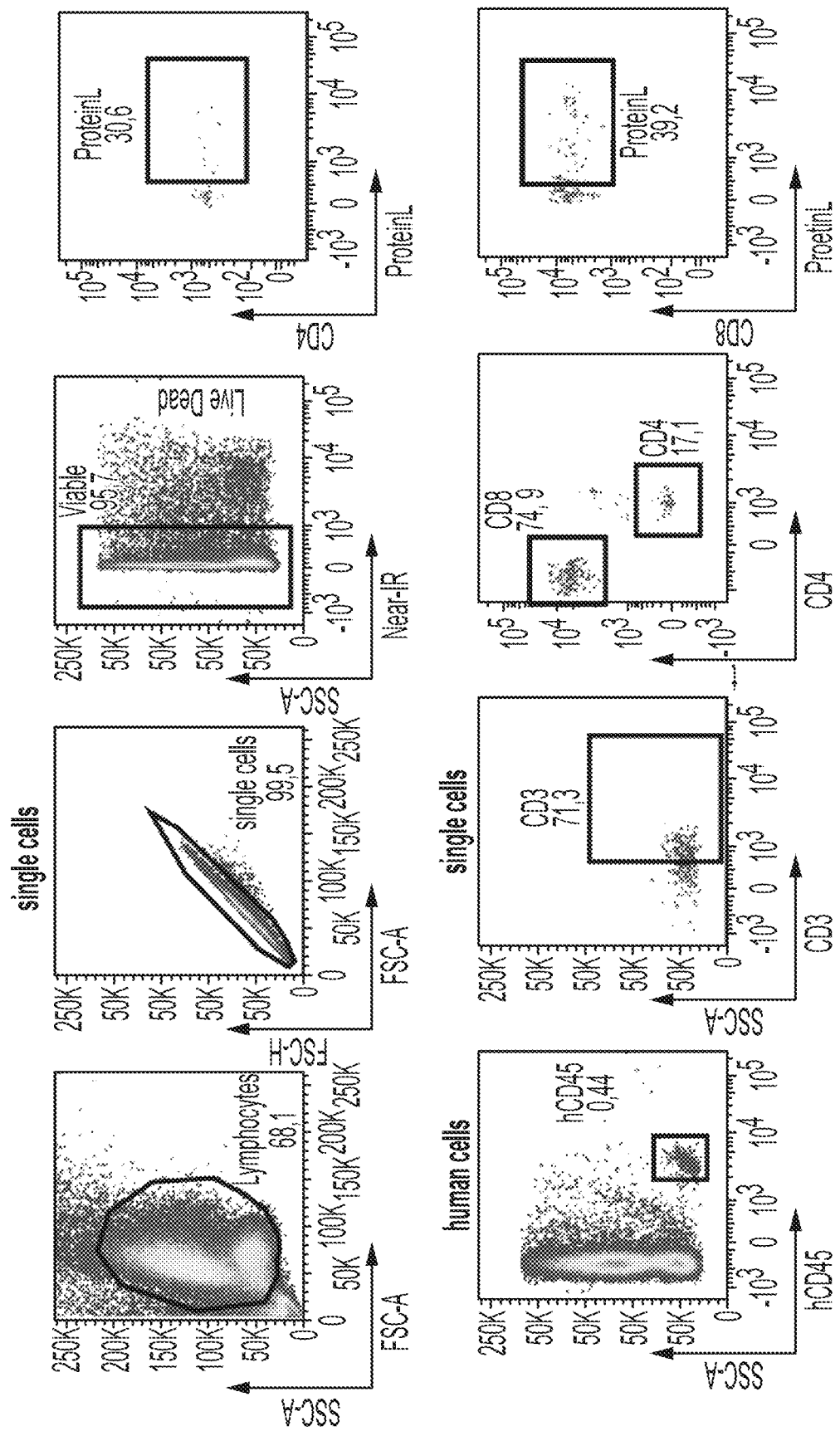

FIG. 21 and FIG. 22 illustrate dose dependency, dose regime (split or single) and expansion of CD19-TAC-expressing T cells in a NALM-6 cancer model. FIG. 21A illustrates experimental design. Mice received either a single dose of CD19-TAC-expressing T cells on day four post-tumor inoculation, or a split dose delivered seven days apart. Multiple CD19-TAC-expressing T cells doses were tested: $0.5 \times 10^6$, $1 \times 10^6$, and $4 \times 10^6$ cells. FIG. 21B control groups of mice receive $4 \times 10^6$ non-transduced cells, or freezing media (vehicle control).

FIG. 21B illustrate survival of mice after NALM-6 injection and CD19-TAC injection. Dose-dependent promotion of survival were observed both in the single dose and split dose groups, with the highest single administration dose limiting tumor growth and promoting survival the mouse.

FIG. 22A illustrates the gating strategy used to assess T cell proliferation. Cells were first selected based on forward and sideways scatter to select for the lymphocyte population. Singlet cells were identified via a forward scatter area over height gate. Live cells were identified via near IR gating. Human cells were identified via a hCD45 gate. The resulting subset of cells was further divided into CD3 positive cells. These cells were then gated on CD4/CD8 and Protein L. The staining strategy also contained muCD45_1 to identify murine blood cells. CD19 was included to stain for NALM-6 cells.

Figure 22B:
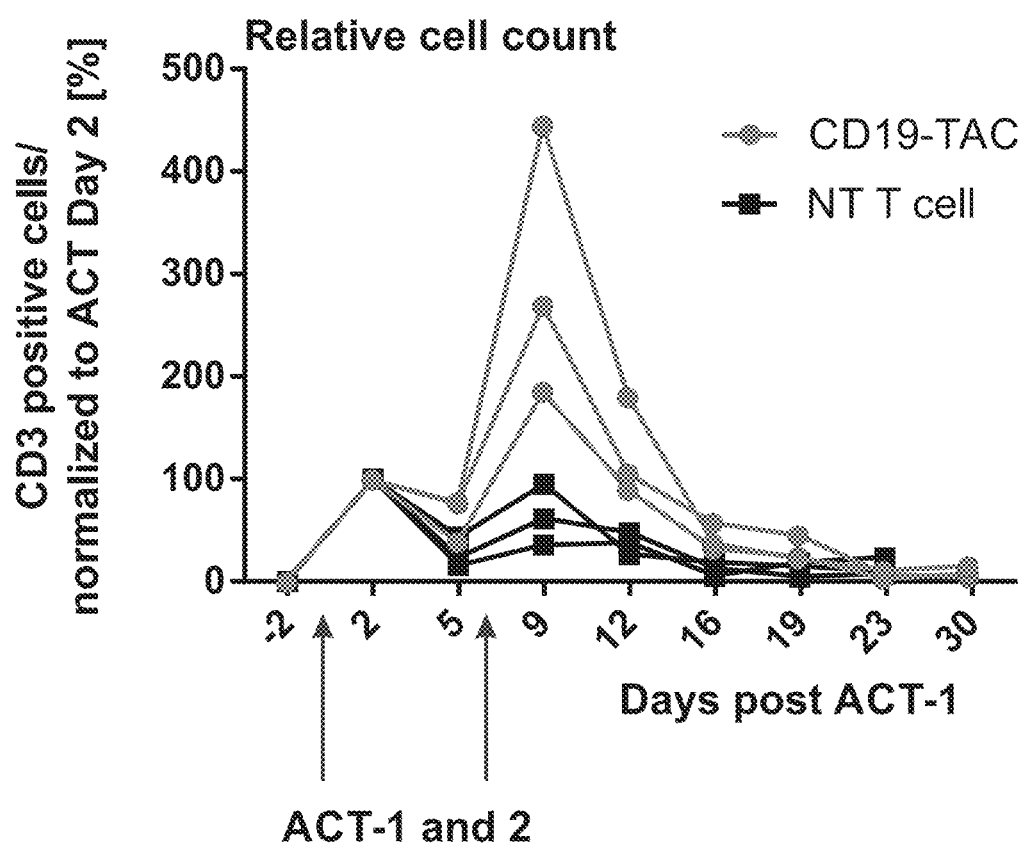

FIG. 22B expansion of T cells in mice after split dose adoptive T cell transfer (ACT). After ACT, blood samples were taken regularly and analyzed via flow cytometry. Values were normalized to the number of total T cells present in the blood post ACT1. Values were also normalized to the total number of CD45.1+(murine) cells to account for differences in blood draw. T cells in mice treated with CD19-TAC engineered cells were shown to expand in recipient mice within approximately 1-2 weeks after the first ACT (FIG. 22B). Non-transduced cells did not expand (FIG. 22B).

The results of the various doses, dose regimen (FIG. 21B) and T cell counts (FIG. 22B) suggest that CD19-TAC efficacy is dose dependent, that engineered T cells expand in vivo, and that this expansion is specific to CD19-TAC engineered cells in animals carrying CD19-positive tumors.

Example 10. In Vivo Efficacy, Long Term Efficacy and Safety CD19-TAC Treatment

Figure 23A:
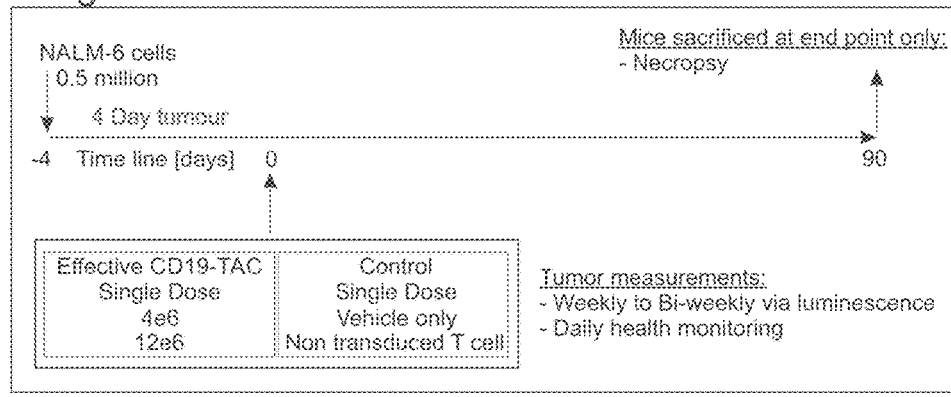
FIG. 23A-FIG. 23C illustrate long term in vivo studies of TAC-CD19 in mice.
Figure 23B:
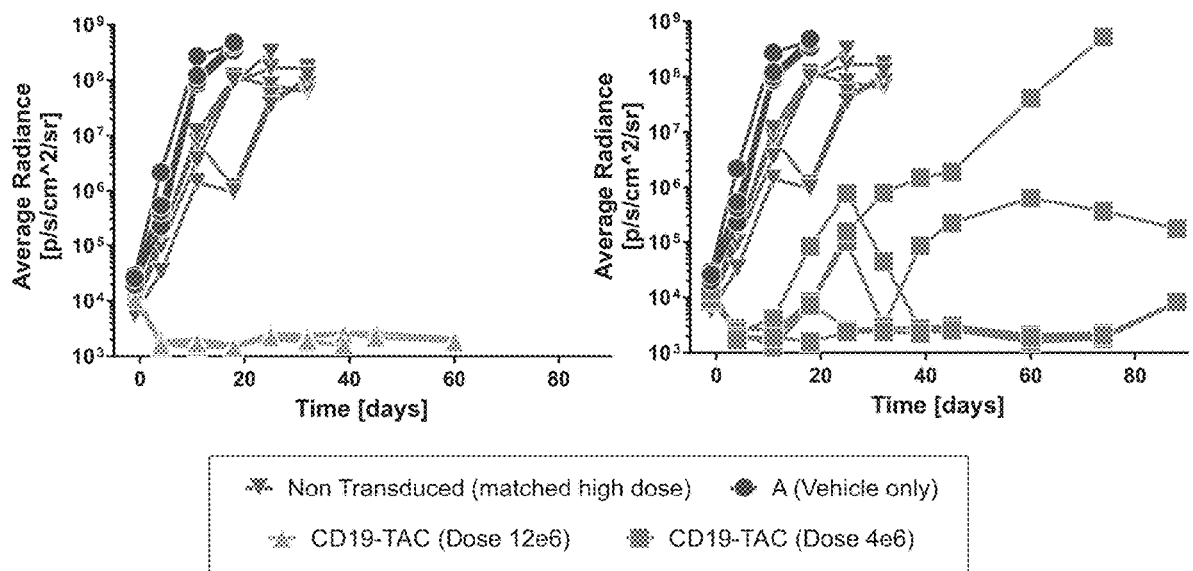
Figure 23C:
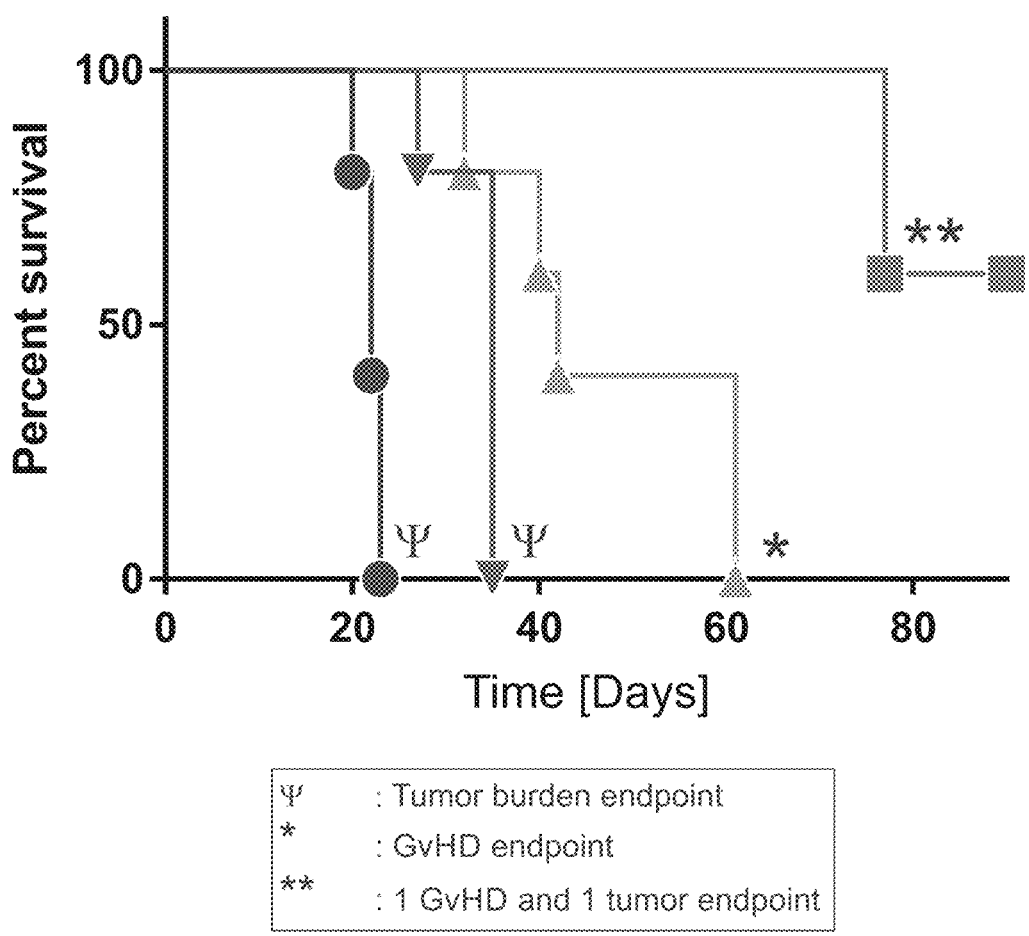
Figure 24:
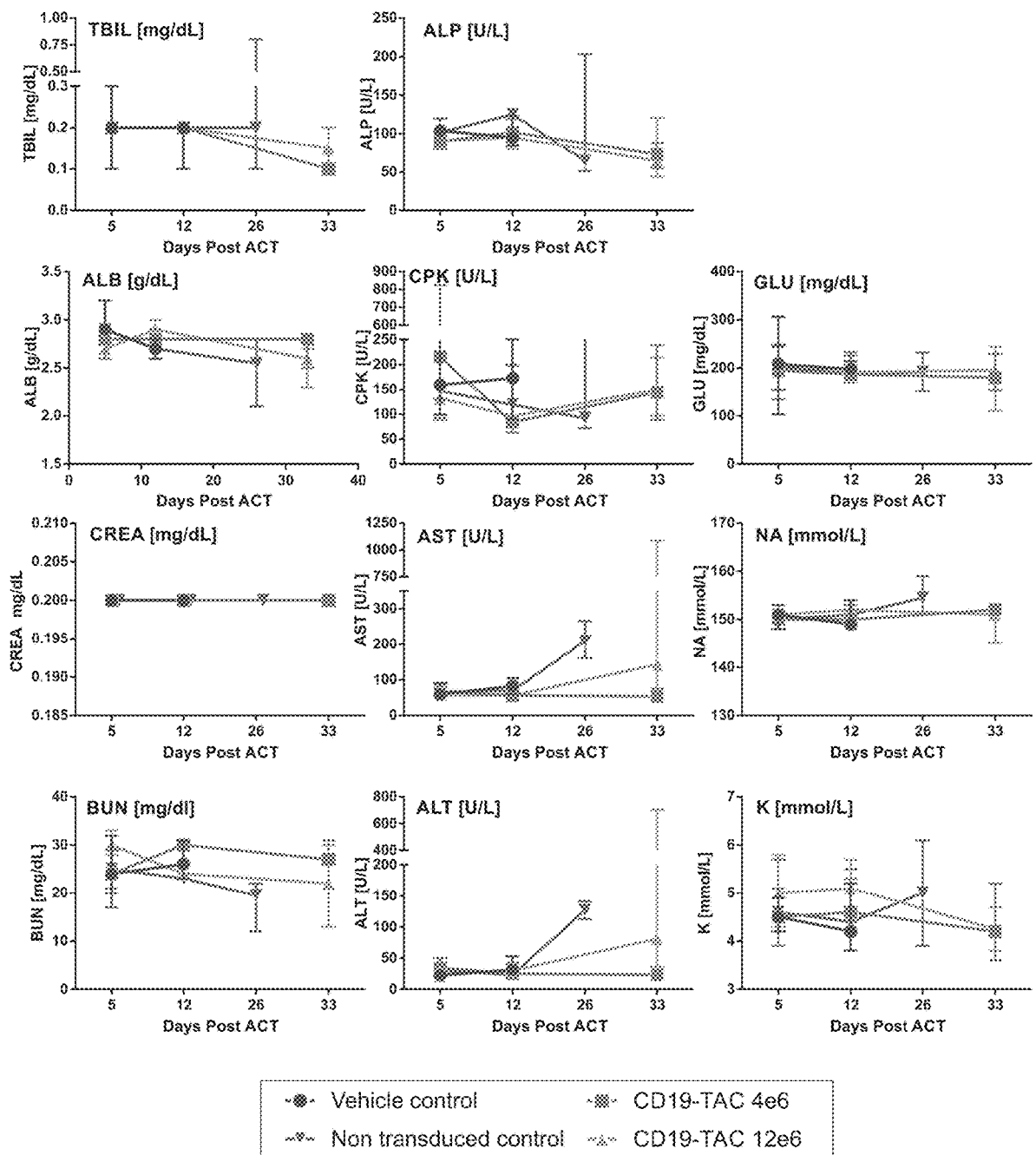
FIG. 24 illustrates clinical chemistry analysis results from mice treated with TAC-CD19 or non-transduced T cells.

FIG. 23-FIG. 25 demonstrate the long-term safety and efficacy (FIG. 23) and in the absence of any acute treatment associated toxicities (FIG. 24-FIG. 25).

FIG. 23A illustrates the experiment design. Mice were injected with 0.5×10⁶ enhanced luciferase engineered NALM-6 cells, which were allowed to engraft for 4 days. Mice are then treated with two dose levels (4 and 12×10⁶ engineered cells) of CD19-TAC-engineered T cells in a single dose administration. Tumor growth was then followed via regular luminesce measurements. Mouse health was regularly assessed via inspection of mouse behavior and physical characteristics (grooming, motility, fur integrity)

FIG. 23B illustrates the tumor burden via luminescence following treatment with either vehicle alone (Freezing media), non-engineered control cells (Total T cell dose equal to total T cell dose of highest engineered treatment group) and either 4 or 12×10⁶ engineered CD19-TAC engineered T cells. Both controls show rapid tumor outgrowth and no anti-tumor efficacy. The control dose results in a delay in tumor outgrowth relative to vehicle alone, presumably due to competition between high dose T cell and tumor cells for engraftment niches. Engineered T cell show tumor regression in all cases. High dose treatment groups show complete tumor control in all cases. The 4×10⁶ treatment group shows 3 mice with complete control, one with delayed tumor outgrowth and one with controlled but high tumor burden.

FIG. 23C illustrates overall survival of the different treatment groups. In both, the vehicle and non-engineered control mice, all mice succumb to the tumor within 23 to 35 days respectively. In case of high dose CD19-TAC treatment all mice develop GvHD symptoms and succumb to GvHD within 61 days. GvHD is a consequence of the mouse model itself and not the treatment with the modified T cells. Low dose mice show survival of 3 mice until end of study at 90 days, one mouse succumbs to high tumor burden, one mouse succumbs to GvHD.

FIG. 24 and FIG. 25 illustrates clinical chemistry parameters and cytokine levels from vehicle control, non-engineered and CD19-TAC (4 and 12×10⁶ effective CD19-TAC engineered cells) treated mice. Mice were followed for 33 days with blood samples taken 5, 12 and 33 days post ACT. Only CD19-TAC treated mice survived for 33 days. Vehicle control mice succumbed to tumor burden before a 3$^{rd}$ blood sample could be collected, non-engineered cells were sacrificed early on day 26, immediately prior to mice reaching tumor burden related endpoint. All blood samples were analyzed for several clinical chemistry parameters and cytokine levels.

FIG. 24 illustrates that at day 5 and 12 CD19-TAC treated mice show no parameter that is significantly higher compared to control groups. At day 33 all treated mice show clinical chemistry parameters comparable to early treatment time points, with the exception of Alanine Aminotransferase (ALT) and Aspartate Aminotransferase (AST) where some mice experience high levels, similar to mice treated with non-engineered cells sampled on day 26.

Figure 29:
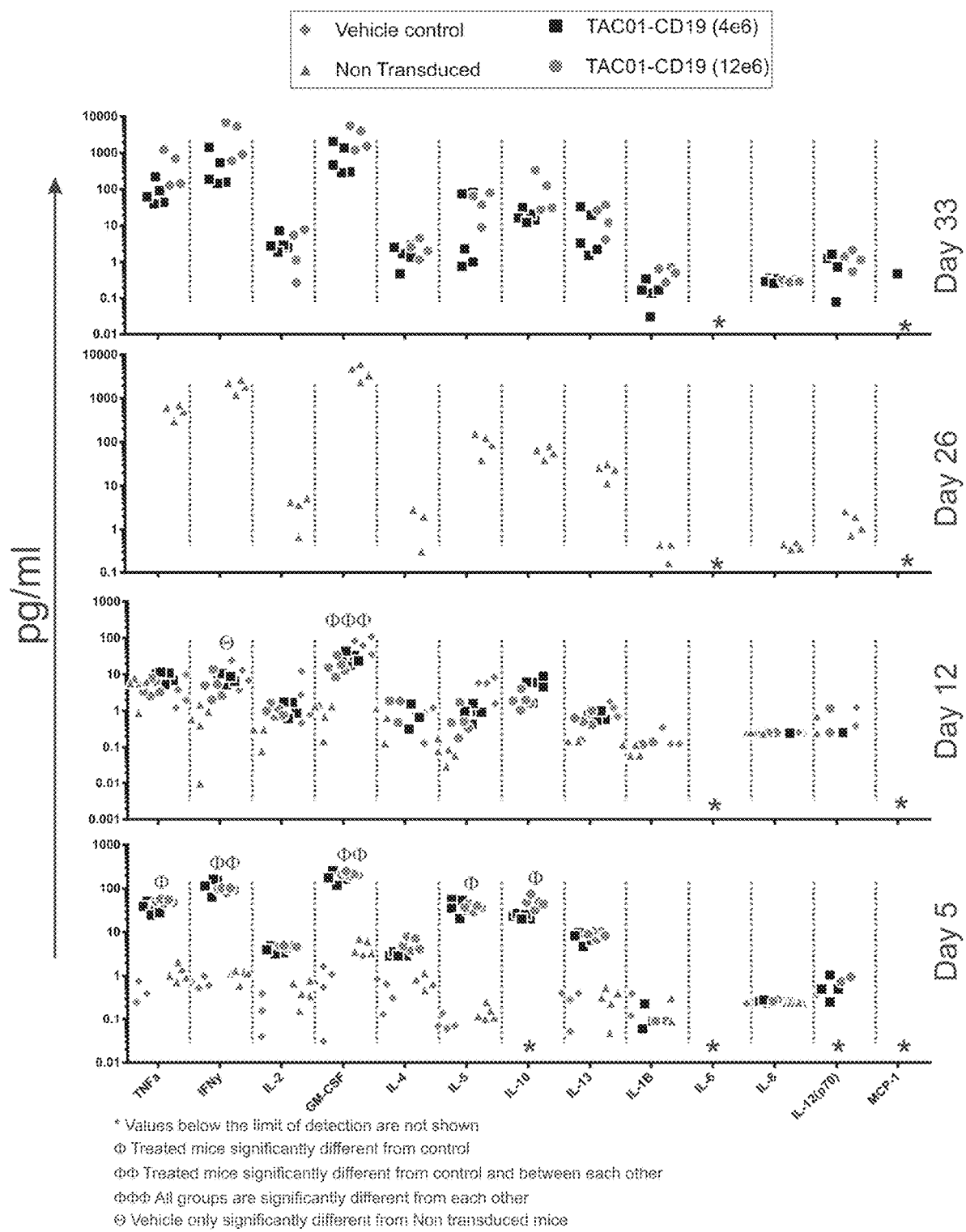
FIG. 29 illustrates human cytokine released in mice blood following treatment with TAC-CD19 or non-transduced T cells.

FIG. 25 illustrates the cytokine response on day 5, 12 and 33. On day 5 post ACT CD19-TAC but not control mice show elevation in all cytokines tested. The cytokine increase is in agreement with an inflammatory response of CD19-TAC engineered T cells recognizing and reacting to antigen positive NALM-6 tumor cells. Following their initial reaction by day 12 cytokine levels subside, which correlates with the by then induced tumor regression and generally low tumor burden. On day 12 cytokine levels between CD19-TAC treated are either similar or lower than non-engineered T cells except for IL10. At the later stage all mice treated with non-transduced or CD19-TAC engineered T cells show an increase in cytokines, presumably associated with GvHD onset. See also FIG. 29, which illustrates cytokine response on day 5, 12, 26 and 33.

The results of the long-term follow up of mice treated with CD19-TAC and their clinical chemistry profile demonstrate that engineered T cells are safe to use and do not show any indication of toxicity caused specifically by CD19-TAC engineering. The results of the cytokine study demonstrate an early inflammatory response associated with anti-tumor efficacy, following by a drop in all cytokine levels, suggesting that a controlled inflammatory response.

Example 11. In Vivo Efficacy of Several BCMA Tri-TAC Variants

Figures 26A, 26B:
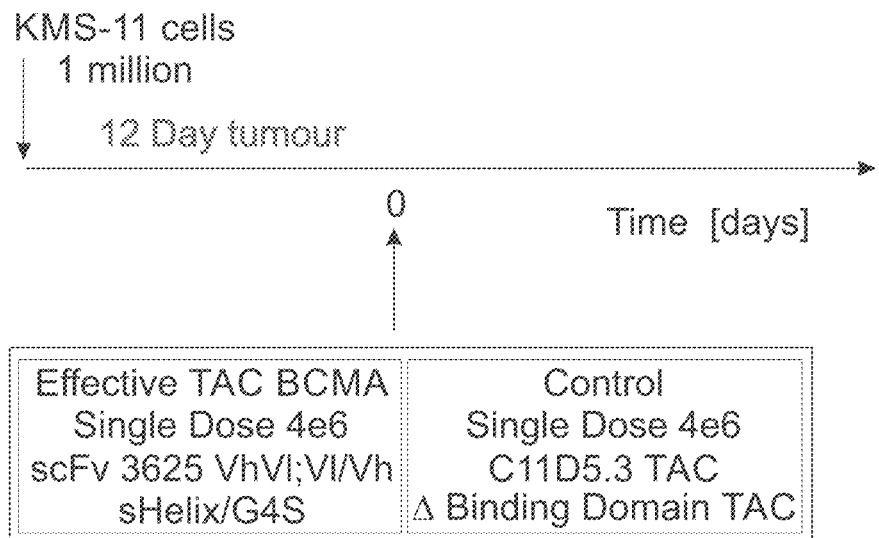
FIG. 26A-FIG. 26C illustrates efficacy of BCMA-TAC in different configurations.

FIG. 26 illustrates an in vivo efficacy study of various BCMA Tri-TAC constructs. FIG. 26A illustrates the overall experimental design. 1 million luciferase-engineered KMS11 (BCMA positive) tumor cells were allowed to engraft for 12 days. Mice were then treated with a single effective dose of 4 million BCMA constructs and controls (FIG. 26B). Tumor burden was regularly assessed via luminescence measurements. All mice that showed tumor regression and tumor control were then re-challenged on day 25 post ACT with 1 million KMS11 cells.

Figure 26C:
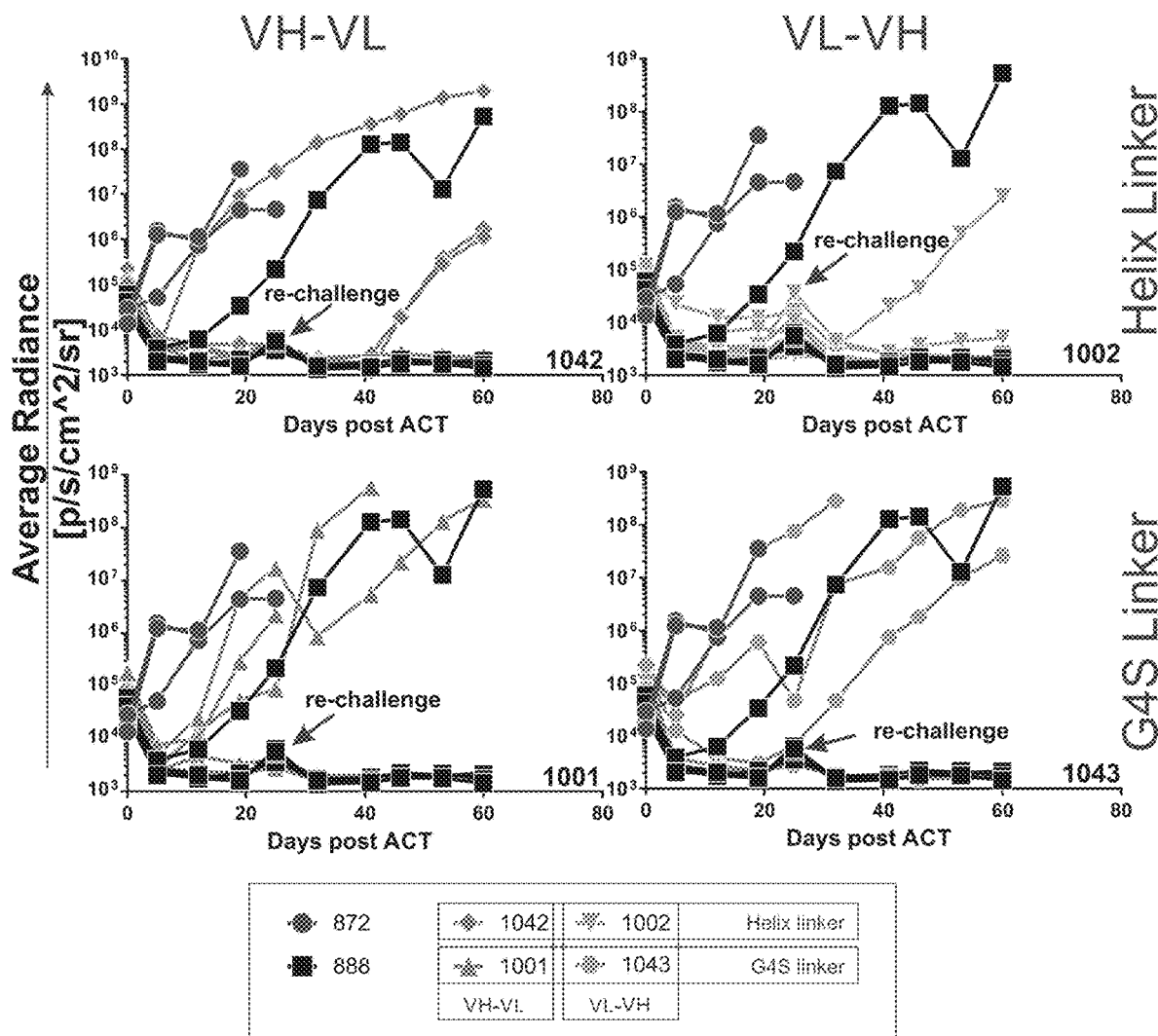

FIG. 26C: Following ACT, control mice exhibited a rapid outgrowth of tumor cells reaching tumor associated endpoint within 19 to 25 days. In contrast all BCMA-TAC treated mice showed initial tumor regression. Tumor control varied across constructs with the G₄S (SEQ ID NO: 73) 3625VH-VL showing the lowest level of initial tumor control and Short Helix 3625 VL-VH showing the highest level of initial tumor control. Following re-challenge, a majority of all constructs that had maintained tumor control until day 25 remained protected against re-challenge.

The results of this in vivo study demonstrate, that a variety of BCMA Tri-TAC constructs are effective in controlling KMS11 (BCMA positive) liquid tumors. But that certain preferred configurations provide superior efficacy. In general, the helical connector region provided a relative benefit when compared to the flexible linker within the same scFv configuration.

Example 12. In Vivo of TAC-Her2

Mice are inoculated at the hind flank with OVCAR3 solid tumors. Tumors are allowed to establish and grow to a size of 100 mm³. Mice are then treated with a tail vain injection of TAC-Her2 engineered T cells. Tumor volume is measured regularly.

Example 13. Clinical Trial

A clinical study is undertaken wherein subjects of at least 18 years of age with CD19-positive Diffuse Large B-cell Lymphoma who have failed at least two prior lines of therapies including ASCT or who are ineligible for ASCT are treated with CD19-TAC-expressing T cells. The study is an open label, single arm, Phase ½ two-stage trial, featuring a dose escalation stage to determine the maximum tolerated dose (MTD) or recommended phase II dose (RPh2D), followed by an expansion cohort at the selected dose.

Upon enrollment, subjects undergo leukapheresis to obtain T cells for manufacture of CD19-TAC-expressing T cells. Upon successful manufacture, subjects enter the treatment phase. This phase involves a lymphodepleting chemotherapy with fludarabine and cyclophosphamide, followed by intravenous (IV) administration of CD19-TAC-expressing T cells. After treatment with CD19-TAC-expressing T cells, subjects enter post-treatment follow-up and are followed for safety, disease status, and survival for 2 years after their last dose of CD19-TAC-expressing T cells. After study completion, subjects are followed for survival, long-term toxicity, and viral vector safety in a separate long-term follow up protocol for up to 15 years after their last dose of CD19-TAC-expressing T cells.

In all groups, safety is assessed throughout the study. T cell expansion is assessed from the time of the first dose of CD19-TAC-expressing T cells until cells are no longer detectable. Radiographic disease assessment is performed by positron emission tomography (PET) and/or computed tomography (CT) scans pre-treatment and approximately 3, 6, 9, 12, 18, and 24 months following the last dose of CD19-TAC-expressing T cells, or until progressive disease, or treatment with additional anti-cancer therapy.

Example 14. Manufacturing of CD19-TAC-Expressing T Cell Drug Products

The manufacturing process of CD19-TAC-expressing T cells drug products involves selecting CD4/CD8 T cells from a leukapheresis product, activating the CD4/CD8 positive cells, transducing the cells with a lentiviral vector comprising the CD19-TAC construct (as described in example 5), expanding the transduced cells to level adequate for the proposed dosing schedule, and harvesting and cryopreserving the final product.

The patient's leukapheresis material with its associated unique subject identifier (UPN) is received into a manufacturing site and given a unique specimen number (ISN). The CD4/CD8 cells are selected are cryopreserved until initiation of the culture process steps.

The cryopreserved CD4/CD8 positively selected T cells are thawed at 37° C., resuspended in appropriate medium and seeded into culture bags with activating reagents, the cultures are incubated overnight at 37° C./5% CO2.

The cells are transduced with the CD19-TAC lentiviral vector at an appropriate multiplicity of infection (MOI) and incubated overnight at 37° C./5% CO2. On subsequent days, the culture is supplemented with complete medium to maintain a desired cell concentration and eventually pooled into transfer bags, pelleted, resuspended and seeded to larger culture bags at the targeted cell density.

For drug product formulation, the harvested cell suspension is resuspended in excipient and cryopreserved with a controlled-rate freezer then transferred to LN2 storage.

The product is shipped to the clinical site in its frozen state, thawed at the bedside and administered intravenously.

Prior to the clinical trial, engineering manufacturing runs are conducted inclusive of all in-process and release testing using healthy donor leukapheresis material. In addition to in-process and release testing, studies supportive of regulatory filings are conducted on final drug product from these engineering runs. These studies include post-thaw stability, initiation of long-term stability, residual testing to assure the clearance of growth-promoting cytokines and early assessment of potential functional/potency indicating assays.

Figure 27:
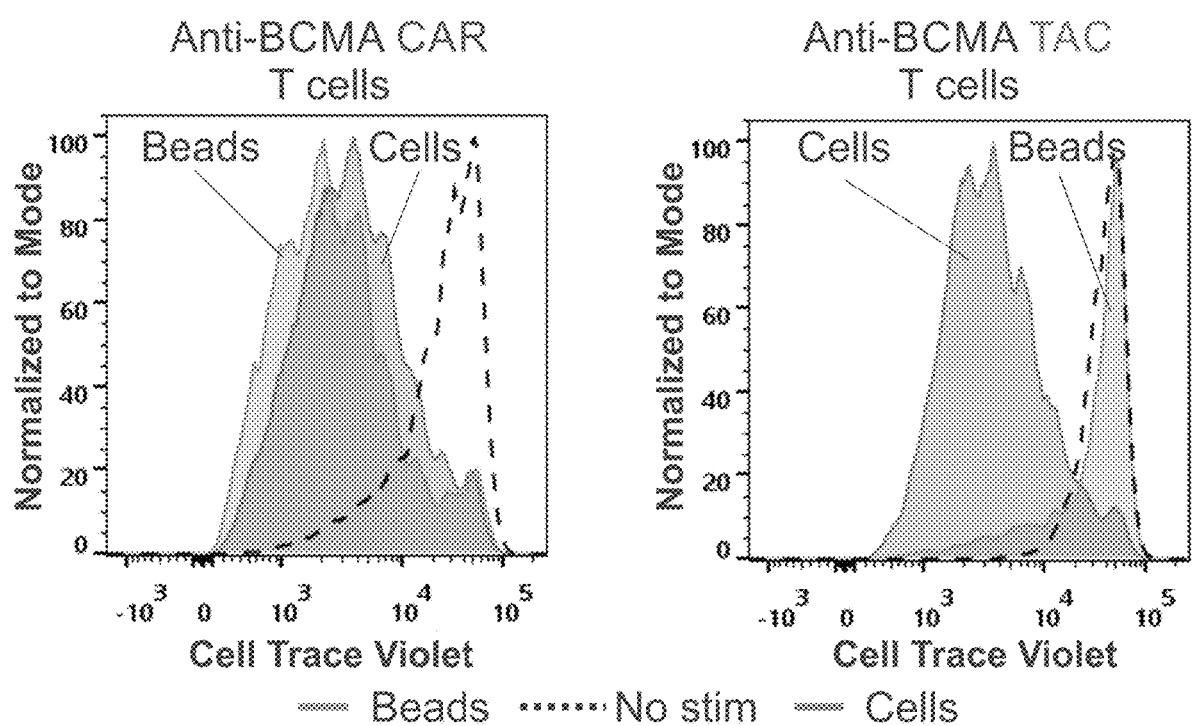
FIG. 27 illustrates that TACs proliferate when encountering antigen on cells, but not when the antigen is presented on artificial beads; but CARs proliferate irrespective if antigens are presented on beads or cells.

Example 15. Preclinical Development of BCMA Specific T-Cell Antigen Coupler (TAC) Therapy for the Treatment of BCMA Positive Malignancies FIG. 27 illustrates that TACs proliferate when encountering antigen on cells, but not when the antigen is presented on artificial beads; but CARs proliferate irrespective if antigens are presented on beads or cells.

FIG. 28A-FIG. 28B illustrate TAC engineered T cells expand in vivo and provide long term protection, indicating cell persistence in a model of myeloma. FIG. 28A-FIG. 28B illustrate BCMA-TAC T cells reject multiple myeloma tumors in a KMS-11 xenograft model engineered with NanoLuc (KMS 11-NanoLuc) (BCMA$^{pos}$). Following tumor engraftment mice were treated with BCMA TAC-T cells (carrying Firefly Luciferase). TAC-T cells expand significantly following administration. This correlates with tumor regression. Treated mice were resistant to tumor rechallenge indicating long term persistence of TAC-T cells.

The data illustrates that TAC-T cells destroy tumor cells likely via a mechanism that mimics the natural process of T cell activation. The TAC technology illustrates 1) strong efficacy in liquid, 2) in vivo proliferation, 3) T cell persistence, protecting mice from re-challenge, and 4) cell expansion following T cell administration.

Example 16. In Vivo and In Vitro Activity of Hu- or muIgκ HER2-TAC with MSCV or EF1α Promoter CD4 and CD8 T cells were engineered with a variety of TAC expressing viruses. One set of cells was engineered with a lentivirus that employed the MSCV promoter to express a TAC specific for HER-2 that employed the murine IgG signal peptide [muIgG TAC (MSCV)]. Another set of cells was engineered with a lentivirus that employed the MSCV promoter to express a TAC specific for HER-2 that employed the human IgG signal peptide [huIgG TAC (MSCV)]. A third set of cells was engineered with a lentivirus that employed the EF1α promoter to express a TAC specific for HER-2 that employed the murine IgG signal peptide [muIgG TAC (EF1α)]. As negative control, a TAC construct lacking the HER2 binding domain (Δbinding domain TAC) was used. Engineered cells were then characterized in vitro for resurface expression and specific activity and in vivo for activity in the OVCAR3 HER2-positive solid tumor model.

Figure 30:
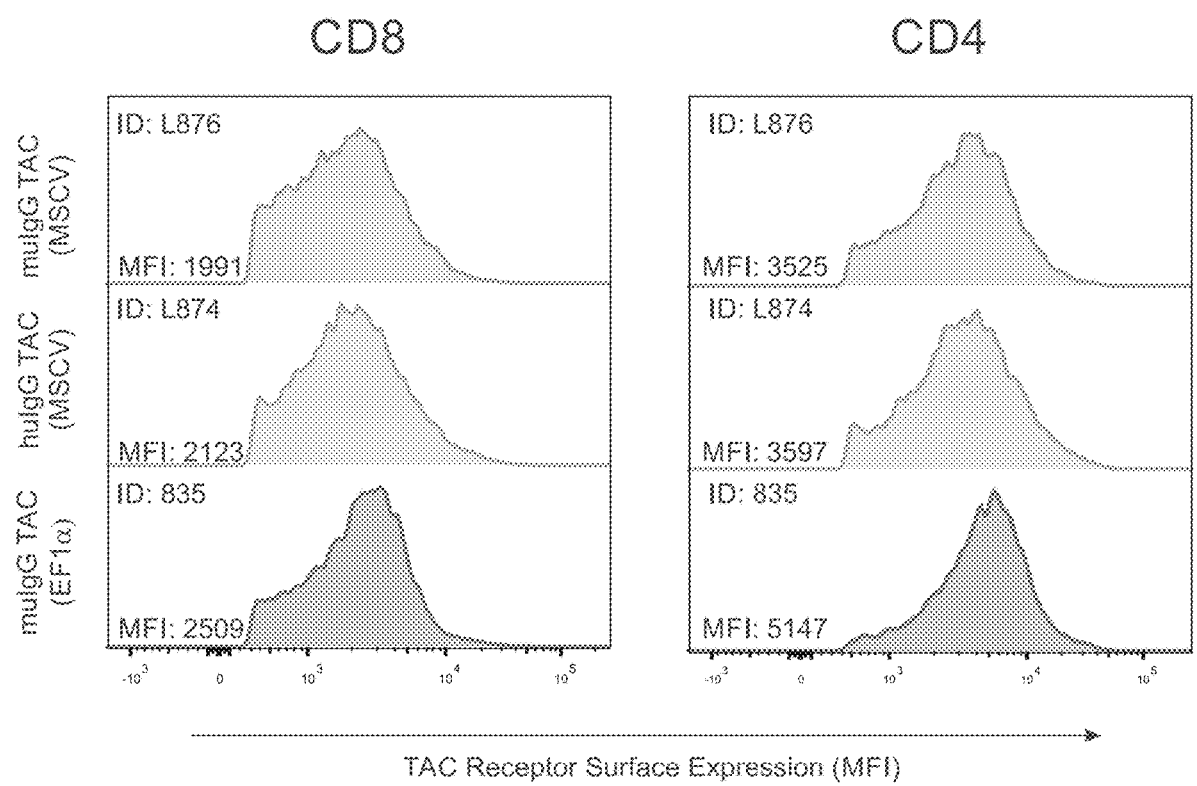
FIG. 30 illustrates exemplary histograms of TAC receptor surface expression in CD4 and CD8 engineered T cells. Cells were engineered with the muIgG HER2 TAC (EF1α promoter), the huIgG HER2 TAC (MSCV promoter) and muIgG HER2 TAC (MSCV promoter). Following engineering, T cells were stained with a TAC specific reagent and measured using flow cytometry. All constructs show comparable levels of surface expression, with EF1α driven expression being higher compared to the MSCV constructs.

FIG. 30 illustrates T cell surface expression of either human or murine IgG leader HER2 TAC receptors, under control of a MCSV or EF1α promoter. Surface expression is a key requirement for biological activity and this illustrates that the HER2 TAC receptors expression is not influenced by the species source of the IgG signal peptide.

Figure 31:
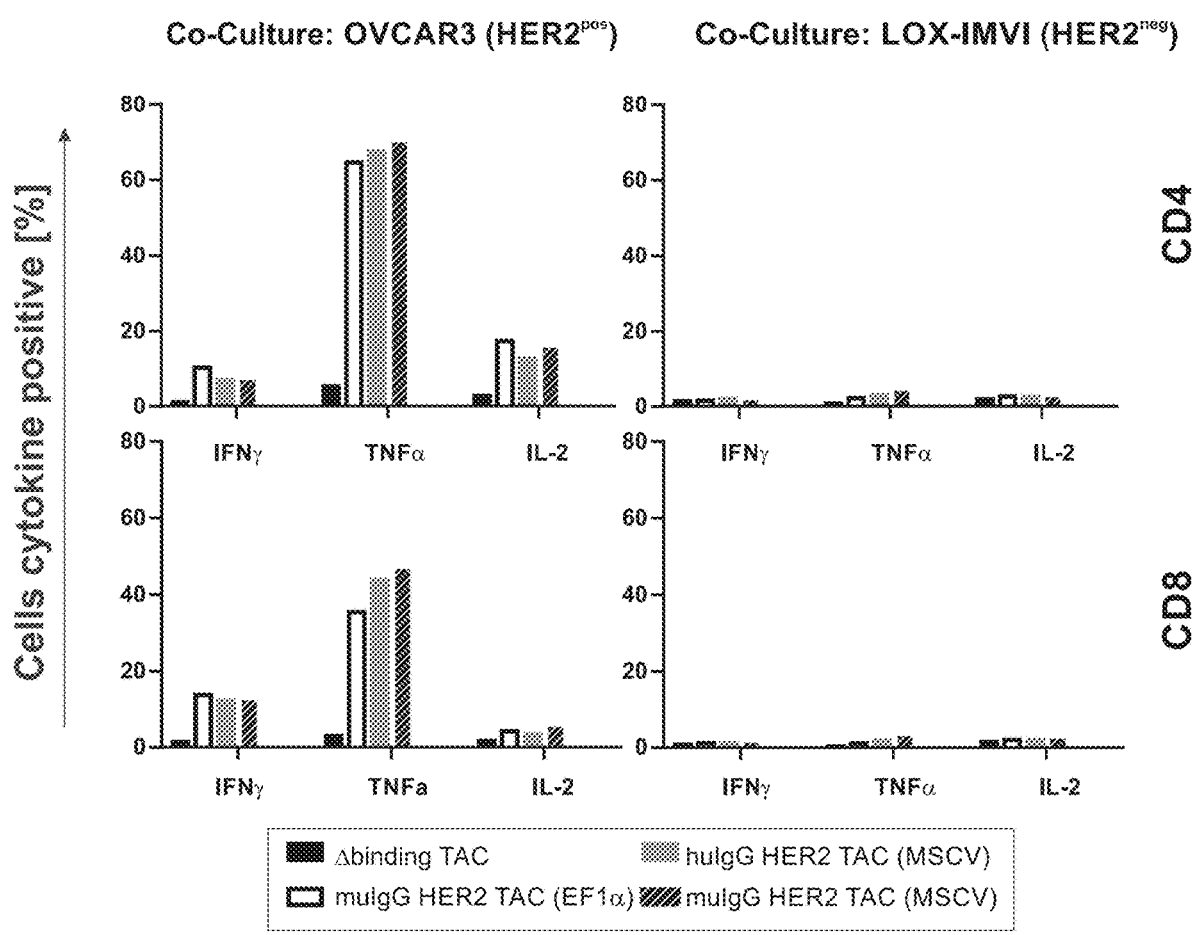
FIG. 31 illustrates the relative percentage of T cells expressing either TNFα, IFNγ or IL-2 following co-cultured either with OVCAR3 (HER2 positive) or LOX IMVI (HER2 negative) cells. T cells were engineered with the muIgG HER2 TAC (EF1α promoter), a TAC construct lacking the HER2 binding domain (Δbinding TAC; EF1α promoter), the huIgG HER2 TAC (MSCV promoter) or the muIgG HER2 TAC (MSCV promoter). When co-cultured with LOX-IMVI (HER2$^{neg}$), Δbinding TAC control and HER2 TAC cells do not show meaningful cytokine expression. All HER2 TAC engineered constructs co-cultured with OVCAR3(HER2$^{pos}$) show similar ability to produce cytokines while control T cells engineered with Δbinding TAC show no meaningful cytokine production.

FIG. 31 demonstrates that T cells engineered with either human or murine IgG leader HER2 TAC constructs, under control of a MCSV or EF1α promoter induce cytokine production, when co-cultured with HER2 positive target cells (OVCAR3) but not with HER2 negative cells (LOX IMVI). This illustrates that HER2 TAC receptor engineered T cells are capable of specifically engaging HER2 expressing target cells but are non-reactive against antigen negative cells.

Figure 32:
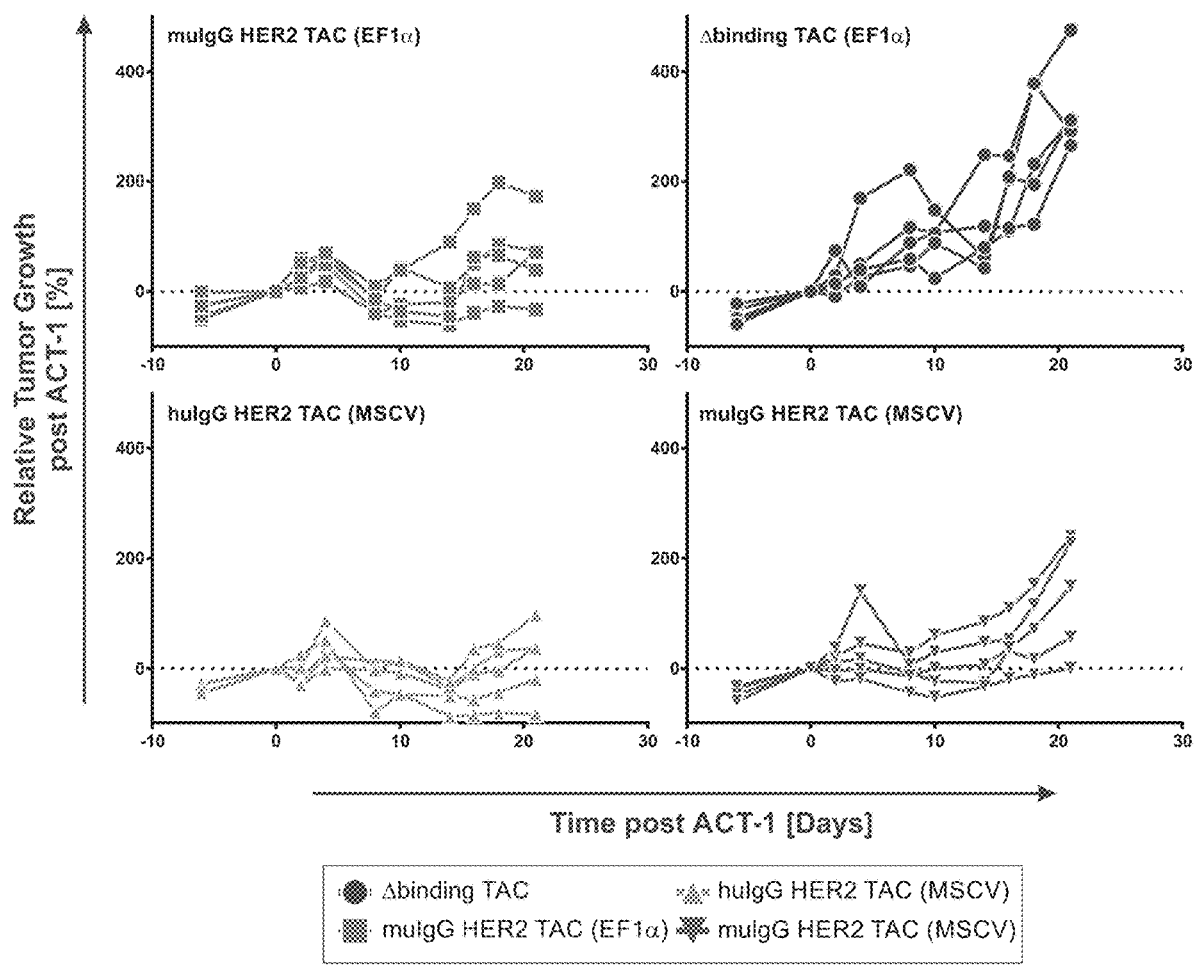
FIG. 32. Illustrates in vivo efficacy of TAC engineered T cells in the OVCAR3 solid tumor model. T cells were engineered with the Δbinding TAC (EF1α promoter), the muIgG HER2 TAC (EF1α promoter), the huIgG HER2 TAC (MSCV promoter) or the muIgG HER2 TAC (MSCV promoter). Mice had been inoculated subcutaneously with OVCAR3 (HER-2-positive) tumors. These were grown to about 100 mm$^3$ in size. Mice were then treated with a split dose of 6 million total HER2 TAC engineered, or Δbinding TAC control T cells 48 h apart via tail vain injection. Tumor progression was followed by biweekly measurements. Δbinding TAC showed no tumor control or tumor regression. All HER2 TAC engineered T cells showed significantly reduced tumor progression, including tumor regression, relative to control mice. All HER2 TAC engineered T cells had similar anti-tumor activity.

FIG. 32. demonstrates the in vivo efficacy of human or murine IgG leader HER2 TAC constructs, under control of a MCSV or EF1α promoter. Following split dose administration of engineered T cells, HER2 TAC engineered cells show significant impact on tumor growth, including tumor regression, relative to the negative control Δbinding TAC. This in vivo experiment demonstrates that all HER2 TAC engineered cells show significant activity against a solid tumor model in vivo.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An engineered γδT cell comprising an expression vector comprising a nucleic acid encoding a human epidermal growth factor receptor (HER2) T cell-antigen coupler (HER2-TAC) polypeptide having the amino acid sequence of SEQ ID NO: 66, SEQ ID NO: 68, or SEQ ID NO: 76, wherein the HER2-TAC polypeptide is expressed by the engineered γδT cell.

2. The engineered γδT cell of claim 1, wherein the amino acid sequence of SEQ ID NO: 66 is encoded by the nucleic acid sequence of SEQ ID NO: 65, the amino acid sequence of SEQ ID NO: 68 is encoded by the nucleic acid sequence of SEQ ID NO: 67, and the amino acid sequence of SEQ ID NO: 76 is encoded by the nucleic acid sequence of SEQ ID NO: 75.

3. A pharmaceutical composition, comprising the γδT cell of claim 1, and a pharmaceutically acceptable excipient.

4. A method of providing a cancer immunotherapy for treating a HER2-expressing cancer in a subject in need thereof, the method comprising administering to the subject a therapeutically effective amount of the engineered γδT cell of claim 1, wherein an antigen binding antibody fragment of the HER2-TAC polypeptide binds to a HER2 antigen expressed by the cancer, wherein administration of said engineered γδT cell results in a reduction in cancer cells in the subject.

5. The method of claim 4, wherein the cancer is breast cancer, bladder cancer, pancreatic cancer, ovarian cancer, glioblastoma, or gastric cancer.

6. The method of claim 4, wherein the cancer is a carcinoma, a blastoma, or a sarcoma.

* * * * *